United States Patent
Campagne et al.

(10) Patent No.: US 10,720,226 B2
(45) Date of Patent: Jul. 21, 2020

(54) METHOD TO MATCH ORGAN DONORS TO RECIPIENTS FOR TRANSPLANTATION

(71) Applicant: Cornell University, Ithaca, NY (US)

(72) Inventors: Fabien Campagne, Astoria, NY (US); Laurent Mesnard, New York, NY (US); Manikkam Suthanthiran, New York, NY (US); Thangamani Muthukumar, New York, NY (US)

(73) Assignee: Cornell University, Ithaca, NY (US)

( * ) Notice: Subject to any disclaimer, the term of this patent is extended or adjusted under 35 U.S.C. 154(b) by 816 days.

(21) Appl. No.: 15/112,105

(22) PCT Filed: Jan. 15, 2015

(86) PCT No.: PCT/US2015/011611
§ 371 (c)(1),
(2) Date: Jul. 15, 2016

(87) PCT Pub. No.: WO2015/109097
PCT Pub. Date: Jul. 23, 2015

(65) Prior Publication Data
US 2016/0328515 A1    Nov. 10, 2016

Related U.S. Application Data

(60) Provisional application No. 61/928,785, filed on Jan. 17, 2014.

(51) Int. Cl.
*G16B 30/00*    (2019.01)
*G16B 40/00*    (2019.01)
(Continued)

(52) U.S. Cl.
CPC .......... *G16B 30/00* (2019.02); *C12Q 1/6883* (2013.01); *G16B 20/00* (2019.02); *G16B 40/00* (2019.02);
(Continued)

(58) Field of Classification Search
None
See application file for complete search history.

(56) References Cited

U.S. PATENT DOCUMENTS

2004/0215487 A1    10/2004  Murphey
2007/0244927 A1    10/2007  Lee et al.

FOREIGN PATENT DOCUMENTS

WO    WO-2007070280 A2    6/2007
WO    WO-2012058689 A2    5/2012
(Continued)

OTHER PUBLICATIONS

Duquesnoy. HLAMatchmaker: A Molecularly Based Donor Selection Algorithm for Highly Alloimmunized Patients. Transplantation Proceedings, vol. 33, pp. 493-497 (Year: 2001).*
(Continued)

*Primary Examiner* — Olivia M. Wise
(74) *Attorney, Agent, or Firm* — Schwegman Lundberg & Woessner, P.A.

(57) ABSTRACT

This invention describes an allogenomics mismatch scoring method that estimates the genomic incompatibility between potential organ donors and a transplant recipient. The allogenomics method addresses immunological concerns and compares genotype information from matched, or potential, donors and recipients. The allogenomics method uses genomic data available before transplantation and predicts kidney graft function for greater than three years after transplantation. The strength of the inverse correlation between pre-transplantation genomic mismatches and transplant organ function increases with the time after transplantation: a low allogenomics mismatch score correlates with better acceptance and function of a donor transplant over time.

12 Claims, 18 Drawing Sheets

(51) Int. Cl.
*C12Q 1/6883* (2018.01)
*G16B 20/00* (2019.01)

(52) U.S. Cl.
CPC .. *C12Q 2600/106* (2013.01); *C12Q 2600/118* (2013.01); *C12Q 2600/156* (2013.01)

(56) References Cited

FOREIGN PATENT DOCUMENTS

| WO | WO-2014011735 A1 | 1/2014 |
|----|------------------|--------|
| WO | WO-2015109097 A1 | 7/2015 |

OTHER PUBLICATIONS

Bentley et al. High-resolution, high-throughput HLA genotyping by next-generation sequencing. Tissue Antigens 2009, vol. 74, pp. 393-403 (Year: 2009).*

"European Application Serial No. 15702069.4, Communication Pursuant to Article 94(3) EPC dated Sep. 22, 2017", 6 pgs.

"European Application Serial No. 15702069.4, Communication Pursuant to Article 94(3) EPC dated Apr. 26, 2018", 6 pgs.

"International Application Serial No. PCT/US2015/011611, International Search Report dated May 4, 2015", 4 pgs.

"International Application Serial No. PCT/US2015/011611, Written Opinion dated May 4, 2015", 10 pgs.

Duquesnoy, René J, et al., "Clinical usefulness of HLAMatchmaker in HLA epitope matching for organ transplantation", Current Opinion in Immunology vol. 20, No. 5,, (Oct. 1, 2008), 594-601.

Joris, Monique M, et al., "A Proposed Algorithm Predictive for Cytotoxic T Cell Alloreactivity", The Journal of Immunology vol. 188, No. 4, (Jan. 18, 2012), 1868-1873.

Kosmoliaptsis, Vasilis, et al., "Predicting HLA Class II Alloantigen Immunogenicity From the Number and Physiochemical Properties of Amino Acid Polymorphisms", Transplantation vol. 91, No. 2,, (Jan. 1, 2011), 183-190.

"International Application Serial No. PCT/US2015/011611, International Preliminary Report on Patentability dated Jul. 28, 2016", 11 pgs.

"Application No. 15702069.4, Response filed Mar. 27, 2017 to European Office Action dated Sep. 16, 2016", 19 pgs.

"European Application Serial No. 15702069.4, Response filed Jan. 19, 2018 to Communication Pursuant to Article 94(3) EPC dated Sep. 22, 2017", 8 pgs.

Opelz, G, "Strength of HLA-A, HLA-B, and HLA-DR mismatches in relation to short- and Long-term Kidney graft survival. Collaborative Transplant Study", Transplant international : official journal of the European Society for Organ Transplantation, vol. 5 Suppl 1, 1992 US National Library of Medicine (NLM), Bethesda, MD, US, Database accession no. NLM14628741, ISSN: 0934-0874, (1992), 1 pg.

"European Application Serial No. 15702069.4, Response filed Aug. 1, 2018 to Communication Pursuant to Article 94(3) EPC dated Apr. 26, 2018", 14 pgs.

"European Application Serial No. 15702069.4, Communication Pursuant to Article 94(3) EPC dated Dec. 13, 2018", 3 pgs.

"European Application Serial No. 15702069.4, Response Filed Apr. 22, 2019 to Communication Pursuant to Article 94(3) EPC dated Dec. 13, 2018", 268 pgs.

* cited by examiner

| Donor amino-acids | Recipient amino-acids | Allogenomics score contribution $\delta_p$ |
|---|---|---|
| {Ala,Phe} | {Ala,Phe} | 0 |
| {Ala} | {Phe} | 1 |
| {Phe} | {Ala,Phe} | 0 |
| {Ala,Phe} | {Asp} | 2 |

Fig. 1B $$\Delta(r,d) = \sum_{p \in P} \delta_p(G_{rp}, G_{dp}) \quad \text{Eqn 1}$$

$$\delta_p(G_{rp}, G_{dp}) = \sum_{a \in G_{dp}} \begin{cases} 0 \text{ if } a \in G_{rp} \\ 1 \text{ otherwise} \end{cases} \quad \text{Eqn 2}$$

Fig. 1C

MODEL BUILT FROM THE
VALIDATION COHORT (eGFR)

e+f * ALLOGENOMICS MISMATCH SCORE

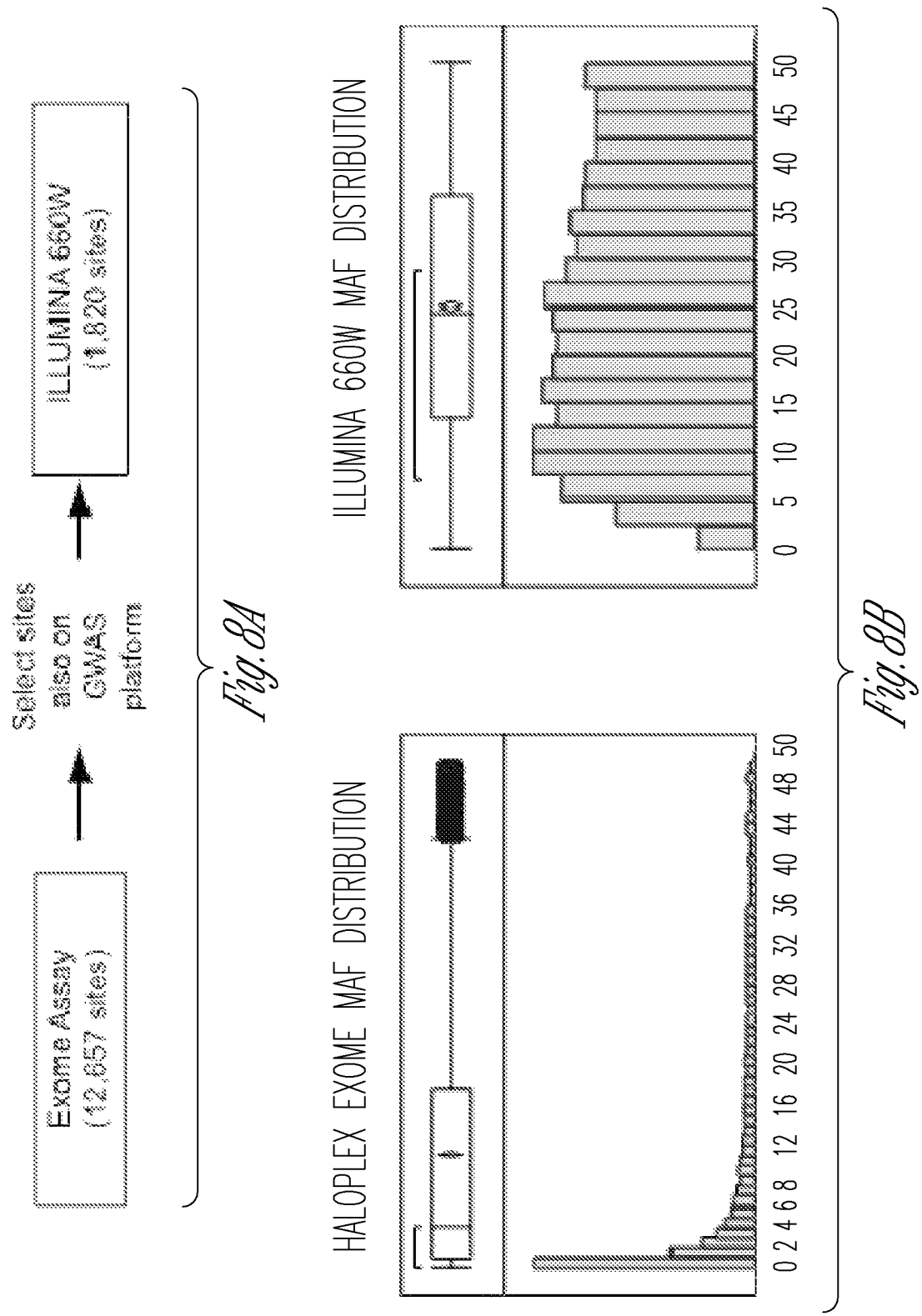

METHOD TO MATCH ORGAN DONORS TO RECIPIENTS FOR TRANSPLANTATION

This application is a U.S. National Stage Filing under 35 U.S.C. 371 from international Application No, PCT/US2015/011611, filed Jan. 15, 2015, and published as WO 2015/109097 on Jul. 23, 2015, which claims benefit of priority to the filing date of U.S. Provisional Application Ser. No. 61/928,785, filed Jan. 17, 2014, the contents of which are specifically incorporated by reference herein in their entity.

BACKGROUND

Most patients who experience End Stage Renal Disease (ESRD) can benefit from kidney transplantation. The initial series of kidney transplants were performed in the 1950s in the USA and France and between identical twins. The introduction of potent immunosuppressive regimens, human leukocyte antigen (HLA)-typing for matching of recipients with donors, and cross matching (testing of recipient's serum against donor's cells for the presence of preformed antibodies) in the 1960s and 1970s made it possible to extend kidney transplantation to unrelated living donors and organs from deceased donors. The short-term outcomes of renal grafts have steadily improved since the early transplants with the refinement of immunosuppressive regimens, HLA compatibility, and a better understanding of when and how immunosuppressive drugs can be used to manage the health of the recipient and function of the graft. See, Opelz et al. Collaborative Transplant Study. Rev Immunogenet. 1(3):334-42 (1999); Angaswamy et al., Human Immunology 74(11):1478-85 (2013); Leventhal et al., J Am Soc Nephrol. 24(9):1376-85 (2013).

Despite these advances, data collected across the USA shows that 50% of kidney allografts fail within ten years of transplantation (Handbook of clinical transplantation. 4th edition ed. Danovitch G M, editor.: Lippincott Williams & Wilkins; 2009). Hence, yet uncharacterized genomic loci may influence donor/recipient compatibility.

Kidney transplant recipients suffer from a number of complications. Many renal transplant recipients experience an episode of acute cellular rejection (ACR), when the immune system of the recipient targets the transplanted donor organ. Adjusting the patient's immunosuppressive regiment may control episodes of ACR. Many transplant patients develop chronic rejection/chronic allograft nephropathy (CAN), which manifest itself in the graft by interstitial fibrosis and tubular atrophy (IF/TA) and a decline in graft function over time. ACR and CAN are routinely diagnosed by histopathological analysis of graft biopsies. While ACR is mostly a reversible adverse event, CAN, at the present time, is a relentlessly progressive condition for which no treatment is available. CAN progression is associated with loss of graft function, which eventually leads to graft loss. Chronic allograft nephropathy is poorly understood, and explains more than 50% of kidney graft losses.

Past studies have demonstrated the importance of HLA-mismatches on graft outcome, leading to important clinical strategies for graft allocation in many countries, including the U.S. As these strategies developed, it has become clearer that HLA mismatches represent only a component, albeit an important component, of the mismatches between donor and recipient. This suggests that mismatch at other loci in the genome, even remote from the HLA locus, may play a role influencing graft outcome. Indeed, fully HLA-matched kidney grafts may still develop acute cellular rejection as well as chronic allograft nephropathy, and more importantly every transplant, including recipients of fully HLA matched transplants need to be treated with chronic/maintenance immunosuppressive therapy to prevent rejection.

Hence, improved methods for matching donor organs to recipients are needed.

SUMMARY

This application discloses a method, called the allogenomics method, to determine the best match of a donor organ to a recipient in need of a transplanted organ that compares the genomes of potential donors with the genome of a transplant recipient. The method estimates the incompatibility between pairs of potential donors and transplant recipients by counting the number of protein fragments encoded by the donor genome that may be recognized as non-self by the recipient immune system. The method defines a quantitative estimate of the allogenomics incompatibility, called the allogenomics mismatch score. This estimate can be used to predict which donors are better candidates for providing organs for transplantation to a given recipient, in order to minimize loss of graft function and graft loss post-transplantation.

One aspect is a method for identifying at least one match among multiple potential organ donors for at least one recipient in need of a transplanted organ, where the method comprises:
 (a) assaying to determine amino acid mismatches encoded by the donor genomes that at least one selected recipient immune system could recognize as non-self;
 (b) separately summing the number of amino acid mismatches for each donor compared to at least one selected recipient where the mismatches can be recognized as non-self by the selected recipient(s);
 (c) determining an allogenomics mismatch score $\Delta(r,d)$ for each selected recipient r and each donor d, which is a sum of mismatches as shown in Equation 1:

$$\Delta(r, d) = \sum_{p \in P} \delta_p [G_{rp} = \text{genotype}(r, p), G_{dp} = \text{genotype}(d, p)] \quad \text{Equation 1}$$

where:
 $\delta_p$ is defined in Equation 2;
 P is a set of all genomic positions of interest;
 p is a polymorphic site in a set P;
 $G_{rp}$ is the genotype of the recipient r at genomic site/position p;
 $G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
 a is an allele; and
 (d) identifying a match among the multiple potential organ donors for at least one recipient in need of a transplanted organ by identifying one or more donor with an allogenomics mismatch score that is below a threshold value, or by identifying the donor with the lowest allogenomics score for a selected recipient.

Another aspect is a method that includes:
(a) assaying to determine amino acid mismatches encoded a donor organ genome that the immune system of the recipient of the donor organ could recognize as non-self;
(b) summing the number of donor amino acid mismatches compared to the recipient where the mismatches can be recognized as non-self by recipient;
(c) determining an allogenomics mismatch score Δ(r,d) for the recipient r and the donor d, which is a sum of mismatches as shown in Equation 1:

$$\Delta(r, d) = \sum_{p \in P} \delta_p [G_{rp} = \text{genotype}(r, p), G_{dp} = \text{genotype}(d, p)] \quad \text{Equation 1}$$

where:
  $\delta_p$ is defined in Equation 2;
  P is a set of all genomic positions of interest;
  p is a polymorphic site in a set P;
  $G_{rp}$ is the genotype of the recipient r at genomic site/position p;
  $G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
  a is an allele;
(d) determining whether the allogenomics mismatch score is greater than a threshold; and
(e) identifying whether the recipient is in need of treatment, or may develop a need for treatment, when the allogenomics mismatch score is greater than a threshold value.

Another aspect is an apparatus that includes:
(a) a component for separately assaying amino acid mismatches encoded by multiple donor genomes that at least one selected recipient immune system could recognize as non-self;
(b) a component for separately summing the donor amino acid mismatches assayed by comparison to amino acids encoded by each selected recipient;
(c) a component for determining an allogenomics mismatch score Δ(r,d) for at least one recipient r and one or more donor d, which is a sum of mismatches as shown in Equation 1:

$$\Delta(r, d) = \sum_{p \in P} \delta_p [G_{rp} = \text{genotype}(r, p), G_{dp} = \text{genotype}(d, p)] \quad \text{Equation 1}$$

where:
  $\delta_p$ is defined in Equation 2;
  P is a set of all genomic positions of interest;
  p is a polymorphic site in a set P;
  $G_{rp}$ is the genotype of the recipient r at genomic site/position p;
  $G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where a is an allele; and
(d) a component for determining a match among potential organ donors for at least one recipient in need of a transplanted organ by identifying one or more donor with a allogenomics mismatch score less than a threshold value, or by identifying the donor with the lowest allogenomics mismatch score for a selected recipient.

The methods described herein can be used to evaluate a variety of donor organs for transplantation into recipients who may have need therefor. For example, the donor organ can be a kidney, a heart, a liver, a lung, a bladder, an intestine, a trachea, an esophagus, a pancreas, a stomach, a thymus, an ovary, a cervix, a uterus, a vagina, a penis, a prostate, a testes, or any combination or part thereof. Tissues from donors can also be evaluated to identify a match for transplantation into a recipient. For example, donor tissues such as vascular tissues, neuronal tissues, muscular tissues, adipose tissues, pancreatic islet tissues, bone tissues, bone marrow, skin, dermal tissues, stem cells, connective tissues, or a combination thereof can be evaluated and compared to potential recipients using the methods described herein.

BRIEF DESCRIPTION OF THE DRAWINGS

FIG. 1A-1C illustrates that recipient/donor incompatibility can be quantified by exome sequencing and calculation of allogenomics mismatch score. FIG. 1A is a schematic diagram illustrating the inventive concept that post-transplant kidney graft function is associated with the number of amino acids coded by the donor genome that the recipient immune system would recognize as non-self. FIG. 1B is an example of donor/recipient amino-acid mismatches at one protein position, and resulting allogenomics score contributions. The allogenomics mismatch score is calculated by summing contributions over a set of genomic polymorphisms (see, e.g., Example 5 for details). FIG. 1C shows equations for the allogenomics model. Score contributions are summed across all genomic positions of interest (set P) to yield the allogenomics score Δ(r,d). $G_{rp}$: genotype of the recipient r at genomic site/position p. $G_{dp}$: genotype of the donor d at site p. Alleles of a genotype are denoted with the letter a.

FIG. 3A graphically illustrates the relationship between the allogenomics mismatch score and recipient serum creatinine levels at 12 months post-transplantation. FIG. 3B graphically illustrates the relationship between the allogenomics mismatch score and recipient serum creatinine levels at 24 months post-transplantation. FIG. 3C graphically illustrates the relationship between the allogenomics mismatch score and recipient serum creatinine levels at 36 months post-transplantation. FIG. 3D graphically illustrates the relationship between the allogenomics mismatch score and recipient estimated glomerular filtration rate (eGFR) levels at 12 months post-transplantation. FIG. 3E graphically illustrates the relationship between the allogenomics mismatch score and recipient estimated glomerular filtration rate (eGFR) levels at 24 months post-transplantation. FIG. 3F graphically illustrates the relationship between the allogenomics mismatch score and recipient estimated glomerular filtration rate (eGFR) levels at 36 months post-transplantation. DNA was isolated from 10 pairs of kidney graft recipients and their living kidney donors (Discovery set). Whole exome sequencing of the donor genomes and recipient genomes was performed and the sequencing information was used to calculate allogenomics mismatch scores based on amino acid mismatches in transmembrane proteins. The graft function markers correlate in a time dependent fashion with the allogenomics mismatch score. The strongest correlations were observed at 36 months post-transplantation.

FIG. 4A graphically illustrates the relationship between the allogenomics mismatch score and recipient serum creatinine levels at 12 months post-transplantation. FIG. 4B graphically illustrates the relationship between the allogenomics mismatch score and recipient serum creatinine levels at 24 months post-transplantation. FIG. 4C graphically illustrates the relationship between the allogenomics mismatch score and recipient serum creatinine levels at 36 months post-transplantation. FIG. 4D graphically illustrates the relationship between the allogenomics mismatch score and recipient serum creatinine levels at 48 months post-transplantation. FIG. 4E graphically illustrates the relationship between the allogenomics mismatch score and recipient estimated glomerular filtration rate (eGFR) levels at 12 months post-transplantation. FIG. 4F graphically illustrates the relationship between the allogenomics mismatch score and recipient estimated glomerular filtration rate (eGFR) levels at 24 months post-transplantation. FIG. 4G graphically illustrates the relationship between the allogenomics mismatch score and recipient estimated glomerular filtration rate (eGFR) levels at 36 months post-transplantation. FIG. 4H graphically illustrates the relationship between the allogenomics mismatch score and recipient estimated glomerular filtration rate (eGFR) levels at 48 months post-transplantation. DNA was isolated from 24-pairs of kidney graft recipients and their living kidney donors (Validation set). Whole exome sequencing of the donor genomes and recipient genomes was performed and the sequencing information was used to calculate allogenomics mismatch scores based on amino acid mismatches in transmembrane proteins. The graft function markers correlate in a time dependent fashion with the allogenomics mismatch score. The strongest correlations were observed at 36 and 48 months post-transplantation.

FIG. 5A is a schematic diagram of the method that was used to train a model to predict eGFR on the discovery cohort (using eGFR at 36 months) and used the trained, fixed, model to predict eGFR at 36 months and 48 months for recipients of the Validation cohort. The trained model was eGFR=109.031825038751- 0.0404193475856964*allogenomics_mismatch_score. FIG. 5B graphically illustrates correlation between predicted eGFR and observed eGFR on the Validation cohort at 36 months post transplantation. FIG. 5B graphically illustrates correlation between predicted eGFR and observed eGFR on the Validation cohort at 48 months post transplantation.

FIG. 6A is a schematic diagram illustrating the process of training models to predict serum creatinine and eGFR on the Validation cohort and then using the trained, fixed, model to predict serum creatinine and eGFR for recipients of the Discovery cohort. FIG. 6B graphically illustrates correlation between the eGFR predicted by the fixed model and that observed in the Validation cohort. Parameters of the trained models were: a=82.12310, b=−0.002528.

FIG. 7A graphically illustrates the allogenomics mismatch scores calculated over all transmembrane proteins (Panel A). FIG. 7B graphically illustrates the allogenomics mismatch scores restricted to the HLA A, HLA B, and HLA DR loci. FIG. 7C graphically illustrates serum creatinine levels correlated with the allogenomics mismatch scores relating to the number of mismatches in the A,B, and DR HLA loci for the complete cohort. FIG. 8D graphically illustrates estimated glomerular filtration rate (eGFR) levels correlated with the allogenomics mismatch scores relating to the number of mismatches in the A,B, and DR HLA loci for the complete cohort. However, these correlations do not explain the association with post-transplantation graft function because when the HLA loci (A/B/DR/DQ/DP/C) are excluded from the sites included in the calculation of the allogenomics mismatch score, a significant correlation is still observed with serum creatinine level (FIG. 7C) and eGFR (FIG. 7D) at 36 months post transplantation.

FIG. 8A-8C illustrates how well the allogenomics mismatch score could be evaluated with the genotyping array technology frequently used in GWAS studies. Analysis are done on the Validation cohort (n=24 pairs, 48 exomes). FIG. 8A is a schematic diagram illustrating that evaluation of the allogenomics mismatch score with the Agilent Haloplex exome platform takes advantage of 17,025 genomic sites to estimate allogenomic contributions in transmembrane proteins. Only sites where an allogenomics mismatch score contribution was different from zero are counted. The exome genomic sites were filtered to exclude sites not found on the Illumina 660W genotyping platform (used in Franklin et al., A genome-wide association study of kidney transplant survival: Donors recipients and interactions. In: American Conference of Human Genetics. 2012. Available from the website at ashg.org/2012meeting/abstracts/fulltext/f120120818.htm). After filtering, the allogenomics score is estimated with 1,797 remaining genomic sites. FIG. 8B shows histograms graphically illustrating the minor allele frequency (MAF) of the alleles described at each set of genomic sites (MAF is estimated from the EVP database, see Example 5). Exome sequencing is an assay that directly observes variations in an individual DNA sample. The MAF distributions confirm that exome sequencing helps estimate contributions from many rare (MAF<5%) polymorphisms, whereas the chip genotyping platform estimates the score from contributions from frequent alleles. FIG. 8C graphically illustrates the correlation obtained with the score estimated from the exome sites and the subset of sites also measured by the GWAS platform. While some trend is still visible with sites measured on the GWAS platform, more samples would be needed to reach significance in the combined Discovery and Validation cohorts (n=34 pairs). Note that the magnitude of the scores is smaller on the GWAS platforms because fewer contributions are summed. In contrast, the exome assays (Illumina TrueSeq for the Discovery cohort or Agilent Haloplex for the Validation cohort) result in stronger and significant correlation on the same set of samples.

FIG. 9A is a diagram of a system that can perform the methods described herein. FIG. 9B is a block diagram of a machine in the example form of a computer system.

DETAILED DESCRIPTION

The applicants here present a new method to estimate the genomic incompatibility between the organ graft recipient and potential donors. This method is referred to as allogenomics. The allogenomics method predicts kidney graft function three years or longer after transplantation by using data on the genomic dissimilarity of donors and recipients that is available before the transplantation. The strength of the correlation increases with the time after transplantation. As described and tested in the Examples, the inventors have shown for the first time it is possible to predict renal graft function at three years or longer post-transplant by using genomic data available before the transplant surgery is performed. The method therefore has a direct application to help match potential donor organs to patients in need of organ transplantation in order to maximize transplant outcome for the patients.

A few factors have been established as predictors of post-transplant renal graft function. These factors include the organ donor type, either from a living donor or from a deceased donor and the cold ischemia time (the time the harvested organ is preserved prior to transplantation). Blood group compatibility is a prerequisite unless pre-conditioning of the recipient is undertaken to facilitate blood group incompatible kidney transplantation. While HLA compatibility is a necessary requirement for successful bone marrow transplants, full HLA compatibility is not an absolute prerequisite for tissue transplant function. In view of better patient survival following transplantation compared to dialysis, kidney transplants are routinely performed with varying degrees of HLA-mismatches including HLA mismatches for all HLA-class I and II antigens. Although, graft outcome is better with better HLA-matching, excellent long-term graft outcome with stable graft function have been observed when HLA mismatches occur. Loci other than HLA compatibility may influence the long-term clinical outcome of kidney allografts.

The allogenomics method relates to quantification of potential immune responses in the transplant recipient by considering the potential origin of the immune response: the immune system of the recipient mounts against the donor organ. Alleles present in the donor genome, but not in the recipient genome, have a potential to produce epitopes that the recipient genome would recognize as non-self. Thus the focus of the current methods is on what new epitopes a donor organ may present to a recipient, rather than on what are the total of recipient and donor differences. This explains why the allogenomics score is not equivalent to the genetic measures of allele sharing distance, which have been used for instance, to perform genetic clustering of individuals (Suthanthiran et al., N Engl J Med. 369(1):20-31 (2013)).

Figure 1A:
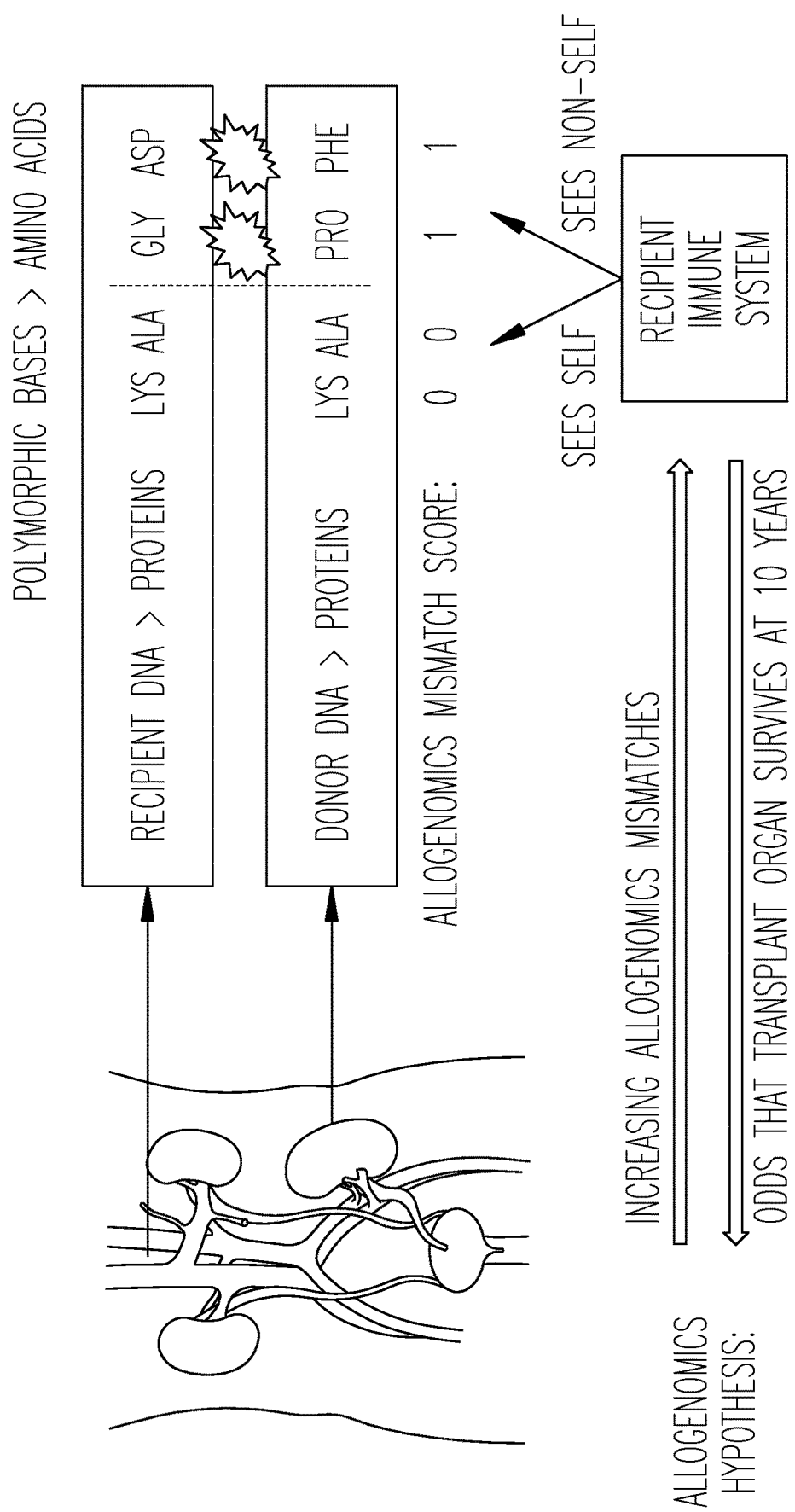

The allogenomics method involves evaluation of the number of amino acid differences encoded by the donor genome that the recipient immune system could recognize as non-self and the recognition that such differences contribute to immune events such as acute or chronic rejection and graft function. FIG. 1 is a schematic illustration of the allogenomics method. A greater number of genomic mismatches in a donor relative to a recipient indicates that an organ from that donor will have a greater potential for rejection than an organ from a donor with a lower number of mismatches. A low allogenomics mismatch score correlates with better acceptance and function of a donor transplant over time.

Because human autosomes have two copies of each gene, two possible alleles are considered for the donor and recipient genomes. An allogenomics score estimates contributions between zero and two, depending on the number of different amino acids that the donor genome encodes for at a given protein position. For example, Table 1 shows the possible allogenomics score contributions when the amino acids in question are either an Alanine or a Phenylalanine or an Aspartate amino acid. The allogenomics mismatch score is the sum of all amino acid mismatch contributions between the recipient and the donor that can be recognized as non-self by the recipient (see Equations 1 and 2).

TABLE 1

Examples of donor/recipient amino-acid mismatches at one protein position, and resulting allogenomic score contributions.

| Donor amino-acids | Recipient amino-acids | Number of amino acids recipients sees as non-self, and the corresponding allogenomic score contribution |
| --- | --- | --- |
| {Ala, Phe} | {Ala, Phe} | 0 |
| {Ala} | {Phe} | 1 |
| {Phe} | {Ala, Phe} | 0 |
| {Ala, Phe} | {Asp} | 2 |

The allogenomics mismatch score $\Delta(r,d)$ is estimated for a recipient r and donor d as a sum of score mismatch contributions as shown in Equation 1.

$$\Delta(r, d) = \sum_{p \in P} \delta_p[G_{rp} = \text{genotype}(r, p), G_{dp} = \text{genotype}(d, p)] \quad \text{Equation 1}$$

where:
$\delta_p$ is defined in Equation 2;
P is a set of all genomic positions of interest;
p is a polymorphic site in a set P;
$G_{rp}$ is the genotype of the recipient r at genomic site/position p; and
$G_{dp}$ is the genotype of the donor d at site p.

The individual score mismatch contributions $\delta_p(G_{rp}, G_{dp})$ can be calculated at a polymorphic site of interest as shown in Equation 2.

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
a is an allele;
P is a set of all genomic positions of interest;
p is a polymorphic site in a set P;
$G_{rp}$ is the genotype of the recipient r at genomic site/position p; and
$G_{dp}$ is the genotype of the donor d at site p.

Contributions are observed for each polymorphic site p in a set P, where P is determined by the genotyping assay and analysis methods, and can be further restricted (e.g., to polymorphisms within genes that code for membrane proteins). Score mismatch contributions $\delta_p(G_{rp}, G_{dp})$ are calculated using the recipient genotype $G_{rp}$ and the donor genotype $G_{dp}$ at the polymorphic site p. A genotype can be represented as a set of alleles that were assayed in a given genome. For instance, if a subject has two alleles at one polymorphic site, that are denoted allele A or B, the genotype at p is represented by the set {A,B}. This representation is general and sufficient to process polymorphic sites with single nucleotide polymorphisms or insertion/deletions.

Table 2 presents examples of donor and recipient genotypes and indicates the resulting score contribution (the subscript p is omitted for conciseness). Score contributions are summed across all polymorphism sites in the set P to yield the allogenomic mismatch score (see Equation 1).

TABLE 2

Examples of donor/recipient mismatches allogenomic score contribution

| Gd = {A, B} | Gr = {A, B} | (Gr, Gd) = 0 |
|---|---|---|
| Gd = {A} | Gr = {B} | (Gr, Gd) = 1 |
| Gd = {B} | Gr = {A, B} | (Gr, Gd) = 0 |
| Gd = {A, B} | Gr = {C} | (Gr, Gd) = 2 |

A strong correlation exists between the allogenomics score estimated with the approach and graft function measured with eGFR or creatinine levels (e.g., shown in FIGS. 2-8 and described in the Examples). This correlation would be sufficient for the allogenomics mismatch score to be used for predicting optimal pairs of donor/recipients for transplantation. The method and this correlation are the basis of our invention to improve the matching of donor and recipients to maximize transplant clinical outcome years post-transplantation.

A threshold allogenomics mismatch score can be used to distinguish an acceptable donor organ from an unacceptable donor organ for a selected recipient. In some instances the threshold allogenomics mismatch score identifies transplant recipients who would benefit from treatment, or who may develop the need for treatment. Such a threshold can be developed using raw allogenomics mismatch scores, or on at set of normalized allogenomics mismatch scores. Normalization removes the impact of reduced set of genomic sites. The range of the score depends on the specific assay used, so normalization is preferably used if a different set of polymorphic sites is assayed. For example, if 6000 sites are typically assayed for mismatches, a raw threshold value based upon an "acceptable" number of mismatches with 6000 sites would likely be different from an "acceptable" number of mismatches within a smaller number of assayed sites (e.g., 4000 sites) or within a larger number of assayed sites (e.g., 8000 sites). Hence, normalization can be used when using a raw threshold score is based on assays of different numbers of site.

A more objective and precise decision threshold can be identified by measuring the allogenomics mismatch score for a number of donor-recipient pairs (e.g., more than 100, or more than 200, or more than 300), and fitting a linear model with the scores to predict eGFR at a selected time such as at four years post-translation. For example, such a threshold can be obtained as the value of the allogenomics mismatch score that would yield a four year eGRF of 40 ml/min/1.73 m. This procedure would yield a threshold of 1400 according to the methods described herein and by using the data in FIG. 4H. Such analysis can also be performed on other graft survival time periods, for example graft survival for ten years. When organ selection and matching is performed using HLA, 40-50% of patients have lost the graft at 10 years. A good threshold allogenomics mismatch score would, for example, be below or equal to a mean or median allogenomics mismatch score obtained for 80% of subjects who still have a functioning graft (eGRF>20 ml/min/1.73 m). Eighty percent graft retention at 10 years post-translation would be a significant improvement over the 50% to 60% graft retention observed when the graft was selected using HLA matching.

It is also possible to estimate a model of the rate of eGFR change per year. This can be done by fitting a linear model using the allogenomics mismatch score and considering how much the score has decreased between two time points (e.g., change between year 4 and year 1 would provide data to calculate the rate of change: (eGFR_1y−eGFR_4y)/4, or rate of change per year following transplantation. The rate of change can be used to estimate how many years the graft will survive post-transplantation in a given patient, knowing that patients require dialysis when eGFR<15 ml/min/1.73 m.

An allogenomics mismatch score of less than about 1600 identifies a donor organ that will likely function well for 3 or more years. For example, allogenomics mismatch scores of less than about 1500, or less than about 1450, or less than about 1400, or less than 1350, or less than about 1300, or less than about 1250, or less than about 1200, or less than about 1100 identifies a donor organ that will likely function well for 3 or more years.

A variety of methods can be used to identify the differences between donors and recipients. For example, the allogenomics method can involve sequencing coding sequences (the exome) of the genomes of both the donor and measuring genomic differences. Although HLA loci can be included in the sites that are assayed for mismatches between donor and recipient, it is not necessary to include HLA in the loci assayed. Sites remote from the classical HLA loci can be assayed and will yield reliable allogenomics mismatch scores that identify whether or not a donor organ is acceptable for a recipient.

The allogenomics method makes it possible to generate a quantitative compatibility score between the genomes of a recipient and potential donor that is calculated from the genotypes and genome annotations available before transplantation. The allogenomics approach does not assume a Mendelian inheritance model but integrates the unique features of transplantation such as the existence of two genomes in a single individual and the recipient's immune system mounting an immune response directed at antigens displayed by the donor kidney.

These new methods can predict long-term transplant function from the genomic information available prior to transplantation, allowing improved selection of donor organs that are optimally compatible with the recipient. Although, the experimental data shown in the Examples relates to kidney grafts, the method relates to identifying immunological differences in a donor compared to a recipient. Hence, the method is applicable to a variety of donor organs for transplantation into recipients who may have need therefor. For example, the donor organ can be a kidney, a heart, a liver, a lung, a bladder, an intestine, a trachea, an esophagus, a pancreas, a stomach, a thymus, an ovary, a cervix, a uterus, a vagina, a penis, a prostate, a testes, or any combination or part thereof. Tissues from donors can also be evaluated to identify a match for transplantation into a recipient. For example, donor tissues such as vascular tissues, neuronal tissues, muscular tissues, adipose tissues, pancreatic islet tissues, bone tissues, bone marrow, skin, dermal tissues, stem cells, connective tissues, or a combination thereof can be evaluated and compared to potential recipients using the methods described herein. A threshold value for identifying an acceptable donor—recipient match, or for identifying a problem with an existing transplant organ can readily be established by correlating functional characteristics of the organ type with allogenomics mismatch scores, in a manner similar to the correlations shown herein in the Examples and Figures.

Preparation of DNA for Sequencing

Genomic DNA is isolated from tissue or bodily fluid samples obtained from the donor(s) and recipient(s) using available methods to separate DNA from other cellular components such as proteins, lipids, RNA, and carbohydrates. The procedure can involve tissue/sample disruption, lysis of cells, removal of proteins and other contaminants, and recovery of DNA. Nuclease inhibitors are generally employed such as protein denaturing agents, proteinases (e.g., proteinase K), detergents, and cation chelators can be used to prevent enzymatic digestion of the DNA. In some instances, the tissue/fluid samples are heated to disrupt proteins but DNA purification can also be performed in temperatures below 45° C. to prevent the denaturation of short, AT-rich, fragments. Denaturation of dsDNA fragments in a complex mixture can result in single stranded DNA fragments that may not anneal back to its complement. Increased temperatures during isolation can decrease the efficiency of the procedure before ligation, because the ssDNA fragments cannot be ligated to double-stranded adaptors efficiently.

The genomic DNA can be fragmented to generate double-stranded DNA fragments of a convenient size for amplification and sequencing. For example, the genomic DNA can be sheared to a fragment size of about 125 bp to about 300 bp, or about 150 bp to about 250 bp. Fragmentation can be achieved by mechanical processes (e.g., physically shearing the DNA using sonication), or by enzymatic cleavage. Enzymatic cleavage can involve use of a dsDNA-specific nuclease such as shrimp nuclease and/or DFF40 nuclease, which generates DNA with blunt ends, so they do not need repairing or a fill-in step. Mechanical and many other types of nucleases or enzymes can create single-stranded extensions that can be blunted by the action of T4 polymerase and exonuclease. Single-stranded extensions can be more prone to the oxidative damage than dsDNA. Although such oxidative damage can only occasionally damage some of the bases in the single-stranded extension, in changes the template that T4 polymerase uses for generating double-stranded, blunt ends can occur. T4 polymerase encounters a damaged base in the template and introduces its partner—a complementary base. The damage may change the pattern of the preferred hydrogen bonds, which may result in the stabilization of interactions with an incorrect nucleotide in the complementary position. After blunt-ending and ligation of Y-adapters, this error can be amplified during PCR, and may result in a false mutation call. Hence, using nucleases that provide blunt DNA ends during fragmentation can obviate this problem. Small products of less than about 125 bp or less than about 75 bp can be removed using available size fractionation methods.

The ends of the double-stranded DNA fragments can be tailed to generate a short single-stranded region to which adaptors or linkers can be ligated. The adaptors or linkers allow capture of the DNA fragments and separation from impurities and fragments that were not properly processed. The adaptors/linkers also allow each fragment to be hybridized to a solid surface (e.g., within a reaction chamber or flowcell), where subsequent processing can occur. For example, the adaptors/linkers can provide primer hybridization sites for DNA amplification or sequencing.

The DNA fragment pool from a specific donor or recipient is thus a library of DNA fragments that are unique to that individual donor or recipient.

DNA Amplification and Sequencing

The different libraries of genomic DNA fragments can be amplified if desired to provide a larger sample for evaluation. However, the libraries are generally subjected to minimal PCR cycling. The amount of amplification can be quantified. Libraries can be combined into pools that contain small numbers of either donor or recipient libraries. Such pooling can reduce the number of samples that are sequenced. When a pool contains a library of interest (e.g., from a donor or recipient of interest), the individual libraries in the pool can be further evaluated, for example, to ascertain which donor best matched with a particular recipient.

Sequencing can be performed using any available procedures. For example, a pool of primers that specifically recognize all the various exons of interest can be employed. Thus, specific primer pools can be employed for sequencing essentially all exons, or for sequencing only some exons that are of particular interest. In some cases, the primer pool can include primers for sequencing all human exons. However, in other cases, the primer pool can include primers for sequencing only selected classes or types of exons.

For example, the primer pool can include primers for sequencing all human exons except those that specifically bind to and would facilitate sequencing of HLA exons. As shown herein, when HLA primers are eliminated from the primer pool, the method still identifies excellent long-term graft outcome with stable graft function. The success of these transplants shows that loci other than the HLA loci influence the long-term clinical outcome of kidney allografts.

Table 5 provides a list of some genes that can be evaluated in the methods described herein. These genes have the names defined by the HUGO Gene Nomenclature Committee (see website at genenames.org/). Sequences for these genes are also available through links provided by the genenames.org website. A portion or all of the genes listed in Table 5 can be assayed to determine the number of amino acid differences encoded by the donor genome that the recipient immune system could recognize as non-self.

In another example, the primer pool can include primers for sequencing exons encoding membrane proteins. Such proteins are likely to be more immunologically visible than intracellular proteins. Hence, membrane proteins are a class of proteins that may influence whether or not a donor transplant is recognized as having foreign antigens or as having 'self' antigens.

Sequencing can be performed using any convenient procedure. For example, automated sequencing devices and procedures can be employed. The nucleic acid sequencer can be configured to analyze (e.g., interrogate) a nucleic acid fragment utilizing all available varieties of techniques, platforms, or technologies to obtain nucleic acid sequence information. For example, the sequencer can perform sequencing by synthesis of DNA from primers that selectively bind to selected DNA sequences. The sequencer can also perform sequencing by fragmenting the DNA in the library that is being sequenced and then determining the molecular weight and sequence by physical measurement (e.g., mass spectroscopy). In general automated sequencers are preferred.

The sequencer can also perform sequencing, and be integrated with components that store the sequencing information, and assemble sequencing information into complete sequences for the individual exons. For example, the nucleic acid sequencer can be in communications with the sample sequence data storage either directly via a data cable (e.g., a serial cable, a direct cable connection, etc.) or bus linkage or, alternatively, through a network connection (e.g., Internet, LAN, WAN, VPN, etc.). In various embodiments, the network connection can be a "hardwired" physical connection. For example, the nucleic acid sequencer can be communicatively connected (via Category 5 (CATS), fiber optic, or equivalent cabling) to a data server that can be communicatively connected (via CATS, fiber optic, or equivalent cabling) through the internet and to the sample sequence data storage. The network connection can be a wireless network connection (e.g., Wi-Fi, WLAN, etc.), for example, utilizing an 802.11b/g or equivalent transmission format. In practice, the network connection utilized is dependent upon the particular requirements of the system. In some cases, the sample sequence data storage can be an integrated part of the nucleic acid sequencer.

In the Examples described herein, samples were processed through flow cells such as those provided by the Illumina HiSeq2000 platform.

Alternative Genotyping Methods.

The allogenomics mismatch score is based on the number of epitopes encoded by the donor genome that the recipient's immune system could recognize as non-self. The method is illustrated in FIG. 1. Hence, the allogenomics method is not limited to using exome assays or DNA sequencing methods, because other approaches can be used to determine genotypes in the recipient and donor genomes that would be sufficient to use as input to the method. Alternative methods of genotyping calling can be used with the invention, and relate to the type of genotyping assay employed. There is no strong requirement placed on the analysis methods other than the ability to call genotypes accurately with data produced by the genotyping assay.

The allogenomics mismatch score can be optimized by defining a subset of polymorphisms that has the largest predictive ability for graft function and/or graft loss. The methods described herein can facilitate analysis of large datasets of genotypes from matched donor and recipient transplants. Sites with genotypes that associate the most with the clinical endpoint of interest can be evaluated using procedures described herein such as those used for evaluating the effect of HLA loci on the allogenomics mismatch score.

Various approaches are available to make this selection when a suitable dataset of genotype has been collected and matching clinical information is available. A simple approach consists in comparing the allogenomics mismatch score contributions summed over all polymorphisms of a gene in groups of matched transplants with extreme phenotype. For instance, comparing the score contributions between groups of transplants with high graft function at three years to transplants with poor graft function at three years will produce sets of genes that contain polymorphisms most predictive of graft function. It is likely that different subsets of polymorphisms will be obtained in this way to predict clinical outcome optimally for different types of graft. These subsets derive directly from this invention and the availability of matched genotype datasets for donor and recipient individuals.

Alternative methods for genotyping are also compatible with the methods described herein. For instance, hybridization of DNA to microarrays, hybridization to or beads, sequencing, primer extension, microarray sequence analysis, SNP analysis, polymerase chain reaction, or a combination thereof. Other methods that can recognize and/or identify a large number of polymorphisms present in the human population would also be suitable as a genotyping assay to use with this approach. Whole genome sequencing is a suitable approach that makes it possible to determine the genotypes of the donor and recipients genomes.

Allogenomics System

An allogenomics apparatus is described herein for performing methods for evaluating with which donor tissues are acceptable for transplantation into a recipient. The apparatus includes a series of components for:

(a) assaying the number of amino acid differences encoded by one or more donor genome that at least one recipient immune system could recognize as non-self;

(b) summing of amino acid mismatches assayed (and detected) in the donor(s) relative to each selected recipient, where the mismatches can be recognized as non-self by the recipient;

(c) determining an allogenomics mismatch score $\Delta(r,d)$ for at least one recipient r and one or more donor d, where the allogenomics mismatch score $\Delta(r,d)$ is a sum of mismatches as shown in Equation 1:

$$\Delta(r, d) = \sum_{p \in P} \delta_p[G_{rp} = \text{genotype}(r, p), G_{dp} = \text{genotype}(d, p)] \quad \text{Equation 1}$$

where:
$\delta_p$ is defined in Equation 2;
P is a set of all genomic positions of interest;
p is a polymorphic site in a set P;
$G_{rp}$ is the genotype of the recipient rat genomic site/position p; $G_{dp}$ is the genotype of the donor d at site p; and (d) determining whether a match exists among one or more potential organ donors for a recipient in need of a transplanted organ by identifying one or more donors with low allogenomics mismatch score(s).

The individual score mismatch contributions can be calculated at a polymorphic site of interest as shown in Equation 2.

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
a is an allele;
P is a set of all genomic positions of interest;
p is a polymorphic site in a set P;
$G_{rp}$ is the genotype of the recipient r at genomic site/position p; and
$G_{dp}$ is the genotype of the donor d at site p.

A contribution of 1 is therefore added to the score for each polymorphic site where the donor genome has an allele ($a_{dp}$) that is not also present in the recipient genome. When both donor and recipient genome are assayed to be the same at polymorphic site P, no contribution is added. If the recipient has a difference that is not present in the donor at site P, the donor would contribute no added immunological feature to the recipient, so no contribution is added to the mismatch score. Another example is where the donor genome has two alleles, i.e., $G_{dp}=\{A,B\}$, at a particular genomic site and the recipient genome is homozygote with $G_{rp}=\{A\}$ at that site. In this case, $(G_{rp},G_{dp})=1$, because the donor has a polymorphism or a mismatch that is not present in the recipient.

The component that assays the number of amino acid differences encoded by the donor genome that the recipient immune system could recognize as non-self can include one or more sequencers, microarrays, mass spectrometer, or other apparatuses that can detect a large number of polymorphisms. The component that assays the number of amino acid differences encoded by the donor genome that the recipient immune system could recognize as non-self can include a data storage unit or be operably linked to a data storage unit that stores number of amino acid differences encoded by the donor genome that the recipient immune system could recognize as non-self. For example, the data storage unit can store the exome and/or selected exon sequences assayed by a sequencer where the sequences are identified as being from the donor or the recipient.

The component that assays the number of amino acid differences encoded by the donor genome that the recipient immune system could recognize as non-self can also include a sequence data assembly unit that assembles the sequence data so that, for example, fragmented sequence data for an exon is assembled into a complete exon sequence. Such an assembly unit may not be needed because the method focuses on recognizing differences at polymorphic sites and sequence fragments accomplish this task without the need for assembly of the entire sequence of a gene, or an entire exon, that includes such a polymorphism.

The component that sums amino acid mismatches (between the recipient and the donor that can be recognized as non-self by the recipient) can be a processor. The processor can receive data from a data storage unit that is either part of the processor, part of the component that assays the number of amino acid differences encoded by the donor genome (relative to the recipient), or that is operably linked to both of these two components.

The component that sums the individual score mismatch contributions assayed at a polymorphic site of interest can utilize Equation 2 to do so.

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where a is an allele;

P is a set of all genomic positions of interest;

p is a polymorphic site in a set P;

$G_{rp}$ is the genotype of the recipient r at genomic site/position p; and $G_{dp}$ is the genotype of the donor d at site p.

The processor can determine an allogenomics mismatch score $\Delta(r,d)$ for a recipient r and donor d, which is a sum of mismatches as shown in Equation 1.

$$\Delta(r,d) = \sum_{p \in P} \delta_p[G_{rp} = \text{genotype}(r, p), G_{dp} = \text{genotype}(d, p)] \quad \text{Equation 1}$$

where:

$\delta_p$ is defined in Equation 2;

P is a set of all genomic positions of interest;

p is a polymorphic site in a set P;

$G_{rp}$ is the genotype of the recipient r at genomic site/position p; and $G_{dp}$ is the genotype of the donor d at site p.

The functions or algorithms described herein may be implemented in software or a combination of software and human implemented procedures, for example. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system. For example, multiple such computer systems can be utilized in a distributed network to implement multiple analyses, draw upon information from distributed sources, or facilitate transaction based usage. An object-oriented, service-oriented, or other architecture may be used to implement such functions and communicate between the multiple systems and components.

The processor or computer can operate in a networked environment using a communication connection to connect to one or more remote computers, such as database servers. The remote computer may include a personal computer (PC), server, router, network PC, a peer device or other common network node, or the like. The communication connection may include a Local Area Network (LAN), a Wide Area Network (WAN) or other networks.

Datasets of information can be in different forms and from different sources. For example, datasets can be stored and updated in the form of computer-accessible storage. Computer-accessible storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer-readable instructions (e.g., for summing up differences between donors and recipients at various polymorphic sites and/or for determining an allogenomics mismatch score) can be stored on a computer-readable medium and can be executable by a processing unit of the computer. A hard drive, CD-ROM, and RAM are some examples of articles including a non-transitory computer-readable medium. For example, a computer program linked to, or including, the instructions for determining an allogenomics mismatch score can be capable of providing a generic technique to perform an access control check for data access and/or for doing an operation on one of the servers in a component object model (COM) based system, or can be included on a CD-ROM and loaded from the CD-ROM to a hard drive. The computer-readable instructions allow computer to provide generic access controls in a COM based computer network system having multiple users and servers.

A system bus can be any of several types of bus structures including a memory bus or memory controller, a peripheral bus, and a local bus using any of a variety of bus architectures. The system memory can also be referred to as simply the memory, and, in some embodiments, includes read-only memory (ROM) and random-access memory (RAM). A basic input/output system (BIOS) program, containing the basic routines that help to transfer information between elements within the computer, such as during start-up, may be stored in ROM. A computer that includes the allogenomics process can further include a hard disk drive for reading from and writing to a hard disk, a magnetic disk drive for reading from or writing to a removable magnetic disk, and an optical disk drive for reading from or writing to a removable optical disk such as a CD ROM or other optical media.

Such a hard disk drive, magnetic disk drive, and optical disk drive can couple with a hard disk drive interface, a magnetic disk drive interface, and an optical disk drive interface, respectively. The drives and their associated computer-readable media provide non-volatile storage of computer-readable instructions, data structures, program modules and other data for the computer. It should be appreciated by those skilled in the art that any type of computer-readable media which can store data that is accessible by a computer, such as magnetic cassettes, flash memory cards, digital video disks, Bernoulli cartridges, random access memories (RAMs), read only memories (ROMs), redundant arrays of independent disks (e.g., RAID storage devices) and the like, can be used in the exemplary operating environment.

A plurality of program modules can be stored on the hard disk, magnetic disk, optical disk, ROM, or RAM, including an operating system, one or more application programs, other program modules, and program data. Programming for implementing one or more processes or method described herein may be resident on any one or number of these computer-readable media.

A user may enter commands and information into computer through input devices such as a keyboard and pointing device. Other input devices (not shown) can include a microphone, touch screen, joystick, game pad, satellite dish, scanner, or the like. These other input devices are often connected to the processing unit through a serial port interface that is coupled to the system bus, but can be connected by other interfaces, such as a parallel port, game port, or a universal serial bus (USB). A monitor or other type of display device can also be connected to the system bus via an interface, such as a video adapter. The monitor can display a graphical user interface for the user, and may include a touchscreen, allowing user interactions to select functions and enter data. In addition to a monitor, computers typically include other peripheral output devices, such as speakers and printers.

The computer may operate in a networked environment using logical connections to one or more remote computers or servers, such as remote computer. These logical connections are achieved by a communication device coupled to or a part of the computer; the invention is not limited to a particular type of communications device. Such a remote computer can be another computer, a server, a router, a network PC, a client, a peer device or other common network node, and typically includes many or all of the elements described above relative to the computer. The logical connections include a local area network (LAN) and/or a wide area network (WAN). Such networking environments are commonplace in office networks, enterprise-wide computer networks, intranets and the internet, which are all types of networks.

When used in a LAN-networking environment, the computer can be connected to the LAN through a network interface or adapter, which is one type of communications device. In some embodiments, when used in a WAN-networking environment, the computer typically includes a modem (another type of communications device) or any other type of communications device, e.g., a wireless transceiver, for establishing communications over the wide-area network, such as the internet. Such a modem, which may be internal or external, is connected to the system bus via the serial port interface. In a networked environment, program modules depicted relative to the computer can be stored in the remote memory storage device of remote computer, or server. It is appreciated that the network connections described are exemplary and other means of, and communications devices for, establishing a communications link between the computers may be used including hybrid fiber-coax connections, T1-T3 lines, DSL's, OC-3 and/or OC-12, TCP/IP, microwave, wireless application protocol, and any other electronic media through any suitable switches, routers, outlets and power lines, as the same are known and understood by one of ordinary skill in the art.

Example embodiments may therefore be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 9A:
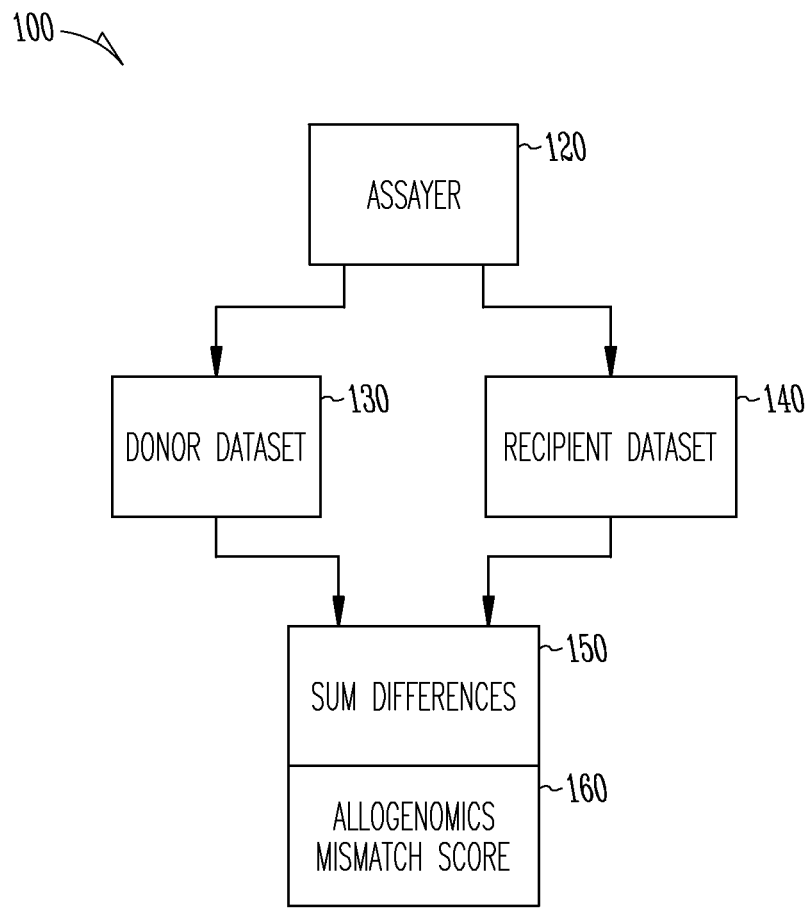
FIG. 9A-9B are diagrams illustrating features of exemplary systems for performing the methods described herein.

An example of an apparatus (100) is shown in FIG. 9A, that includes at least one assayer component (120) for assaying the number of amino acid differences (mismatches) encoded by one or more donor genome that at least one recipient immune system could recognize as non-self. The apparatus can also include a component for summing of amino acid differences (mismatches) between the recipient(s) and the donor(s) that can be recognized as non-self by the recipient (150) by comparing a donor dataset (130) and a recipient dataset (140) and summing the differences. The apparatus can also include a component for determining an allogenomics mismatch score $\Delta(r,d)$ for at least one recipient r and one or more donor d (160).

Example Processing Machine Architecture and Machine-Readable Medium

Figure 9B:
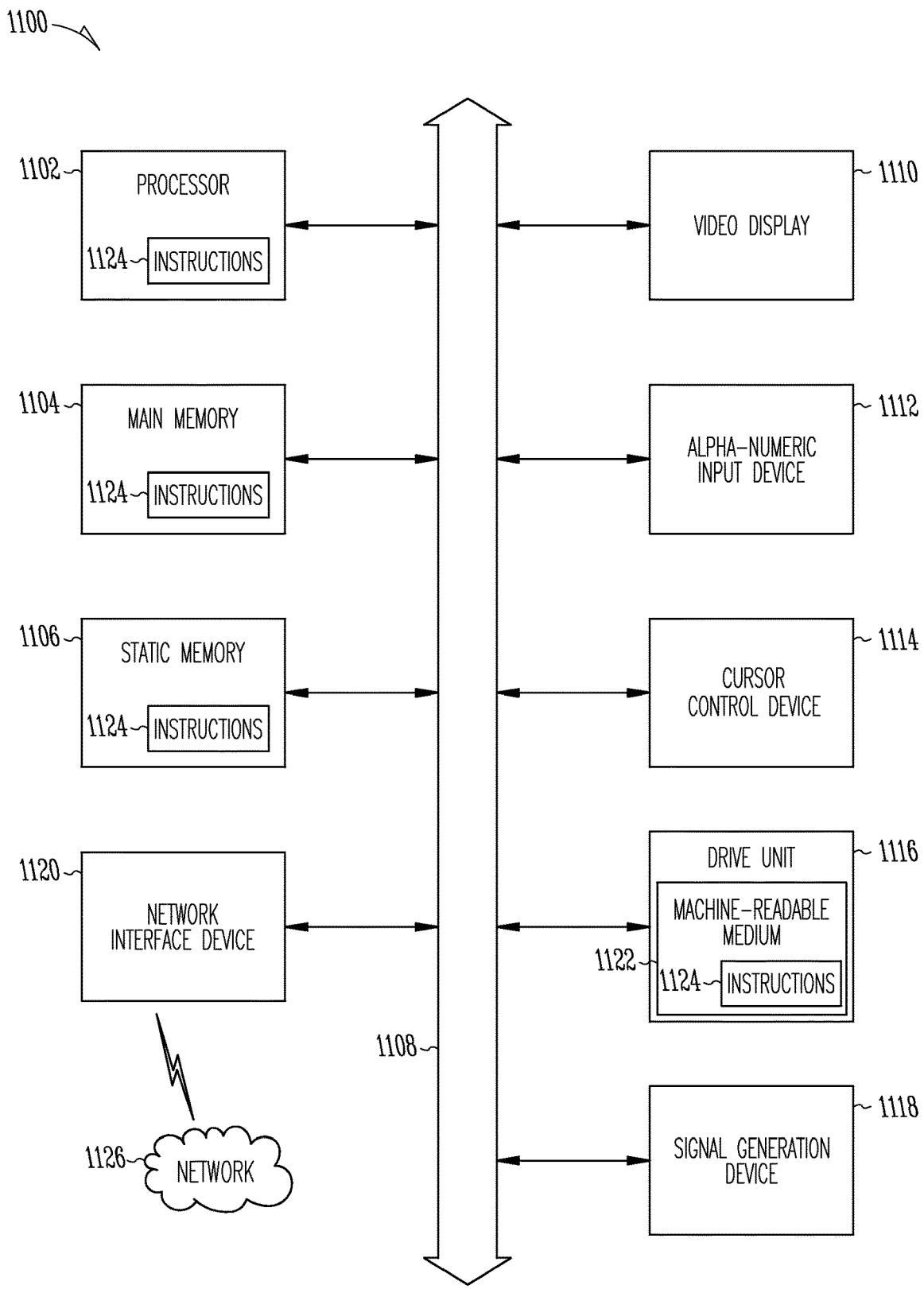

FIG. 9B is a block diagram of machine in the example form of a computer system 1100 within which there may be executed instructions 1124 for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1100 includes a processor 1102 (e.g., a central processing unit (CPU), a graphics processing unit (GPU) or both), a main memory 1104 and a static memory 1106, which communicate with each other via a bus 1108. The computer system 1100 may further include a video display unit 1110 (e.g., a liquid crystal display (LCD) or a cathode ray tube (CRT)). The computer system 1100 also includes an alphanumeric input device 1112 (e.g., a keyboard), a cursor control device 1114 (e.g., user interface (UI) navigation device or computer mouse), a disk drive unit 1116, a signal generation device 1118 (e.g., a speaker) and a network interface device 1120.

Machine Readable Medium

The disk drive unit 1116 includes a machine-readable medium 1122 on which is stored one or more sets of data structures and instructions 1124 (e.g., software) embodying or used by any one or more of the methodologies or functions described herein. The instructions 1124 may also reside, completely or at least partially, within the main memory 1104, static memory 1106, and/or within the processor 1102 during execution thereof by the computer system 1100, the main memory 1104 and the processor 1102 also constituting machine-readable media.

While the machine-readable medium 1122 is shown in an example embodiment to be a single medium, the term "machine-readable medium" may include a single medium or multiple media (e.g., a centralized or distributed database, and/or associated caches and servers) that store the one or more instructions 1124 or data structures. The term "machine-readable medium" shall also be taken to include any tangible medium that is capable of storing, encoding or carrying instructions for execution by the machine and that cause the machine to perform any one or more of the methodologies of the embodiments of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

Transmission Medium

The instructions 1124 may further be transmitted or received over a communications network 1126 using a transmission medium. The instructions 1124 may be transmitted using the network interface device 1120 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and WiMax networks). The term "transmission medium" shall be taken to include any intangible medium that is capable of storing, encoding or carrying instructions for execution by the machine, and includes digital or analog communications signals or other intangible media to facilitate communication of such software.

Treatment

The allogenomics method can also be employed to identify and optimize treatment of transplant recipients who may need, or who may develop a need for, treatment for rejection of a transplanted organ. For example, medical personnel can assess whether a patient may benefit from an immunosuppressive regimen by determining the allogenomics mismatch score of the recipient and the donor organ. When the allogenomics mismatch score is greater than a selected threshold, treatment of the transplant recipient can be initiated. For example, a threshold of greater than about 1600, or greater than about 1500, or greater than about 1450, or greater than about 1400, or greater than about 1350, or greater than about 1300, or greater than about 1250, or greater than about 1200, or greater than about 1100 identifies a recipient with a donor organ who can benefit from treatment.

Such treatment can include immunosuppression drugs, or anti-rejection treatment. The higher the allogenomics mismatch score, the more aggressive the therapy can be at the outset. Hence, rather than waiting for kidney damage to indicate therapeutic intervention is needed, medical personnel can evaluate and predict the need for therapy before significant damage has occurred.

The transplant recipients can include any recipient of a transplanted organ. In some instances, the allogenomics mismatch score of the recipient/donor organ was not determined before transplantation of the donor organ. For example, in some instances the recipient received an HLA matched organ from a living or deceased donor.

The methods can include informing medical personnel or the patient about the test results. Information about whether the patient will have acute rejection can also be communicated. If the patient is likely to develop kidney dysfunction, the patient can be prescribed and/or administered a treatment to delay rejection of the transplanted organ.

The methods can further include treatment of kidney conditions such as kidney transplant rejection, acute cellular rejection (ACR), or antibody-mediated rejection (AMR). Such treatment can include increased or decreased dose of an anti-rejection agent or an anti-rejection agent can be added. Anti-rejection agents, include for example, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof.

For example, if acute rejection is predicted, a steroid pulse therapy can be started and may include the administration for three to six days of a high dose corticosteroid (e.g., greater than 100 mg). An antibody can be added. An example of an antibody therapy includes the administration for seven to fourteen days of the polyclonal antibody Thymoglobin or the monoclonal antibody, OT3.

Another example of a treatment that can be administered is plasmapheresis. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded.

The present description is further illustrated by the following examples, which should not be construed as limiting in any way. The contents of all cited references (including literature references, issued patents, published patent applications as cited throughout this application) are hereby expressly incorporated by reference.

Example 1: Predicting Post-Transplantation Graft Function with the Allogenomics Method The inventors have developed and implemented a method that utilizes a computational tool to estimate the allogenomics mismatch score from genotypes derived for pairs of donor and recipient genomes. Example 1 describes some of the procedures in more detail and the software for implementation. The method is designed to consider the entire set of protein positions measured by a genotyping assay, or restrict the analysis to a subset of positions Pin the genome.

This Example describes analysis of DNA isolated from 24 kidney graft recipients and their donors, and whole exome sequencing. The exome data was analyzed for the 24 matched recipient and donor genomes (48 genomes measured with exome sequencing technology) using the allogenomics scoring tool.

Patient Cohorts and DNA Extraction.

DNA samples from 24 kidney graft recipients for whom donor DNA was available were selected based on the occurrence of a biopsy confirmed acute cellular rejection within the first 15 months post-transplantation (n=12 recipient/donor pairs) or without an episode of acute cellular rejection during the same time interval (n-12 recipient/donor combinations). These patients were a subset of patients enrolled in a multicenter Clinical Trial in Organ Transplantation-04 (CTOT-04) study of urinary cell mRNA profiling and from whom tissue/cells were collected for future mechanistic studies (Suthanthiran et al., N Engl J Med. 369(1): 20-31 (2013 Jul. 4). The kidney allograft biopsies were classified using Banff classification schema (Mengel et al., Am J Transplant. 12(3):563-70 (2011). Clinical data were collected for the 24 matched donors of these recipients. Informed consent was obtained for all participants according to the respective IRBs of the CTOT-4 study centers. All recipients or living donors were at least 18 years old. DNA extraction from total blood was done using the EZ1 DNA blood kit (Qiagen®) based on the manufacturer recommendation.

Exome Sequencing.

In the pilot study that generated data for FIG. 2, DNA was enriched for exon regions with the TruSeq exome enrichment kit v3 and primary sequence data analyses were conducted with GobyWeb (Dorff et al., PLoS ONE. 2013; 8 (7):e69666 (2013)). Briefly, 1.8 µg of genomic DNA was sheared to average fragment size of 200 bp using the Covaris E220 (Covaris, Woburn, Mass., USA). Fragments were purified using AmpPureXP beads (Beckman Coulter, Brae, Calif., USA) to remove small products (<100 bp), yielding 1 µg of material that was end-polished, A-tailed and adapter ligated according to the manufacturer's protocol. Libraries were subjected to minimal PCR cycling and quantified using the Agilent High Sensitivity DNA assay (Agilent, Santa Clara, Calif., USA). Libraries were combined into pools of six for solution phase hybridization using the Illumina (Illumina, San Diego, Calif., USA) TruSeq Exome Enrichment Kit. Captured libraries were assessed for both quality and yield using the Agilent High Sensitivity DNA assay Library Quantification Kit. Sequencing was performed with six samples per flow cell lane using the Illumina HiSeq2000 platform and version 2 sequencing-by-synthesis reagents to generate 100 bp single-end reads (1×100 SE).

Table 5 provides a list of some genes that can be evaluated in the methods described herein. These genes have the names defined by Gene Nomenclature Committee (see website at genenames.org/). Sequences for these genes are also available through links provided by the genenames.org website. A portion or all of the genes listed in Table 5 can be assayed to determine the number of amino acid differences encoded by the donor genome that the recipient immune system could recognize as non-self.

General Exome Sequence Data Analysis.

Illumina Data Analysis Pipeline software (CASAVA 1.8.2) was used for the sample de-multiplexing step. Sequence data in FASTQ format were transformed to compact-reads format using the Goby framework (Campagne et al. PLoS One 8 (11):e79871 (2013)). Compact-reads were aligned to the current build of the human genome (hg19, released in February 2009) using the Burrows-Wheeler Aligner (BWA v 0.7.3 SW) with the GobyWeb software (Suthanthiran et al., N Engl J Med [Internet] 369(1):20-31

(2013)). Single nucleotide polymorphisms (SNPs) and genotypes involving small insertion/deletion polymorphisms (indels) were called using GobyWeb with the Goby sequence variation discovery mode and annotated using the Variant Effect Predictor (VEP version 73) from Ensembl. The data were written to an output file in the Variant Calling format (VCF) (Poge et al., Am J Transpl [Internet] 5(6):1306-11 (2005)).

Glomerular Filtration Rates.

Kidney graft function is a continuous phenotype that can be objectively quantified by estimating the glomerular filtration rate (GFR, i.e., the volume of blood that the kidney filtrates per minute). The GFR can be estimated (eGFR) from creatinine levels in blood and several clinical variables (Poge et al., Am J Transplant 5(6):1306-11 (2005)). Creatinemia refers to the amount of creatinine in the urine, where an excess of creatinine (creatinemia) is an indicator of poor kidney function. The GFR estimates are denoted as eGFR and were used routinely to monitor graft function in patients, where a greater GFR/eGFR rate is an indicator of better kidney function. Healthy, non-transplanted individuals have eGFR value 90 ml/min Kidney transplant recipients with an eGFR larger than 60 ml/min are considered to have excellent graft function (these patients have only one functioning kidney), while a value below 15 ml/min indicates that the patient may require dialysis.

Results

The allogenomics mismatch score was examined to ascertain whether it is associated with kidney allograft function, as characterized by serum creatinine levels and eGFR measurement at 12, 24 or 36 months post-transplantation. Renal allograft function data were recorded as part of clinical care and the data were stored in the CTOT-04 clinical database.

Figure 2A:
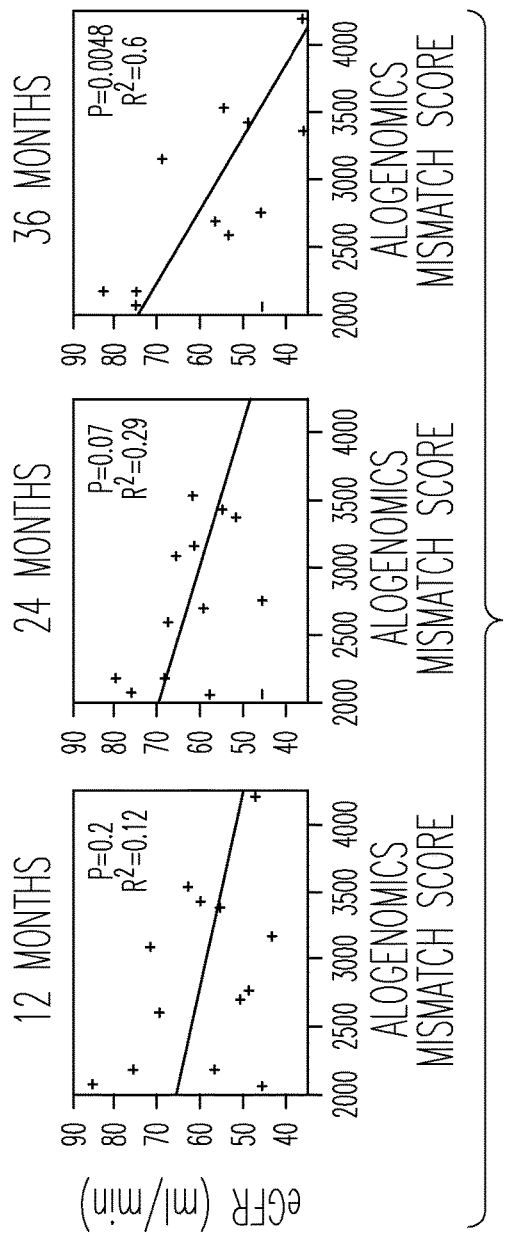
FIG. 2A-2B graphically illustrate the correlation between the allogenomics mismatch score estimated with the method and graft function post transplantation. Both estimated glomerular filtration rate (eGFR, FIG. 2A) and creatinemia (FIG. 2B) are shown. Both eGFR and creatinemia are clinical markers of graft function and are also predictors of future graft loss. The plots show that these graft function markers correlate in a time dependent fashion with the allogenomics mismatch score estimated with the method described in this application. The strongest correlations are observed at 36 months post-transplantation.
Figure 2B:
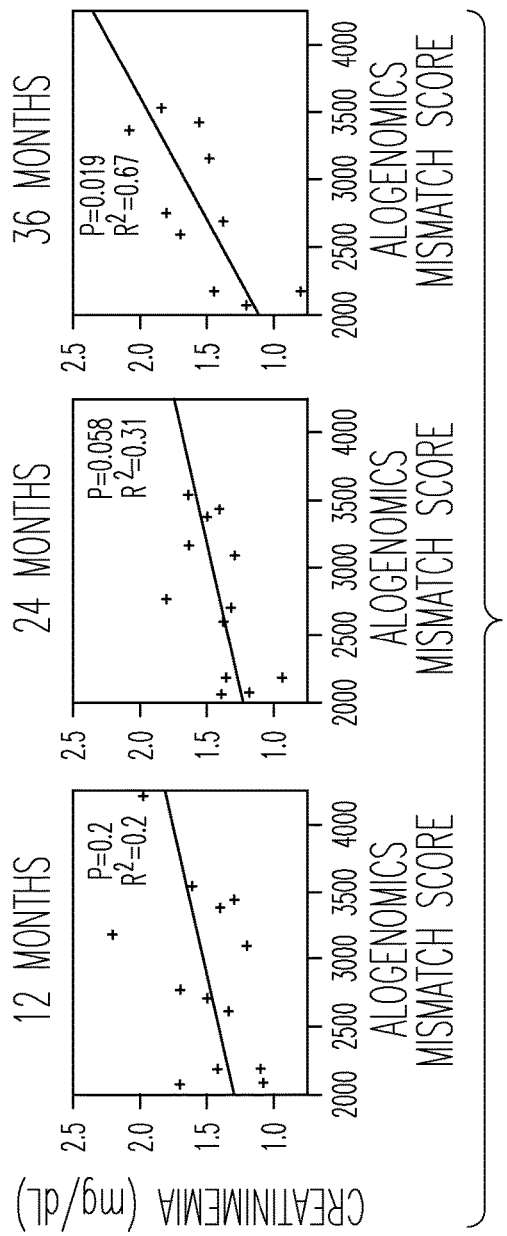

A linear correlation was present between the allogenomics mismatch score and both eGFR (FIG. 2A) and creatinine levels (FIG. 2B). The level of correlation increased with time from transplant, to reach $r^2>0.6$ at 36 months post-transplant.

This example illustrates that the allogenomics method described herein is able to estimate a quantitative score, the allogenomics mismatch score, from genomic data available before a transplant is performed, and that this score correlates with graft function several years after transplantation.

Example 2: Implementation of the Method in the Allogenomics Scoring Tool

An allogenomics scoring tool has been developed to process genotypes in the Variant Calling Format and produce allogenomics mismatch score estimates for specific pairs of genomes in the input file. The allogenomics scoring tool was implemented in Java with the Goby framework and is designed to read VCF files produced by GobyWeb (Suthanthiran et al., N Engl J Med [Internet] 369(1):20-31 (2013)).

Example 3: Selection of Informative Polymorphisms

The selection of the set of polymorphic sites P can contribute to the effectiveness of the approach. In the current method, exonic polymorphic sites were selected that are predicted to create non-synonymous change in a protein sequence. Additional filters can be applied to restrict P, which may lead to improved prediction of transplant clinical endpoints. Some filters may also be applied to restrict the set of polymorphisms to a set easier or faster to measure. The inventors have restricted P to a set of non-synonymous polymorphisms in transmembrane proteins and have obtained results similar to those shown in FIG. 2.

Example 4: Tuning of the Polymorphism Set P for Different Types of Graft or Clinical Outcome and Endpoints The methods of the allogenomics scoring tool were implemented to obtain score contributions for regions of the genome that span multiple polymorphic sites in P. For instance, the allogenomics scoring tool can produce estimates of allogenomics mismatch score over gene regions. This is useful to obtain data about the immunogenic potential of specific genes, and can be used to optimize the set of polymorphisms measured and used in the allogenomics method described in this invention. Analysis of data produced with this tool when analyzing matched donor recipient genomic information illustrates how to define subset of polymorphisms that are tuned to predict specific clinical outcomes for specific graft types (e.g., kidney, liver, solid organ transplantations, bone marrow, stem cell transplantations, etc.). These subsets of polymorphisms follow directly from the invention disclosed herein.

Example 5: Materials and Methods

This Example describes some of the materials and methods used in the development of the invention.

Discovery Cohort: Transplant Recipients and DNA Samples.

Ten kidney transplant recipients were randomly selected from those who had consented to participate in the Clinical Trials in Organ Transplantation-04 (CTOT-04), a multicenter observational study of noninvasive diagnosis of renal allograft rejection by urinary cell mRNA profiling. The only recipients included were those who had a living donor transplant and, along with their donors, had provided informed consent for the use of their stored biological specimens for future research. The demographic information is shown in Table 3.

TABLE 3

Kidney transplant recipient and their donor characteristics.

| Characteristic | Discovery cohort | Validation cohort |
|---|---|---|
| Number of Transplant Pairs with living donors | 10/10 | 24/24 |
| Clinical factors | | |
| Age | | |
| Donor | — | 45.5 (9.3) |
| Recipient (SD) | 48 (10) | 51 (13.4) |
| Living Donor type | | |
| Living related (allogenomic score) | — | 13 (939 (218)) |
| Living unrelated (allogenomic score) | — | 11 (1277 (170)) |
| Donor sex | | |
| Male | — | 8 |
| Female | — | 16 |
| Recipient sex | | |
| Male (%) | 9 (90%) | 13 (54%) |
| Female (%) | 1 (10%) | 11 (46%) |
| Recipient Ethnicity | | |
| Black (%) | 4 (40%) | 7 (29%) |
| Non-Black (%) | 6 (60%) | 17 (71%) |

TABLE 3-continued

Kidney transplant recipient and their donor characteristics.

| Characteristic | Discovery cohort | Validation cohort |
|---|---|---|
| Ethnicity "Mismatches" | — | 5 |
| Gender "Mismatches" on Y | — | 2 |
| Number of HLA mismatches ABDR (SD) | 3.9 (1.8) | 3.6 (1.93) |
| Functional Factors | | |
| Patient number 12 months | 10 | 24 |
| Creatininemia-12 Months mg/dL (SD) | 1.51 (0.32) | 1.44 (0.40) |
| Estimated eGFR-12 ml/min/1.73 m2 months (SD) | 54.3 (10) | 52.5 (16.5) |
| Patient number 24 months | 9 | 23 |
| Creatininemia-24 Months mg/dL (SD) | 1.35 (0.17) | 1.46 (0.48) |
| Estimated eGFR-24 ml/min/1.73 m2 months (SD) | 59 (7.4) | 52.7 (16.5) |
| Patient number 36 months | 8 | 24 |
| Creatininemia-36 Months mg/dL (SD) | 1.62 (0.47) | 1.40 (0.41) |
| Estimated eGFR-36 months ml/min/1.73 m2 (SD) | 53.4 (15) | 54.5 (16.5) |
| Number of patient with an Acute Cellular rejection episode before the first year Total (%) | 3 (30%) | 5 (20%) |
| Calcineurin Inhibitor use Total | — | |
| Cyclosporine | — | 0 |
| Tacrolimus | — | 24 (100%) |
| Antiproliferative use Total (%) | | |
| Azathioprine | — | 0 |
| Mycophenolic acid | — | 24 (100%) |
| Neither | — | 0 |
| Corticosteroid use at 36 months Total (%) | — | 5 (21%) |

DNA was extracted from stored peripheral blood using the EZ1 DNA blood kit (Qiagen®) based on the manufacturer recommendation.

Discovery Cohort: Whole Exome Sequencing.

DNA was enriched for exon regions with the TruSeq exome enrichment kit v3. Sequencing libraries were constructed using the Illumina TruSeq kit DNA sample preparation kit. Briefly, 1.8 µg of genomic DNA was sheared to average fragment size of 200 bp using the Covaris E220 (Covaris, Woburn, Mass., USA). Fragments were purified using AmpPureXP beads (Beckman Coulter, Brae, Calif., USA) to remove small products (<100 bp), yielding 1 µg of material that was end-polished, A-tailed and adapter ligated according to the manufacturer's protocol.

Libraries were subjected to minimal PCR cycling and quantified using the Agilent High Sensitivity DNA assay (Agilent, Santa Clara, Calif., USA). Libraries were combined into pools of six for solution phase hybridization using the Illumina (Illumina, San Diego, Calif., USA) TruSeq Exome Enrichment Kit. Captured libraries were assessed for both quality and yield using the Agilent High Sensitivity DNA assay Library Quantification Kit. Sequencing was performed with six samples per lane using the Illumina HiSeq 2000 sequencer and version 2 of the sequencing-by-synthesis reagents to generate 100 bp single-end reads (1×100 SE).

Validation Cohort: Transplant Recipients and DNA Samples.

Twenty-four kidney transplant recipients were studied who had a living donor transplant at the Cornell University Medical Center. This was an independent cohort and none of the recipients had participated in the CTOT-04 trial. Recipients were selected randomly based on the availability of archived paired recipient-donor DNA specimens obtained at the time of transplantation at the Cornell Immunogenetics and Transplantation Laboratory. The Institutional Review Board at Cornell approved the study. DNA extraction from peripheral blood was done using the EZ1 DNA blood kit) (QIAGEN®) based on the manufacturer recommendation.

Validation Cohort: Whole Exome Sequencing.

The validation cohort was assayed with the Agilent Haloplex exome sequencing assay. The Haloplex assay enriches 37 Mb of coding sequence in the human genome and was selected for the validation cohort because it provides a strong and consistent exon enrichment efficiency for regions of the genome most likely to contribute to the allogenomics contributions in protein sequences. In contrast, the TrueSeq assay (used for the Discovery Cohort) enriches 63 Mb of sequence and includes regions in untranslated regions (5' and 3' UTRs), which do not contribute to allogenomics scores and therefore do not need to be sequenced to estimate the score. Libraries were prepared as per the Agilent recommended protocol. Sequencing was performed on an Illumina 2500 sequencer with the 100 bp paired-end protocol recommended by Agilent for the Haloplex assay. Libraries were multiplexed 6 per lane to yield approximately 30 million PE reads per sample.

Allogenomics Site Minor Allele Frequencies.

The minor allele frequency of sites used in the calculation of the allogenomics mismatch score was determined using data from the NHLBI Exome Sequencing Project (ESP) release ESP6500SI-V2. The data file ESP6500SI-V2-SSA137.protein-hgvs-update.snps_indels.txt.tangz was downloaded and extracted minor allele frequency (MAF) in the European American population (EA) and in the African American population (AA) (Exome Variant Server, NHLBI GO Exome Sequencing Project (ESP) [Internet]. 2014 (Jun. 20, 2014). Available from the following website: evs.gs.washington.edu/EVS/. The ESP measured genotypes in a population of 6,503 individuals across the EA and AA populations using an exome-sequencing assay (id.). This resource made it possible to estimate minor allele frequency for most of the variations that are observed in the subjects included in our discovery and validation cohort.

Overlap with EVP Variants.

Of 12,457 sites measured in the validation cohort with an allogenomics contribution strictly larger than zero (48 exomes, sites with contributions across 24 clinical pairs of transplants), 9,765 (78%) have also been reported in EVP (6,503 exomes).

Sequence Data Analysis.

Illumina sequence base calling was performed in the Weill Cornell Genomics Core Facility. Sequence data in FASTQ format were converted to the compact-reads format using the Goby framework (Goldfarb-Rumyantzev & Naiman, Curr Opin Nephrol Hypertens 17(6):573-9 (2008)). Compact-reads were uploaded to the GobyWeb (Dorff et al., PLoS One 8 (7):e69666 (2013)) system and aligned to the 1000 genome reference build for the human genome (corresponding to hg19, released in February 2009) using the Last (Frith et al., BMC Bioinformatics 11(1):80 (2010); Kielbasa et al., Genome Res 21(3):487-93 (2011)) aligner (parallelized in a GobyWeb plugin; Dorff et al., PLoS One 8 (7):e69666 (2013)). Single nucleotide polymorphisms (SNPs) and small indels genotype were called using Goby-Web with the Goby (Campagne et al., PLoS One 8 (11): e79871 (2013)) discover-sequence-variants mode and annotated using the Variant Effect Predictor (McLaren et al., Bioinformatics 26(16):2069-70 (2010), VEP version 75) from Ensembl. The data were downloaded as a Variant Calling format (VCF) file from GobyWeb (Dorff et al., PLoS One 8 (7):e69666 (2013)) and further processed with the allogenomics scoring tool (see website at allogenomics.campagnelab.org).

Estimation of the Allogenomics Mismatch Score.

The allogenomics mismatch score Δ(r,d) is estimated for a recipient r and donor d as a sum of score mismatch contributions (see Equation 1).

$$\Delta(r, d) = \sum_{p \in P} \delta_p [G_{rp} = \text{genotype}(r, p), G_{dp} = \text{genotype}(d, p)] \quad \text{Equation 1}$$

where:
$\delta_p$ is defined in Equation 2;
P is a set of all genomic positions of interest;
p is a polymorphic site in a set P;
$G_{rp}$ is the genotype of the recipient r at genomic site/position p; and
$G_{dp}$ is the genotype of the donor d at site p.

Contributions are observed for each polymorphic site p in a set P, where P is determined by the genotyping assay and analysis methods, and can be further restricted (e.g., to polymorphisms within genes that code for membrane proteins). Score mismatch contributions $\delta_p(G_{rp}, G_{dp})$ is calculated using the recipient genotype $G_{rp}$ and the donor genotype $G_{dp}$ at the polymorphic site p. Here, a genotype can be represented as a set of alleles that were called in a given genome. For instance, if a subject has two alleles at one polymorphic site, and each allele is denoted A or B, the genotype at p is represented by the set {A,B}. This representation is general and sufficient to process polymorphic sites with single nucleotide polymorphisms or insertion/deletions.

Equation 2 describes how the individual score mismatch contributions $\delta_p(G_{rp}, G_{dp})$ are calculated at a polymorphic site of interest.

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
a is an allele;
P is a set of all genomic positions of interest;
p is a polymorphic site in a set P;
$G_{rp}$ is the genotype of the recipient r at genomic site/position p; and
$G_{dp}$ is the genotype of the donor d at site p.

A contribution of 1 is added to the score for each polymorphic site where the donor genome has an allele ($a_{dp}$) that is not also present in the recipient genome. When both donor and recipient genome are called at polymorphic site P (i.e., both have the same polymorphism or sequence), no contribution is added. However, for a genomic site where the donor genome has two alleles, i.e., $G_{dp}$={A,B}, and the recipient genome is homozygote with $G_{rp}$={A}, then ($G_{rp}$, $G_{dp}$) is 1 for that site.

Table 4 presents additional examples of donor and recipient genotypes and indicates the resulting score contribution (the subscript p is omitted for conciseness). Score contributions are summed across all polymorphism sites in the set P to yield the allogenomic mismatch score (see Equation 1).

TABLE 4

Examples of recipient/donor mismatches allogenomic score contributions.

| Gd | Gr | (Gr, Gd) |
|---|---|---|
| Gd = {A, B} | Gr = {A, B} | (Gr, Gd) = 0 |
| Gd = {A} | Gr = {B} | (Gr, Gd) = 1 |
| Gd = {B} | Gr = {A, B} | (Gr, Gd) = 0 |
| Gd = {A, B} | Gr = {C} | (Gr, Gd) = 2 |

Selection of Informative Polymorphisms.

The selection of the set of polymorphic sites P contributes to the effectiveness of the approach. In the current method, exonic polymorphic sites were selected that are (1) predicted to create non-synonymous changes protein sequences, (2) are located in genes that code for one or more membrane proteins (defined as any protein with at least one predicted transmembrane segment, information obtained from Biomart, Ensembl database 75; Haider et al., Nucleic Acids Res [Internet] 37 (Jul. 1, 2009). Additional filters can be applied to restrict P, which may lead to improved prediction of transplant clinical endpoints. Constructing additional filters will require the study of a larger training set of matched recipient and donor genotypes, which currently does not exist. It is possible that such study will indicate that other criteria than (2) also lead to predictive scores.

Implementation: The Allogenomics Scoring Tool.

An allogenomics scoring tool was developed to process genotypes in the VCF format and produce allogenomics mismatch score estimates for specific pairs of genomes in the input file. The allogenomics scoring tool was implemented in Java with the Goby framework and is designed to read VCF files produced by Goby and GobyWeb. The source code of the allogenomics scoring tools is distributed for academic and non-commercial purposes at the allogenomics.campagnelab.org website.

The following command line arguments were used to generate the estimates described herein and can be run from an Allogenomics_Package file available from the inventors. The genotype input file for reproducing these results (GobyWeb tag: JEOHQUR) will be distributed through dbGAP (at the ncbi.nlm.nih.gov/gap website) to control access to these private genotype human subject data. A copy of the file can be obtained from the inventors upon condition of confidentiality.

As a pre-requisite to running the command lines: (1) the Java runtime environment should be installed on your computer (the software has been tested with version 1.6); (2) the environment variable ALLO should be defined to the location where the distribution of the allogemomics scoring tool has been downloaded; and (3) the input VCF file has been obtained and placed under: ${ALLO}/VCF_files_input/JEOHQUR-stats.vcf.gz Estimating Allogenomics Mismatch Scores on the Discovery Cohort:

```
java -Xmx4g -jar allogenomics-1.1.7-scoring-tool.jar \
    --input ${ALLO}/VCF_files_input/JEOHQUR-stats.vcf.gz \
    -p ${ALLO}/Pair_files/Discovery_cohort.pairs.tsv \
    -a Annotation_files/All_protein_coding_Ensembl_75.gtf \
    --output ${ALLO}/Output/TM-Discovery.tsv \
    --output-format TSV --only-non-synonymous-coding --vep \
    --consider-indels --minimum-depth 10 --max-depth 500 \
    -t ${ALLO}/Annotation_files/TrM-Transcript_Ensembl_75.tsv \
    --clinical
```

Estimating Allogenomics Mismatch Scores on the Validation Cohort:

```
java -Xmx4g -jar allogenomics-1.1.7-scoring-tool.jar \
    --input ${ALLO}/VCF_files_input/JEOHQUR-stats.vcf.gz \
    -p ${ALLO}/Pair_files/Validation_cohort.pairs.tsv \
    -a ${ALLO}/Annotation_files/
All_protein_coding_Ensembl_75.gtf \
    --output ${ALLO}/Output/TM-Validation.tsv \
    --output-format TSV --only-non-synonymous-coding --vep \
    --consider-indels --minimum-depth 10 --max-depth 500 \
    -t ${ALLO}/Annotation_files/TrM-Transcript_Ensembl_75.tsv \
    --clinical --measured-sites SitesHaloplexExome.tsv
```

Estimating Allogenomics Mismatch Scores on Merged Discovery and Validation Cohorts:

```
java -Xmx4g -jar allogenomics-1.1.7-scoring-tool.jar \
    --input ${ALLO}/VCF_files_input/JEOHQUR-stats.vcf.gz\
    -p Pair_files/Discovery+Validation_cohort.pairs.tsv \
    -a ${ALLO}/Annotation_files/
All_protein_coding_Ensembl_75.gtf \
    --output ${ALLO}/Output/TM-Discovery+Validation.tsv \
    --output-format TSV --only-non-synonymous-coding \
    --vep --consider-indels --minimum-depth 10 \
    --max-depth 500 \
    -t ${ALLO}/Annotation_files/TrM-Transcript_Ensembl_75.tsv
    --clinical
```

Estimating Allogenomics Mismatch Score Limited to Illumina GeneChip660W Loci on the Validation Cohort:

```
java -Xmx4g -jar allogenomics-1.1.7-scoring-tool.jar \
    --input ${ALLO}/VCF_files_input/JEOHQUR-stats.vcf.gz \
    -p ${ALLO}/Pair_files/Validation_cohort.pairs.tsv \
    -a ${ALLO}/Annotation_for_660W/
Human660W_Gene_Annotation_hg19-ilmn.tsv \
    --output ${ALLO}/Output/TM-Validation_Illumina660W.tsv \
    --output-format TSV --only-non-synonymous-coding --vep \
    --consider-indels --minimum-depth 10 --max-depth 500 \
    -t ${ALLO}/Annotation_for_660W/
TM-as-gene-names_for_Illumina660W.tsv \
    --clinical --measured-sites sites-660W.tsv
```

Example 6: The Allogenomics Mismatch Score Correlates with Graft Function Post Transplantation This Example describes some of the results of an additional study illustrating the allogenomics methods. The procedures described in Example 5 were used during this study.

In order to test the allogenomics hypothesis, DNA from 10 kidney graft recipients and their living donors (Discovery Cohort) was isolated, whole exome sequencing was performed, and genotype data for these matched recipient and donor genomes (20 exomes) was analyzed. These patients were a subset of patients enrolled in a multicenter Clinical Trial in Organ Transplantation-04 (CTOT-04) study of urinary cell mRNA profiling and from whom tissue/cells were collected for future mechanistic studies (Suthanthiran et al. N Engl J Med 369(1):20-31 (2013)). Table 3 provides demographics information about the patients included in the Discovery Cohort. Exome data were obtained with the Illumina TrueSeq exome enrichment kit v3. Primary sequence data analyses were conducted with GobyWeb (data and analysis management; see, Dorff et al., PLoS One 8 (7):e69666 (2013)), Last (alignment to the genome; see Kielbasa et al., Genome Res 21(3):487-93 (2011)) and Goby (genotype calls; see Campagne et al., PLoS One 8 (11): e79871 (2013)).

Kidney graft function is a continuous phenotype and is clinically evaluated by measuring serum creatinine levels or using estimated glomerular filtration rate (eGFR; see Poge et al., Am J Transpl 5(6):1306-11 (2005)). In this study, kidney graft function was evaluated at months 12, 24, 36 or 48 following transplantation using serum creatinine levels and eGFR, calculated using the 2011 MDRD formula (see Levey et al., Ann Intern Med 154(1):65-7 (2011)). The allogenomics mismatch score was examined to ascertain whether it is associated with post-transplant allograft function.

Figure 3A:
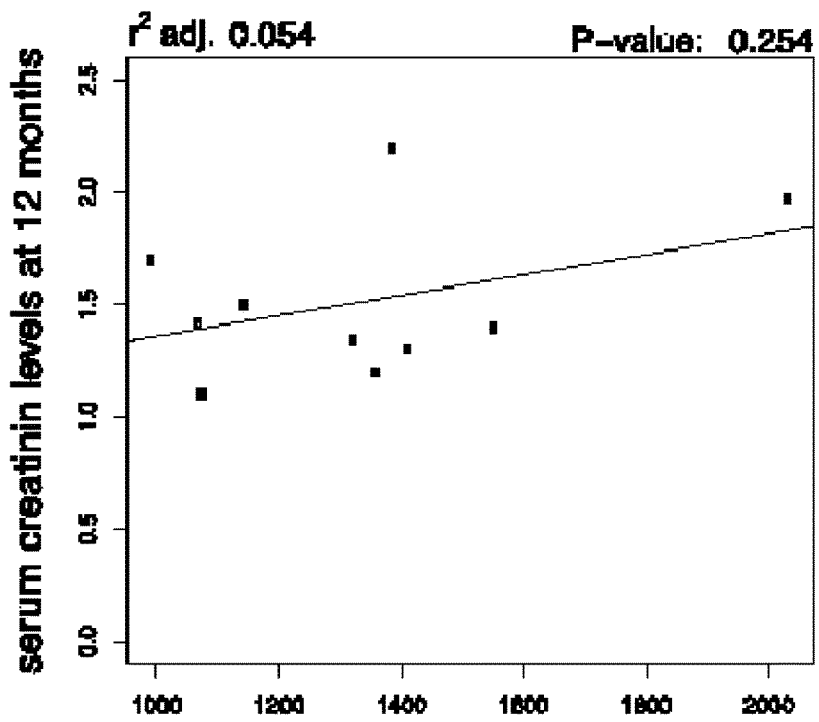
FIG. 3A-3F graphically illustrate the relationship between the allogenomics mismatch score and kidney graft function at 12, 24 or 36 months following transplantation in the Discovery cohort.
Figure 3B:
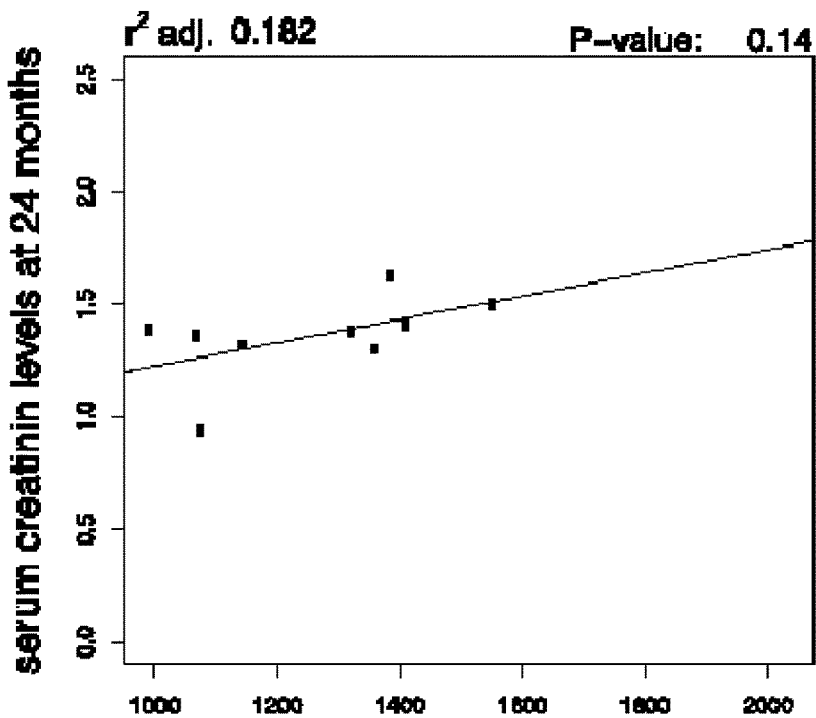
Figure 3C:
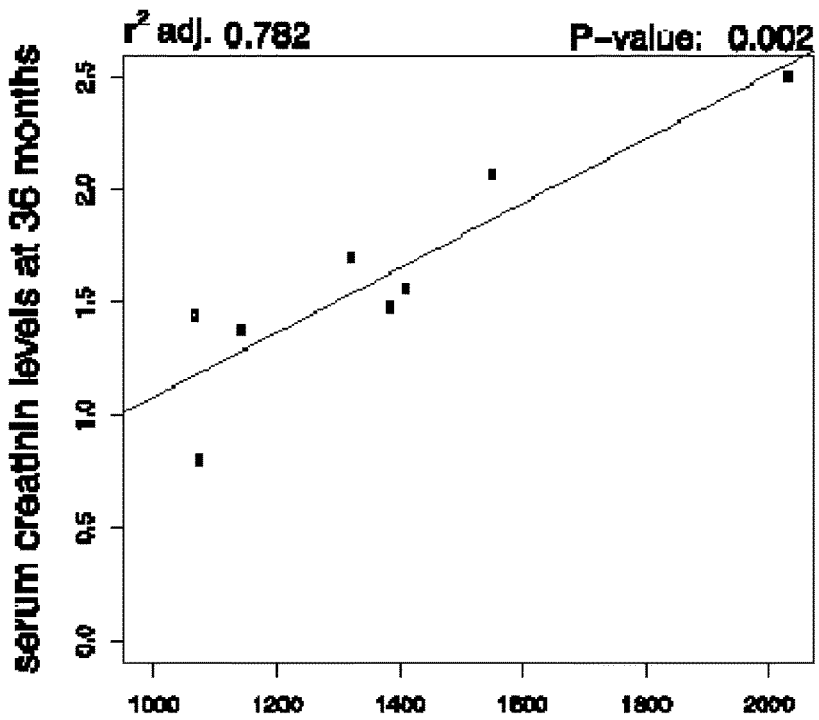
Figure 3D:
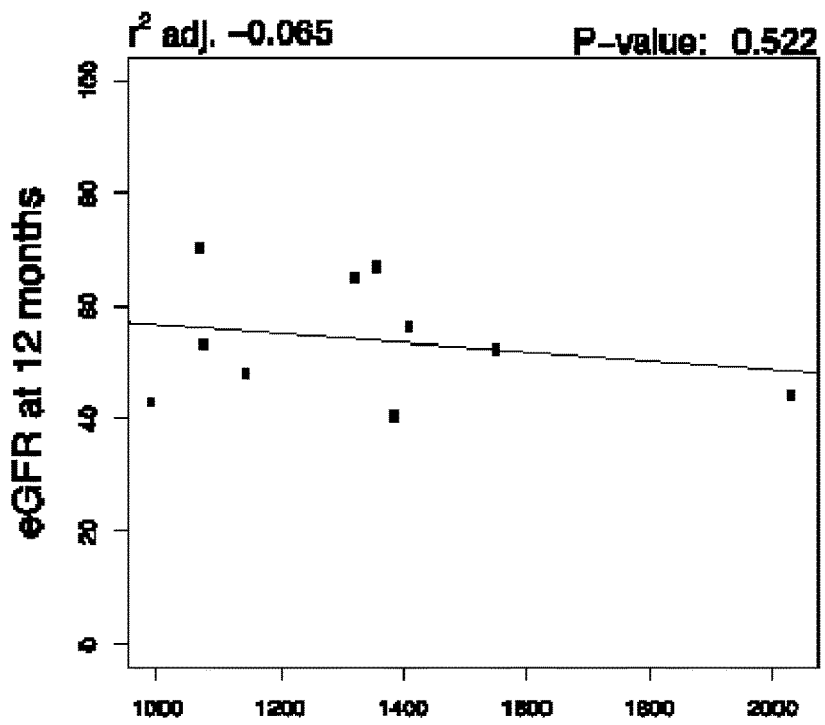
Figure 3E:
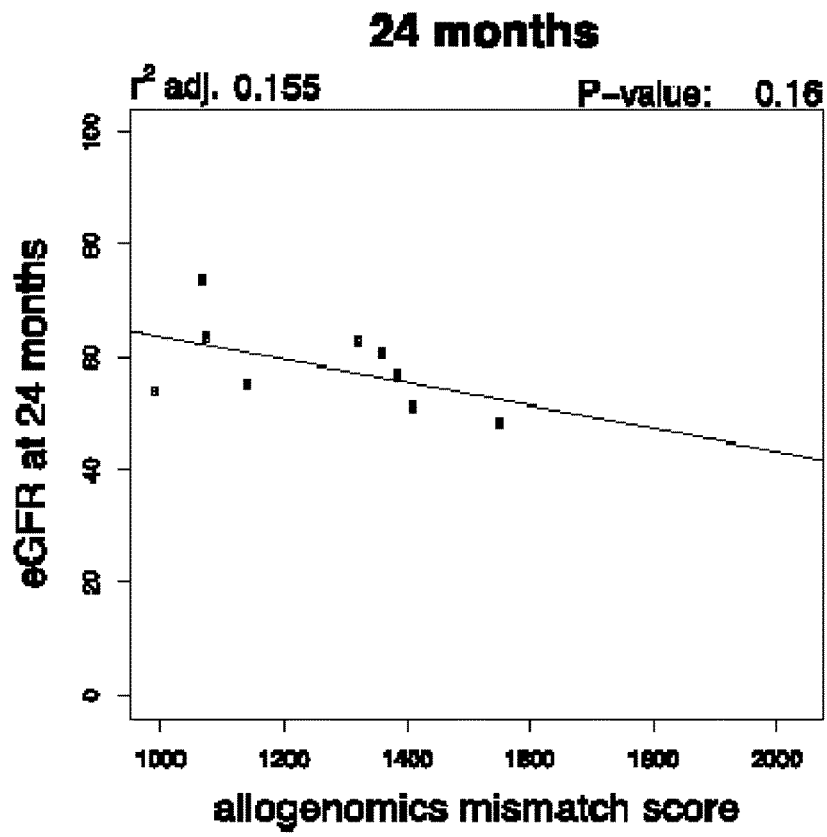
Figure 3F:
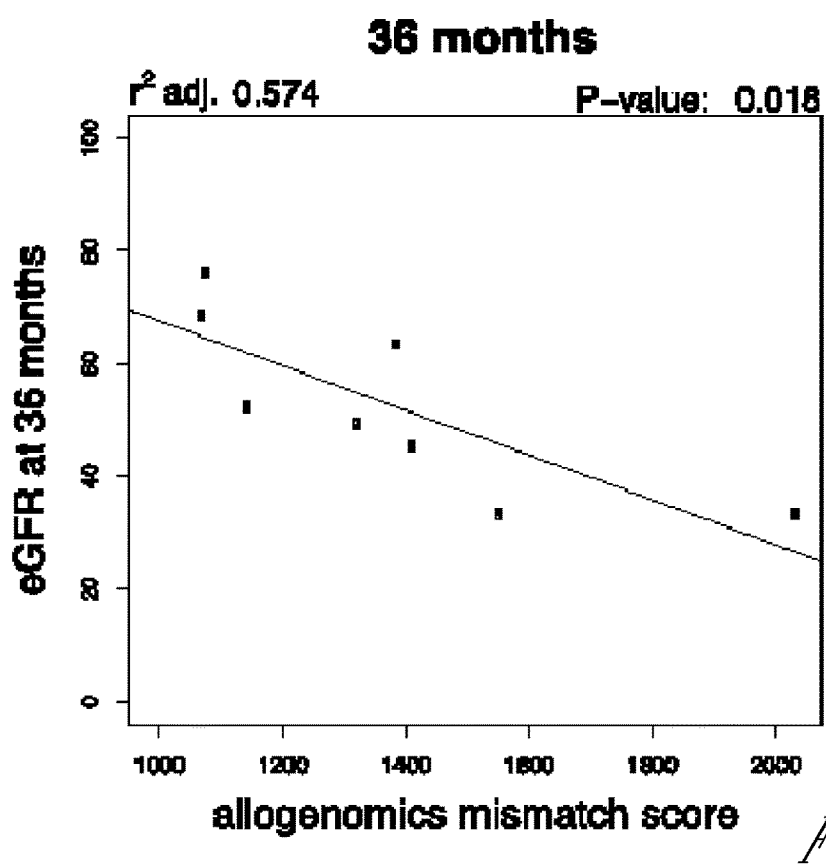
Figure 4A:
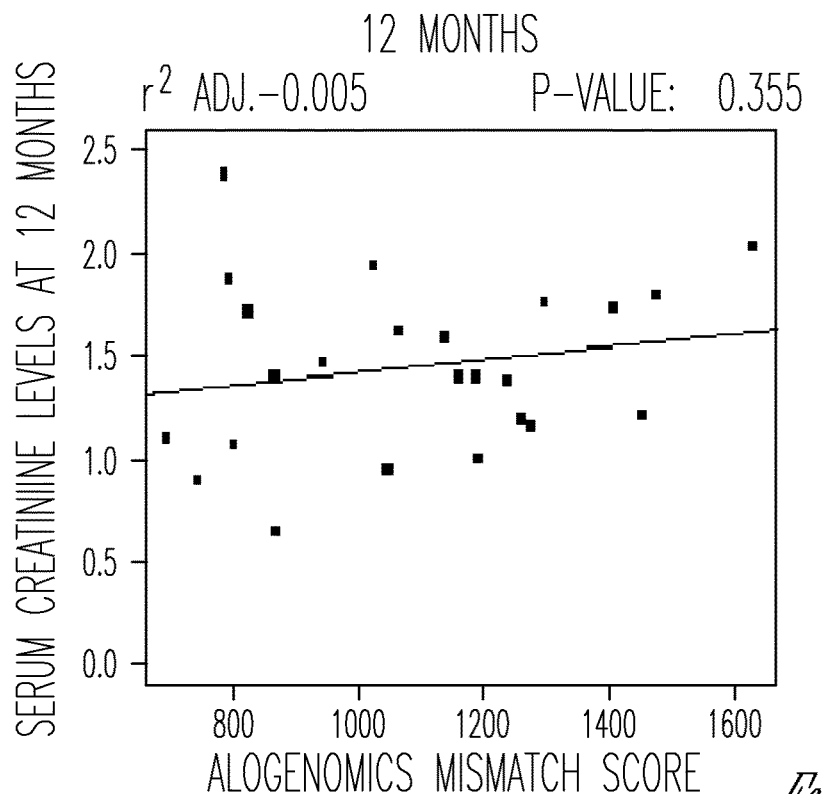
FIG. 4A-4H graphically illustrates the relationships between allogenomics mismatch scores and kidney graft function at 12, 24, 36 or 48 months following transplantation in the Validation Cohort.
Figure 4B:
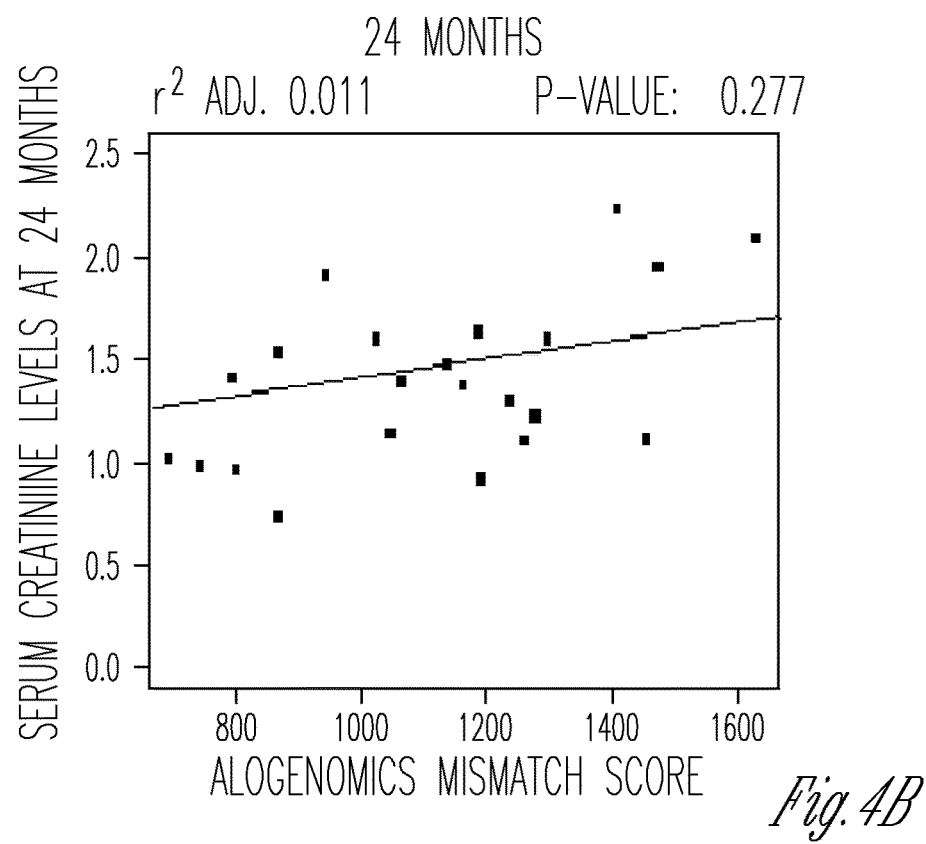
Figure 4C:
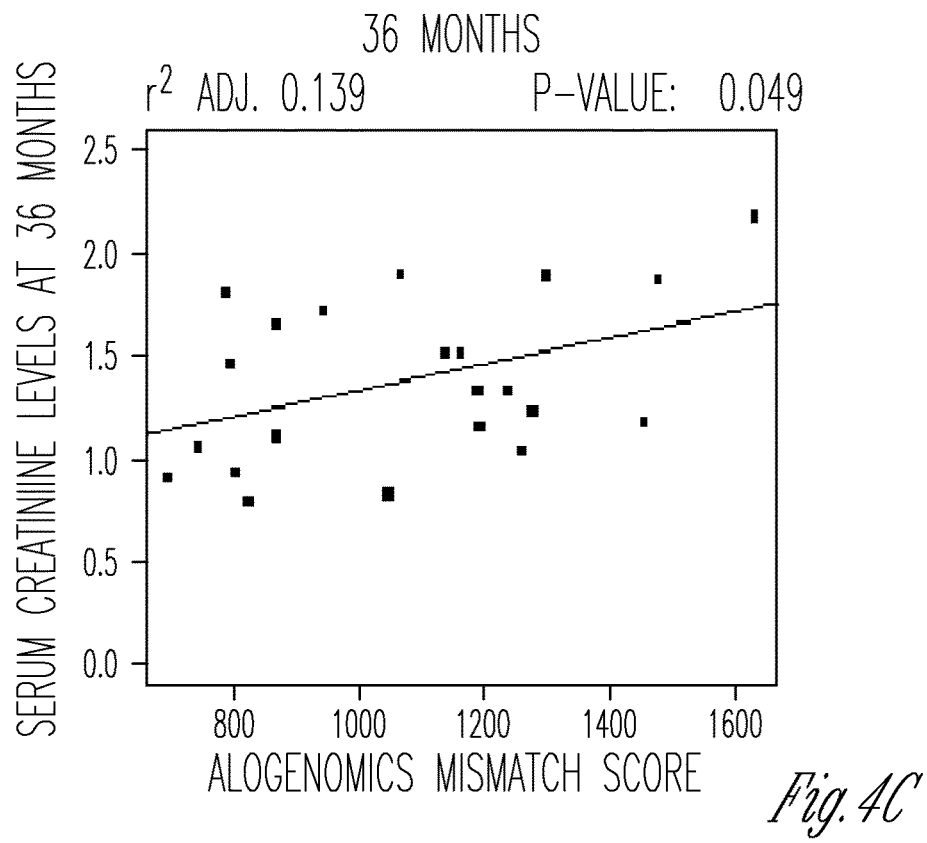
Figure 4D:
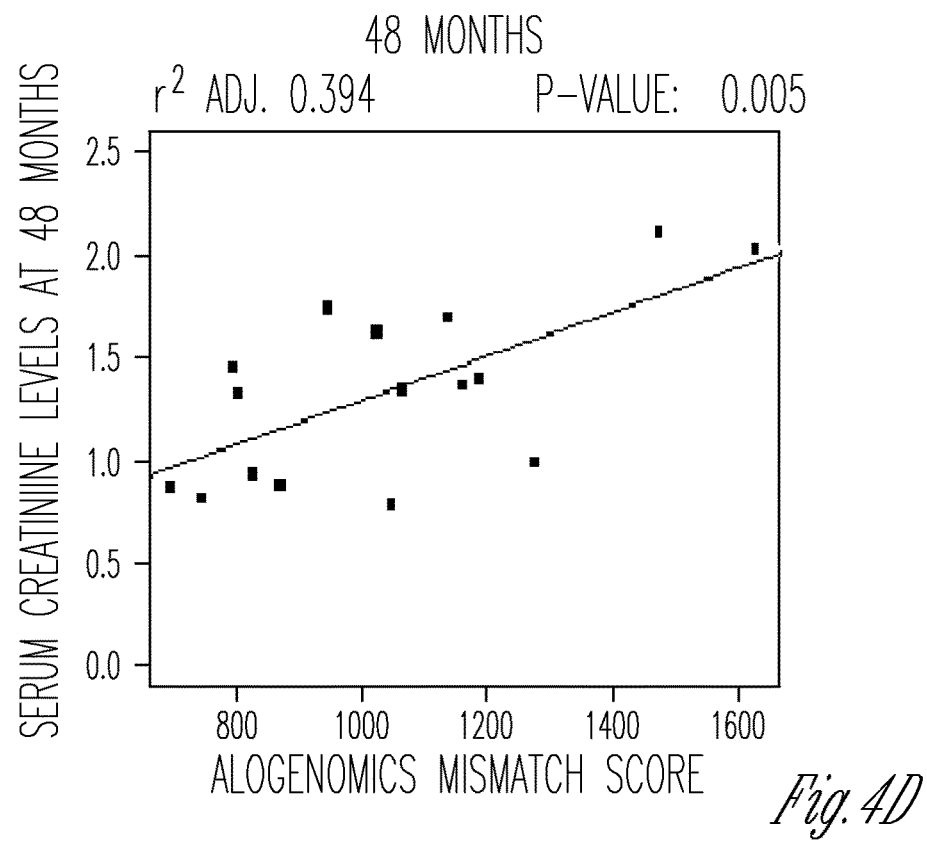
Figure 4E:
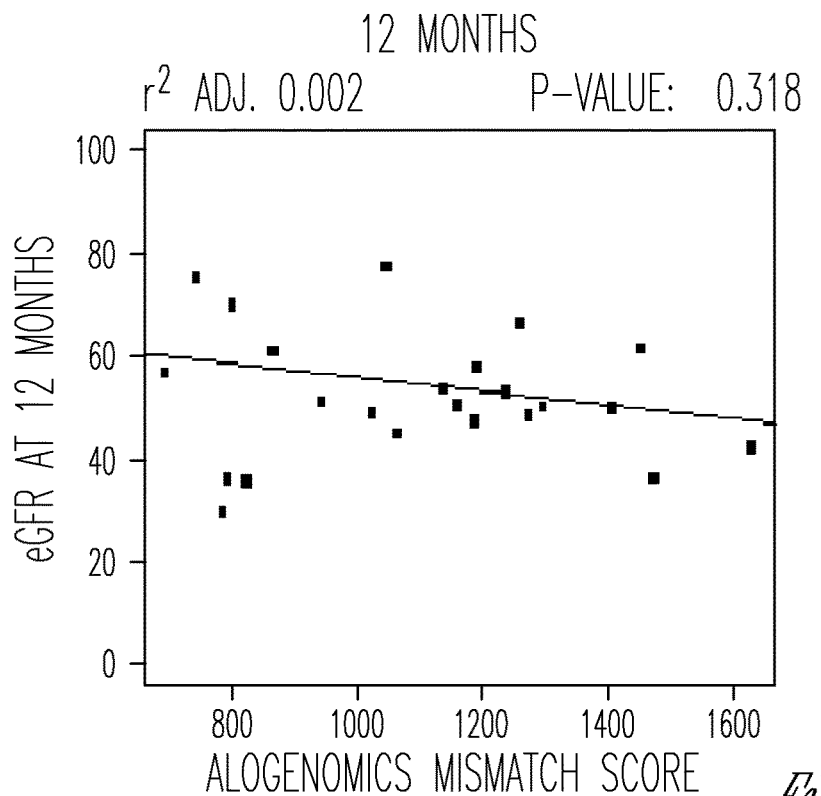
Figure 4F:
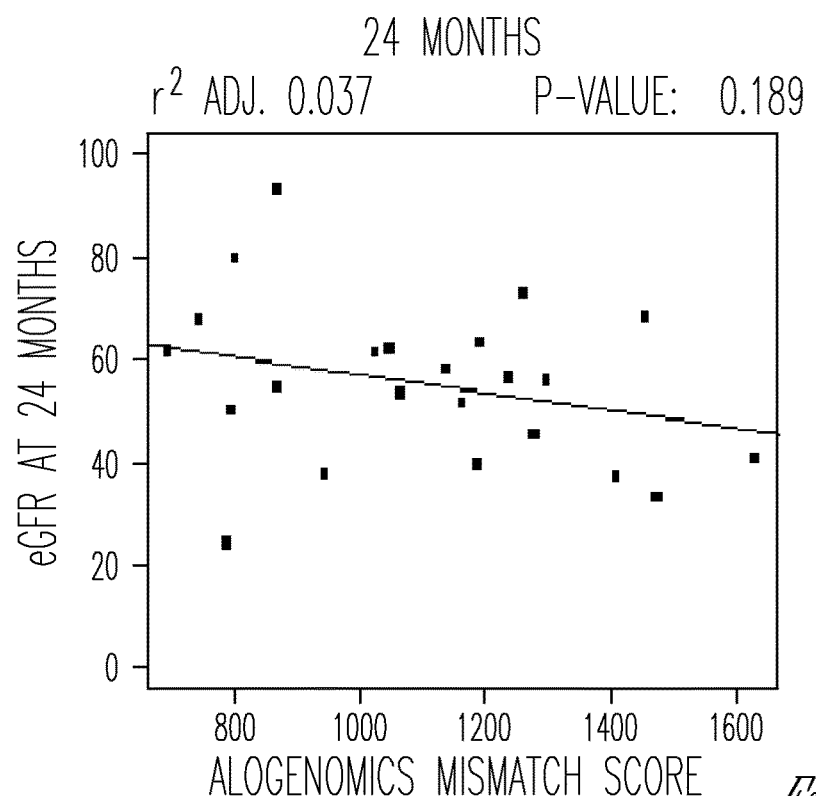
Figure 4G:
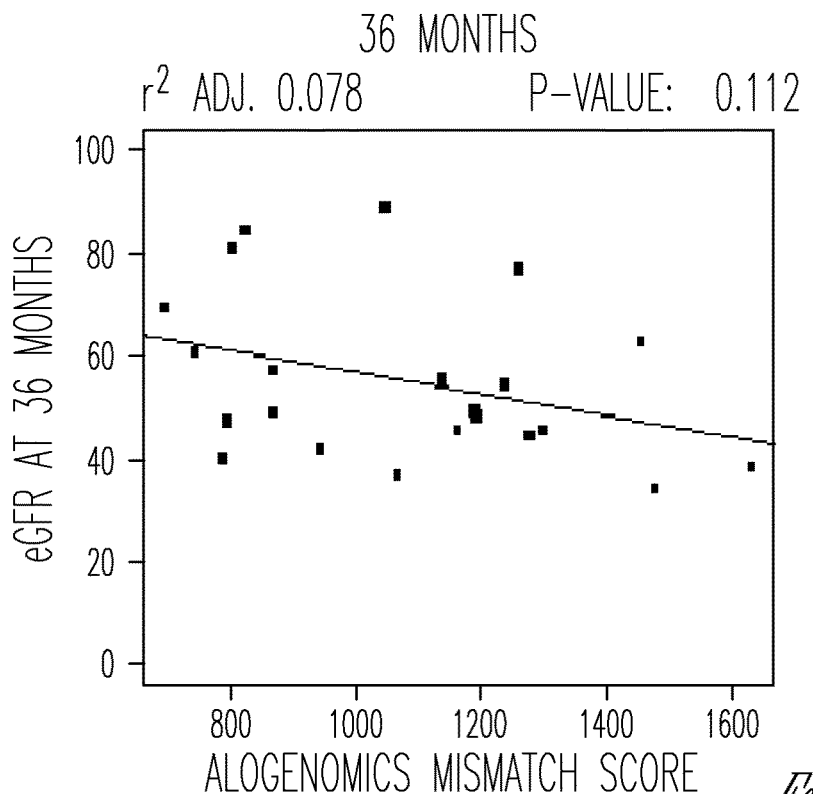
Figure 4H:
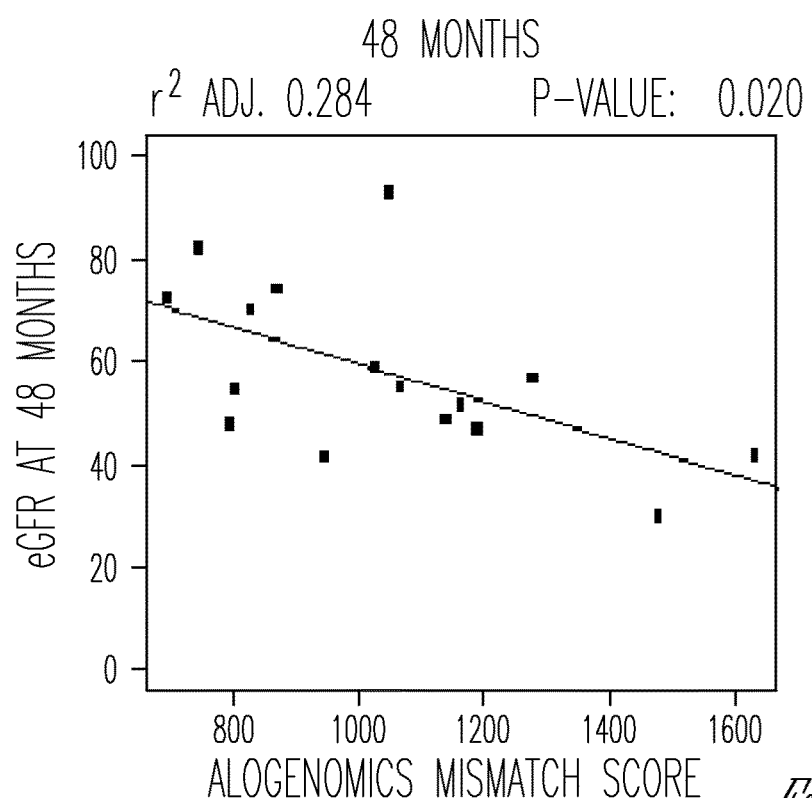

Positive linear associations between the allogenomics mismatch score and serum creatinine levels at 36 months post transplantation ($R^2$ adj.=0.78, P<0.01, n=10, at 36 months) were obtained but not 12 or 24 months following kidney transplantation (FIG. 3A-3C). A negative linear relationship was found between the score and eGFR at 36 months post transplantation ($R^2$ adj.=0.57, P=0.02) but not at 12 or 24 months following kidney transplantation (FIG. 3D-3F). The association between the score and graft function suggests that the allogenomics score is predictive of long-term graft function rather than short-term function.

Example 7: The Allogenomics Mismatch Score Associates with Graft Function in an Independent Cohort of Kidney Recipient-Donor Pairs This Example describes some of the results of an additional study illustrating the allogenomics methods. The procedures described in Example 5 were used during this study.

To validate the finding that the allogenomics mismatch score is associated with post-transplant kidney graft function the association in an independent cohort of kidney transplant patients was tested. DNA was collected from 24 additional kidney recipient-donor pairs (see Table 3 for demographic information of subjects included in the Validation cohort) and sequenced. DNA sequencing was performed using the Agilent Haloplex assay covering 37 Mb of the coding sequence of the human genome. The genotypes were identified and the allogenomics mismatch score was estimated as described in Example 5).

FIG. 4 shows that, as observed with the Discovery cohort, the allogenomics mismatch score correlates progressively better with kidney graft function with increase in the time following transplantation. At 36 months post-transplantation, a moderate positive association was observed between the allogenomics mismatch score and the serum creatinine levels ($R^2$ adj. 0.139, P=0.049) (FIG. 4C) and eGFR ($R^2$ adj. 0.078, P=0.11) (FIG. 4G). The association between the score and graft function was stronger and reached significance at 48 months post-transplantation for both creatinine levels ($R^2$ adj. 0.394, P<0.01) (FIG. 4D), and eGFR ($R^2$ adj. 0.284, P=0.02) (FIG. 4H), further validating the association in the Validation cohort.

Figure 5A:
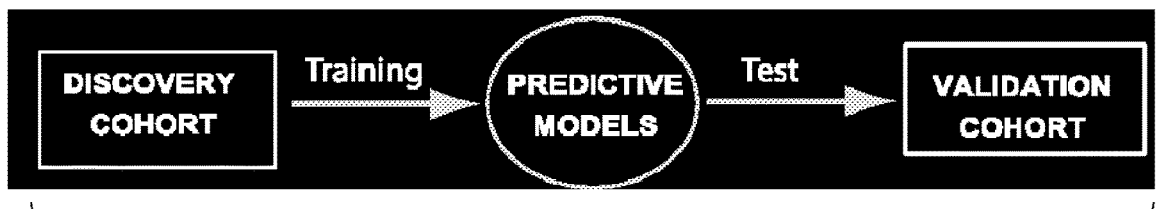
FIG. 5A-5C illustrates the model trained on the Discovery cohort applied to the Validation cohort.
Figure 5B:
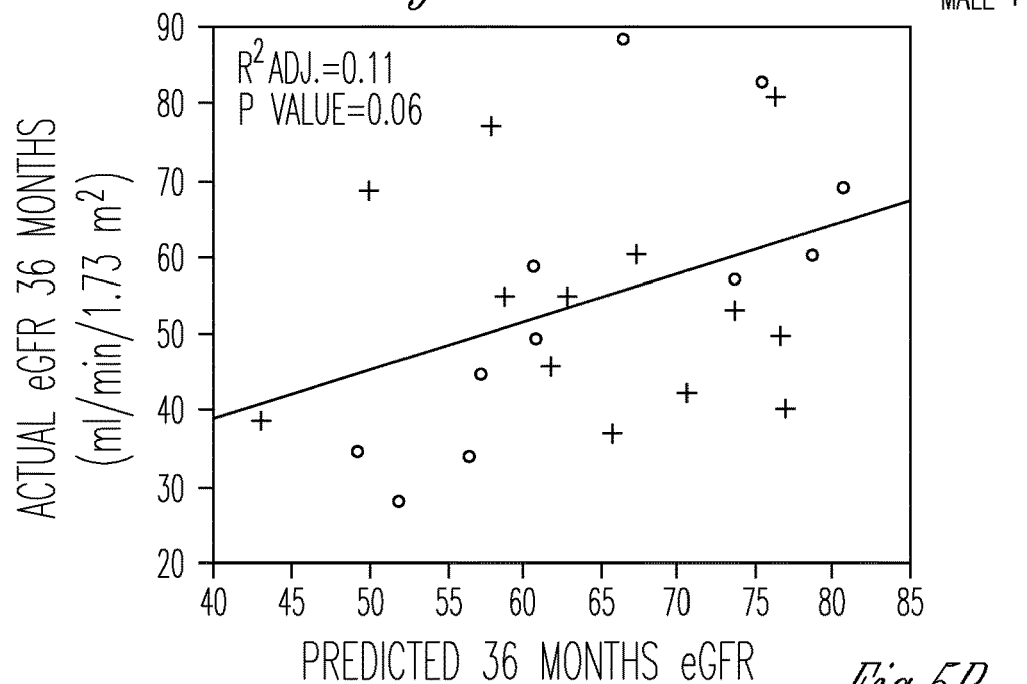
Figure 5C:
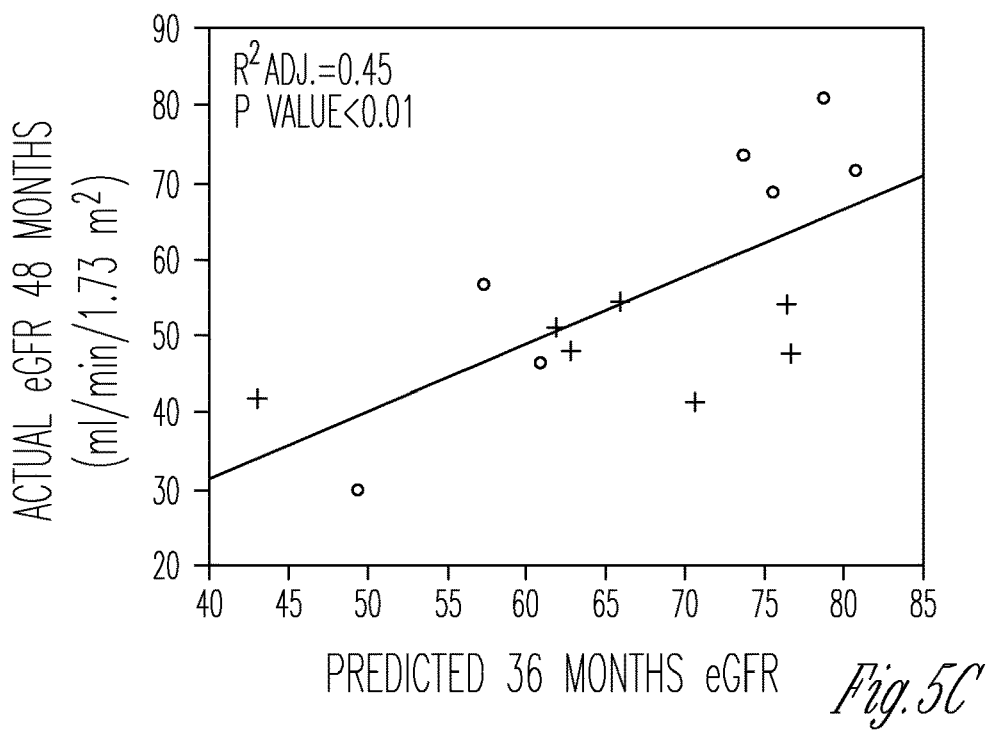
Figure 6A:
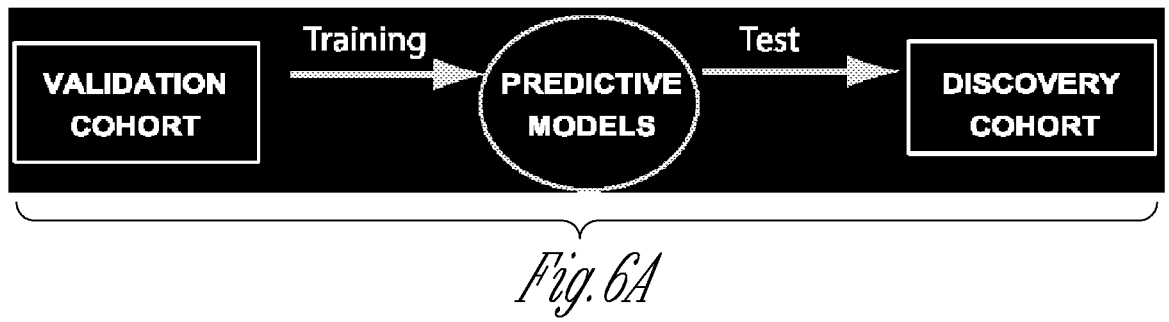
FIG. 6A-6B illustrates the model trained on the Validation cohort applied to the Discovery cohort.
Figure 6B:
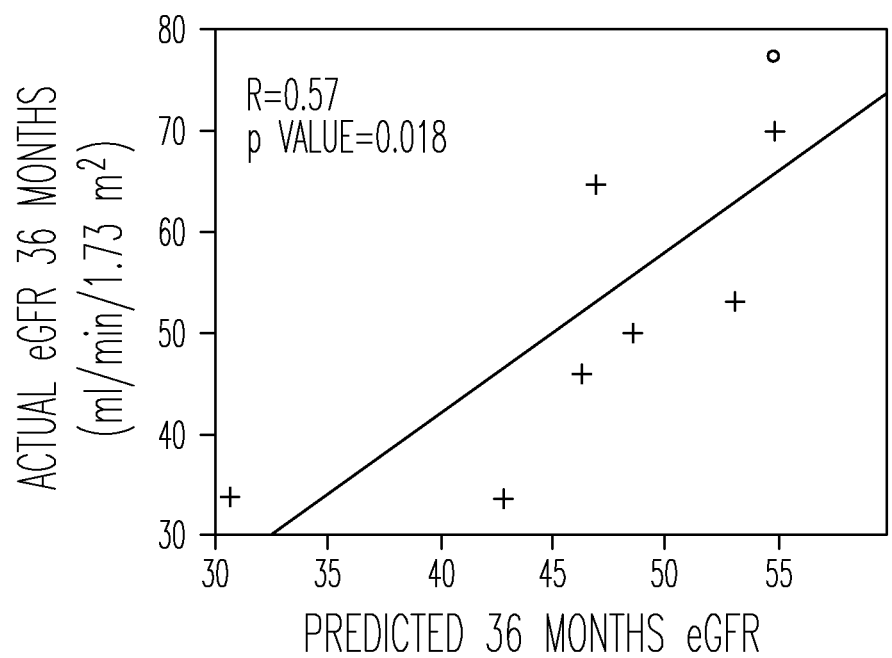
Figure 7A:
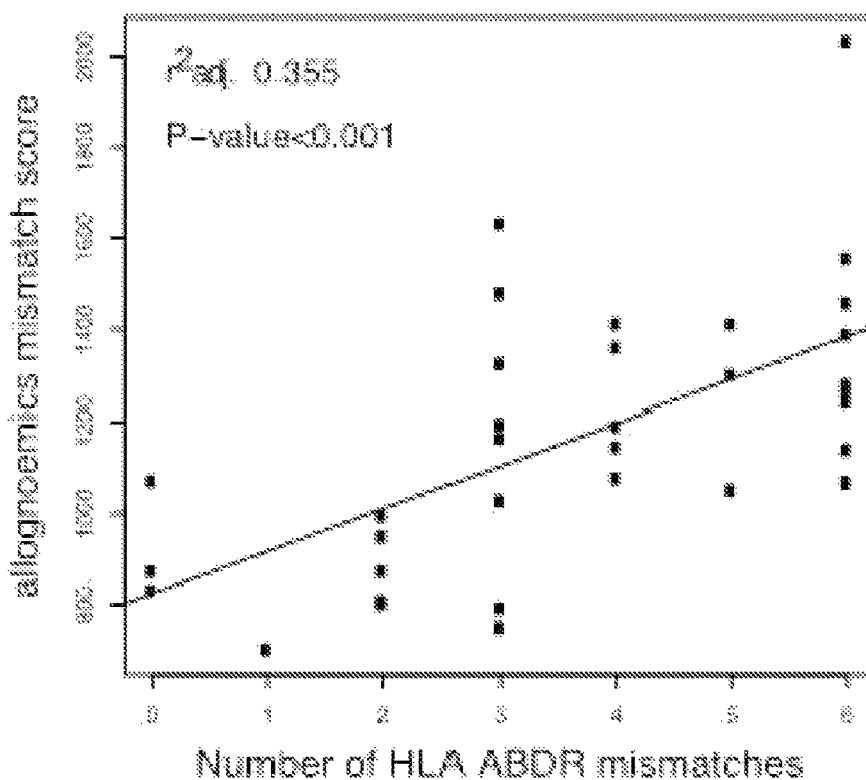
FIG. 7A-7D graphically illustrates relationships between allogenomics mismatch scores and the HLA loci. Discovery and Validation cohorts were combined to examine the relationship of the allogenomics mismatch score to the HLA-A, B and DR mismatch between the recipient and the kidney donor.
Figure 7B:
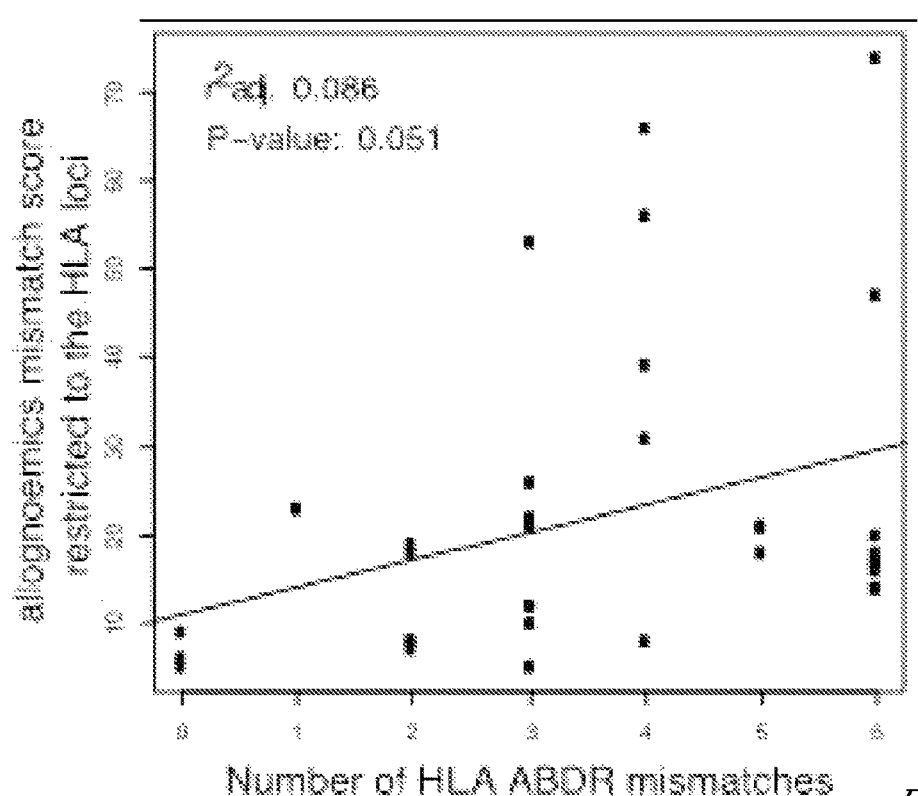
Figure 7C:
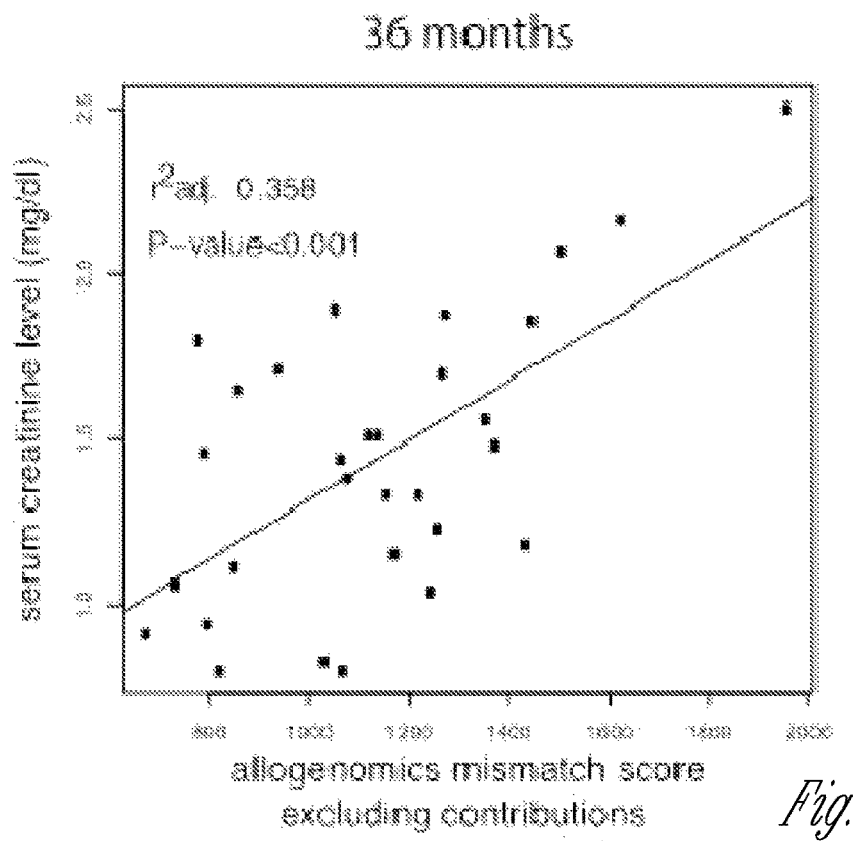
Figure 7D:
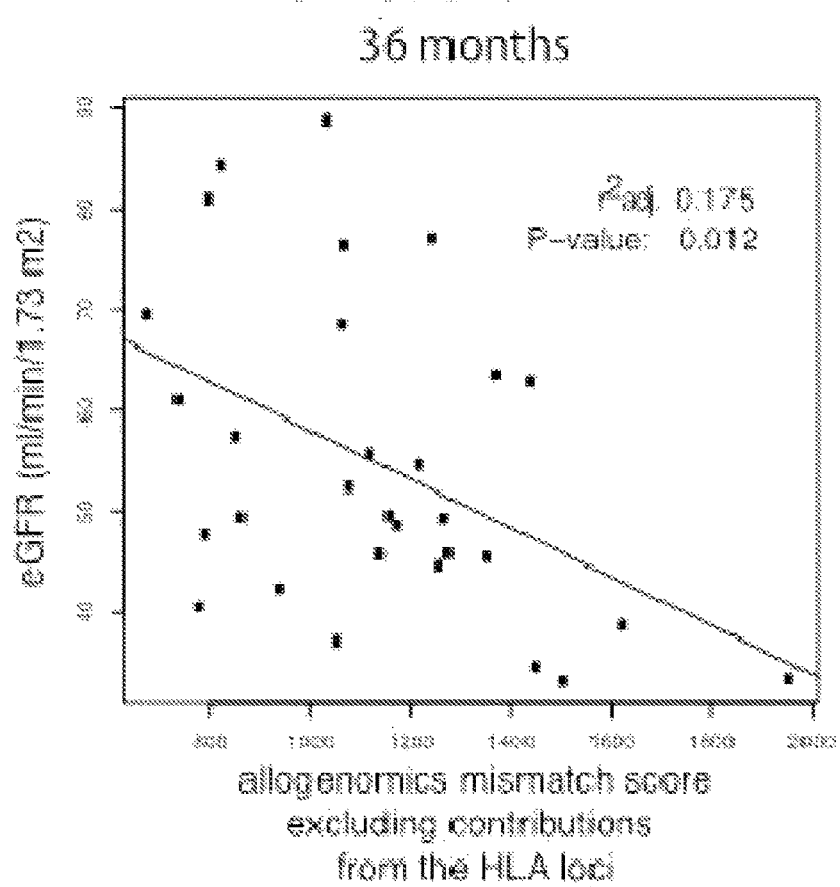

To test whether models trained on one cohort would generalize to another cohort, models were trained on the Discovery cohort and the fixed model was used to predict graft function in the Validation cohort. FIG. 5 shows that such a fixed model does generalize when presented with new recipient-donor pairs, and that the fixed model also exhibited better fit to the longer 48 month time-point compared to the earlier time-point (FIG. 5B vs. 5C) Similarly, models trained on the Validation cohort generalize to the Discovery cohort (FIG. 6A-6B). These results establish that the parameters of the models are stable, despite the relatively small numbers of kidney recipient-donor pairs included in the Discovery and Validation cohorts.

Example 8: Relation of Allogenomics Mismatch Scores to HLA Mismatches

This Example describes some of the results of an additional study illustrating the allogenomics methods. The procedures described in Example 5 were used during this study.

FIG. 7 presents an analysis where the Discovery and Validation cohorts (34 transplant kidney recipient-donor pairs) were combined, and the allogenomics scores were compared to the number of mismatches at the HLA-A, B and DR loci. The allogenomics mismatch score is moderately correlated with the number of mismatches at the HLA loci (FIG. 7A, $R^2$ adj.=0.36, P<0.001). However, the number of HLA mismatches correlates poorly with an allogenomics score estimated from exome data when restricting the sites to the HLA loci (FIG. 7B, $R^2$ adj.=0.1, P=0.03). Furthermore, the allogenomics mismatch score estimated outside of the HLA loci still significantly associates with serum creatinine levels (FIG. 7C) and eGFR (FIG. 7D). These data indicate that the allogenomics method does not rely upon data from the HLA loci, and is mostly independent of the HLA loci.

Example 9: Final Models

This Example describes some of the results of an additional study illustrating the allogenomics methods. The procedures described in Example 5 were used during this study.

Models were fitted across the combined cohorts to yield final models with fixed parameters. These models are trained across the 32 pairs of the Discovery and Validation cohorts against serum creatinine levels at 36 months:

$$creatinine\_at\_36\_months = 0.3823513 + 0.0009216 * allogenomics\_mismatch\_score;$$

and eGFR at 36 months:

$$eGFR\_at\_36\ months = 83.802675 - 0.0254203 * allogenomics\_mismatch\_score.$$

The equations and parameters are provided to enable testing of these models on independent cohorts of transplant pairs genotyped with exome sequencing. Fit parameter values were estimated with JMP Pro release 11, Fit X by Y, Fit Line. Note that the parameters of this model are sensitive to the exact analysis pipeline used to align reads to the genome and to call genotypes and that a test of this model will require following the exact analysis protocol we have used.

Example 10: Impact of Genotyping Platform and Rare Polymorphisms

This Example describes some of the results of an additional study illustrating the allogenomics methods. The procedures described in Example 5 were used during this study.

Figure 8C:
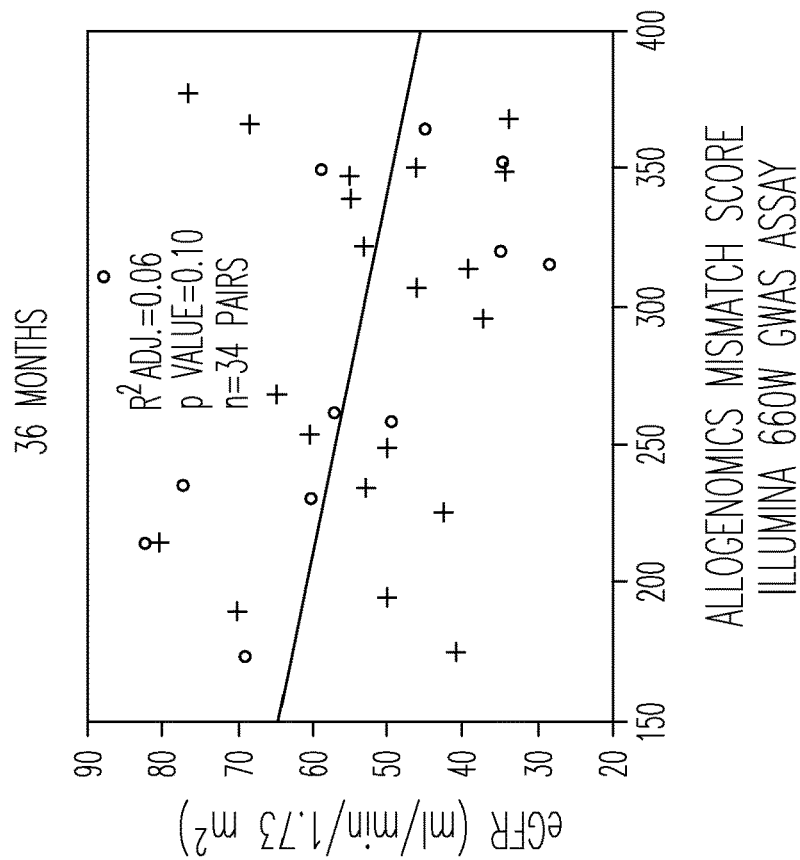
Figure 8C:
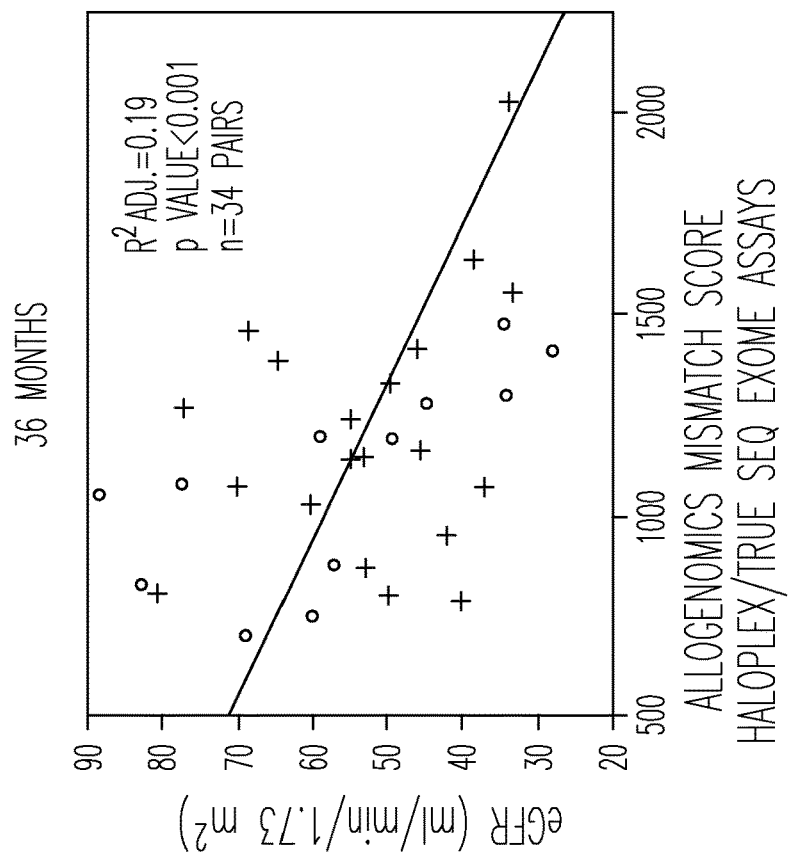

The impact of the genotyping platform on the estimation of the allogenomics mismatch score was evaluated as illustrated in FIG. 8. Large cohorts of matched recipient and donor DNA are being assembled and genotyped with SNP chip array technology such as the Illumina 660W bead array platform (Franklin et al., A genome-wide association study of kidney transplant survival: Donors recipients and interactions. In: American Conference of Human Genetics. 2012. Available from the website ashg.org/2012meeting/abstracts/fulltext/f120120818.htm). In this study, the inventors asked whether such platforms would be appropriate to validate the allogenomics model in large cohorts. FIG. 8A documents the number of sites that contribute to the allogenomics score on each platform. FIG. 8B shows that the exome assay captures many more sites with rare polymorphisms (minor allele frequency <5%) than the GWAS array platform. This is because exome assays directly sequence an individual DNA, while GWAS platforms are designed with a fixed set of polymorphisms and will not include many of the rare polymorphisms any given individual may carry. FIG. 8C compares the correlations measured with the exome assay or that could have been obtained if the allogenomics mismatch score had been measured with the Illumina 660W assay. The weak correlations obtained strongly suggest that GWAS platforms are not ideal for future tests of the allogenomics model.

Table 5 provides a list of some genes that can be evaluated in the methods described herein.

TABLE 5

| Gene List | | | |
|---|---|---|---|
| HGNC symbol ID | Ensembl Gene | HGNC symbol ID | Ensembl Gene |
| KIR2DL3 | ENSG00000275008 | SDK1 | ENSG00000267001 |
| KIR2DS3 | ENSG00000277657 | PIANP | ENSG00000139200 |
| NEU1 | ENSG00000228691 | OR12D2 | ENSG00000168787 |
| OR51Q1 | ENSG00000167360 | RYR3 | ENSG00000198838 |
| P2RX5-TAX1BP3 | ENSG00000257950 | C3orf35 | ENSG00000279651 |
| KIR3DL1 | ENSG00000274920 | STX16 | ENSG00000124222 |
| KIR3DL3 | ENSG00000274394 | | ENSG00000250264 |
| PRNP | ENSG00000171867 | CRHR1 | ENSG00000278232 |
| ARSE | ENSG00000157399 | CD96 | ENSG00000153283 |
| C6orf10 | ENSG00000232106 | ARMCX1 | ENSG00000126947 |
| LILRB2 | ENSG00000275463 | TMEM17 | ENSG00000186889 |
| TAS2R14 | ENSG00000212127 | | ENSG00000278904 |
| NFE2L3 | ENSG00000050344 | SPPL3 | ENSG00000157837 |
| PRLR | ENSG00000113494 | SLC7A8 | ENSG00000092068 |
| ZG16B | ENSG00000162078 | SYT10 | ENSG00000110975 |
| C10orf105 | ENSG00000214688 | KCNJ2 | ENSG00000123700 |
| CLDN10 | ENSG00000134873 | | ENSG00000280442 |
| HLA-DRA | ENSG00000204287 | ITPR3 | ENSG00000096433 |
| HLA-DOA | ENSG00000204252 | OR2F1 | ENSG00000279723 |

TABLE 5-continued

Gene List

| HGNC symbol ID | Ensembl Gene | HGNC symbol ID | Ensembl Gene |
|---|---|---|---|
| MOG | ENSG00000234096 | TAS2R10 | ENSG00000121318 |
| ERVMER34-1 | ENSG00000226887 | OR8D4 | ENSG00000181518 |
| KCNV2 | ENSG00000168263 | | ENSG00000279545 |
| HRASLS2 | ENSG00000133328 | KIR3DL3 | ENSG00000274511 |
| SLC39A9 | ENSG00000029364 | TAS2R50 | ENSG00000212126 |
| NFXL1 | ENSG00000170448 | CPD | ENSG00000108582 |
| LGR4 | ENSG00000205213 | LILRB4 | ENSG00000278555 |
| STRAP | ENSG00000023734 | GPHB5 | ENSG00000179600 |
| SLC27A4 | ENSG00000167114 | TAS2R31 | ENSG00000256436 |
| CATSPER4 | ENSG00000188782 | APLP2 | ENSG00000084234 |
| P2RX5 | ENSG00000083454 | OR2S2 | ENSG00000122718 |
| GGT5 | ENSG00000099998 | PCDH11Y | ENSG00000280342 |
| SLC5A2 | ENSG00000140675 | | ENSG00000279896 |
| HLA-DQA2 | ENSG00000231526 | UGT1A5 | ENSG00000240224 |
| OCLM | ENSG00000262180 | NOX1 | ENSG00000007952 |
| SLC26A8 | ENSG00000112053 | | ENSG00000279823 |
| ABCC6 | ENSG00000091262 | AGPAT1 | ENSG00000228892 |
| ATRNL1 | ENSG00000107518 | | ENSG00000278906 |
| TAPBP | ENSG00000206281 | OR4D5 | ENSG00000171014 |
| HSD3B1 | ENSG00000203857 | | ENSG00000279596 |
| GNS | ENSG00000135677 | | ENSG00000279449 |
| PAQR9 | ENSG00000188582 | OR6T1 | ENSG00000181499 |
| GPR160 | ENSG00000173890 | | ENSG00000279052 |
| CDH5 | ENSG00000179776 | LCT | ENSG00000115850 |
| | ENSG00000278440 | OR10S1 | ENSG00000196248 |
| C1orf27 | ENSG00000157181 | TPBG | ENSG00000146242 |
| HLA-DMA | ENSG00000242685 | | ENSG00000279938 |
| OR51B2 | ENSG00000279012 | B3GAT2 | ENSG00000112309 |
| KIR3DL3 | ENSG00000278729 | TRAF3IP3 | ENSG00000009790 |
| OR52B4 | ENSG00000280253 | OR10G6 | ENSG00000198674 |
| C4orf3 | ENSG00000279402 | SULF2 | ENSG00000196562 |
| SDK1 | ENSG00000146555 | OR10G4 | ENSG00000254737 |
| TRPM6 | ENSG00000119121 | FPR2 | ENSG00000171049 |
| OR10G9 | ENSG00000236981 | DEFB4B | ENSG00000275444 |
| OR10G8 | ENSG00000234560 | ADAM10 | ENSG00000137845 |
| SLC25A25 | ENSG00000148339 | SCN3A | ENSG00000153253 |
| C10orf35 | ENSG00000171224 | SORCS2 | ENSG00000184985 |
| SLC35D1 | ENSG00000116704 | ADCY1 | ENSG00000164742 |
| SLC16A12 | ENSG00000152779 | SMN2 | ENSG00000277773 |
| ANGPTL1 | ENSG00000116194 | RAMP1 | ENSG00000132329 |
| ELOVL3 | ENSG00000119915 | HTR2B | ENSG00000135914 |
| PAQR7 | ENSG00000182749 | FAM73B | ENSG00000148343 |
| ZP3 | ENSG00000188372 | | ENSG00000279871 |
| TNFSF15 | ENSG00000181634 | LMBR1L | ENSG00000139636 |
| TMEM52B | ENSG00000165685 | ANO5 | ENSG00000171714 |
| CLDN17 | ENSG00000156282 | OR2J2 | ENSG00000226347 |
| PTCH2 | ENSG00000117425 | GRIK1 | ENSG00000171189 |
| SCD | ENSG00000099194 | ICOSLG | ENSG00000160223 |
| TMEM74B | ENSG00000125895 | LRP8 | ENSG00000157193 |
| | ENSG00000275249 | CACNA1E | ENSG00000198216 |
| | ENSG00000276613 | NDUFA3 | ENSG00000275605 |
| CASD1 | ENSG00000127995 | NDST1 | ENSG00000070614 |
| GALR1 | ENSG00000166573 | TSPAN12 | ENSG00000106025 |
| KIR3DL3 | ENSG00000242019 | CHSY3 | ENSG00000198108 |
| ALB | ENSG00000163631 | MAS1L | ENSG00000228515 |
| VSTM1 | ENSG00000276363 | LHFPL3 | ENSG00000187416 |
| CPED1 | ENSG00000106034 | MET | ENSG00000105976 |
| GABBR1 | ENSG00000232632 | TMC4 | ENSG00000277789 |
| NDUFA3 | ENSG00000277722 | LINGO3 | ENSG00000220008 |
| OR5A1 | ENSG00000172320 | OR2L3 | ENSG00000198128 |
| EXTL2 | ENSG00000162694 | LAIR1 | ENSG00000276053 |
| IGDCC3 | ENSG00000174498 | SMIM2 | ENSG00000139656 |
| OR4D6 | ENSG00000166884 | PNISR | ENSG00000132424 |
| OR10G7 | ENSG00000182634 | OR2L8 | ENSG00000279263 |
| KLK4 | ENSG00000167749 | PIGB | ENSG00000069943 |
| CYP2S1 | ENSG00000167600 | SYVN1 | ENSG00000162298 |
| TTYH1 | ENSG00000167614 | GPR143 | ENSG00000101850 |
| PLOD2 | ENSG00000152952 | OR2T3 | ENSG00000278377 |
| FPR1 | ENSG00000171051 | SLC45A1 | ENSG00000162426 |
| | ENSG00000276289 | TAS2R46 | ENSG00000226761 |
| CWH43 | ENSG00000109182 | LINC00116 | ENSG00000175701 |
| TNFRSF8 | ENSG00000120949 | TBC1D2B | ENSG00000167202 |
| OR2S2 | ENSG00000278889 | SLC7A3 | ENSG00000165349 |
| CCDC108 | ENSG00000181378 | RHAG | ENSG00000112077 |
| SMIM20 | ENSG00000250317 | OR8U1 | ENSG00000172199 |

TABLE 5-continued

Gene List

| HGNC symbol ID | Ensembl Gene | HGNC symbol ID | Ensembl Gene |
|---|---|---|---|
| FPR3 | ENSG00000187474 | CACNG6 | ENSG00000130433 |
| EGFLAM | ENSG00000164318 | SYP | ENSG00000102003 |
| SLC36A4 | ENSG00000180773 | ICAM2 | ENSG00000108622 |
| MCHR2 | ENSG00000152034 | SMDT1 | ENSG00000272835 |
| IL18RAP | ENSG00000115607 | HLA-DQA1 | ENSG00000232062 |
| LRP5 | ENSG00000162337 | TRDN | ENSG00000186439 |
| FZD1 | ENSG00000157240 | TARM1 | ENSG00000275384 |
| CACNG1 | ENSG00000108878 | SEL1L3 | ENSG00000091490 |
| METTL2B | ENSG00000165055 | ATP2A3 | ENSG00000074370 |
| SLC13A4 | ENSG00000164707 | OR2T6 | ENSG00000278689 |
| PIGBOS1 | ENSG00000225973 | CCR3 | ENSG00000183625 |
| TSHR | ENSG00000165409 | ST3GAL4 | ENSG00000110080 |
| DEFB4A | ENSG00000275444 | KCNE3 | ENSG00000175538 |
| CDH26 | ENSG00000124215 | ABCG2 | ENSG00000118777 |
| SLC13A3 | ENSG00000158296 | SLC44A4 | ENSG00000204385 |
| CD47 | ENSG00000196776 | LRRC59 | ENSG00000108829 |
| TAS2R20 | ENSG00000255837 | SLC35A1 | ENSG00000164414 |
| FURIN | ENSG00000140564 | | ENSG00000261958 |
| SLC39A2 | ENSG00000165794 | TAS2R14 | ENSG00000276541 |
| TAS2R13 | ENSG00000212128 | | ENSG00000257046 |
| KIR2DS2 | ENSG00000275737 | CACNA1A | ENSG00000141837 |
| HLA-DRA | ENSG00000234794 | ITIH1 | ENSG00000055957 |
| SLC44A1 | ENSG00000070214 | TMEM101 | ENSG00000091947 |
| RHCG | ENSG00000140519 | SEMA3B | ENSG00000012171 |
| OR5T2 | ENSG00000262851 | ABCA1 | ENSG00000165029 |
| OR5T3 | ENSG00000261897 | KIAA1549L | ENSG00000110427 |
| CHRFAM7A | ENSG00000275917 | KCNMB3 | ENSG00000171121 |
| KRTCAP2 | ENSG00000163463 | CCR1 | ENSG00000163823 |
| | ENSG00000257062 | POMT2 | ENSG00000009830 |
| KCNJ5 | ENSG00000120457 | KIR2DL4 | ENSG00000274609 |
| KIR2DL4 | ENSG00000277850 | PPIL3 | ENSG00000240344 |
| MFSD10 | ENSG00000109736 | NYX | ENSG00000188937 |
| LAPTM5 | ENSG00000162511 | SLC25A20 | ENSG00000178537 |
| | ENSG00000278776 | | ENSG00000278194 |
| DEFB105A | ENSG00000274729 | SLC38A6 | ENSG00000139974 |
| DEFB105B | ENSG00000274729 | OR4D10 | ENSG00000254466 |
| TMEM184C | ENSG00000164168 | | ENSG00000274699 |
| KIR3DL1 | ENSG00000276501 | SLC25A23 | ENSG00000125648 |
| GABRA4 | ENSG00000109158 | OR2T4 | ENSG00000275617 |
| HLA-DOB | ENSG00000243612 | GLCE | ENSG00000138604 |
| CLRN3 | ENSG00000180745 | TAP2 | ENSG00000225967 |
| ABCC1 | ENSG00000278183 | CYB561D2 | ENSG00000114395 |
| GABRD | ENSG00000187730 | KDSR | ENSG00000119537 |
| | ENSG00000278307 | APOL1 | ENSG00000100342 |
| LAT | ENSG00000213658 | CYHR1 | ENSG00000187954 |
| TMC4 | ENSG00000274873 | DHRS11 | ENSG00000275397 |
| OR8K3 | ENSG00000262755 | NCR1 | ENSG00000273506 |
| DHODH | ENSG00000102967 | OR2T3 | ENSG00000277113 |
| OR9G4 | ENSG00000262647 | SLC1A5 | ENSG00000105281 |
| MYRF | ENSG00000124920 | OR51J1 | ENSG00000184321 |
| TBL2 | ENSG00000106638 | NRXN3 | ENSG00000021645 |
| SLC30A9 | ENSG00000014824 | TMEM26 | ENSG00000196932 |
| ABCC3 | ENSG00000108846 | LY6G6E | ENSG00000206401 |
| CD200R1L | ENSG00000206531 | ATP5J2 | ENSG00000241468 |
| OR8K1 | ENSG00000263328 | | ENSG00000259784 |
| SLC1A1 | ENSG00000106688 | NPC1L1 | ENSG00000015520 |
| FMO4 | ENSG00000076258 | OFCC1 | ENSG00000181355 |
| NPBWR2 | ENSG00000277339 | CFAP61 | ENSG00000089101 |
| MALRD1 | ENSG00000204740 | STX17 | ENSG00000136874 |
| OR56A4 | ENSG00000183389 | | ENSG00000278303 |
| OR3A3 | ENSG00000159961 | BPIFB2 | ENSG00000078898 |
| OR2M5 | ENSG00000162727 | COQ7 | ENSG00000167186 |
| RXFP3 | ENSG00000182631 | ABHD16A | ENSG00000224552 |
| | ENSG00000275331 | SLC51A | ENSG00000163959 |
| FAM210B | ENSG00000124098 | HLA-DQA2 | ENSG00000233192 |
| NPY2R | ENSG00000185149 | HOGA1 | ENSG00000241935 |
| GJB3 | ENSG00000188910 | TAS2R43 | ENSG00000255374 |
| PROCR | ENSG00000101000 | GJB4 | ENSG00000189433 |
| | ENSG00000113811 | LY6G6E | ENSG00000236210 |
| TAS2R8 | ENSG00000277316 | C20orf24 | ENSG00000101084 |
| NXPE1 | ENSG00000095110 | SPPL2B | ENSG00000005206 |
| FLVCR1 | ENSG00000162769 | LILRA6 | ENSG00000275584 |
| TAS2R30 | ENSG00000256188 | CD72 | ENSG00000137101 |
| MBOAT7 | ENSG00000277025 | ST8SIA6 | ENSG00000148488 |

TABLE 5-continued

Gene List

| HGNC symbol ID | Ensembl Gene | HGNC symbol ID | Ensembl Gene |
|---|---|---|---|
| SLC45A2 | ENSG00000164175 | ARSK | ENSG00000164291 |
|  | ENSG00000277044 | TAS2R9 | ENSG00000273713 |
| SLC22A7 | ENSG00000137204 | SPN | ENSG00000197471 |
| ST8SIA1 | ENSG00000111728 | OR9G9 | ENSG00000262191 |
|  | ENSG00000280108 | OR5P2 | ENSG00000276025 |
| TMEM64 | ENSG00000180694 | OR2M3 | ENSG00000228198 |
|  | ENSG00000279380 | ATP6V0C | ENSG00000185883 |
| SMIM12 | ENSG00000163866 | LY75-CD302 | ENSG00000248672 |
| GAL | ENSG00000069482 | KCNMB4 | ENSG00000135643 |
| P2RY6 | ENSG00000171631 | TMC4 | ENSG00000277996 |
| TMC4 | ENSG00000278363 | GUCA2B | ENSG00000044012 |
| MDGA2 | ENSG00000139915 | PPAP2B | ENSG00000162407 |
| OR2M2 | ENSG00000198601 | CD22 | ENSG00000012124 |
| C17orf78 | ENSG00000278145 | KIAA1024L | ENSG00000186367 |
| SLC33A1 | ENSG00000169359 | HS6ST1 | ENSG00000136720 |
| CRLS1 | ENSG00000088766 | SLC26A1 | ENSG00000145217 |
| TMC1 | ENSG00000165091 | TNFRSF14 | ENSG00000273936 |
| TAS2R10 | ENSG00000277238 | FKBP14 | ENSG00000106080 |
| OR2T2 | ENSG00000275754 | SEMA6D | ENSG00000137872 |
| LY6G6F | ENSG00000239741 | OR4A47 | ENSG00000237388 |
| OR2T1 | ENSG00000275244 |  | ENSG00000259522 |
| OR5P3 | ENSG00000278253 | NPBWR2 | ENSG00000125522 |
| POMK | ENSG00000185900 | CRY2 | ENSG00000121671 |
| PRPF38B | ENSG00000134186 | SERPINA9 | ENSG00000170054 |
| KIR2DL2 | ENSG00000278692 | OR4C6 | ENSG00000181903 |
| KIR2DL2 | ENSG00000276126 | UBA5 | ENSG00000081307 |
| ISM2 | ENSG00000100593 | SEC61A2 | ENSG00000065665 |
| OR5AK2 | ENSG00000181273 | ICOSLG | ENSG00000277117 |
| RYR2 | ENSG00000198626 | DHRS13 | ENSG00000167536 |
| SLC22A14 | ENSG00000144671 | TMEM115 | ENSG00000126062 |
|  | ENSG00000279282 | HRH2 | ENSG00000113749 |
| CD4 | ENSG00000010610 | PIGW | ENSG00000275600 |
| TARM1 | ENSG00000275123 | FER1L5 | ENSG00000249715 |
| EPHA10 | ENSG00000183317 |  | ENSG00000258635 |
| KIR3DL2 | ENSG00000276739 | IFNL1 | ENSG00000182393 |
| OR10A6 | ENSG00000276451 | TAS2R50 | ENSG00000276167 |
| SLC44A4 | ENSG00000228263 | PQLC2 | ENSG00000040487 |
| GRM1 | ENSG00000152822 | B4GALNT4 | ENSG00000182272 |
| AMN | ENSG00000166126 | HILPDA | ENSG00000135245 |
| IFI27L2 | ENSG00000119632 | VNN3 | ENSG00000093134 |
| KCNQ5 | ENSG00000185760 | CXCR3 | ENSG00000186810 |
| OTOF | ENSG00000115155 | KIR2DS4 | ENSG00000275353 |
| UGT1A4 | ENSG00000244474 | HLA-DOB | ENSG00000241910 |
| PTGER3 | ENSG00000050628 | STIM2 | ENSG00000109689 |
| OR10A3 | ENSG00000273953 | KIR2DS2 | ENSG00000275452 |
| PTPLAD1 | ENSG00000074696 |  | ENSG00000279342 |
| BLCAP | ENSG00000166619 | QPCTL | ENSG00000011478 |
| EVC | ENSG00000072840 | OR2T4 | ENSG00000274870 |
| HLA-E | ENSG00000225201 | CLCNKA | ENSG00000186510 |
|  | ENSG00000279096 | SYPL1 | ENSG00000008282 |
| PRSS16 | ENSG00000112812 | MYOF | ENSG00000138119 |
| TMEM100 | ENSG00000166292 | DENND5A | ENSG00000184014 |
|  | ENSG00000279214 | AREL1 | ENSG00000119682 |
| LY6G6F | ENSG00000243804 | DNASE2B | ENSG00000137976 |
| COL26A1 | ENSG00000160963 | OR4C13 | ENSG00000258817 |
| DDR1 | ENSG00000215522 | BPIFB1 | ENSG00000125999 |
| TAS2R19 | ENSG00000212124 | OR10C1 | ENSG00000220550 |
| UCN2 | ENSG00000145040 | PLD5 | ENSG00000180287 |
| OR56A1 | ENSG00000180934 |  | ENSG00000204422 |
| TMEM63A | ENSG00000196187 |  | ENSG00000279374 |
| OR2H2 | ENSG00000224319 | METTL16 | ENSG00000127804 |
| RETSAT | ENSG00000042445 | TARM1 | ENSG00000275806 |
| OR2M4 | ENSG00000171180 | CD163 | ENSG00000177575 |
| SSTR4 | ENSG00000132671 | CTXN3 | ENSG00000205279 |
| CELSR2 | ENSG00000143126 | OR4N4 | ENSG00000274792 |
| SLC35A3 | ENSG00000117620 | MAS1L | ENSG00000233141 |
| KIR3DL1 | ENSG00000275717 | OR51M1 | ENSG00000184698 |
| EVC2 | ENSG00000173040 | GGCX | ENSG00000115486 |
|  | ENSG00000250641 | LY6G6E | ENSG00000237482 |
| LY6G6F | ENSG00000243003 | EREG | ENSG00000124882 |
| SLC22A18 | ENSG00000110628 | HLA-DMB | ENSG00000241674 |
| GDPD3 | ENSG00000102886 | TMEM147 | ENSG00000105677 |
|  | ENSG00000272000 | SCAMP3 | ENSG00000116521 |
| GDPD3 | ENSG00000198064 | BTNL3 | ENSG00000168903 |
| KIR3DL2 | ENSG00000278710 | OR2T12 | ENSG00000177201 |

TABLE 5-continued

Gene List

| HGNC symbol ID | Ensembl Gene | HGNC symbol ID | Ensembl Gene |
|---|---|---|---|
| ABCC9 | ENSG00000069431 | ARSF | ENSG00000062096 |
| OR4B1 | ENSG00000175619 | CYB561A3 | ENSG00000162144 |
| TRIM59 | ENSG00000213186 | TM4SF19-TCTEX1D2 | ENSG00000273331 |
| CCL4 | ENSG00000275824 | SEC22C | ENSG00000093183 |
| MGST1 | ENSG00000008394 | TYROBP | ENSG00000011600 |
| KIR3DL2 | ENSG00000274722 | OR2M7 | ENSG00000177186 |
| TAS2R45 | ENSG00000278111 | TM4SF19 | ENSG00000145107 |
| GP1BA | ENSG00000185245 | SLC25A31 | ENSG00000151475 |
| IL2RA | ENSG00000134460 | FUT3 | ENSG00000171124 |
| OR2T33 | ENSG00000177212 | OR14C36 | ENSG00000177174 |
| CLCN6 | ENSG00000011021 | ATP6V0E1 | ENSG00000113732 |
| SLC9C1 | ENSG00000172139 | | ENSG00000278742 |
| KIR3DL1 | ENSG00000167633 | TMEM156 | ENSG00000121895 |
| SLC41A1 | ENSG00000133065 | PKHD1 | ENSG00000170927 |
| KCNH6 | ENSG00000173826 | ARMCX6 | ENSG00000198960 |
| SLC6A1 | ENSG00000157103 | OR13A1 | ENSG00000277495 |
| OR5I1 | ENSG00000167825 | CTNS | ENSG00000040531 |
| EMR1 | ENSG00000174837 | P2RY8 | ENSG00000182162 |
| POLR2J3 | ENSG00000168255 | SLC10A4 | ENSG00000145248 |
| KIR2DS5 | ENSG00000274739 | GP6 | ENSG00000275633 |
| TMEM132B | ENSG00000139364 | ENTPD6 | ENSG00000197586 |
| SHH | ENSG00000164690 | GLRA1 | ENSG00000145888 |
| OR11A1 | ENSG00000206517 | C3orf80 | ENSG00000180044 |
| MS4A3 | ENSG00000149516 | ABCG1 | ENSG00000160179 |
| CEACAM21 | ENSG00000278565 | ZNF708 | ENSG00000182141 |
| MAATS1 | ENSG00000183833 | TAS2R39 | ENSG00000236398 |
| MUC4 | ENSG00000275164 | GRM3 | ENSG00000198822 |
| KCNJ3 | ENSG00000162989 | CRIM1 | ENSG00000277354 |
| UGT8 | ENSG00000174607 | OR8U8 | ENSG00000262315 |
| LEPROTL1 | ENSG00000104660 | OR8U9 | ENSG00000262315 |
| CLCN2 | ENSG00000114859 | ATP11A | ENSG00000068650 |
| OR4A5 | ENSG00000221840 | SPATA31A1 | ENSG00000204849 |
| OR5K2 | ENSG00000231861 | KIR2DL3 | ENSG00000277924 |
| GABRB1 | ENSG00000163288 | TMEFF1 | ENSG00000241697 |
| | ENSG00000259101 | OR10A6 | ENSG00000279000 |
| SLC7A1 | ENSG00000139514 | HPN | ENSG00000105707 |
| SCRG1 | ENSG00000164106 | MPEG1 | ENSG00000197629 |
| TMEM2 | ENSG00000135048 | HSPA13 | ENSG00000155304 |
| OR2J3 | ENSG00000226271 | CRB3 | ENSG00000130545 |
| MFSD7 | ENSG00000169026 | VSTM1 | ENSG00000274887 |
| LRRN3 | ENSG00000173114 | GAA | ENSG00000171298 |
| HHIP | ENSG00000164161 | MBOAT7 | ENSG00000274194 |
| ITPRIPL1 | ENSG00000198885 | SLC35F6 | ENSG00000213699 |
| FUT10 | ENSG00000172728 | KIR2DL2 | ENSG00000277725 |
| SLC39A7 | ENSG00000112473 | SLC17A9 | ENSG00000101194 |
| MUC15 | ENSG00000169550 | TNFSF13B | ENSG00000102524 |
| STX4 | ENSG00000103496 | LY6G6E | ENSG00000224708 |
| LHFPL4 | ENSG00000156959 | GPNMB | ENSG00000136235 |
| PLXDC2 | ENSG00000120594 | OR10A3 | ENSG00000170683 |
| SLC25A22 | ENSG00000177542 | METTL7A | ENSG00000185432 |
| FAM189A2 | ENSG00000135063 | GJA4 | ENSG00000187513 |
| EMC7 | ENSG00000134153 | TLR8 | ENSG00000101916 |
| OR2T4 | ENSG00000196944 | COX8C | ENSG00000277018 |
| LY6G6D | ENSG00000206402 | OR8J1 | ENSG00000262796 |
| TAS2R40 | ENSG00000221937 | SGCG | ENSG00000102683 |
| IL22RA1 | ENSG00000142677 | TGIF2-C20orf24 | ENSG00000259399 |
| ABHD16A | ENSG00000204427 | MGAT5B | ENSG00000167889 |
| KIR2DL5A | ENSG00000275436 | OR2T1 | ENSG00000175143 |
| OR2T6 | ENSG00000198104 | MGAT5 | ENSG00000152127 |
| MS4A18 | ENSG00000214782 | NDUFA3 | ENSG00000276220 |
| HLA-DRB1 | ENSG00000228080 | DNAJB9 | ENSG00000128590 |
| SLITRK4 | ENSG00000179542 | PCDH8 | ENSG00000136099 |
| SDC2 | ENSG00000169439 | XKR6 | ENSG00000171044 |
| MBOAT7 | ENSG00000277923 | | ENSG00000262302 |
| GANAB | ENSG00000089597 | | ENSG00000277221 |
| OR7G3 | ENSG00000170920 | THSD7B | ENSG00000144229 |
| RNF222 | ENSG00000189051 | OR2J3 | ENSG00000229866 |
| ADRA1D | ENSG00000171873 | CHL1 | ENSG00000134121 |
| YIPF6 | ENSG00000181704 | CISD1 | ENSG00000122873 |
| MOSPD2 | ENSG00000130150 | OR8K5 | ENSG00000181752 |
| KIR2DL4 | ENSG00000275237 | FAM20C | ENSG00000177706 |
| ANO3 | ENSG00000134343 | PPAPDC2 | ENSG00000205808 |
| | ENSG00000262611 | SOX1 | ENSG00000182968 |
| OR4A16 | ENSG00000181961 | MMP16 | ENSG00000156103 |
| EPGN | ENSG00000182585 | TAS2R42 | ENSG00000186136 |

TABLE 5-continued

Gene List

| HGNC symbol ID | Ensembl Gene | HGNC symbol ID | Ensembl Gene |
|---|---|---|---|
| NDUFA1 | ENSG00000125356 | CCKAR | ENSG00000163394 |
| NNAT | ENSG00000053438 | IL9R | ENSG00000124334 |
| GPR151 | ENSG00000173250 | SLC30A2 | ENSG00000158014 |
| FAAH | ENSG00000117480 | OR4A15 | ENSG00000181958 |
| PYY | ENSG00000131096 | OR6S1 | ENSG00000181803 |
| HLA-DOA | ENSG00000231558 | LY6G6D | ENSG00000226603 |
| PTGIS | ENSG00000124212 | TUBB3 | ENSG00000198211 |
| PLXND1 | ENSG00000004399 | PCDHB3 | ENSG00000113205 |
|  | ENSG00000129951 | FGF7 | ENSG00000140285 |
| KCNK16 | ENSG00000095981 | ABCC8 | ENSG00000006071 |
|  | ENSG00000277737 | PROM1 | ENSG00000007062 |
| KIR2DL5A | ENSG00000274143 | OR2T7 | ENSG00000227152 |
| MC5R | ENSG00000176136 | MSANTD3-TMEFF1 | ENSG00000251349 |
| TMEM179 | ENSG00000276342 | OR52W1 | ENSG00000175485 |
| TREML1 | ENSG00000161911 | OR9K2 | ENSG00000170605 |
| GJB5 | ENSG00000189280 | UST | ENSG00000111962 |
| MC1R | ENSG00000258839 | TMC5 | ENSG00000103534 |
| NDUFB6 | ENSG00000165264 | BVES | ENSG00000112276 |
| KIR3DL1 | ENSG00000275545 | MEP1A | ENSG00000112818 |
| TEX38 | ENSG00000186118 | TARM1 | ENSG00000274889 |
| SLC24A2 | ENSG00000155886 | HVCN1 | ENSG00000122986 |
| THBD | ENSG00000178726 | KIR3DL2 | ENSG00000278403 |
| GLRA4 | ENSG00000188828 | COX4I1 | ENSG00000131143 |
| TMEM39B | ENSG00000121775 | DEFB103A | ENSG00000273641 |
| S1PR5 | ENSG00000180739 | DEFB103B | ENSG00000273641 |
| OR5J2 | ENSG00000174957 | LY6G6F | ENSG00000240008 |
| HAUS2 | ENSG00000137814 |  | ENSG00000273822 |
| SLC44A4 | ENSG00000231479 | FXYD4 | ENSG00000150201 |
| C4orf3 | ENSG00000164096 | TMEM258 | ENSG00000134825 |
| TAAR2 | ENSG00000146378 | PCDHB13 | ENSG00000187372 |
| KREMEN1 | ENSG00000183762 | STOML1 | ENSG00000067221 |
| SLC27A1 | ENSG00000130304 | CSF2RA | ENSG00000198223 |
| MAS1 | ENSG00000130368 | RBM3 | ENSG00000102317 |
| NDUFA3 | ENSG00000276766 | UGT1A7 | ENSG00000244122 |
|  | ENSG00000250349 | SSMEM1 | ENSG00000165120 |
| TMEM194A | ENSG00000166881 | GRID2 | ENSG00000152208 |
| OR2T2 | ENSG00000196240 | ARHGAP1 | ENSG00000175220 |
| GPR126 | ENSG00000112414 | PCGF3 | ENSG00000185619 |
|  | ENSG00000272104 | FRMD5 | ENSG00000171877 |
| RDM1 | ENSG00000278023 | SLC12A7 | ENSG00000276482 |
| SLC6A3 | ENSG00000276996 | TNFRSF18 | ENSG00000186891 |
| OR9Q2 | ENSG00000186513 | AXL | ENSG00000167601 |
| HLA-E | ENSG00000236632 | ZNF286A | ENSG00000187607 |
| SLC6A18 | ENSG00000164363 | SLC27A3 | ENSG00000263163 |
| TMEM230 | ENSG00000089063 | PTDSS2 | ENSG00000174915 |
| DKKL1 | ENSG00000104901 | MANEA | ENSG00000172469 |
| MTHFD1 | ENSG00000100714 | CACNA1G | ENSG00000006283 |
| ALG10B | ENSG00000175548 | SLC12A8 | ENSG00000221955 |
| TRAC | ENSG00000277734 | LY75 | ENSG00000054219 |
| CCR2 | ENSG00000121807 | CYB561D1 | ENSG00000174151 |
| KIR3DL2 | ENSG00000278726 | ZDHHC23 | ENSG00000184307 |
| TMEM158 | ENSG00000249992 | FAM47E-STBD1 | ENSG00000118804 |
| GRM4 | ENSG00000124493 | HLA-G | ENSG00000230413 |
| PON2 | ENSG00000105854 | CRB1 | ENSG00000134376 |
| ELANE | ENSG00000277571 | MARVELD2 | ENSG00000274671 |
| CYYR1 | ENSG00000166265 | FAS | ENSG00000026103 |
| TPST1 | ENSG00000169902 | PRRG1 | ENSG00000130962 |
| TMPRSS6 | ENSG00000187045 | SYT9 | ENSG00000170743 |
| LILRB1 | ENSG00000274669 | KLRF2 | ENSG00000256797 |
| OR2H1 | ENSG00000204688 | USMG5 | ENSG00000173915 |
|  | ENSG00000278563 | SLC17A2 | ENSG00000112337 |
| HAVCR1 | ENSG00000113249 | CR2 | ENSG00000117322 |
| OR2D3 | ENSG00000178358 | ZNRF3 | ENSG00000183579 |
| VSIG2 | ENSG00000019102 | GP6 | ENSG00000276065 |
| NLGN2 | ENSG00000169992 | OR2H1 | ENSG00000206471 |
| FGFRL1 | ENSG00000127418 | LRMP | ENSG00000118308 |
|  | ENSG00000237962 | UGT1A3 | ENSG00000243135 |
| CYP19A1 | ENSG00000137869 | SCARA5 | ENSG00000168079 |
| AGPAT4 | ENSG00000026652 | LRRTM1 | ENSG00000162951 |
| EDNRB | ENSG00000136160 | SEMA4C | ENSG00000168758 |
| WNT3 | ENSG00000277626 | B3GNT7 | ENSG00000156966 |
| SLC25A53 | ENSG00000269743 | KIR2DS2 | ENSG00000274518 |
| MARCH1 | ENSG00000145416 | TMEM184A | ENSG00000164855 |
| HLA-DQB1 | ENSG00000233209 | ADCY8 | ENSG00000155897 |
| CD37 | ENSG00000104894 | POPDC3 | ENSG00000132429 |

TABLE 5-continued

Gene List

| HGNC symbol ID | Ensembl Gene | HGNC symbol ID | Ensembl Gene |
|---|---|---|---|
| UXS1 | ENSG00000115652 | B4GALT5 | ENSG00000158470 |
| IFITM1 | ENSG00000185885 | TAS2R7 | ENSG00000274327 |
| PCDHB6 | ENSG00000113211 | C14orf180 | ENSG00000274126 |
|  | ENSG00000275621 | LRFN3 | ENSG00000126243 |
| OR2J2 | ENSG00000225550 | OR5L1 | ENSG00000279395 |
| PCDHB14 | ENSG00000120327 | TMEM61 | ENSG00000143001 |
| GPER1 | ENSG00000164850 | FCRLA | ENSG00000132185 |
| IFITM2 | ENSG00000185201 | OR10AG1 | ENSG00000174970 |
| COL17A1 | ENSG00000065618 | GALNT9 | ENSG00000182870 |
| HIGD2B | ENSG00000175202 | KIAA1715 | ENSG00000144320 |
| CXCL8 | ENSG00000169429 | DEFB4B | ENSG00000177257 |
| OR2J2 | ENSG00000232945 | OR13A1 | ENSG00000256574 |
| PARP16 | ENSG00000138617 | SLC19A2 | ENSG00000117479 |
| ARHGAP36 | ENSG00000147256 | HCN2 | ENSG00000099822 |
| LMF1 | ENSG00000103227 | SFXN2 | ENSG00000156398 |
| DHCR7 | ENSG00000172893 | PRRT1 | ENSG00000235956 |
| KIR2DL4 | ENSG00000277750 | HAS2 | ENSG00000170961 |
| GP6 | ENSG00000274566 | DAGLA | ENSG00000134780 |
| LRP3 | ENSG00000130881 | EMP2 | ENSG00000213853 |
| VN1R1 | ENSG00000178201 | CATSPERD | ENSG00000174898 |
| RTN1 | ENSG00000139970 | SLC25A43 | ENSG00000077713 |
| OR2T3 | ENSG00000196539 | CLCN1 | ENSG00000188037 |
| MALL | ENSG00000144063 | TAS2R42 | ENSG00000273505 |
| NRSN1 | ENSG00000152954 | MGAT4A | ENSG00000071073 |
| TNFRSF4 | ENSG00000186827 | SYT11 | ENSG00000132718 |
| AGPAT1 | ENSG00000235758 | ELFN1 | ENSG00000225968 |
| FAT4 | ENSG00000196159 | TMEM31 | ENSG00000179363 |
| ABHD16A | ENSG00000235676 | GCLC | ENSG00000001084 |
| SELL | ENSG00000188404 |  | ENSG00000280174 |
|  | ENSG00000279988 | NRM | ENSG00000228867 |
| OSMR | ENSG00000145623 | OCEL1 | ENSG00000099330 |
| HLA-G | ENSG00000235680 | TMEM38A | ENSG00000072954 |
| VSTM5 | ENSG00000214376 | PDGFRB | ENSG00000113721 |
| SVOP | ENSG00000166111 | CYP7B1 | ENSG00000172817 |
|  | ENSG00000279909 | PCDHB5 | ENSG00000113209 |
| NCSTN | ENSG00000162736 | TAPT1 | ENSG00000169762 |
| MMEL1 | ENSG00000277131 | MBOAT7 | ENSG00000277733 |
| TRGC2 | ENSG00000227191 | C6orf25 | ENSG00000230060 |
| TMTC3 | ENSG00000139324 | KIR3DL1 | ENSG00000276423 |
| IFNK | ENSG00000147896 | NXPE4 | ENSG00000137634 |
| CDHR5 | ENSG00000273572 | GALNT10 | ENSG00000164574 |
| OR5R1 | ENSG00000279961 | SLC8A3 | ENSG00000100678 |
| LY6G6C | ENSG00000236183 | KIR2DS1 | ENSG00000278120 |
| KCNV1 | ENSG00000164794 | SYNGR1 | ENSG00000100321 |
| ENPP5 | ENSG00000112796 | SEMA4G | ENSG00000095539 |
| FAT2 | ENSG00000086570 | TMEM119 | ENSG00000183160 |
| VSIG4 | ENSG00000155659 | TM4SF18 | ENSG00000163762 |
| GCNT2 | ENSG00000111846 | TMEM65 | ENSG00000164983 |
| C6orf25 | ENSG00000204420 | VSTM1 | ENSG00000275577 |
| QSOX2 | ENSG00000165661 | TMEM38B | ENSG00000095209 |
| TVP23A | ENSG00000166676 | HLA-DRA | ENSG00000226260 |
| KIR2DL4 | ENSG00000276979 | PM20D1 | ENSG00000162877 |
| OR4K1 | ENSG00000155249 | BMP10 | ENSG00000163217 |
| GALR3 | ENSG00000128310 | MUC4 | ENSG00000145113 |
| OR4D11 | ENSG00000176200 | RHBDD1 | ENSG00000144468 |
| ANTXR2 | ENSG00000163297 | CATSPER3 | ENSG00000152705 |
| HERC4 | ENSG00000148634 | ADCYAP1R1 | ENSG00000078549 |
| TMCO2 | ENSG00000188800 | SERINC5 | ENSG00000164300 |
| B3GNT5 | ENSG00000176597 |  | ENSG00000276825 |
| PTPRU | ENSG00000060656 | MYADM | ENSG00000179820 |
| OR1S2 | ENSG00000197887 | ST6GAL1 | ENSG00000073849 |
| EMC6 | ENSG00000127774 | GXYLT1 | ENSG00000151233 |
| OR5M9 | ENSG00000150269 | YIPF1 | ENSG00000058799 |
| PCDHB16 | ENSG00000272674 | STXBP2 | ENSG00000076944 |
| NCR1 | ENSG00000275156 | OR52E4 | ENSG00000180974 |
| TLR3 | ENSG00000164342 | NXPE2 | ENSG00000204361 |
| PLA2G16 | ENSG00000176485 | MLF2 | ENSG00000089693 |
| ITGA4 | ENSG00000115232 | GABRE | ENSG00000102287 |
| IGDCC4 | ENSG00000103742 | MGAT3 | ENSG00000128268 |
| C1orf185 | ENSG00000204006 | SLC7A10 | ENSG00000130876 |
| HCRTR1 | ENSG00000121764 | CYP20A1 | ENSG00000119004 |
| CHRNE | ENSG00000108556 | OR2T29 | ENSG00000182783 |
| OR2T5 | ENSG00000203661 | FITM2 | ENSG00000197296 |
| ZDHHC1 | ENSG00000159714 | OR2J1 | ENSG00000204702 |
| MLANA | ENSG00000120215 | UGT1A1 | ENSG00000242366 |

TABLE 5-continued

Gene List

| HGNC symbol ID | Ensembl Gene | HGNC symbol ID | Ensembl Gene |
| --- | --- | --- | --- |
| PCDHB9 | ENSG00000177839 | SSR3 | ENSG00000114850 |
| OPN5 | ENSG00000124818 | OR2J3 | ENSG00000204701 |
| HLA-DQA1 | ENSG00000206305 | OR8K3 | ENSG00000280314 |
| GABRG1 | ENSG00000163285 | ANTXR1 | ENSG00000169604 |
| TSPAN19 | ENSG00000231738 | IL27 | ENSG00000197272 |
| SLC35A2 | ENSG00000102100 | VSTM1 | ENSG00000277607 |
| GRIN3A | ENSG00000198785 | GPR20 | ENSG00000275181 |
| OR2B3 | ENSG00000204703 | VSTM1 | ENSG00000276159 |
| ST3GAL2 | ENSG00000157350 | ALG10 | ENSG00000139133 |
| OR51I2 | ENSG00000187918 | HLA-DQB2 | ENSG00000230675 |
| FRAS1 | ENSG00000138759 | SERINC4 | ENSG00000184716 |
| ENTPD3 | ENSG00000168032 | GUCA2A | ENSG00000197273 |
| SLC6A15 | ENSG00000072041 | SPNS1 | ENSG00000169682 |
| KIR2DL4 | ENSG00000189013 | KIR2DL2 | ENSG00000276731 |
| CST11 | ENSG00000125831 | SLC35B4 | ENSG00000205060 |
| GPR31 | ENSG00000120436 | NTF3 | ENSG00000185652 |
| TMEM243 | ENSG00000135185 | NALCN | ENSG00000102452 |
| SLC39A6 | ENSG00000141424 | FAM24B | ENSG00000213185 |
| C5AR2 | ENSG00000134830 | GPR119 | ENSG00000147262 |
| SNRNP40 | ENSG00000060688 | LRFN1 | ENSG00000128011 |
| OR6B2 | ENSG00000182083 | MFSD12 | ENSG00000161091 |
| CCDC90B | ENSG00000137500 | FCAR | ENSG00000275269 |
| OR2G6 | ENSG00000188558 | NMUR1 | ENSG00000171596 |
| TMC4 | ENSG00000167608 | SLC17A4 | ENSG00000146039 |
| CPM | ENSG00000135678 | KDELR3 | ENSG00000100196 |
| PTCHD3 | ENSG00000276595 | CD247 | ENSG00000198821 |
| SYNGR4 | ENSG00000105467 | TMEM211 | ENSG00000206069 |
| ST8SIA5 | ENSG00000101638 | NPPA | ENSG00000175206 |
| METTL15 | ENSG00000169519 | OR52B6 | ENSG00000187747 |
| SUN1 | ENSG00000164828 | RDH14 | ENSG00000240857 |
| SLC26A10 | ENSG00000135502 | CD5 | ENSG00000110448 |
| IL17D | ENSG00000172458 | KIR2DL4 | ENSG00000275699 |
| KLK1 | ENSG00000167748 | CUZD1 | ENSG00000138161 |
| MS4A4E | ENSG00000214787 | TSPAN15 | ENSG00000099282 |
| SORCS1 | ENSG00000108018 | TENM3 | ENSG00000218336 |
| SLC12A9 | ENSG00000146828 | COX8C | ENSG00000187581 |
| COQ2 | ENSG00000173085 | GPR20 | ENSG00000204882 |
| OR51B4 | ENSG00000183251 | OR2T10 | ENSG00000184022 |
| SLC5A3 | ENSG00000198743 | OR5B3 | ENSG00000172769 |
| KCNQ1 | ENSG00000053918 | ACSS3 | ENSG00000111058 |
| PPT2 | ENSG00000231618 | OR5B2 | ENSG00000172365 |
| CYP4F11 | ENSG00000171903 | OR5M10 | ENSG00000254834 |
| EPHB6 | ENSG00000106123 | KEL | ENSG00000197993 |
| IFNAR1 | ENSG00000142166 | C8B | ENSG00000021852 |
| TMEM78 | ENSG00000177800 | PTGS1 | ENSG00000095303 |
| TLR2 | ENSG00000137462 | ZPBP | ENSG00000042813 |
|  | ENSG00000277361 | REEP6 | ENSG00000115255 |
| MIP | ENSG00000135517 | GLCCI1 | ENSG00000106415 |
| NPHP4 | ENSG00000131697 | DEFB105B | ENSG00000186599 |
| OR2T34 | ENSG00000183310 | IGFL1 | ENSG00000188293 |
| CD163L1 | ENSG00000177675 | ADAM32 | ENSG00000197140 |
| RCE1 | ENSG00000173653 | KIRREL3 | ENSG00000149571 |
|  | ENSG00000262535 | C6orf10 | ENSG00000206245 |
| OR9G1 | ENSG00000174914 | OR2T1 | ENSG00000273508 |
| VSTM1 | ENSG00000275330 | RNASE4 | ENSG00000258818 |
| FZD9 | ENSG00000188763 | EDEM1 | ENSG00000134109 |
| B3GNT3 | ENSG00000179913 | NDUFB3 | ENSG00000119013 |
| OR2J2 | ENSG00000231676 | PLD4 | ENSG00000166428 |
| GALNT16 | ENSG00000100626 | SEC22A | ENSG00000121542 |
| WFDC11 | ENSG00000180083 | OR6C2 | ENSG00000179695 |
| RAD51B | ENSG00000182185 | OR6C4 | ENSG00000179626 |
| ANKRD22 | ENSG00000152766 | SPATA31A6 | ENSG00000185775 |
| TRPM1 | ENSG00000274965 | LRRC4B | ENSG00000131409 |
| MCTP2 | ENSG00000140563 | OR5B12 | ENSG00000172362 |
| ABCB1 | ENSG00000085563 |  | ENSG00000280316 |
| BCS1L | ENSG00000074582 | LNPEP | ENSG00000113441 |
| UGT2A3 | ENSG00000135220 | TRGC1 | ENSG00000211689 |
| ACVR2B | ENSG00000114739 | SMIM18 | ENSG00000253457 |
| KIR3DL3 | ENSG00000275513 | TSPAN31 | ENSG00000135452 |
| C1GALT1C1 | ENSG00000171155 | OR2T11 | ENSG00000279301 |
| TSPAN5 | ENSG00000168785 | OPRD1 | ENSG00000116329 |
| OR51B5 | ENSG00000242180 | VSTM1 | ENSG00000189068 |
| UTS2B | ENSG00000188958 | OR2T35 | ENSG00000177151 |
| CHRM5 | ENSG00000184984 | NMU | ENSG00000109255 |
| UNC50 | ENSG00000115446 | ADCY3 | ENSG00000138031 |

TABLE 5-continued

Gene List

| HGNC symbol ID | Ensembl Gene | HGNC symbol ID | Ensembl Gene |
|---|---|---|---|
| OR5M11 | ENSG00000255223 | | ENSG00000259171 |
| MICA | ENSG00000204520 | | ENSG00000273984 |
| SCFD1 | ENSG00000092108 | HLA-DRB1 | ENSG00000236884 |
| | ENSG00000277065 | HLA-DRB4 | ENSG00000231021 |
| DYNAP | ENSG00000178690 | MPC1 | ENSG00000060762 |
| TMC4 | ENSG00000274905 | CTDNEP1 | ENSG00000175826 |
| TMEM53 | ENSG00000126106 | LRCH3 | ENSG00000186001 |
| DAK | ENSG00000149476 | SIGLEC1 | ENSG00000088827 |
| C1orf210 | ENSG00000253313 | RBFOX3 | ENSG00000167281 |
| THSD4 | ENSG00000187720 | KCNA4 | ENSG00000182255 |
| OR1A1 | ENSG00000172146 | DAG1 | ENSG00000173402 |
| KIR3DS1 | ENSG00000275608 | DENND5B | ENSG00000170456 |
| RDM1 | ENSG00000276432 | GABRB2 | ENSG00000145864 |
| SURF4 | ENSG00000148248 | ANK1 | ENSG00000029534 |
| MEGF11 | ENSG00000157890 | ZP4 | ENSG00000116996 |
| FAM213A | ENSG00000122378 | KIR3DL3 | ENSG00000276806 |
| RNF148 | ENSG00000235631 | SLC12A5 | ENSG00000124140 |
| | ENSG00000278088 | DLL1 | ENSG00000275555 |
| TEDDM1 | ENSG00000203730 | CELSR1 | ENSG00000075275 |
| KIR2DL4 | ENSG00000276779 | PCDHB8 | ENSG00000120322 |
| CYP2D6 | ENSG00000100197 | CS | ENSG00000062485 |
| GUSB | ENSG00000169919 | TMC2 | ENSG00000149488 |
| DGAT2 | ENSG00000062282 | B3GALNT1 | ENSG00000169255 |
| ANG | ENSG00000214274 | SLC17A3 | ENSG00000124564 |
| WFIKKN2 | ENSG00000173714 | RHOT1 | ENSG00000126858 |
| NDUFA3 | ENSG00000170906 | OR2T27 | ENSG00000187701 |
| TMCO5A | ENSG00000166069 | DTD1 | ENSG00000125821 |
| GPR146 | ENSG00000164849 | TMEM127 | ENSG00000135956 |
| ST14 | ENSG00000149418 | CLEC2A | ENSG00000188393 |
| OR2H1 | ENSG00000206516 | HLA-DPB1 | ENSG00000230763 |
| | ENSG00000277106 | ADAMTS4 | ENSG00000158859 |
| HLA-DOA | ENSG00000230141 | ATP2C1 | ENSG00000017260 |
| DERL3 | ENSG00000274437 | ENTPD4 | ENSG00000197217 |
| TMEFF2 | ENSG00000144339 | MARCH9 | ENSG00000139266 |
| LY6G5C | ENSG00000206404 | | ENSG00000228144 |
| IGSF3 | ENSG00000143061 | TMED3 | ENSG00000166557 |
| APOLD1 | ENSG00000178878 | | ENSG00000227506 |
| EDAR | ENSG00000135960 | DBH | ENSG00000123454 |
| TARM1 | ENSG00000277178 | TMEM257 | ENSG00000221870 |
| SLC22A12 | ENSG00000197891 | TSPAN1 | ENSG00000117472 |
| SLC24A3 | ENSG00000185052 | | ENSG00000276469 |
| SCN7A | ENSG00000136546 | CLEC9A | ENSG00000197992 |
| SLC5A7 | ENSG00000115665 | STRA6 | ENSG00000137868 |
| CLDN15 | ENSG00000106404 | KIR3DL2 | ENSG00000276357 |
| TTYH1 | ENSG00000275650 | LPAR1 | ENSG00000198121 |
| ABCC5 | ENSG00000114770 | CD82 | ENSG00000085117 |
| BTNL2 | ENSG00000224770 | SEC22B | ENSG00000265808 |
| ICAM5 | ENSG00000105376 | NDUFA3 | ENSG00000273642 |
| KCNS2 | ENSG00000156486 | GPM6A | ENSG00000150625 |
| CHST3 | ENSG00000122863 | NCR1 | ENSG00000277824 |
| HLA-DRB4 | ENSG00000227357 | TEX261 | ENSG00000144043 |
| KIR2DS2 | ENSG00000274438 | ADAM29 | ENSG00000168594 |
| MS4A10 | ENSG00000172689 | NCR1 | ENSG00000273535 |
| NT5E | ENSG00000135318 | SMCO4 | ENSG00000166002 |
| SLC41A2 | ENSG00000136052 | TMEM200C | ENSG00000206432 |
| OR6C70 | ENSG00000184954 | TMTC4 | ENSG00000125247 |
| MAN1B1 | ENSG00000177239 | SLCO2A1 | ENSG00000174640 |
| TEK | ENSG00000120156 | OR5M3 | ENSG00000174937 |
| OR2AP1 | ENSG00000179615 | KIR3DL1 | ENSG00000273775 |
| DENND1B | ENSG00000213047 | TARM1 | ENSG00000273875 |
| TOMM70A | ENSG00000154174 | OR9G4 | ENSG00000172457 |
| CLIP4 | ENSG00000115295 | RNF5 | ENSG00000227277 |
| ERLIN1 | ENSG00000107566 | HHAT | ENSG00000054392 |
| MICA | ENSG00000183214 | KIR3DL1 | ENSG00000278368 |
| C16orf54 | ENSG00000185905 | TBC1D7 | ENSG00000145979 |
| CDON | ENSG00000064309 | CHST1 | ENSG00000175264 |
| SLC35B3 | ENSG00000124786 | CES3 | ENSG00000172828 |
| TMPRSS9 | ENSG00000178297 | GRAMD2 | ENSG00000175318 |
| CLDN24 | ENSG00000185758 | PCDHB2 | ENSG00000112852 |
| SLC9A1 | ENSG00000090020 | | ENSG00000234195 |
| FCRL3 | ENSG00000160856 | TIMM22 | ENSG00000278501 |
| TMEM234 | ENSG00000160055 | MPL | ENSG00000117400 |
| SLC11A2 | ENSG00000110911 | ADIG | ENSG00000182035 |
| TMEM138 | ENSG00000149483 | MAG | ENSG00000105695 |
| TMPRSS13 | ENSG00000137747 | SLC45A4 | ENSG00000022567 |

TABLE 5-continued

Gene List

| HGNC symbol ID | Ensembl Gene | HGNC symbol ID | Ensembl Gene |
|---|---|---|---|
| XK | ENSG00000047597 | GP6 | ENSG00000276211 |
| CCDC141 | ENSG00000163492 | GPR107 | ENSG00000148358 |
| OR51E1 | ENSG00000180785 | HLA-DMA | ENSG00000241394 |
| ALG11 | ENSG00000253710 | CHST4 | ENSG00000140835 |
| MINOS1 | ENSG00000173436 | SMPD3 | ENSG00000103056 |
|  | ENSG00000234469 | CD164L2 | ENSG00000174950 |
| SLC4A7 | ENSG00000033867 | ADAM22 | ENSG00000008277 |
| KIR3DL3 | ENSG00000276930 | ZMPSTE24 | ENSG00000084073 |
| FSHR | ENSG00000170820 | OR14J1 | ENSG00000234100 |
| CHRM2 | ENSG00000181072 | TMEM255A | ENSG00000125355 |
| OR6B3 | ENSG00000178586 | TMEM81 | ENSG00000174529 |
| HLA-DQA2 | ENSG00000206301 | NPTXR | ENSG00000221890 |
| SUSD5 | ENSG00000173705 | CHRNA7 | ENSG00000274542 |
| OR2F2 | ENSG00000221910 | TM6SF2 | ENSG00000213996 |
| GABBR1 | ENSG00000206466 | CD248 | ENSG00000174807 |
| MLLT10 | ENSG00000078403 | AGER | ENSG00000231268 |
| CGRRF1 | ENSG00000100532 | ACP1 | ENSG00000143727 |
| GZMK | ENSG00000113088 | SLAMF1 | ENSG00000117090 |
| OR14I1 | ENSG00000189181 | MOG | ENSG00000237834 |
| RPRM | ENSG00000177519 | TMEM242 | ENSG00000215712 |
| PTGER2 | ENSG00000125384 | IGHG1 | ENSG00000211896 |
| UQCC3 | ENSG00000204922 | UGT1A8 | ENSG00000241635 |
| SLC22A2 | ENSG00000112499 | CD300LG | ENSG00000161649 |
| OR2T6 | ENSG00000278659 | HLA-DQB1 | ENSG00000231286 |
| CDIP1 | ENSG00000274336 | TMPPE | ENSG00000188167 |
| SLC4A10 | ENSG00000144290 | AGTR2 | ENSG00000180772 |
| CHRNA6 | ENSG00000147434 | KCNK6 | ENSG00000099337 |
| C1GALT1 | ENSG00000106392 | SMIM8 | ENSG00000111850 |
| VRK1 | ENSG00000100749 | LRTM2 | ENSG00000166159 |
| SERP2 | ENSG00000151778 | IL10RB | ENSG00000243646 |
| MAGT1 | ENSG00000102158 | ITGA3 | ENSG00000005884 |
| TRPV6 | ENSG00000276971 | B4GALNT1 | ENSG00000135454 |
| MTNR1A | ENSG00000168412 | ABCD4 | ENSG00000119688 |
| CNST | ENSG00000162852 | LPCAT2 | ENSG00000087253 |
|  | ENSG00000276539 | CYP4V2 | ENSG00000145476 |
| FAM173A | ENSG00000103254 | RTP1 | ENSG00000175077 |
| SEZ6L | ENSG00000100095 | TMEM120A | ENSG00000189077 |
| GRIK2 | ENSG00000164418 | NTRK1 | ENSG00000198400 |
| CYBB | ENSG00000165168 | TMEM185B | ENSG00000226479 |
| C5orf46 | ENSG00000178776 | OR4C12 | ENSG00000221954 |
| MAGEH1 | ENSG00000187601 | RHBDD2 | ENSG00000005486 |
| MYRFL | ENSG00000166268 | ANTXRL | ENSG00000274209 |
| PIGN | ENSG00000197563 | RNF5 | ENSG00000225452 |
| OR6C68 | ENSG00000205327 | KIR2DL3 | ENSG00000243772 |
| NCR3 | ENSG00000223833 | GJB7 | ENSG00000164411 |
| TMC4 | ENSG00000276260 | C1orf233 | ENSG00000228594 |
| CHRNA5 | ENSG00000169684 | RNF144B | ENSG00000137393 |
| SLC26A7 | ENSG00000147606 | WBP1 | ENSG00000239779 |
| NDUFA3 | ENSG00000274359 | CCL4L1 | ENSG00000276125 |
| GHITM | ENSG00000165678 | CCL4L2 | ENSG00000276125 |
| HCN3 | ENSG00000143630 | KEL | ENSG00000276615 |
| LRAT | ENSG00000121207 | SLC26A3 | ENSG00000091138 |
| SRP14 | ENSG00000140319 | MINOS1-NBL1 | ENSG00000270136 |
| ZNF559-ZNF177 | ENSG00000270011 | TRPV4 | ENSG00000111199 |
| RGS9BP | ENSG00000186326 | TBXA2R | ENSG00000006638 |
| GABRA6 | ENSG00000145863 | KCNA1 | ENSG00000111262 |
| CAV2 | ENSG00000105971 | RNF122 | ENSG00000133874 |
| ERMAP | ENSG00000164010 | SLC17A6 | ENSG00000091664 |
| EXD2 | ENSG00000081177 | C2orf40 | ENSG00000119147 |
| OR2K2 | ENSG00000171133 | LRCOL1 | ENSG00000204583 |
| SYT12 | ENSG00000173227 | UGT1A10 | ENSG00000242515 |
| MUC21 | ENSG00000204544 | SLC9A7 | ENSG00000065923 |
| C16orf52 | ENSG00000185716 | MANBAL | ENSG00000101363 |
| GP6 | ENSG00000277439 | HAPLN4 | ENSG00000187664 |
| RGSL1 | ENSG00000121446 | TMEM261 | ENSG00000137038 |
| ILDR1 | ENSG00000145103 | HLA-DMB | ENSG00000226264 |
| CXCR4 | ENSG00000121966 | LTB | ENSG00000236925 |
| CEACAM20 | ENSG00000273777 | TMEM185A | ENSG00000269556 |
| WBSCR17 | ENSG00000185274 | TMBIM4 | ENSG00000155957 |
| ARMCX2 | ENSG00000184867 | PCDHB10 | ENSG00000120324 |
| STARD3NL | ENSG00000010270 | HLA-DMA | ENSG00000204257 |
|  | ENSG00000274332 | NTN4 | ENSG00000074527 |
| KIR3DL1 | ENSG00000275659 | CD48 | ENSG00000117091 |
| LY6G6C | ENSG00000204421 | NFAT5 | ENSG00000102908 |
| FJX1 | ENSG00000179431 | LRRC25 | ENSG00000175489 |

TABLE 5-continued

Gene List

| HGNC symbol ID | Ensembl Gene | HGNC symbol ID | Ensembl Gene |
|---|---|---|---|
| SELE | ENSG00000007908 | LY6G6E | ENSG00000255552 |
| MSLN | ENSG00000102854 | LTB4R | ENSG00000213903 |
| SLC2A11 | ENSG00000133460 | SLC3A1 | ENSG00000138079 |
| HM13 | ENSG00000101294 | KIAA0247 | ENSG00000100647 |
| IFI27L1 | ENSG00000276880 | BFAR | ENSG00000275618 |
| COL4A2 | ENSG00000134871 | INSL3 | ENSG00000248099 |
| INSRR | ENSG00000027644 | LINC00493 | ENSG00000232388 |
| TP53I13 | ENSG00000167543 | ADPGK | ENSG00000159322 |
| TNMD | ENSG00000000005 | IL10RA | ENSG00000110324 |
| SERF1A | ENSG00000277429 | ATRIP | ENSG00000164053 |
| SERF1B | ENSG00000277429 | LY6G6F | ENSG00000204424 |
| PTCHD1 | ENSG00000165186 | SLC16A4 | ENSG00000168679 |
| KIR2DL3 | ENSG00000277317 | WNT3 | ENSG00000277641 |
| ABO | ENSG00000175164 | FATE1 | ENSG00000147378 |
| WNT9B | ENSG00000276799 | MAS1L | ENSG00000206470 |
| GOLT1A | ENSG00000174567 | OR10A7 | ENSG00000179919 |
| HLA-DQB1 | ENSG00000231939 | OR6C74 | ENSG00000197706 |
| GYLTL1B | ENSG00000165905 | MAL2 | ENSG00000147676 |
| OCA2 | ENSG00000104044 | RXFP3 | ENSG00000277069 |
| HLA-C | ENSG00000206435 | KIR3DL3 | ENSG00000274480 |
|  | ENSG00000168824 | IFNAR2 | ENSG00000159110 |
| CHRNB2 | ENSG00000160716 | KIR2DL4 | ENSG00000276044 |
| HLA-F | ENSG00000137403 | STX10 | ENSG00000104915 |
| CD164 | ENSG00000135535 | PTPRN | ENSG00000054356 |
| TMIGD2 | ENSG00000167664 | KCNJ11 | ENSG00000187486 |
| GLB1 | ENSG00000170266 | LST1 | ENSG00000230791 |
| IL1RAPL1 | ENSG00000169306 | PIGH | ENSG00000100564 |
| TREX1 | ENSG00000213689 | HLA-DQA1 | ENSG00000236418 |
| TAS2R13 | ENSG00000277254 | FFAR2 | ENSG00000126262 |
| CD302 | ENSG00000241399 | KIR3DL3 | ENSG00000277552 |
| SHISA7 | ENSG00000187902 | SLC1A2 | ENSG00000110436 |
|  | ENSG00000276130 | OR52N2 | ENSG00000180988 |
| ZP2 | ENSG00000103310 | GPR52 | ENSG00000203737 |
| SUN3 | ENSG00000164744 | LHFPL5 | ENSG00000197753 |
| MOSPD3 | ENSG00000106330 | TRHR | ENSG00000174417 |
| LPHN1 | ENSG00000072071 | GPR6 | ENSG00000146360 |
| SCCPDH | ENSG00000143653 | TGFBR3L | ENSG00000260001 |
| C6orf25 | ENSG00000237459 | ITGAX | ENSG00000140678 |
| MMGT1 | ENSG00000169446 | SLC37A1 | ENSG00000160190 |
| KCTD8 | ENSG00000183783 | CD69 | ENSG00000110848 |
| GABBR1 | ENSG00000237051 | PQLC1 | ENSG00000122490 |
| MPZ | ENSG00000158887 | ABHD6 | ENSG00000163686 |
| LMAN1 | ENSG00000074695 | UBE2W | ENSG00000104343 |
| EPHX4 | ENSG00000172031 | SIT1 | ENSG00000137078 |
| TNFRSF19 | ENSG00000127863 | PLXNA4 | ENSG00000221866 |
| GPRC5B | ENSG00000167191 | PIGA | ENSG00000165195 |
| C2orf82 | ENSG00000182600 | SLC2A3 | ENSG00000059804 |
| ITGA11 | ENSG00000137809 | KIAA1024 | ENSG00000169330 |
| WNT9B | ENSG00000158955 | TTYH1 | ENSG00000276887 |
| TUSC3 | ENSG00000104723 | PPAP2C | ENSG00000141934 |
| TMEM55B | ENSG00000165782 | UPK3B | ENSG00000276184 |
| IFI27 | ENSG00000165949 | TNFRSF13C | ENSG00000159958 |
| GPR35 | ENSG00000178623 | CYP2R1 | ENSG00000186104 |
| ABHD12 | ENSG00000100997 | OR10G2 | ENSG00000255582 |
| ADAM18 | ENSG00000168619 | TMEM14A | ENSG00000096092 |
| VSTM1 | ENSG00000274953 | ANKRD46 | ENSG00000186106 |
| GAL3ST1 | ENSG00000128242 | LTB | ENSG00000236237 |
| FXR1 | ENSG00000114416 | ST3GAL3 | ENSG00000126091 |
|  | ENSG00000278923 | YIPF4 | ENSG00000119820 |
| CHRNA3 | ENSG00000080644 | LRRC66 | ENSG00000188993 |
| TMEM108 | ENSG00000144868 | ADAM32 | ENSG00000275594 |
| P2RX7 | ENSG00000089041 | CATSPERB | ENSG00000274338 |
| CDSN | ENSG00000137197 | KIR2DL1 | ENSG00000278755 |
| ABCG8 | ENSG00000143921 | RNF19A | ENSG00000034677 |
| ETNK1 | ENSG00000139163 | GPR17 | ENSG00000144230 |
| GABRQ | ENSG00000268089 | STARD3 | ENSG00000131748 |
| PCDHB4 | ENSG00000081818 | TMEM110-MUSTN1 | ENSG00000248592 |
| CDH10 | ENSG00000040731 | OR11G2 | ENSG00000196832 |
| CLDN8 | ENSG00000156284 | GALNT1 | ENSG00000141429 |
| OR2W1 | ENSG00000228977 | RARA | ENSG00000131759 |
| TSPAN14 | ENSG00000108219 | FAM162B | ENSG00000183807 |
| ERMP1 | ENSG00000099219 | STAB2 | ENSG00000136011 |
| FAM151A | ENSG00000162391 | CACNA1C | ENSG00000151067 |
| PCDHB12 | ENSG00000120328 | TAS2R5 | ENSG00000127366 |
| WNT5A | ENSG00000114251 | SFXN3 | ENSG00000107819 |

TABLE 5-continued

Gene List

| HGNC symbol ID | Ensembl Gene | HGNC symbol ID | Ensembl Gene |
|---|---|---|---|
| SRD5A3 | ENSG00000128039 | AGPAT1 | ENSG00000227642 |
| LMAN2L | ENSG00000114988 | HLA-DRA | ENSG00000228987 |
| OR2T5 | ENSG00000275102 | | ENSG00000273554 |
| TAAR1 | ENSG00000146399 | KIR3DS1 | ENSG00000275434 |
| NKAIN1 | ENSG00000084628 | CSPG4 | ENSG00000173546 |
| OR52E5 | ENSG00000277932 | GDI1 | ENSG00000203879 |
| CLEC4D | ENSG00000166527 | OR13C9 | ENSG00000136839 |
| TMIE | ENSG00000181585 | TMEM71 | ENSG00000165071 |
| SLC6A14 | ENSG00000268104 | CYP39A1 | ENSG00000146233 |
| DSC2 | ENSG00000134755 | OR14J1 | ENSG00000236927 |
| GPR3 | ENSG00000181773 | DHRS7B | ENSG00000109016 |
| PCDHB15 | ENSG00000113248 | SLC16A13 | ENSG00000174327 |
| | ENSG00000198832 | DRD2 | ENSG00000149295 |
| KCNA7 | ENSG00000104848 | ARSB | ENSG00000113273 |
| OR56B1 | ENSG00000181023 | HLA-DQA1 | ENSG00000228284 |
| TMEM187 | ENSG00000177854 | FKBP8 | ENSG00000105701 |
| DSEL | ENSG00000171451 | STX18 | ENSG00000168818 |
| CLDN7 | ENSG00000181885 | PDCD1 | ENSG00000276977 |
| PSENEN | ENSG00000205155 | OR5D18 | ENSG00000186119 |
| LRRC4C | ENSG00000148948 | OR5L2 | ENSG00000205030 |
| AMIGO3 | ENSG00000176020 | BAI2 | ENSG00000121753 |
| HLA-DMB | ENSG00000242574 | PCDHGC4 | ENSG00000242419 |
| FAM159A | ENSG00000182183 | PCDHB11 | ENSG00000197479 |
| NDST4 | ENSG00000138653 | GPR110 | ENSG00000153292 |
| CXCR2 | ENSG00000180871 | LRRN1 | ENSG00000175928 |
| POTEM | ENSG00000187537 | UPK3A | ENSG00000100373 |
| LRP4 | ENSG00000134569 | ZDHHC17 | ENSG00000186908 |
| KCNH1 | ENSG00000143473 | CD79A | ENSG00000105369 |
| PEX10 | ENSG00000157911 | NPY | ENSG00000122585 |
| GP6 | ENSG00000278316 | PMCH | ENSG00000183395 |
| APELA | ENSG00000248329 | ERMARD | ENSG00000276187 |
| MFAP3 | ENSG00000037749 | SLC24A4 | ENSG00000140090 |
| PIGW | ENSG00000277161 | KIDINS220 | ENSG00000134313 |
| CLCN5 | ENSG00000171365 | SI | ENSG00000090402 |
| CSF2RB | ENSG00000100368 | VASN | ENSG00000274334 |
| TPO | ENSG00000115705 | MDM1 | ENSG00000111554 |
| LRRC8E | ENSG00000171017 | BRI3 | ENSG00000164713 |
| AJAP1 | ENSG00000196581 | KIR2DS5 | ENSG00000275047 |
| GP6 | ENSG00000275931 | GRAMD3 | ENSG00000155324 |
| SLC35E2 | ENSG00000215790 | MPDU1 | ENSG00000129255 |
| KIR2DL1 | ENSG00000273510 | IL23R | ENSG00000162594 |
| PTCHD4 | ENSG00000244694 | UNC5B | ENSG00000107731 |
| ZNF559 | ENSG00000188321 | REEP4 | ENSG00000168476 |
| OR10H1 | ENSG00000186723 | ANKLE1 | ENSG00000160117 |
| GP2 | ENSG00000169347 | TRAM2 | ENSG00000065308 |
| DEFB107B | ENSG00000198129 | FAM171A2 | ENSG00000161682 |
| LY6G5C | ENSG00000237495 | CCL15 | ENSG00000275528 |
| KLHL2 | ENSG00000109466 | OR52E8 | ENSG00000183269 |
| HLA-DPA1 | ENSG00000168384 | TMBIM1 | ENSG00000135926 |
| KIR3DL3 | ENSG00000276084 | KIR2DL4 | ENSG00000273498 |
| MUC13 | ENSG00000173702 | HSD17B2 | ENSG00000086696 |
| KCNK13 | ENSG00000152315 | GABRA5 | ENSG00000186297 |
| MCAM | ENSG00000076706 | USE1 | ENSG00000053501 |
| RNF5 | ENSG00000228405 | CNGB3 | ENSG00000170289 |
| KCNK18 | ENSG00000186795 | TMEM229B | ENSG00000198133 |
| C4orf32 | ENSG00000174749 | TAP1 | ENSG00000227816 |
| TMEM150B | ENSG00000180061 | SLC24A5 | ENSG00000188467 |
| PCDHB1 | ENSG00000171815 | TARM1 | ENSG00000276145 |
| ORMDL3 | ENSG00000172057 | RNF133 | ENSG00000188050 |
| B3GALT4 | ENSG00000235155 | B3GALT5 | ENSG00000183778 |
| KIR2DS1 | ENSG00000273603 | SLC14A1 | ENSG00000141469 |
| OR4X2 | ENSG00000172208 | POR | ENSG00000127948 |
| CD33 | ENSG00000105383 | C3orf35 | ENSG00000198590 |
| OR52N4 | ENSG00000181074 | OR10C1 | ENSG00000235441 |
| CYP4Z1 | ENSG00000186160 | FAM162A | ENSG00000114023 |
| SERF1A | ENSG00000275581 | DHRS9 | ENSG00000073737 |
| SERF1B | ENSG00000275581 | ZMYND11 | ENSG00000015171 |
| C17orf62 | ENSG00000178927 | SLC7A13 | ENSG00000164893 |
| STOM | ENSG00000148175 | FCGR1B | ENSG00000198019 |
| RAET1L | ENSG00000155918 | LTF | ENSG00000012223 |
| FAM73A | ENSG00000180488 | BST2 | ENSG00000130303 |
| NUDC | ENSG00000090273 | STEAP1B | ENSG00000105889 |
| CD1C | ENSG00000158481 | TMEM30B | ENSG00000182107 |
| OR2T5 | ENSG00000273827 | LILRB5 | ENSG00000274311 |
| COL11A2 | ENSG00000204248 | HMOX2 | ENSG00000277424 |

TABLE 5-continued

Gene List

| HGNC symbol ID | Ensembl Gene | HGNC symbol ID | Ensembl Gene |
|---|---|---|---|
| PKD2L1 | ENSG00000107593 | OR4Q2 | ENSG00000196383 |
| SLC2A10 | ENSG00000197496 | CHRNA10 | ENSG00000129749 |
| OR6V1 | ENSG00000277378 | TFR2 | ENSG00000106327 |
| GLIPR1 | ENSG00000139278 | SLC28A1 | ENSG00000156222 |
| OR10H5 | ENSG00000172519 | LY6K | ENSG00000160886 |
| HLA-E | ENSG00000204592 | OR12D2 | ENSG00000225247 |
| SLC16A2 | ENSG00000147100 | CHRM3 | ENSG00000133019 |
| PRCP | ENSG00000137509 | ACMSD | ENSG00000153086 |
| ABCB8 | ENSG00000197150 | ELOVL6 | ENSG00000170522 |
| LYPLA1 | ENSG00000120992 | OR11A1 | ENSG00000223898 |
| CYP4F2 | ENSG00000186115 | SMAD2 | ENSG00000175387 |
| C11orf24 | ENSG00000171067 | OMA1 | ENSG00000162600 |
| TMEM251 | ENSG00000275947 | RNF186 | ENSG00000178828 |
| VMA21 | ENSG00000160131 | | ENSG00000268400 |
| FAM20B | ENSG00000116199 | LAPTM4A | ENSG00000068697 |
| CLECL1 | ENSG00000184293 | GRIK4 | ENSG00000149403 |
| DMRT2 | ENSG00000173253 | ATP2B2 | ENSG00000157087 |
| CACNA1F | ENSG00000102001 | SGCB | ENSG00000163069 |
| TRBC1 | ENSG00000276849 | OR10C1 | ENSG00000230505 |
| CDHR3 | ENSG00000128536 | SLC47A1 | ENSG00000142494 |
| SLC37A4 | ENSG00000137700 | ZNF566 | ENSG00000186017 |
| LHFP | ENSG00000183722 | TMPRSS7 | ENSG00000176040 |
| ATP4A | ENSG00000105675 | OR11A1 | ENSG00000232289 |
| PEAR1 | ENSG00000187800 | OR2F1 | ENSG00000213215 |
| B4GALT7 | ENSG00000027847 | OR52N5 | ENSG00000181009 |
| SLC5A11 | ENSG00000158865 | | ENSG00000277585 |
| KRTAP19-4 | ENSG00000186967 | MOG | ENSG00000234623 |
| OR52N1 | ENSG00000181001 | SLC38A4 | ENSG00000139209 |
| OR5AS1 | ENSG00000181785 | FXYD3 | ENSG00000089356 |
| | ENSG00000273993 | RNFT1 | ENSG00000189050 |
| LTB4R2 | ENSG00000213906 | CD1B | ENSG00000158485 |
| GPR137 | ENSG00000173264 | ABCA6 | ENSG00000154262 |
| HLA-A | ENSG00000224320 | VLDLR | ENSG00000147852 |
| PCDHB7 | ENSG00000113212 | OR7E24 | ENSG00000237521 |
| DPCR1 | ENSG00000232308 | ANO2 | ENSG00000047617 |
| ATL3 | ENSG00000184743 | MGAT4B | ENSG00000161013 |
| CLCNKB | ENSG00000184908 | NCR3 | ENSG00000204475 |
| CR1 | ENSG00000203710 | PLP1 | ENSG00000123560 |
| M6PR | ENSG00000003056 | TMEM132C | ENSG00000181234 |
| ENG | ENSG00000106991 | MBTPS2 | ENSG00000012174 |
| C10orf128 | ENSG00000204161 | SLC44A2 | ENSG00000129353 |
| LILRB3 | ENSG00000277816 | CUTA | ENSG00000112514 |
| OR12D3 | ENSG00000250364 | CEACAM4 | ENSG00000274131 |
| PRRT1 | ENSG00000227122 | CHST2 | ENSG00000175040 |
| C1orf43 | ENSG00000143612 | TMC4 | ENSG00000277667 |
| GJC1 | ENSG00000182963 | LST1 | ENSG00000204482 |
| DPEP2 | ENSG00000167261 | | ENSG00000277603 |
| | ENSG00000274360 | B3GALT4 | ENSG00000226936 |
| CDH11 | ENSG00000140937 | BTNL9 | ENSG00000165810 |
| ADAM18 | ENSG00000278548 | PPT2 | ENSG00000168452 |
| ELOVL7 | ENSG00000164181 | TUBD1 | ENSG00000108423 |
| GIPR | ENSG00000010310 | VKORC1L1 | ENSG00000196715 |
| CYP4A22 | ENSG00000162365 | EDDM3B | ENSG00000181552 |
| | ENSG00000205236 | PCDHGA3 | ENSG00000254245 |
| UBA6 | ENSG00000033178 | MYB | ENSG00000118513 |
| CDH17 | ENSG00000079112 | OR6B1 | ENSG00000221813 |
| SLC6A7 | ENSG00000011083 | OR4D9 | ENSG00000172742 |
| HTR1A | ENSG00000178394 | MXRA7 | ENSG00000182534 |
| CPT1A | ENSG00000110090 | CNTNAP4 | ENSG00000152910 |
| KIR2DL4 | ENSG00000277362 | MS4A12 | ENSG00000071203 |
| TMEM30A | ENSG00000112697 | MTDH | ENSG00000147649 |
| TSPAN7 | ENSG00000156298 | OR4K14 | ENSG00000169484 |
| NLGN4X | ENSG00000146938 | LILRB4 | ENSG00000276042 |
| CD28 | ENSG00000178562 | ACER3 | ENSG00000078124 |
| CPT1B | ENSG00000205560 | HLA-F | ENSG00000237508 |
| CCDC167 | ENSG00000198937 | PCDH18 | ENSG00000189184 |
| SLC26A9 | ENSG00000174502 | TMEM167A | ENSG00000174695 |
| FUT5 | ENSG00000130383 | OR3A1 | ENSG00000180090 |
| ENTPD2 | ENSG00000054179 | VSTM4 | ENSG00000165633 |
| SLC5A10 | ENSG00000154025 | ASTN1 | ENSG00000152092 |
| OR5V1 | ENSG00000227137 | OR3A2 | ENSG00000221882 |
| TOMM20L | ENSG00000196860 | CERS1 | ENSG00000223802 |
| TMEM25 | ENSG00000149582 | KLRG2 | ENSG00000188883 |
| PGAP1 | ENSG00000197121 | B3GAT3 | ENSG00000149541 |
| TMEM67 | ENSG00000164953 | XKRX | ENSG00000182489 |

TABLE 5-continued

Gene List

| HGNC symbol ID | Ensembl Gene | HGNC symbol ID | Ensembl Gene |
|---|---|---|---|
| CDH8 | ENSG00000150394 | LRTM1 | ENSG00000144771 |
| KIR3DL1 | ENSG00000275288 | RYR1 | ENSG00000196218 |
| PF4 | ENSG00000163737 | CLRN1 | ENSG00000163646 |
| SLC35E3 | ENSG00000175782 | TLL1 | ENSG00000038295 |
| PGAP2 | ENSG00000148985 | HIGD1A | ENSG00000181061 |
| TGOLN2 | ENSG00000152291 | LDLR | ENSG00000130164 |
| EMD | ENSG00000102119 | CCL4L1 | ENSG00000275313 |
| SPATA9 | ENSG00000145757 | CCL4L2 | ENSG00000275313 |
| MIEF1 | ENSG00000100335 | ITGAE | ENSG00000083457 |
| NPHS2 | ENSG00000116218 | MAN2A1 | ENSG00000112893 |
| MANEAL | ENSG00000185090 | FAXDC2 | ENSG00000170271 |
| GP6 | ENSG00000278670 | ABCB5 | ENSG00000004846 |
| B4GALNT3 | ENSG00000139044 | ZDHHC20 | ENSG00000180776 |
| HLA-B | ENSG00000228964 | TMCO4 | ENSG00000162542 |
| MBTPS1 | ENSG00000140943 | SLC46A3 | ENSG00000139508 |
| OR5P2 | ENSG00000183303 | PIGF | ENSG00000151665 |
| GRIN3B | ENSG00000116032 | ACSL6 | ENSG00000164398 |
| SLC25A5 | ENSG00000005022 | NDUFA11 | ENSG00000174886 |
| OR5P3 | ENSG00000182334 | PRRT1 | ENSG00000204314 |
| ADCY4 | ENSG00000129467 | OR5M1 | ENSG00000255012 |
| ZDHHC6 | ENSG00000023041 | TIMM22 | ENSG00000277649 |
| TMEM175 | ENSG00000127419 | OR2B3 | ENSG00000233687 |
| MSI1 | ENSG00000135097 | OR2A25 | ENSG00000221933 |
| CYP4F3 | ENSG00000186529 | ATP13A4 | ENSG00000127249 |
| PTPRR | ENSG00000153233 | LY6G6C | ENSG00000228250 |
| BEST2 | ENSG00000039987 | PNPLA6 | ENSG00000032444 |
| ANO6 | ENSG00000177119 | S1PR1 | ENSG00000170989 |
| NMBR | ENSG00000135577 | PRRG4 | ENSG00000135378 |
| KIR3DL2 | ENSG00000277181 | EMCN | ENSG00000164035 |
| UGT2B10 | ENSG00000275190 | NDUFC2 | ENSG00000151366 |
| OR1K1 | ENSG00000165204 | RAMP3 | ENSG00000122679 |
| BAI3 | ENSG00000135298 | SLC1A7 | ENSG00000162383 |
| PCDHGC5 | ENSG00000240764 | PRRG2 | ENSG00000126460 |
| UQCR11 | ENSG00000127540 | SNX13 | ENSG00000071189 |
| RER1 | ENSG00000157916 | KCNE1 | ENSG00000180509 |
| PRLHR | ENSG00000119973 | OR52B4 | ENSG00000221996 |
| SLC7A2 | ENSG00000003989 | TSPAN33 | ENSG00000158457 |
| MOG | ENSG00000230885 | FCRL2 | ENSG00000132704 |
|  | ENSG00000273526 | DNAJC30 | ENSG00000176410 |
| KIR3DL2 | ENSG00000275083 | ATP5G1 | ENSG00000159199 |
| KIR3DL3 | ENSG00000274696 | CTXN1 | ENSG00000178531 |
| RHBDL1 | ENSG00000103269 | OR1J1 | ENSG00000136834 |
| VIMP | ENSG00000131871 | PANX2 | ENSG00000073150 |
| SLITRK1 | ENSG00000178235 | ABHD16A | ENSG00000231488 |
| CHIC1 | ENSG00000204116 | EFNB1 | ENSG00000090776 |
| LDLRAD3 | ENSG00000179241 | HLA-A | ENSG00000227715 |
| DAPL1 | ENSG00000163331 | PTH2 | ENSG00000142538 |
| TMPO | ENSG00000120802 | HLA-C | ENSG00000228299 |
| PCNXL3 | ENSG00000197136 | FXYD2 | ENSG00000137731 |
| SERINC2 | ENSG00000168528 | FNDC4 | ENSG00000115226 |
| ABCB10 | ENSG00000135776 | ADCK5 | ENSG00000173137 |
| EPHB4 | ENSG00000196411 | UQCR11 | ENSG00000267059 |
| CCDC67 | ENSG00000165325 | C16orf91 | ENSG00000174109 |
| GLTPD2 | ENSG00000182327 | SLC6A2 | ENSG00000103546 |
| IL1RAPL2 | ENSG00000189108 |  | ENSG00000278468 |
| TNFRSF10D | ENSG00000173530 | FCER1G | ENSG00000158869 |
| PEX11A | ENSG00000166821 | OR2H2 | ENSG00000229680 |
| FTHL17 | ENSG00000132446 | TMPRSS11A | ENSG00000187054 |
|  | ENSG00000260234 | DEFB107A | ENSG00000277530 |
| DIO2 | ENSG00000211448 | DEFB107B | ENSG00000277530 |
| GDPD1 | ENSG00000153982 | HHATL | ENSG00000010282 |
| CEP170 | ENSG00000143702 | METTL21A | ENSG00000144401 |
| PLA2G2E | ENSG00000188784 | STRBP | ENSG00000165209 |
| PRIMA1 | ENSG00000274089 | ZNRF4 | ENSG00000105428 |
| TMEM259 | ENSG00000182087 | XKR3 | ENSG00000172967 |
| TMEM181 | ENSG00000146433 | CSF1R | ENSG00000182578 |
| PIGU | ENSG00000101464 | LILRB5 | ENSG00000105609 |
| MBOAT7 | ENSG00000278519 | MTFP1 | ENSG00000242114 |
| TM2D2 | ENSG00000169490 | B4GALT2 | ENSG00000117411 |
| KIR2DS2 | ENSG00000275583 | OR13H1 | ENSG00000171054 |
| LTB | ENSG00000204487 | KIR2DL1 | ENSG00000277356 |
| LRRC3B | ENSG00000179796 | TM9SF2 | ENSG00000125304 |
| OR8K1 | ENSG00000150261 | TNFRSF10B | ENSG00000120889 |
| ZNF7 | ENSG00000147789 | SAMD8 | ENSG00000156671 |
| SRD5A2 | ENSG00000277893 | AGPAT1 | ENSG00000204310 |

TABLE 5-continued

Gene List

| HGNC symbol ID | Ensembl Gene | HGNC symbol ID | Ensembl Gene |
| --- | --- | --- | --- |
| LRRC3C | ENSG00000204913 | ECEL1 | ENSG00000171551 |
| HLA-DQB2 | ENSG00000226165 | STX1A | ENSG00000106089 |
| LRRC52 | ENSG00000162763 | STYK1 | ENSG00000060140 |
| CYP2D6 | ENSG00000275211 | FZD7 | ENSG00000155760 |
| KIR3DL1 | ENSG00000278079 | OR5AC2 | ENSG00000196578 |
| KHDC1 | ENSG00000135314 | HLA-DMB | ENSG00000242386 |
| S1PR3 | ENSG00000213694 | OR11H6 | ENSG00000176219 |
| BTN3A1 | ENSG00000026950 | LETM2 | ENSG00000165046 |
| DOLPP1 | ENSG00000167130 | OR11A1 | ENSG00000237258 |
| NOX5 | ENSG00000255346 | EI24 | ENSG00000149547 |
| GRINA | ENSG00000178719 | C4orf26 | ENSG00000174792 |
| BANP | ENSG00000172530 | RELT | ENSG00000054967 |
| PCDHGB2 | ENSG00000253910 | | ENSG00000267740 |
| MEGF8 | ENSG00000105429 | SLC39A7 | ENSG00000226614 |
| ESAM | ENSG00000149564 | PCDHGB6 | ENSG00000253305 |
| HBS1L | ENSG00000112339 | TMEM50A | ENSG00000183726 |
| AGER | ENSG00000206320 | CYP4F8 | ENSG00000186526 |
| WNT1 | ENSG00000125084 | SLC26A4 | ENSG00000091137 |
| OR1E2 | ENSG00000127780 | | ENSG00000279018 |
| LRRC70 | ENSG00000186105 | AWAT2 | ENSG00000147160 |
| DIO1 | ENSG00000211452 | VAMP7 | ENSG00000124333 |
| OR1I1 | ENSG00000094661 | TMEM150A | ENSG00000168890 |
| MUC22 | ENSG00000261272 | KCNF1 | ENSG00000162975 |
| TMEM42 | ENSG00000169964 | LDHC | ENSG00000166796 |
| HS6ST3 | ENSG00000185352 | SLC35F5 | ENSG00000115084 |
| PLIN1 | ENSG00000166819 | NDUFC2-KCTD14 | ENSG00000259112 |
| ADRA1A | ENSG00000120907 | CELF4 | ENSG00000101489 |
| ETV6 | ENSG00000139083 | OR12D3 | ENSG00000224487 |
| SSTR5 | ENSG00000162009 | PCDHGA4 | ENSG00000262576 |
| ST3GAL6 | ENSG00000064225 | HEPH | ENSG00000089472 |
| OCLN | ENSG00000273814 | GFY | ENSG00000261949 |
| PPP1R3F | ENSG00000049769 | EVA1A | ENSG00000115363 |
| | ENSG00000273564 | JKAMP | ENSG00000050130 |
| GSG1L | ENSG00000169181 | OR4K2 | ENSG00000165762 |
| RNASE1 | ENSG00000129538 | KIR2DL1 | ENSG00000274782 |
| HTR3D | ENSG00000186090 | LRIG2 | ENSG00000198799 |
| STAB1 | ENSG00000010327 | TTYH2 | ENSG00000141540 |
| SMDT1 | ENSG00000274112 | NAALAD2 | ENSG00000077616 |
| TNFRSF10C | ENSG00000173535 | CXCR1 | ENSG00000163464 |
| ATCAY | ENSG00000167654 | PLB1 | ENSG00000163803 |
| B3GNT4 | ENSG00000176383 | ITSN1 | ENSG00000205726 |
| CD63 | ENSG00000135404 | LTA | ENSG00000238130 |
| WISP1 | ENSG00000104415 | ASIC5 | ENSG00000256394 |
| CEPT1 | ENSG00000134255 | TMEM37 | ENSG00000171227 |
| OR12D2 | ENSG00000233481 | DUSP13 | ENSG00000079393 |
| LILRB3 | ENSG00000274587 | OR6C6 | ENSG00000188324 |
| ACVR2A | ENSG00000121989 | GABRB3 | ENSG00000166206 |
| IMPG2 | ENSG00000081148 | KL | ENSG00000133116 |
| TMEM43 | ENSG00000170876 | PTGES | ENSG00000148344 |
| TMEM192 | ENSG00000170088 | OR4K13 | ENSG00000176253 |
| TMEM170B | ENSG00000205269 | ANO7 | ENSG00000146205 |
| CDH2 | ENSG00000170558 | OR10C1 | ENSG00000232397 |
| MPZL2 | ENSG00000149573 | SLC38A1 | ENSG00000111371 |
| OR5V1 | ENSG00000243441 | LSMEM2 | ENSG00000179564 |
| CD97 | ENSG00000123146 | MUC16 | ENSG00000181143 |
| SLC13A1 | ENSG00000081800 | COX8A | ENSG00000176340 |
| FRRS1L | ENSG00000260230 | HRH3 | ENSG00000101180 |
| IFNE | ENSG00000184995 | KCNE2 | ENSG00000159197 |
| PCDHGB1 | ENSG00000254221 | IL13 | ENSG00000169194 |
| OR2J1 | ENSG00000226931 | CEACAM3 | ENSG00000170956 |
| TENM1 | ENSG00000009694 | ADRA2C | ENSG00000184160 |
| SSTR3 | ENSG00000278195 | LMO7 | ENSG00000136153 |
| BCL2L13 | ENSG00000099968 | KIR2DL3 | ENSG00000277484 |
| TMEM88 | ENSG00000167874 | TNFRSF13B | ENSG00000240505 |
| SLC9A9 | ENSG00000181804 | GP6 | ENSG00000274050 |
| ROMO1 | ENSG00000125995 | SERPINB13 | ENSG00000197641 |
| PPT2 | ENSG00000236649 | TMEM204 | ENSG00000131634 |
| OR5H1 | ENSG00000231192 | NCR2 | ENSG00000096264 |
| OR9A2 | ENSG00000273914 | MUL1 | ENSG00000090432 |
| ADCY9 | ENSG00000162104 | PLAUR | ENSG00000011422 |
| SEMA6A | ENSG00000092421 | NDUFA3 | ENSG00000275724 |
| SLC39A7 | ENSG00000206288 | C17orf80 | ENSG00000141219 |
| SLC38A3 | ENSG00000188338 | TMED2 | ENSG00000086598 |
| GSG1 | ENSG00000111305 | KCNQ4 | ENSG00000117013 |
| VAMP4 | ENSG00000117533 | NPR3 | ENSG00000113389 |

TABLE 5-continued

Gene List

| HGNC symbol ID | Ensembl Gene | HGNC symbol ID | Ensembl Gene |
|---|---|---|---|
| ATP13A5 | ENSG00000187527 | RNF183 | ENSG00000165188 |
| OR14J1 | ENSG00000225291 | NCR1 | ENSG00000275822 |
| TMEM106B | ENSG00000106460 | ARSH | ENSG00000205667 |
| OR14J1 | ENSG00000237777 | SCN9A | ENSG00000169432 |
| TENM4 | ENSG00000149256 | TMEM247 | ENSG00000187600 |
| UGT2B15 | ENSG00000196620 | SCUBE2 | ENSG00000175356 |
| LTA | ENSG00000226979 | ORMDL1 | ENSG00000128699 |
| ZDHHC15 | ENSG00000102383 | CHODL | ENSG00000154645 |
| SMIM9 | ENSG00000203870 | TSPO | ENSG00000100300 |
| DEFB107A | ENSG00000186572 | SMCO2 | ENSG00000165935 |
| CCL4 | ENSG00000277943 | KIR2DL1 | ENSG00000276310 |
| CKAP4 | ENSG00000136026 | C1orf15 | ENSG00000162817 |
| B3GALT4 | ENSG00000206285 | TMUB2 | ENSG00000168591 |
| LTB | ENSG00000206437 | TREM2 | ENSG00000095970 |
| IL1R2 | ENSG00000115590 | GLRA2 | ENSG00000101958 |
| BCL2 | ENSG00000171791 | GALNT2 | ENSG00000143641 |
| ATP6AP1L | ENSG00000205464 | AGTRAP | ENSG00000177674 |
| SLC6A20 | ENSG00000163817 | FCRL1 | ENSG00000163534 |
| ACACB | ENSG00000076555 | AMICA1 | ENSG00000160593 |
| DSC1 | ENSG00000134765 | EXTL3 | ENSG00000012232 |
| SIGLECL1 | ENSG00000179213 | RDH11 | ENSG00000072042 |
| SCAMP2 | ENSG00000140497 | CDH7 | ENSG00000081138 |
|  | ENSG00000275482 | NCR1 | ENSG00000277629 |
| HEXB | ENSG00000049860 | TM4SF1 | ENSG00000169908 |
| LRRC4 | ENSG00000128594 | CDHR2 | ENSG00000074276 |
|  | ENSG00000250232 | GPR101 | ENSG00000165370 |
| PKD1L2 | ENSG00000166473 | ANPEP | ENSG00000166825 |
| DSCAML1 | ENSG00000177103 | DCHS2 | ENSG00000197410 |
| TLCD2 | ENSG00000275246 | DHRS3 | ENSG00000162496 |
| SEMA5A | ENSG00000112902 | OR5T2 | ENSG00000181718 |
| GPR18 | ENSG00000125245 | PCDHGA11 | ENSG00000253873 |
| DNAJC22 | ENSG00000178401 | ALDH3A2 | ENSG00000072210 |
| TMEM178B | ENSG00000261115 | OR2H2 | ENSG00000204657 |
| GABBR1 | ENSG00000237112 | GPR137B | ENSG00000077585 |
| LMTK3 | ENSG00000142235 | INSIG2 | ENSG00000125629 |
| TAS1R3 | ENSG00000169962 | LETM1 | ENSG00000168924 |
| PCSK1N | ENSG00000102109 | LMTK2 | ENSG00000164715 |
| MRGPRD | ENSG00000172938 | TGFBR2 | ENSG00000163513 |
| GJB1 | ENSG00000169562 | TAPBP | ENSG00000236490 |
| MCUR1 | ENSG00000050393 | UBAC2 | ENSG00000134882 |
| MGAT4D | ENSG00000205301 | HTATIP2 | ENSG00000109854 |
| LIME1 | ENSG00000203896 | FICD | ENSG00000198855 |
| HLA-G | ENSG00000237216 | GDPD4 | ENSG00000178795 |
| GPR22 | ENSG00000172209 | MARC1 | ENSG00000186205 |
|  | ENSG00000278178 | DNAJC10 | ENSG00000077232 |
| KIR3DL2 | ENSG00000278707 | FAM173B | ENSG00000150756 |
| PNKD | ENSG00000127838 | KCNK7 | ENSG00000173338 |
| DNAJC14 | ENSG00000135392 | FAM134B | ENSG00000154153 |
| HLA-B | ENSG00000234745 | ELMO2 | ENSG00000062598 |
| ICA1 | ENSG00000003147 | TMEM68 | ENSG00000167904 |
| ADAM23 | ENSG00000114948 | KIR3DL1 | ENSG00000275486 |
| SLC14A2 | ENSG00000132874 | GCNT1 | ENSG00000187210 |
| PPBP | ENSG00000163736 | CLN8 | ENSG00000278220 |
| OR1J2 | ENSG00000197233 | CDCP1 | ENSG00000163814 |
| MBOAT7 | ENSG00000278322 | RTN3 | ENSG00000133318 |
| UGT2B17 | ENSG00000197888 | PODXL | ENSG00000128567 |
| FGG | ENSG00000171557 | DPY19L1 | ENSG00000173852 |
| UGT2B15 | ENSG00000277132 | TAS2R7 | ENSG00000273326 |
| TMEM99 | ENSG00000167920 | LRRC8D | ENSG00000171492 |
| TMEM190 | ENSG00000160472 | CDH9 | ENSG00000113100 |
| DERL1 | ENSG00000136986 | SPAG8 | ENSG00000137098 |
| ICAM4 | ENSG00000105371 | TMEM240 | ENSG00000205090 |
| MARC2 | ENSG00000117791 | RTP2 | ENSG00000198471 |
| AQP2 | ENSG00000167580 | NIPA1 | ENSG00000170113 |
| SC5D | ENSG00000109929 | SLC50A1 | ENSG00000169241 |
| LPCAT4 | ENSG00000176454 | CNNM3 | ENSG00000168763 |
| TMEM252 | ENSG00000181778 | ABHD16A | ENSG00000230475 |
| ABHD16A | ENSG00000236063 | LY6G5C | ENSG00000228883 |
| OR5AP2 | ENSG00000172464 | TMEM59L | ENSG00000105696 |
| IL6ST | ENSG00000134352 | TCIRG1 | ENSG00000110719 |
| LILRB2 | ENSG00000131042 | KIR2DL2 | ENSG00000274412 |
| BTN2A1 | ENSG00000112763 | ADSSL1 | ENSG00000185100 |
| OLFML2B | ENSG00000162745 | DRAM2 | ENSG00000156171 |
| PRRT1 | ENSG00000229488 | CLPTM1L | ENSG00000274811 |
| DIABLO | ENSG00000184047 | ITM2B | ENSG00000136156 |

TABLE 5-continued

Gene List

| HGNC symbol ID | Ensembl Gene | HGNC symbol ID | Ensembl Gene |
|---|---|---|---|
| SDHC | ENSG00000143252 | POMT1 | ENSG00000130714 |
| ICAM1 | ENSG00000090339 | BCL2L2 | ENSG00000129473 |
| KIAA1324 | ENSG00000116299 | IL13RA2 | ENSG00000123496 |
| DCUN1D5 | ENSG00000137692 | NEU1 | ENSG00000184494 |
| MBOAT7 | ENSG00000273592 | PCDH11X | ENSG00000102290 |
| NCR1 | ENSG00000273916 | OR7C1 | ENSG00000127530 |
| RABGAP1L | ENSG00000152061 | VIP | ENSG00000146469 |
|  | ENSG00000188223 | FMO5 | ENSG00000131781 |
| KIR2DL4 | ENSG00000274955 | KIR2DL4 | ENSG00000277540 |
| SSTR2 | ENSG00000180616 | GNL2 | ENSG00000134697 |
| RNF223 | ENSG00000237330 | GNL2 | ENSG00000117600 |
| RHCE | ENSG00000188672 | KIR2DL2 | ENSG00000273661 |
| PXDN | ENSG00000130508 | SYT6 | ENSG00000134207 |
| DEFB134 | ENSG00000205882 | MAS1L | ENSG00000206515 |
| ADAM33 | ENSG00000149451 | LRRC38 | ENSG00000162494 |
| SLITRK6 | ENSG00000184564 |  | ENSG00000275079 |
| OR7A5 | ENSG00000188269 | MGST3 | ENSG00000143198 |
| OR5B21 | ENSG00000198283 | KIR3DL2 | ENSG00000275262 |
| IGFLR1 | ENSG00000126246 | SLC39A14 | ENSG00000104635 |
| C3orf18 | ENSG00000088543 | ALOX5AP | ENSG00000132965 |
| ANGPTL7 | ENSG00000171819 | KIR2DL4 | ENSG00000278430 |
| DEFB115 | ENSG00000215547 | SLC6A9 | ENSG00000196517 |
| ITGA10 | ENSG00000143127 | MAN1A2 | ENSG00000198162 |
| HLA-E | ENSG00000230254 | HLA-A | ENSG00000206505 |
| ABHD1 | ENSG00000143994 | LRCH1 | ENSG00000136141 |
| JAG1 | ENSG00000101384 | ORMDL2 | ENSG00000123353 |
| AADACL4 | ENSG00000204518 | SCN1B | ENSG00000105711 |
| TMEM238 | ENSG00000233493 | SLC18A2 | ENSG00000165646 |
| TMEM244 | ENSG00000203756 | KCND2 | ENSG00000184408 |
| TMEM132D | ENSG00000151952 | FITM1 | ENSG00000139914 |
| FXYD6-FXYD2 | ENSG00000255245 | ENHO | ENSG00000168913 |
| AQP8 | ENSG00000103375 | F2RL1 | ENSG00000164251 |
| TMEM168 | ENSG00000146802 | CNIH1 | ENSG00000100528 |
| APH1A | ENSG00000117362 | ATP8A1 | ENSG00000124406 |
| BOC | ENSG00000144857 | ADRB1 | ENSG00000043591 |
| CATSPERB | ENSG00000133962 | C1orf95 | ENSG00000203685 |
| LILRB1 | ENSG00000277807 | GAL3ST3 | ENSG00000175229 |
| PDZD8 | ENSG00000165650 | OR4L1 | ENSG00000176246 |
| ST7 | ENSG00000004866 | FCER1A | ENSG00000179639 |
| CLSTN2 | ENSG00000158258 | TMEM110 | ENSG00000213533 |
| CCR5 | ENSG00000160791 | OR5H15 | ENSG00000233412 |
| NDUFA4L2 | ENSG00000185633 | BTNL2 | ENSG00000224242 |
| WNT7B | ENSG00000188064 | LILRB4 | ENSG00000278279 |
| SPPL2C | ENSG00000185294 | HIGD1C | ENSG00000214511 |
| FAR2 | ENSG00000064763 | NPSR1 | ENSG00000187258 |
| TMPRSS11F | ENSG00000198092 | HLA-DMA | ENSG00000239463 |
| KIR3DL2 | ENSG00000275626 | UBIAD1 | ENSG00000120942 |
| ATRN | ENSG00000088812 | GPR183 | ENSG00000169508 |
| MFAP3L | ENSG00000198948 | GPR113 | ENSG00000173567 |
| KIR3DL3 | ENSG00000277392 | DGAT1 | ENSG00000185000 |
| ENDOD1 | ENSG00000149218 | SYT3 | ENSG00000213023 |
| TNF | ENSG00000228849 | SMO | ENSG00000128602 |
| VSTM2A | ENSG00000170419 | TP53I11 | ENSG00000175274 |
| OR5H14 | ENSG00000236032 | ASB5 | ENSG00000164122 |
| CERS5 | ENSG00000139624 | CNTNAP3B | ENSG00000154529 |
| AGPAT1 | ENSG00000236873 | CLSTN3 | ENSG00000139182 |
| SYT1 | ENSG00000067715 | CYP26A1 | ENSG00000095596 |
|  | ENSG00000274058 | NAGPA | ENSG00000103174 |
| MFF | ENSG00000168958 | DNAJC16 | ENSG00000116138 |
| TM4SF4 | ENSG00000169903 | FGF19 | ENSG00000162344 |
|  | ENSG00000234137 | TPCN1 | ENSG00000186815 |
| UQCR10 | ENSG00000184076 | BRINP2 | ENSG00000198797 |
| KIR2DL3 | ENSG00000276218 | IGF1R | ENSG00000140443 |
| LRP6 | ENSG00000070018 | ATP1A1 | ENSG00000163399 |
| SLC22A8 | ENSG00000149452 | OR2J3 | ENSG00000230855 |
| UGT2A3 | ENSG00000278216 | FAM200A | ENSG00000221909 |
| PCDH12 | ENSG00000113555 | SLAMF7 | ENSG00000026751 |
| FXYD6 | ENSG00000137726 | SLC28A3 | ENSG00000197506 |
| LHCGR | ENSG00000138039 | EMID1 | ENSG00000186998 |
| SLMAP | ENSG00000163681 | PTPN1 | ENSG00000196396 |
| DOLK | ENSG00000175283 | KANSL1L | ENSG00000144445 |
| COLEC11 | ENSG00000118004 | KDELR1 | ENSG00000105438 |
| TNFSF8 | ENSG00000106952 | ABCA3 | ENSG00000167972 |
| ADAM15 | ENSG00000143537 | SMPD4 | ENSG00000136699 |
| MRGPRF | ENSG00000172935 | CERS3 | ENSG00000154227 |

TABLE 5-continued

Gene List

| HGNC symbol ID | Ensembl Gene | HGNC symbol ID | Ensembl Gene |
|---|---|---|---|
| TNFRSF14 | ENSG00000157873 | TRPA1 | ENSG00000104321 |
| COX6A1 | ENSG00000111775 | KIAA1919 | ENSG00000173214 |
| F10 | ENSG00000126218 | CHRNA7 | ENSG00000175344 |
| ODF4 | ENSG00000184650 | MS4A2 | ENSG00000149534 |
| CD38 | ENSG00000004468 | LPCAT3 | ENSG00000111684 |
| SIRPA | ENSG00000198053 | KIR3DL1 | ENSG00000274036 |
| CLPTM1L | ENSG00000049656 | BMPR1B | ENSG00000138696 |
| ACVR1 | ENSG00000115170 | FBXW7 | ENSG00000109670 |
| ZPLD1 | ENSG00000170044 | SUSD2 | ENSG00000099994 |
| TYR | ENSG00000077498 | SLC35G3 | ENSG00000164729 |
| OR13J1 | ENSG00000168828 | | ENSG00000251357 |
| GABBR1 | ENSG00000204681 | ADAMTS13 | ENSG00000160323 |
| LRRC26 | ENSG00000184709 | KIAA0319 | ENSG00000137261 |
| PHEX | ENSG00000102174 | NDUFB8 | ENSG00000166136 |
| KIR2DL3 | ENSG00000274108 | KCNG1 | ENSG00000026559 |
| DEFB126 | ENSG00000125788 | LHFPL2 | ENSG00000145685 |
| KIR3DL3 | ENSG00000276433 | C6orf10 | ENSG00000226892 |
| ATP1B2 | ENSG00000129244 | CDCA7L | ENSG00000164649 |
| CXorf66 | ENSG00000203933 | CD226 | ENSG00000150637 |
| EMC4 | ENSG00000128463 | SGCA | ENSG00000108823 |
| TMEM251 | ENSG00000153485 | SLC26A11 | ENSG00000181045 |
| CDHR1 | ENSG00000148600 | CYB5A | ENSG00000166347 |
| | ENSG00000258881 | SLC1A3 | ENSG00000079215 |
| OR2J2 | ENSG00000196231 | FAM163A | ENSG00000143340 |
| RABGAP1 | ENSG00000011454 | JAM3 | ENSG00000166086 |
| TMEM171 | ENSG00000157111 | GCGR | ENSG00000215644 |
| GPR19 | ENSG00000183150 | VTI1B | ENSG00000100568 |
| MS4A15 | ENSG00000166961 | TMEM219 | ENSG00000149932 |
| NKAIN4 | ENSG00000101198 | FAM9C | ENSG00000187268 |
| GNRHR | ENSG00000109163 | NUCB2 | ENSG00000070081 |
| XG | ENSG00000124343 | COMMD7 | ENSG00000149600 |
| OR5AU1 | ENSG00000169327 | RET | ENSG00000165731 |
| ELTD1 | ENSG00000162618 | GPR135 | ENSG00000181619 |
| SLC25A6 | ENSG00000169100 | MGAT4C | ENSG00000182050 |
| FUT8 | ENSG00000033170 | ABCC11 | ENSG00000121270 |
| GAPT | ENSG00000175857 | SPTLC3 | ENSG00000172296 |
| CCRL2 | ENSG00000121797 | | ENSG00000255641 |
| LRRC37A | ENSG00000176681 | MTFR1L | ENSG00000117640 |
| GIMAP2 | ENSG00000106560 | CD52 | ENSG00000169442 |
| SLC35G2 | ENSG00000168917 | PIGT | ENSG00000124155 |
| TEX264 | ENSG00000164081 | SLC35B1 | ENSG00000121073 |
| HLA-B | ENSG00000206450 | KLRC3 | ENSG00000205810 |
| LRRC8B | ENSG00000197147 | RNF5 | ENSG00000228907 |
| OR52E6 | ENSG00000205409 | LRTOMT | ENSG00000184154 |
| SLC4A5 | ENSG00000188687 | SUCO | ENSG00000094975 |
| CABP7 | ENSG00000100314 | ROBO2 | ENSG00000185008 |
| OR10J3 | ENSG00000196266 | SLC2A11 | ENSG00000275744 |
| ATP6V0A4 | ENSG00000105929 | SLC22A31 | ENSG00000259803 |
| OR4M2 | ENSG00000182974 | SDC3 | ENSG00000162512 |
| PREB | ENSG00000138073 | EFNA5 | ENSG00000184349 |
| CANT1 | ENSG00000171302 | PCDHGA6 | ENSG00000253731 |
| FDCSP | ENSG00000181617 | THEM6 | ENSG00000130193 |
| TMEM40 | ENSG00000088726 | CLYBL | ENSG00000125246 |
| PRND | ENSG00000171864 | SGCD | ENSG00000170624 |
| LEMD2 | ENSG00000161904 | ADCY7 | ENSG00000121281 |
| PPIB | ENSG00000166794 | KIAA1467 | ENSG00000084444 |
| | ENSG00000259066 | KCND1 | ENSG00000102057 |
| | ENSG00000111780 | GABRA3 | ENSG00000011677 |
| SLC6A8 | ENSG00000130821 | ANO8 | ENSG00000074855 |
| EPT1 | ENSG00000138018 | OR2T2 | ENSG00000276821 |
| MFSD1 | ENSG00000118855 | DGAT2L6 | ENSG00000184210 |
| TRPV5 | ENSG00000274348 | NCR1 | ENSG00000274053 |
| AGER | ENSG00000204305 | KIR3DL3 | ENSG00000276086 |
| TMEM19 | ENSG00000139291 | SLC38A10 | ENSG00000157637 |
| KIR3DL3 | ENSG00000275433 | REEP3 | ENSG00000165476 |
| TMPRSS11D | ENSG00000153802 | CLDN9 | ENSG00000213937 |
| CREG1 | ENSG00000143162 | ITGA5 | ENSG00000161638 |
| GPR84 | ENSG00000139572 | NRM | ENSG00000137404 |
| L3MBTL2 | ENSG00000100395 | KIR3DL3 | ENSG00000275172 |
| SPNS2 | ENSG00000183018 | IL6R | ENSG00000160712 |
| SIRPB1 | ENSG00000101307 | KCNG4 | ENSG00000168418 |
| COA1 | ENSG00000106603 | LRRC8C | ENSG00000171488 |
| LST1 | ENSG00000223465 | CNNM2 | ENSG00000148842 |
| PSEN2 | ENSG00000143801 | LEMD3 | ENSG00000174106 |
| | ENSG00000254778 | TARM1 | ENSG00000276604 |

TABLE 5-continued

Gene List

| HGNC symbol ID | Ensembl Gene | HGNC symbol ID | Ensembl Gene |
|---|---|---|---|
| SLC2A8 | ENSG00000136856 | ZDHHC21 | ENSG00000175893 |
| KIR3DL3 | ENSG00000273502 | SLC15A5 | ENSG00000188991 |
| ALG14 | ENSG00000172339 | IL31RA | ENSG00000164509 |
| CNOT1 | ENSG00000125107 | KIAA0100 | ENSG00000007202 |
| EMB | ENSG00000170571 | KIAA0100 | ENSG00000277263 |
| AGTR1 | ENSG00000144891 | SEC62 | ENSG00000008952 |
| PACRG | ENSG00000112530 | UTY | ENSG00000183878 |
| C12orf76 | ENSG00000174456 | OR1F1 | ENSG00000168124 |
| LRIG3 | ENSG00000139263 | AQP6 | ENSG00000086159 |
| PCDHGA1 | ENSG00000204956 | LTBP3 | ENSG00000168056 |
| ATP5F1 | ENSG00000116459 | GPR56 | ENSG00000205336 |
| THSD1 | ENSG00000136114 |  | ENSG00000255339 |
| USP30 | ENSG00000135093 | KIR3DL1 | ENSG00000277175 |
| TSC2 | ENSG00000103197 | DEFB103B | ENSG00000177243 |
| SIGIRR | ENSG00000185187 | TOMM22 | ENSG00000100216 |
| SCN1A | ENSG00000144285 | LAPTM4B | ENSG00000104341 |
| FKTN | ENSG00000106692 | SLC43A2 | ENSG00000278550 |
| SLC39A7 | ENSG00000229802 | INPP4B | ENSG00000109452 |
| PIGL | ENSG00000108474 |  | ENSG00000274944 |
| STS | ENSG00000101846 | AFG3L2 | ENSG00000141385 |
| PCDHGC3 | ENSG00000240184 | LTA | ENSG00000231408 |
| HLA-F | ENSG00000204642 | UBA2 | ENSG00000126261 |
| IGLV4-3 | ENSG00000211672 | ERN1 | ENSG00000178607 |
|  | ENSG00000272532 | SIRPG | ENSG00000089012 |
| HTR4 | ENSG00000164270 | LRIT2 | ENSG00000204033 |
| CLDN5 | ENSG00000184113 | KIR3DL3 | ENSG00000274724 |
| GRIN2A | ENSG00000183454 | MS4A1 | ENSG00000156738 |
| TVP23B | ENSG00000171928 | C6orf25 | ENSG00000224393 |
| MFGE8 | ENSG00000140545 | IGHD | ENSG00000211898 |
| SLC30A1 | ENSG00000170385 | KIR2DL4 | ENSG00000278606 |
| CCR10 | ENSG00000184451 | KIR3DS1 | ENSG00000275037 |
| GRIN1 | ENSG00000176884 | B3GNT2 | ENSG00000170340 |
| CCL5 | ENSG00000274233 | MPV17 | ENSG00000115204 |
| KCNA5 | ENSG00000130037 | TRAM1L1 | ENSG00000174599 |
| OR5T1 | ENSG00000262784 | SGMS1 | ENSG00000198964 |
| MCOLN1 | ENSG00000090674 | TAP1 | ENSG00000168394 |
| ECE1 | ENSG00000117298 | DPM3 | ENSG00000179085 |
| LY6G5C | ENSG00000231325 | ADAM20 | ENSG00000134007 |
| OR4E2 | ENSG00000221977 | OR2A12 | ENSG00000221858 |
| NEU1 | ENSG00000234343 | PTPRC | ENSG00000081237 |
| TOR1AIP2 | ENSG00000169905 | NDRG1 | ENSG00000104419 |
| HIATL2 | ENSG00000196312 | COX14 | ENSG00000178449 |
| MID1 | ENSG00000101871 | PLA2G10 | ENSG00000069764 |
| OR2Y1 | ENSG00000174339 | CD274 | ENSG00000120217 |
| IF127 | ENSG00000275214 | LMBR1 | ENSG00000105983 |
| TECRL | ENSG00000205678 | CD70 | ENSG00000125726 |
| TMEM164 | ENSG00000157600 | GPR85 | ENSG00000164604 |
| PPT2 | ENSG00000221988 | PGRMC2 | ENSG00000164040 |
| TGFBR1 | ENSG00000106799 | GALNT8 | ENSG00000130035 |
| CDSN | ENSG00000237114 | LILRA6 | ENSG00000244482 |
| ZAN | ENSG00000146839 | SMIM11 | ENSG00000273590 |
| OR2A2 | ENSG00000221989 | ADORA2B | ENSG00000170425 |
| AKAP6 | ENSG00000151320 | RNF144A | ENSG00000151692 |
| OR11A1 | ENSG00000234347 | KLRC1 | ENSG00000134545 |
| SNX14 | ENSG00000135317 | NLGN1 | ENSG00000169760 |
| PLA2G10 | ENSG00000276870 | THOC1 | ENSG00000079134 |
| PCDHA7 | ENSG00000204963 | PTAFR | ENSG00000169403 |
| ADAM21 | ENSG00000139985 | P2RX1 | ENSG00000108405 |
| TMEM59 | ENSG00000116209 | TMEM45A | ENSG00000181458 |
| LILRB5 | ENSG00000277414 | HLA-DQA1 | ENSG00000196735 |
| SLC15A1 | ENSG00000088386 | PRRT1 | ENSG00000238056 |
| CNTNAP1 | ENSG00000108797 | FLRT1 | ENSG00000126500 |
| DERL2 | ENSG00000072849 | POM121C | ENSG00000272391 |
| DKC1 | ENSG00000130826 | DCBLD2 | ENSG00000057019 |
| CD7 | ENSG00000173762 | SUN2 | ENSG00000100242 |
| C6orf10 | ENSG00000237881 | PEBP4 | ENSG00000134020 |
| AGPAT9 | ENSG00000138678 | WSCD2 | ENSG00000075035 |
| CDH18 | ENSG00000145526 | FAM189B | ENSG00000262666 |
| HLA-DQA2 | ENSG00000223793 | STT3A | ENSG00000134910 |
| OR5K4 | ENSG00000196098 | KCNN2 | ENSG00000080709 |
| AASDH | ENSG00000157426 | HSD3B7 | ENSG00000099377 |
| HLA-DQB2 | ENSG00000232629 | PROM2 | ENSG00000155066 |
| CCDC127 | ENSG00000164366 | TAPBP | ENSG00000206208 |
| TMEM41B | ENSG00000166471 | ABCA8 | ENSG00000141338 |
| OR2AT4 | ENSG00000171561 | KIR3DL2 | ENSG00000275566 |

TABLE 5-continued

Gene List

| HGNC symbol ID | Ensembl Gene | HGNC symbol ID | Ensembl Gene |
|---|---|---|---|
| OR5H6 | ENSG00000279922 | OR5K3 | ENSG00000206536 |
| CRHR1 | ENSG00000276191 | OR12D3 | ENSG00000242022 |
| SLC5A5 | ENSG00000105641 | IFNGR2 | ENSG00000262795 |
| SIDT1 | ENSG00000072858 | OPN1LW | ENSG00000102076 |
| RAP1B | ENSG00000127314 | ADCY6 | ENSG00000174233 |
| SLC35A5 | ENSG00000138459 | AGPAT1 | ENSG00000226467 |
| IEI6 | ENSG00000126709 | LILRB2 | ENSG00000277751 |
| SLC15A4 | ENSG00000139370 | TNF | ENSG00000204490 |
| TMEM117 | ENSG00000139173 | PPIC | ENSG00000168938 |
| DSG2 | ENSG00000046604 | HBEGF | ENSG00000113070 |
| SQLE | ENSG00000104549 | PTK7 | ENSG00000112655 |
| B4GALT1 | ENSG00000086062 | TAP1 | ENSG00000230705 |
| FAM19A4 | ENSG00000163377 | OR2A14 | ENSG00000221938 |
| MFN2 | ENSG00000116688 | OR7G2 | ENSG00000170923 |
| KCNB2 | ENSG00000182674 | TSPAN18 | ENSG00000157570 |
| OR6C1 | ENSG00000205330 | ITGAM | ENSG00000169896 |
| RNF225 | ENSG00000269855 | PLGRKT | ENSG00000107020 |
| CD93 | ENSG00000125810 | CYP3A4 | ENSG00000160868 |
| OR1M1 | ENSG00000170929 | B3GNT1 | ENSG00000174684 |
| TNF | ENSG00000228321 | NTSR2 | ENSG00000169006 |
|  | ENSG00000268279 | SPAG4 | ENSG00000061656 |
| TMEM92 | ENSG00000167105 | SLC4A1 | ENSG00000004939 |
| FAM57B | ENSG00000149926 | TNF | ENSG00000230108 |
| GPRC5D | ENSG00000111291 | KRTCAP3 | ENSG00000157992 |
| OR10C1 | ENSG00000229412 | SLC35B2 | ENSG00000157593 |
| ACER2 | ENSG00000177076 | LY9 | ENSG00000122224 |
| ASGR1 | ENSG00000141505 | P4HTM | ENSG00000178467 |
| SLCO1C1 | ENSG00000139155 | PLP2 | ENSG00000102007 |
| PCDHA13 | ENSG00000239389 | HLA-DMB | ENSG00000239329 |
| SLC12A6 | ENSG00000140199 | SERTM1 | ENSG00000180440 |
| KIAA1549 | ENSG00000122778 | IGSF9 | ENSG00000085552 |
| OR5H2 | ENSG00000197938 | RNF182 | ENSG00000180537 |
| CDH1 | ENSG00000039068 | SLC25A17 | ENSG00000100372 |
| SLC30A8 | ENSG00000164756 | BACE2 | ENSG00000182240 |
| FCER2 | ENSG00000104921 | CTAGE1 | ENSG00000212710 |
| FSD1L | ENSG00000106701 | FCAR | ENSG00000274580 |
| ADAM2 | ENSG00000276286 |  | ENSG00000256206 |
| DEGS2 | ENSG00000168350 | CHI3L2 | ENSG00000064886 |
| KIR3DL2 | ENSG00000275416 | PKDREJ | ENSG00000130943 |
| AGPAT5 | ENSG00000155189 | SLC34A2 | ENSG00000157765 |
| ADAM11 | ENSG00000073670 | C1orf186 | ENSG00000263961 |
| OR12D2 | ENSG00000227446 | COX6C | ENSG00000164919 |
| AGPAT2 | ENSG00000169692 | ROM1 | ENSG00000149489 |
| GPR133 | ENSG00000111452 | STX3 | ENSG00000166900 |
| SMIM13 | ENSG00000224531 | PDCD1LG2 | ENSG00000197646 |
| TNFRSF21 | ENSG00000146072 | OR10J5 | ENSG00000184155 |
| SYT4 | ENSG00000132872 | KLRC2 | ENSG00000205809 |
| MRS2 | ENSG00000124532 | IL18R1 | ENSG00000115604 |
| NTSR1 | ENSG00000101188 | CACNA1H | ENSG00000196557 |
| ABCC12 | ENSG00000140798 | TOR1AIP1 | ENSG00000143337 |
| GPX8 | ENSG00000164294 | RXFP4 | ENSG00000173080 |
| ADAM9 | ENSG00000168615 | TMEM213 | ENSG00000214128 |
| KIR2DS2 | ENSG00000276425 | KIR2DL3 | ENSG00000274402 |
| MAP4K2 | ENSG00000168067 | PCDHGA7 | ENSG00000253537 |
| TMEM55A | ENSG00000155099 | LHFPL1 | ENSG00000182508 |
| RABAC1 | ENSG00000105404 | STT3B | ENSG00000163527 |
| CSF3R | ENSG00000119535 | CCDC136 | ENSG00000128596 |
| ERF | ENSG00000105722 | DAPK2 | ENSG00000035664 |
| PIGY | ENSG00000255072 | CD83 | ENSG00000112149 |
| WFDC10B | ENSG00000182931 | SLC7A7 | ENSG00000155465 |
| PNPLA4 | ENSG00000006757 | KRTAP6-1 | ENSG00000184724 |
| STOML3 | ENSG00000133115 | ZDHHC7 | ENSG00000153786 |
| HHIPL2 | ENSG00000143512 | LST1 | ENSG00000226182 |
| DCAKD | ENSG00000172992 | CTLA4 | ENSG00000163599 |
| HYAL4 | ENSG00000106302 | CHIT1 | ENSG00000133063 |
| CYB5D2 | ENSG00000167740 | DNASE1 | ENSG00000213918 |
| DSC3 | ENSG00000134762 | C16orf92 | ENSG00000167194 |
| RAET1E | ENSG00000164520 | CYP4A11 | ENSG00000187048 |
| GPR123 | ENSG00000197177 | GALC | ENSG00000054983 |
| TMCC2 | ENSG00000133069 | MARCH8 | ENSG00000278545 |
| SPATA31A3 | ENSG00000275969 | LARGE | ENSG00000133424 |
|  | ENSG00000277596 | C10orf99 | ENSG00000188373 |
| NCR3 | ENSG00000237808 | OR6C3 | ENSG00000205329 |
| HLA-DMB | ENSG00000234154 | OR2H1 | ENSG00000229408 |
| LAIR1 | ENSG00000167613 | KCNG3 | ENSG00000171126 |

TABLE 5-continued

Gene List

| HGNC symbol ID | Ensembl Gene | HGNC symbol ID | Ensembl Gene |
|---|---|---|---|
| OPCML | ENSG00000183715 | C1QTNF1 | ENSG00000173918 |
| BSCL2 | ENSG00000168000 | ST6GALNAC6 | ENSG00000160408 |
| ERVFRD-1 | ENSG00000244476 | IL17RB | ENSG00000056736 |
| SUMF2 | ENSG00000129103 | DDR1 | ENSG00000204580 |
| OR51L1 | ENSG00000176798 | MT-ND5 | ENSG00000198786 |
| ADTRP | ENSG00000111863 | MT-ND6 | ENSG00000198695 |
| C6orf25 | ENSG00000231003 | IL1RL1 | ENSG00000115602 |
| NTM | ENSG00000182667 | OR2H2 | ENSG00000206467 |
| ABCC2 | ENSG00000023839 | MT-CYB | ENSG00000198727 |
| LINGO4 | ENSG00000213171 | CHST12 | ENSG00000136213 |
| TMEM50B | ENSG00000263160 | GYPC | ENSG00000136732 |
| TLR9 | ENSG00000239732 | TPTE2 | ENSG00000132958 |
| PPT2-EGFL8 | ENSG00000258388 | PTN | ENSG00000105894 |
| AVPR1B | ENSG00000198049 | | ENSG00000279870 |
| FAM8A1 | ENSG00000137414 | TMCO3 | ENSG00000150403 |
| THADA | ENSG00000115970 | FAM209A | ENSG00000124103 |
| ABHD3 | ENSG00000158201 | GJE1 | ENSG00000203733 |
| TMCO1 | ENSG00000143183 | PRLH | ENSG00000071677 |
| FASLG | ENSG00000117560 | UTY | ENSG00000279053 |
| GUCY2C | ENSG00000070019 | | ENSG00000279947 |
| OGFOD3 | ENSG00000181396 | LRPAP1 | ENSG00000163956 |
| MPZL1 | ENSG00000197965 | WNT6 | ENSG00000115596 |
| OST4 | ENSG00000228474 | | ENSG00000279383 |
| SLC44A5 | ENSG00000137968 | PPT2 | ENSG00000206256 |
| FFAR1 | ENSG00000126266 | LILRB3 | ENSG00000204577 |
| VSTM1 | ENSG00000276066 | NLGN4Y | ENSG00000279292 |
| HLA-G | ENSG00000276051 | CYB561 | ENSG00000008283 |
| SLC30A7 | ENSG00000162695 | GPR179 | ENSG00000277399 |
| VSIG10L | ENSG00000186806 | FKBP11 | ENSG00000134285 |
| NPIPB11 | ENSG00000254206 | MEGF11 | ENSG00000277848 |
| CDH6 | ENSG00000113361 | OR10X1 | ENSG00000186400 |
| EFCAB14 | ENSG00000159658 | KLRF1 | ENSG00000150045 |
| ASTL | ENSG00000188886 | OR2L8 | ENSG00000196936 |
| CCDC107 | ENSG00000159884 | OR2T11 | ENSG00000183130 |
| SLC52A1 | ENSG00000132517 | CLSTN1 | ENSG00000171603 |
| NIPAL2 | ENSG00000104361 | OR51F1 | ENSG00000188069 |
| GLRA3 | ENSG00000145451 | OR52R1 | ENSG00000176937 |
| RTN4 | ENSG00000115310 | FUT9 | ENSG00000172461 |
| | ENSG00000273808 | OR51G1 | ENSG00000176879 |
| NCR3 | ENSG00000237103 | ACBD4 | ENSG00000181513 |
| BDKRB2 | ENSG00000168398 | OR2AG1 | ENSG00000170803 |
| ANKAR | ENSG00000151687 | OR4X2 | ENSG00000279556 |
| SDF4 | ENSG00000078808 | OR4X1 | ENSG00000176567 |
| NCAM1 | ENSG00000149294 | OR4C16 | ENSG00000181935 |
| PIGG | ENSG00000174227 | FOLR1 | ENSG00000110195 |
| CUTA | ENSG00000226492 | OR5D13 | ENSG00000198877 |
| CH25H | ENSG00000138135 | OR5L1 | ENSG00000186117 |
| HLA-B | ENSG00000223532 | OR8K3 | ENSG00000181689 |
| MMD2 | ENSG00000136297 | OR5R1 | ENSG00000174942 |
| FAIM3 | ENSG00000162894 | OR5AR1 | ENSG00000279911 |
| LY6G6C | ENSG00000228859 | PSEN1 | ENSG00000080815 |
| MT-ND1 | ENSG00000198888 | OR6Q1 | ENSG00000172381 |
| MT-ND2 | ENSG00000198763 | PTH2R | ENSG00000144407 |
| MT-CO1 | ENSG00000198804 | GPD2 | ENSG00000115159 |
| MT-CO2 | ENSG00000198712 | OR1S1 | ENSG00000172774 |
| MT-ATP8 | ENSG00000228253 | OR8D2 | ENSG00000197263 |
| MT-ATP6 | ENSG00000198899 | OR8B4 | ENSG00000198657 |
| MT-CO3 | ENSG00000198938 | LRP11 | ENSG00000120256 |
| MT-ND3 | ENSG00000198840 | LPGAT1 | ENSG00000123684 |
| MT-ND4L | ENSG00000212907 | ESYT3 | ENSG00000158220 |
| MT-ND4 | ENSG00000198886 | OSTM1 | ENSG00000081087 |
| OR5H6 | ENSG00000230301 | SIGLEC9 | ENSG00000129450 |
| OR10C1 | ENSG00000279941 | ACHE | ENSG00000087085 |
| OR1B1 | ENSG00000171484 | CEACAM4 | ENSG00000105352 |
| KREMEN2 | ENSG00000131650 | GIMAP5 | ENSG00000196329 |
| SRR | ENSG00000167720 | LMLN | ENSG00000185621 |
| GPR97 | ENSG00000182885 | CXADR | ENSG00000154639 |
| INSIG1 | ENSG00000186480 | PTPRF | ENSG00000142949 |
| TNFRSF12A | ENSG00000006327 | OR4D1 | ENSG00000141194 |
| IZUMO1 | ENSG00000182264 | CLDN23 | ENSG00000253958 |
| STX12 | ENSG00000117758 | OR5AR1 | ENSG00000172459 |
| RNF5 | ENSG00000223767 | B3GALT6 | ENSG00000176022 |
| BMPR1A | ENSG00000107779 | OPRK1 | ENSG00000082556 |
| SLCO6A1 | ENSG00000205359 | KCNA10 | ENSG00000143105 |
| PCDHGA12 | ENSG00000253159 | LILRA6 | ENSG00000274148 |

TABLE 5-continued

Gene List

| HGNC symbol ID | Ensembl Gene | HGNC symbol ID | Ensembl Gene |
| --- | --- | --- | --- |
| MCL1 | ENSG00000143384 | MPG | ENSG00000103152 |
| B3GALTL | ENSG00000187676 | RHBDL2 | ENSG00000158315 |
| EPHX3 | ENSG00000105131 | OR8G1 | ENSG00000197849 |
| HLA-DPA1 | ENSG00000229685 | HLA-DRB1 | ENSG00000229074 |
| AMELX | ENSG00000125363 | OR8G5 | ENSG00000255298 |
| ADAM2 | ENSG00000104755 | PCDHGB3 | ENSG00000262209 |
| HLA-DMA | ENSG00000243719 | SLC22A17 | ENSG00000092096 |
| CLEC7A | ENSG00000172243 | KCNA2 | ENSG00000177301 |
| SERF1B | ENSG00000278839 | PAM | ENSG00000145730 |
| PNPLA3 | ENSG00000100344 | CALY | ENSG00000130643 |
| SPEG | ENSG00000072195 | TLR6 | ENSG00000174130 |
| CD300A | ENSG00000167851 | SYT7 | ENSG00000011347 |
| CXCR5 | ENSG00000160683 | TMEM126B | ENSG00000171204 |
| SCN5A | ENSG00000183873 | PCDHA2 | ENSG00000204969 |
| SEMA6B | ENSG00000167680 | NINJ1 | ENSG00000131669 |
| KTN1 | ENSG00000126777 | CATSPER2 | ENSG00000166762 |
| PCDHA3 | ENSG00000255408 | SIGLEC11 | ENSG00000161640 |
| MRAP | ENSG00000170262 | ABCD3 | ENSG00000117528 |
| ATP11B | ENSG00000058063 | TM7SF2 | ENSG00000149809 |
| AMHR2 | ENSG00000135409 | RPN2 | ENSG00000118705 |
| CAMP | ENSG00000164047 | PKN2 | ENSG00000065243 |
| ERGIC2 | ENSG00000087502 | SIGLEC10 | ENSG00000142512 |
| NETO2 | ENSG00000171208 | PCDHA12 | ENSG00000251664 |
| GALNT11 | ENSG00000178234 | EPHA2 | ENSG00000142627 |
| TMEM208 | ENSG00000168701 | BST1 | ENSG00000109743 |
| HTR3C | ENSG00000178084 | SPTSSA | ENSG00000165389 |
| OR10D3 | ENSG00000197309 | CLDN14 | ENSG00000159261 |
| KIR2DL1 | ENSG00000277833 | WNT10A | ENSG00000135925 |
| HLA-F | ENSG00000234487 | SMIM22 | ENSG00000267795 |
| TTC13 | ENSG00000143643 | TM2D3 | ENSG00000184277 |
| ZMYM6 | ENSG00000163867 | SLC35F1 | ENSG00000196376 |
| STX2 | ENSG00000111450 | LRP10 | ENSG00000197324 |
| UPK2 | ENSG00000110375 | GPR83 | ENSG00000123901 |
| CD2 | ENSG00000116824 | CLMP | ENSG00000166250 |
| KCTD20 | ENSG00000112078 | TMEM97 | ENSG00000109084 |
| LMAN2 | ENSG00000169223 | BDKRB1 | ENSG00000100739 |
| SEC61A1 | ENSG00000058262 | CLEC4M | ENSG00000104938 |
| LRRTM3 | ENSG00000198739 | CLDN6 | ENSG00000184697 |
| PVRL1 | ENSG00000110400 | EGFR | ENSG00000146648 |
| KIR2DS1 | ENSG00000275306 | CNTNAP5 | ENSG00000155052 |
| TAOK2 | ENSG00000149930 | OR4X1 | ENSG00000279260 |
| GPR21 | ENSG00000188394 | VAMP2 | ENSG00000220205 |
| PLXNA1 | ENSG00000114554 | UGT3A1 | ENSG00000145626 |
| OPRL1 | ENSG00000125510 | ERBB2 | ENSG00000141736 |
| DTNA | ENSG00000134769 | KIR2DL5A | ENSG00000278116 |
| TMEM201 | ENSG00000188807 | SCIMP | ENSG00000161929 |
| MEGF9 | ENSG00000106780 | CTAGE4 | ENSG00000225932 |
| NAALADL2 | ENSG00000177694 | SLC22A16 | ENSG00000004809 |
| KCNA3 | ENSG00000177272 | SEL1L | ENSG00000071537 |
| KIR3DL2 | ENSG00000278361 | C6orf10 | ENSG00000206310 |
| HIGD1B | ENSG00000131097 | SLC5A8 | ENSG00000256870 |
| RXFP1 | ENSG00000171509 | LRIT3 | ENSG00000183423 |
| HLA-E | ENSG00000229252 | NELL2 | ENSG00000184613 |
| PCDHGA2 | ENSG00000081853 | GPR32 | ENSG00000142511 |
| SMIM10 | ENSG00000184785 | KCNK5 | ENSG00000164626 |
| TMEM154 | ENSG00000170006 | HLA-DPB1 | ENSG00000237710 |
| ADAM19 | ENSG00000135074 | KCNK15 | ENSG00000124249 |
| ABCB7 | ENSG00000131269 | CSGALNACT1 | ENSG00000147408 |
| KCNK2 | ENSG00000082482 | KIR2DS5 | ENSG00000274563 |
| NRCAM | ENSG00000091129 | ABCG4 | ENSG00000172350 |
| TPRA1 | ENSG00000163870 | PTPRD | ENSG00000153707 |
| SLAMF9 | ENSG00000162723 | TMEM212 | ENSG00000186329 |
| RNASE6 | ENSG00000169413 | GPR75 | ENSG00000119737 |
| THAP6 | ENSG00000174796 | ARV1 | ENSG00000173409 |
|  | ENSG00000223590 | NXF5 | ENSG00000126952 |
| HSD11B2 | ENSG00000176387 | OR4D2 | ENSG00000255713 |
| DISP2 | ENSG00000140323 | SEZ6L2 | ENSG00000174938 |
| SYT8 | ENSG00000149043 | TMEM9B | ENSG00000175348 |
| SLCO2B1 | ENSG00000137491 | FAM132A | ENSG00000184163 |
| KRTAP20-1 | ENSG00000244624 | PIGR | ENSG00000162896 |
| SLC2A5 | ENSG00000142583 | SDR42E2 | ENSG00000183921 |
| OR5T1 | ENSG00000181698 | GRM7 | ENSG00000196277 |
| ECHDC1 | ENSG00000093144 | SHISA4 | ENSG00000198892 |
| QRFPR | ENSG00000186867 | ZDHHC18 | ENSG00000204160 |
| OR8H1 | ENSG00000181693 | PRIMA1 | ENSG00000175785 |

TABLE 5-continued

Gene List

| HGNC symbol ID | Ensembl Gene | HGNC symbol ID | Ensembl Gene |
|---|---|---|---|
| TNFSF18 | ENSG00000120337 | SFRP1 | ENSG00000104332 |
| ALG3 | ENSG00000214160 | SYNE3 | ENSG00000176438 |
| SHISA3 | ENSG00000178343 | SLC39A10 | ENSG00000196950 |
| SLC2A7 | ENSG00000197241 | MFSD11 | ENSG00000092931 |
| OR8D1 | ENSG00000196341 | ABHD15 | ENSG00000168792 |
| OR13F1 | ENSG00000186881 | HSD17B12 | ENSG00000149084 |
| GJA9 | ENSG00000131233 | MRPL42 | ENSG00000198015 |
| LRIT1 | ENSG00000148602 | KCNT1 | ENSG00000107147 |
| SEC61B | ENSG00000106803 | CEACAM21 | ENSG00000007129 |
| LECT1 | ENSG00000136110 | SRCAP | ENSG00000080603 |
| GIMAP1 | ENSG00000213203 | MACF1 | ENSG00000127603 |
| DPCR1 | ENSG00000229284 | CALHM1 | ENSG00000185933 |
| BAX | ENSG00000087088 | CASR | ENSG00000036828 |
| TLR1 | ENSG00000174125 | ELANE | ENSG00000197561 |
| PRAF2 | ENSG00000243279 | SGCZ | ENSG00000185053 |
| DRD4 | ENSG00000069696 | TMPRSS11B | ENSG00000185873 |
| NDC1 | ENSG00000058804 | YIPF5 | ENSG00000145817 |
| TAS2R30 | ENSG00000262111 | CACFD1 | ENSG00000160325 |
| SLC12A2 | ENSG00000064651 | SYNGR2 | ENSG00000108639 |
| OR1J4 | ENSG00000239590 | IL21R | ENSG00000103522 |
| ITGB6 | ENSG00000115221 | NAT14 | ENSG00000090971 |
| SCAP | ENSG00000114650 | PQLC3 | ENSG00000162976 |
| CNTN1 | ENSG00000018236 | GPR180 | ENSG00000152749 |
| TYW1B | ENSG00000277149 | OR51A2 | ENSG00000205496 |
| ERP29 | ENSG00000089248 | TM9SF1 | ENSG00000254692 |
| COA3 | ENSG00000183978 | PLVAP | ENSG00000130300 |
| FREM2 | ENSG00000150893 | KIR2DL1 | ENSG00000275522 |
|  | ENSG00000263620 | AQP7 | ENSG00000165269 |
| AQP11 | ENSG00000178301 | DGKE | ENSG00000153933 |
| KIR2DL4 | ENSG00000275732 | KIR2DL5A | ENSG00000276177 |
| GPR150 | ENSG00000178015 | TMEM209 | ENSG00000146842 |
| CLCA4 | ENSG00000016602 | HGF | ENSG00000019991 |
| HTR3E | ENSG00000186038 | RHOT2 | ENSG00000140983 |
| SFTPC | ENSG00000168484 | C6orf10 | ENSG00000234280 |
| GPR64 | ENSG00000173698 | OR4S1 | ENSG00000176555 |
| C12orf49 | ENSG00000111412 | OR11H1 | ENSG00000130538 |
| OR10V1 | ENSG00000172289 | OTOR | ENSG00000125879 |
| TMEM39A | ENSG00000176142 | ALG9 | ENSG00000086848 |
| AQP10 | ENSG00000143595 | OR51A4 | ENSG00000205497 |
| PDE6B | ENSG00000133256 | PCDHGA5 | ENSG00000253485 |
| KIRREL | ENSG00000183853 | TNFRSF25 | ENSG00000215788 |
| PCDHA11 | ENSG00000249158 | OR2H1 | ENSG00000224395 |
| CHRM4 | ENSG00000180720 | BNIP3 | ENSG00000176171 |
| ATP7B | ENSG00000123191 | TGFA | ENSG00000163235 |
| EMR2 | ENSG00000127507 | TMEM159 | ENSG00000011638 |
| NNT | ENSG00000112992 | PCDHGB5 | ENSG00000276547 |
| PCDHGA9 | ENSG00000261934 | MS4A4A | ENSG00000110079 |
| GHRHR | ENSG00000106128 | FCAR | ENSG00000276985 |
| SCARA3 | ENSG00000168077 | TAP2 | ENSG00000228582 |
| TNFSF4 | ENSG00000117586 | DSE | ENSG00000111817 |
| ATP9A | ENSG00000054793 | AGPAT3 | ENSG00000160216 |
| MSMO1 | ENSG00000052802 | PTCRA | ENSG00000171611 |
| PIGM | ENSG00000143315 | SGMS2 | ENSG00000164023 |
| CLN8 | ENSG00000182372 | KLK8 | ENSG00000129455 |
| HTR7 | ENSG00000148680 | TIGIT | ENSG00000181847 |
| RNF19B | ENSG00000116514 | UPK1A | ENSG00000105668 |
| NRP2 | ENSG00000118257 | SMIM7 | ENSG00000214046 |
| SLC25A39 | ENSG00000013306 | SSH1 | ENSG00000084112 |
| PAQR4 | ENSG00000162073 | GALNT13 | ENSG00000144278 |
| UNC5C | ENSG00000182168 | NRM | ENSG00000234809 |
| ETFDH | ENSG00000171503 | GRHL1 | ENSG00000134317 |
| KIR2DL3 | ENSG00000278369 | LY6G6E | ENSG00000226169 |
| FAM3D | ENSG00000198643 | HRCT1 | ENSG00000196196 |
| ERBB4 | ENSG00000178568 | DHCR24 | ENSG00000116133 |
| CDK5RAP2 | ENSG00000136861 | TMEM134 | ENSG00000172663 |
| PLXDC1 | ENSG00000161381 | LY6G6F | ENSG00000241822 |
| C6orf89 | ENSG00000198663 | SLC7A9 | ENSG00000021488 |
| ALG9 | ENSG00000258529 | NDUFA13 | ENSG00000186010 |
| GJA1 | ENSG00000152661 | SYT5 | ENSG00000129990 |
| CYP3A43 | ENSG00000021461 | SLC41A3 | ENSG00000114544 |
| EDDM3A | ENSG00000181562 | HLA-C | ENSG00000206452 |
| HLA-DMA | ENSG00000243215 | ILVBL | ENSG00000105135 |
| ATP2C2 | ENSG00000064270 | RHBDF1 | ENSG00000007384 |
| SLC37A3 | ENSG00000157800 | OR2AG2 | ENSG00000188124 |
| OR2H1 | ENSG00000229125 | TMEM56-RWDD3 | ENSG00000271092 |

TABLE 5-continued

Gene List

| HGNC symbol ID | Ensembl Gene | HGNC symbol ID | Ensembl Gene |
|---|---|---|---|
| POTEH | ENSG00000198062 | CA9 | ENSG00000107159 |
| JPH2 | ENSG00000149596 | PRRT1 | ENSG00000206331 |
| ADCY10 | ENSG00000143199 | ANO9 | ENSG00000185101 |
| SCN2A | ENSG00000136531 | TACR1 | ENSG00000115353 |
| SYPL2 | ENSG00000143028 | ZP1 | ENSG00000149506 |
| GINM1 | ENSG00000055211 | TSPAN17 | ENSG00000048140 |
| CTSH | ENSG00000103811 | ECE2 | ENSG00000145194 |
| P2RX3 | ENSG00000109991 | TMEM56 | ENSG00000152078 |
|  | ENSG00000227826 | OR2AG1 | ENSG00000279486 |
| OR51H1 | ENSG00000176904 | SPCS3 | ENSG00000129128 |
| OXTR | ENSG00000180914 | TEX2 | ENSG00000136478 |
| CHDC2 | ENSG00000176034 | RNFT2 | ENSG00000135119 |
| KIT | ENSG00000157404 | WNT7A | ENSG00000154764 |
| FCGR3A | ENSG00000203747 | KCNJ10 | ENSG00000177807 |
| KIR2DS3 | ENSG00000277163 | CMTM7 | ENSG00000153551 |
| TENM2 | ENSG00000145934 |  | ENSG00000258880 |
| OR51G2 | ENSG00000176893 | SPOCK3 | ENSG00000196104 |
| CD3D | ENSG00000167286 | KCNA6 | ENSG00000151079 |
| AIG1 | ENSG00000146416 | KCNG2 | ENSG00000178342 |
| SLC8A2 | ENSG00000118160 | REEP1 | ENSG00000068615 |
| CD300LF | ENSG00000186074 | TMEM123 | ENSG00000152558 |
| LILRB1 | ENSG00000277134 | CACHD1 | ENSG00000158966 |
| VEZT | ENSG00000028203 | PVRL4 | ENSG00000143217 |
| KMT2E | ENSG00000005483 | FGF4 | ENSG00000075388 |
| KMT2E | ENSG00000278086 | IGSF9B | ENSG00000080854 |
| OR1L1 | ENSG00000173679 | IL17RA | ENSG00000177663 |
| SMN2 | ENSG00000205571 | GPR34 | ENSG00000171659 |
| ADRB3 | ENSG00000188778 | AREG | ENSG00000109321 |
| FIG4 | ENSG00000112367 | PCDHGB7 | ENSG00000254122 |
| KIR2DL5B | ENSG00000278481 | TMEM135 | ENSG00000166575 |
| COQ6 | ENSG00000119723 | KCNH4 | ENSG00000089558 |
| PCDHGA10 | ENSG00000253846 | FKBP1A | ENSG00000088832 |
| OR1L3 | ENSG00000171481 | SLC51B | ENSG00000186198 |
| KIR2DL1 | ENSG00000278248 | OR6A2 | ENSG00000184933 |
| ITGA2 | ENSG00000164171 | CNGA2 | ENSG00000183862 |
| GRIN2C | ENSG00000161509 | OR51G1 | ENSG00000278870 |
| DCST1 | ENSG00000163357 | SLC38A9 | ENSG00000177058 |
| TRPM7 | ENSG00000092439 | SLCO5A1 | ENSG00000137571 |
| TEX29 | ENSG00000153495 | FCAMR | ENSG00000162897 |
| OR5D16 | ENSG00000205029 | LEMD1 | ENSG00000186007 |
| VAMP5 | ENSG00000168899 | DSCAM | ENSG00000171587 |
| PRRT4 | ENSG00000224940 | SLC38A7 | ENSG00000103042 |
| FCGR2B | ENSG00000072694 | RNF130 | ENSG00000113269 |
| PAQR8 | ENSG00000170915 |  | ENSG00000262505 |
| CCKBR | ENSG00000110148 | SMAGP | ENSG00000170545 |
| SLC16A10 | ENSG00000112394 | TYRO3 | ENSG00000092445 |
| TMTC2 | ENSG00000179104 | QSOX1 | ENSG00000116260 |
| SMIM11 | ENSG00000205670 | FGF6 | ENSG00000111241 |
| GPR144 | ENSG00000180264 | ZDHHC12 | ENSG00000160446 |
| TMEM186 | ENSG00000184857 | NGFR | ENSG00000064300 |
| EDA2R | ENSG00000131080 | SLC12A3 | ENSG00000070915 |
| ATP10D | ENSG00000145246 | CATSPERG | ENSG00000099338 |
| GBGT1 | ENSG00000148288 | PRR7 | ENSG00000131188 |
| GABRA1 | ENSG00000022355 | KIR2DL1 | ENSG00000275276 |
| TAP2 | ENSG00000237599 | OR1S1 | ENSG00000280204 |
| CAV3 | ENSG00000182533 | SEMA5B | ENSG00000082684 |
| FAIM2 | ENSG00000135472 | IL4I1 | ENSG00000104951 |
| TMEM216 | ENSG00000187049 | FFAR3 | ENSG00000185897 |
| CD1D | ENSG00000158473 | TMEM121 | ENSG00000184986 |
| CYP1A1 | ENSG00000140465 | TRPM2 | ENSG00000142185 |
| OR12D3 | ENSG00000251394 | IGF2R | ENSG00000197081 |
| TMTC1 | ENSG00000133687 | HLA-A | ENSG00000229215 |
|  | ENSG00000254875 | TMEM169 | ENSG00000163449 |
| STIM1 | ENSG00000167323 | C9orf69 | ENSG00000238227 |
| CDSN | ENSG00000237165 | C6orf25 | ENSG00000228090 |
| TMEM160 | ENSG00000130748 | SLC24A1 | ENSG00000074621 |
| BCL2L1 | ENSG00000171552 | TAS2R46 | ENSG00000262525 |
| KIR3DL3 | ENSG00000276196 | XKR9 | ENSG00000221947 |
| FCAR | ENSG00000275970 | CDH22 | ENSG00000149654 |
| P2RY12 | ENSG00000169313 | SLC46A1 | ENSG00000076351 |
| MIA-RAB4B | ENSG00000268975 | HEG1 | ENSG00000173706 |
| CACNA1B | ENSG00000148408 | AMIGO1 | ENSG00000181754 |
| PAG1 | ENSG00000076641 | ATP9B | ENSG00000166377 |
| CACNG3 | ENSG00000006116 | TMPRSS11E | ENSG00000087128 |
| TAS2R14 | ENSG00000261984 | IL25 | ENSG00000166090 |

TABLE 5-continued

Gene List

| HGNC symbol ID | Ensembl Gene | HGNC symbol ID | Ensembl Gene |
|---|---|---|---|
| ENTPD1 | ENSG00000138185 | CLEC4F | ENSG00000152672 |
| C1orf162 | ENSG00000143110 | | ENSG00000260342 |
| CMTM6 | ENSG00000091317 | ENPP2 | ENSG00000136960 |
| NCR1 | ENSG00000278362 | CCR4 | ENSG00000183813 |
| SLC10A7 | ENSG00000120519 | CRIM1 | ENSG00000150938 |
| FCGR2A | ENSG00000143226 | | ENSG00000258674 |
| CASC4 | ENSG00000166734 | CHRFAM7A | ENSG00000166664 |
| SGPP2 | ENSG00000163082 | GABRA2 | ENSG00000151834 |
| P2RY13 | ENSG00000181631 | C9orf89 | ENSG00000165233 |
| CXCR6 | ENSG00000172215 | TM9SF3 | ENSG00000077147 |
| DST | ENSG00000151914 | DHRS2 | ENSG00000100867 |
| TMEM91 | ENSG00000142046 | CHRNA4 | ENSG00000101204 |
| KIAA1324L | ENSG00000164659 | NRXN2 | ENSG00000110076 |
| CD244 | ENSG00000122223 | OR2W1 | ENSG00000206525 |
| AQP9 | ENSG00000103569 | MTUS1 | ENSG00000129422 |
| CUX1 | ENSG00000257923 | ALPK1 | ENSG00000073331 |
| SPTLC2 | ENSG00000100596 | OR8D2 | ENSG00000279116 |
| SHISA5 | ENSG00000164054 | CST9L | ENSG00000101435 |
| TYW1 | ENSG00000198874 | OR11A1 | ENSG00000230780 |
| MRVI1 | ENSG00000072952 | OR2W1 | ENSG00000227639 |
| PTPRO | ENSG00000151490 | PTGER4 | ENSG00000171522 |
| CTSA | ENSG00000064601 | DYRK2 | ENSG00000127334 |
| OR5V1 | ENSG00000233046 | | ENSG00000259371 |
| KCNJ9 | ENSG00000162728 | OR14J1 | ENSG00000112459 |
| PTPRM | ENSG00000173482 | CHST7 | ENSG00000147119 |
| TAS2R43 | ENSG00000262612 | OR10C1 | ENSG00000224234 |
| COL25A1 | ENSG00000188517 | CD36 | ENSG00000135218 |
| CHST8 | ENSG00000124302 | TRPV3 | ENSG00000167723 |
| DGCR2 | ENSG00000070413 | FDPS | ENSG00000160752 |
| KIR2DL1 | ENSG00000275080 | SLC5A12 | ENSG00000148942 |
| LTB | ENSG00000238114 | OR6J1 | ENSG00000255804 |
| PVRL3 | ENSG00000177707 | LDLRAD4 | ENSG00000168675 |
| TMEM74 | ENSG00000164841 | SLC16A8 | ENSG00000100156 |
| CLEC3A | ENSG00000166509 | SLC35E4 | ENSG00000100036 |
| JAGN1 | ENSG00000171135 | P2RY14 | ENSG00000174944 |
| EPHB2 | ENSG00000133216 | TMEM210 | ENSG00000185863 |
| DNAJC13 | ENSG00000138246 | CHRM1 | ENSG00000168539 |
| FLT4 | ENSG00000037280 | COL24A1 | ENSG00000171502 |
| MMP24 | ENSG00000125966 | OR6V1 | ENSG00000225781 |
| HLA-DQB2 | ENSG00000228254 | METTL7B | ENSG00000170439 |
| DSEL | ENSG00000262102 | TPSG1 | ENSG00000116176 |
| EBPL | ENSG00000123179 | KLHL31 | ENSG00000124743 |
| KCNN3 | ENSG00000143603 | DAD1 | ENSG00000129562 |
| TAS2R13 | ENSG00000273457 | RNF175 | ENSG00000145428 |
| TAS2R10 | ENSG00000272805 | GPM6B | ENSG00000046653 |
| CYP26B1 | ENSG00000003137 | CDRT15L2 | ENSG00000214819 |
| AGPAT1 | ENSG00000206324 | HLA-G | ENSG00000206506 |
| PVR | ENSG00000073008 | PCDHGB4 | ENSG00000253953 |
| CECR6 | ENSG00000183307 | GPR4 | ENSG00000177464 |
| UGT2B28 | ENSG00000135226 | NDUFB1 | ENSG00000183648 |
| TMEM161B | ENSG00000164180 | CARKD | ENSG00000213995 |
| CLPSL2 | ENSG00000196748 | NEU1 | ENSG00000227129 |
| TAS2R20 | ENSG00000273092 | KIR2DL3 | ENSG00000274410 |
| HLA-F | ENSG00000229698 | F2RL3 | ENSG00000127533 |
| PIRT | ENSG00000233670 | MAN2A2 | ENSG00000196547 |
| PRRT1 | ENSG00000229071 | CLDN25 | ENSG00000228607 |
| CYP2U1 | ENSG00000155016 | LSMEM1 | ENSG00000181016 |
| GP6 | ENSG00000088053 | ERGIC3 | ENSG00000125991 |
| OR5M8 | ENSG00000181371 | MBOAT7 | ENSG00000275118 |
| LRFN2 | ENSG00000156564 | KIR2DL4 | ENSG00000278074 |
| FCGR3B | ENSG00000162747 | PCDHGA8 | ENSG00000253767 |
| MCEMP1 | ENSG00000183019 | CHRNA9 | ENSG00000174343 |
| TAS2R19 | ENSG00000263028 | | ENSG00000272305 |
| HLA-DOA | ENSG00000206292 | DUOX1 | ENSG00000137857 |
| WBSCR28 | ENSG00000175877 | SLC1A6 | ENSG00000105143 |
| TSPAN32 | ENSG00000064201 | APOC1 | ENSG00000130208 |
| COL11A2 | ENSG00000206290 | CMTM3 | ENSG00000140931 |
| OR9A2 | ENSG00000179468 | ATP1B4 | ENSG00000101892 |
| SSPN | ENSG00000123096 | JTB | ENSG00000143543 |
| HCST | ENSG00000126264 | TMEM107 | ENSG00000179029 |
| OPN1MW | ENSG00000269433 | SLC9A6 | ENSG00000198689 |
| SIRPB2 | ENSG00000196209 | SLC9A5 | ENSG00000135740 |
| NDUFA3 | ENSG00000276061 | CCL22 | ENSG00000102962 |
| SSR1 | ENSG00000124783 | SLC16A7 | ENSG00000118596 |
| ASB11 | ENSG00000165192 | KIR2DL1 | ENSG00000278821 |

TABLE 5-continued

Gene List

| HGNC symbol ID | Ensembl Gene | HGNC symbol ID | Ensembl Gene |
|---|---|---|---|
| TMEM179B | ENSG00000185475 | REEP2 | ENSG00000132563 |
| EVI5L | ENSG00000142459 | ABCB9 | ENSG00000150967 |
| OR12D2 | ENSG00000235966 | PGAP3 | ENSG00000161395 |
| GRID1 | ENSG00000182771 | LAMP2 | ENSG00000005893 |
| CLN5 | ENSG00000102805 | COL11A2 | ENSG00000223699 |
| OPN1MW2 | ENSG00000166160 | KCNJ4 | ENSG00000168135 |
| CNGA3 | ENSG00000144191 | ACSBG2 | ENSG00000130377 |
| ITGA9 | ENSG00000144668 | ARL6IP1 | ENSG00000170540 |
| TSPO2 | ENSG00000112212 | ITGA6 | ENSG00000091409 |
| SCD5 | ENSG00000145284 | CYP2E1 | ENSG00000130649 |
| OR6C75 | ENSG00000187857 | GPR78 | ENSG00000155269 |
| LRRC37A3 | ENSG00000176809 | LMBRD1 | ENSG00000168216 |
| TMEM98 | ENSG00000006042 | PCDHA5 | ENSG00000204965 |
| LST1 | ENSG00000206433 | LILRA6 | ENSG00000277177 |
| KIR2DS4 | ENSG00000274406 | SPATA31A7 | ENSG00000276040 |
| ALG1 | ENSG00000033011 | GRIK5 | ENSG00000105737 |
| PTPRE | ENSG00000132334 | TMEM87A | ENSG00000103978 |
| SOAT1 | ENSG00000057252 | CNR2 | ENSG00000188822 |
| SPINT1 | ENSG00000166145 | RMDN3 | ENSG00000137824 |
| RELL1 | ENSG00000181826 | EDNRA | ENSG00000151617 |
| USH2A | ENSG00000042781 | PCDHA4 | ENSG00000204967 |
| HLA-DQB1 | ENSG00000225824 | DYSF | ENSG00000135636 |
| HLA-DMB | ENSG00000241296 | BTNL2 | ENSG00000204290 |
| CHRNB4 | ENSG00000117971 | SV2B | ENSG00000185518 |
| RNF26 | ENSG00000173456 | TMEM165 | ENSG00000134851 |
| TMEM63C | ENSG00000165548 | ITGA7 | ENSG00000135424 |
| IFNLR1 | ENSG00000185436 | GPR171 | ENSG00000174946 |
| TMED5 | ENSG00000117500 | ATP12A | ENSG00000075673 |
| SEC11C | ENSG00000166562 | ABCA4 | ENSG00000198691 |
| TIMM21 | ENSG00000075336 | LILRB3 | ENSG00000275019 |
| CNTN6 | ENSG00000134115 | SLC36A1 | ENSG00000123643 |
| KIR2DS1 | ENSG00000275421 | RTP3 | ENSG00000163825 |
| AIFM2 | ENSG00000042286 | LRRC15 | ENSG00000172061 |
| CLRN2 | ENSG00000249581 | CD46 | ENSG00000117335 |
| CYP2A7 | ENSG00000198077 | TAP1 | ENSG00000224748 |
| CCDC112 | ENSG00000164221 | NRG1 | ENSG00000157168 |
| PIGS | ENSG00000087111 | GPR50 | ENSG00000102195 |
| BEAN1 | ENSG00000166546 | IGSF10 | ENSG00000152580 |
| MAS1L | ENSG00000237284 | FCAR | ENSG00000276858 |
| TMEM86A | ENSG00000151117 | STEAP4 | ENSG00000127954 |
| OR2W1 | ENSG00000228652 | XKR4 | ENSG00000206579 |
| CLCN4 | ENSG00000073464 | FADS6 | ENSG00000172782 |
| KIR2DL3 | ENSG00000276459 | KIR2DS3 | ENSG00000277193 |
| ENTPD7 | ENSG00000198018 | ZACN | ENSG00000186919 |
| STX7 | ENSG00000079950 | KIR2DS4 | ENSG00000274957 |
| NIPAL3 | ENSG00000001461 | ABCC4 | ENSG00000125257 |
| CEACAM19 | ENSG00000186567 | LILRB4 | ENSG00000186818 |
| CXCL9 | ENSG00000138755 | GP5 | ENSG00000178732 |
| ABCA12 | ENSG00000144452 | SLC9C2 | ENSG00000162753 |
| CDC14B | ENSG00000081377 | L1CAM | ENSG00000198910 |
| LAMP1 | ENSG00000185896 | ITGB1 | ENSG00000150093 |
| RNF152 | ENSG00000176641 | KIR3DL3 | ENSG00000274763 |
| TMEM178A | ENSG00000152154 | SLC22A6 | ENSG00000197901 |
| SLC35G4 | ENSG00000236396 | KIR2DL4 | ENSG00000277355 |
| KLK5 | ENSG00000167754 | ATG9A | ENSG00000198925 |
| KIR2DL1 | ENSG00000278503 | ROR2 | ENSG00000169071 |
| LYPD6B | ENSG00000150556 | LAYN | ENSG00000204381 |
| SLC39A5 | ENSG00000139540 | OR10Q1 | ENSG00000180475 |
| FCGR2C | ENSG00000244682 | IGSF11 | ENSG00000144847 |
| PIGV | ENSG00000060642 | MIA3 | ENSG00000154305 |
| AGER | ENSG00000234729 | OR2Z1 | ENSG00000181733 |
| AQP3 | ENSG00000165272 | LAIR1 | ENSG00000278154 |
| CD40 | ENSG00000101017 | OR2C1 | ENSG00000168158 |
| CNTNAP3 | ENSG00000106714 | SLITRK5 | ENSG00000165300 |
| KIR2DL4 | ENSG00000274232 | LY6G6C | ENSG00000235452 |
| KIR2DL5B | ENSG00000275946 | ICOS | ENSG00000163600 |
| MGARP | ENSG00000137463 | MS4A8 | ENSG00000166959 |
| KLHL5 | ENSG00000109790 | SIGLEC15 | ENSG00000197046 |
| LGR5 | ENSG00000139292 | C5orf15 | ENSG00000113583 |
| RHBDF2 | ENSG00000129667 | AIFM1 | ENSG00000156709 |
| PTPN5 | ENSG00000110786 | ATP6V0A1 | ENSG00000033627 |
| CD1E | ENSG00000158488 | KITLG | ENSG00000049130 |
| HLA-E | ENSG00000206493 | CALHM3 | ENSG00000183128 |
| TMEM8C | ENSG00000187616 | ZDHHC8 | ENSG00000099904 |
| OR8B2 | ENSG00000204293 | IFNGR1 | ENSG00000027697 |

TABLE 5-continued

Gene List

| HGNC symbol ID | Ensembl Gene | HGNC symbol ID | Ensembl Gene |
|---|---|---|---|
| UPK1B | ENSG00000114638 | ZDHHC9 | ENSG00000188706 |
| OR2A7 | ENSG00000243896 | MAVS | ENSG00000088888 |
| PTCHD2 | ENSG00000204624 | KIR2DL5B | ENSG00000274707 |
| SLC39A1 | ENSG00000143570 | TAS2R31 | ENSG00000263097 |
| GGT7 | ENSG00000131067 | CLEC14A | ENSG00000176435 |
| TMEM256 | ENSG00000205544 | TMEM235 | ENSG00000204278 |
| KIR2DL1 | ENSG00000278805 | KIR3DL2 | ENSG00000278656 |
| ADIPOR1 | ENSG00000159346 | TTYH3 | ENSG00000136295 |
| KCNC2 | ENSG00000166006 | ACBD5 | ENSG00000107897 |
| SMPD2 | ENSG00000135587 | OR51S1 | ENSG00000176922 |
| ITPR2 | ENSG00000123104 | ANO1 | ENSG00000131620 |
| KIR2DS5 | ENSG00000276676 | KIR2DS4 | ENSG00000276885 |
| P2RX2 | ENSG00000187848 | RNASE7 | ENSG00000165799 |
| RNF170 | ENSG00000120925 | TMEM223 | ENSG00000168569 |
| SORL1 | ENSG00000137642 | COX7A2L | ENSG00000115944 |
| GLP2R | ENSG00000065325 | SLC29A2 | ENSG00000174669 |
| PORCN | ENSG00000102312 | ATP2B3 | ENSG00000067842 |
| KCNC1 | ENSG00000129159 | OR51A7 | ENSG00000176895 |
| UGGT1 | ENSG00000136731 | SORT1 | ENSG00000134243 |
| OR2B3 | ENSG00000206524 | DRD1 | ENSG00000184845 |
| C2orf74 | ENSG00000237651 | GLT8D1 | ENSG00000016864 |
| NDFIP2 | ENSG00000102471 | SLC4A2 | ENSG00000164889 |
| SLC29A1 | ENSG00000112759 | HLA-DQA1 | ENSG00000225890 |
| KIR2DL3 | ENSG00000273887 | UNC5CL | ENSG00000124602 |
| TAZ | ENSG00000102125 | TSPAN4 | ENSG00000214063 |
| CTRB1 | ENSG00000168925 | FGFR4 | ENSG00000160867 |
| OR8B3 | ENSG00000196661 | TMPRSS3 | ENSG00000160183 |
| TAP2 | ENSG00000206235 | KIR2DL1 | ENSG00000276820 |
| ALG6 | ENSG00000088035 | HLA-DMB | ENSG00000242092 |
| MOGAT1 | ENSG00000124003 | EDA | ENSG00000158813 |
| OR8B4 | ENSG00000280090 | SLC35A4 | ENSG00000176087 |
| SCAMP3 | ENSG00000263290 | CLDN11 | ENSG00000013297 |
| ADAM12 | ENSG00000148848 | MAS1L | ENSG00000228377 |
| OR8B8 | ENSG00000197125 | PCDHA8 | ENSG00000204962 |
| DCSTAMP | ENSG00000164935 | SMIM21 | ENSG00000206026 |
| MCU | ENSG00000156026 | PPT2 | ENSG00000206329 |
| ABHD14A | ENSG00000248487 | TNFRSF1A | ENSG00000067182 |
| CRLF2 | ENSG00000205755 | CHRNB3 | ENSG00000147432 |
| VIPR2 | ENSG00000106018 | OR2H2 | ENSG00000206512 |
| PTPLAD2 | ENSG00000188921 | RNF5 | ENSG00000183574 |
| KIR2DS1 | ENSG00000276327 | ST6GAL2 | ENSG00000144057 |
| IFI27L1 | ENSG00000165948 | TSPAN13 | ENSG00000106537 |
| BTN3A3 | ENSG00000111801 | LRRC19 | ENSG00000184434 |
| COMT | ENSG00000093010 | IL22 | ENSG00000127318 |
| RNF150 | ENSG00000170153 | PDZK1IP1 | ENSG00000162366 |
| FAM19A3 | ENSG00000184599 | ATP13A3 | ENSG00000133657 |
| OR11H4 | ENSG00000176198 | VTI1A | ENSG00000151532 |
| SMIM4 | ENSG00000168273 | OR8A1 | ENSG00000196119 |
| LRFN4 | ENSG00000173621 | GALNT7 | ENSG00000109586 |
| IFNL2 | ENSG00000183709 | HGFAC | ENSG00000109758 |
| TMEM189 | ENSG00000240849 | OR52R1 | ENSG00000279270 |
| TAS2R50 | ENSG00000273431 | N4BP2L2 | ENSG00000244754 |
| NEO1 | ENSG00000067141 | SIGLEC7 | ENSG00000168995 |
| SYNGR3 | ENSG00000127561 | EMR3 | ENSG00000131355 |
| RNF139 | ENSG00000170881 | HLA-C | ENSG00000233841 |
| CHST15 | ENSG00000182022 | CYSLTR2 | ENSG00000152207 |
| LRFN5 | ENSG00000165379 | PDE3A | ENSG00000172572 |
| ARF4 | ENSG00000168374 | OR11A1 | ENSG00000206472 |
| KIR3DL3 | ENSG00000274639 | SLC34A1 | ENSG00000131183 |
| ADRA1B | ENSG00000170214 | TARM1 | ENSG00000248385 |
| NRM | ENSG00000236843 | MARCH8 | ENSG00000165406 |
| AGER | ENSG00000230514 | IGSF8 | ENSG00000162729 |
| LRRC55 | ENSG00000183908 | SLCO4C1 | ENSG00000173930 |
|  | ENSG00000275500 | MSMP | ENSG00000215183 |
| KIR2DL5B | ENSG00000275937 | PCDHAC1 | ENSG00000248383 |
| CX3CR1 | ENSG00000168329 | ABCA10 | ENSG00000154263 |
| CHIC2 | ENSG00000109220 | ALDH6A1 | ENSG00000119711 |
| SSR2 | ENSG00000163479 | CCDC134 | ENSG00000100147 |
| OR4F17 | ENSG00000176695 | CYSLTR1 | ENSG00000173198 |
| NMB | ENSG00000197696 | LST1 | ENSG00000231048 |
| ATP5G3 | ENSG00000154518 | SLC43A3 | ENSG00000134802 |
| TMEM241 | ENSG00000134490 | CLPS | ENSG00000137392 |
| HEPHL1 | ENSG00000181333 | GZMM | ENSG00000197540 |
| SV2A | ENSG00000159164 | CXCL14 | ENSG00000145824 |
| B4GALT6 | ENSG00000118276 | BSND | ENSG00000162399 |

TABLE 5-continued

Gene List

| HGNC symbol ID | Ensembl Gene | HGNC symbol ID | Ensembl Gene |
|---|---|---|---|
| DIRC2 | ENSG00000138463 | FAP | ENSG00000078098 |
| TOR1B | ENSG00000136816 | HLA-DMA | ENSG00000243189 |
| KIR3DS1 | ENSG00000274465 | GABBR1 | ENSG00000206511 |
| SLC7A14 | ENSG00000013293 | NMUR2 | ENSG00000132911 |
| ADAM30 | ENSG00000134249 | FAM57A | ENSG00000167695 |
| EML2 | ENSG00000125746 | OXGR1 | ENSG00000165621 |
| TBC1D20 | ENSG00000125875 | MARVELD1 | ENSG00000155254 |
| LILRB4 | ENSG00000275730 | TLCD1 | ENSG00000160606 |
| TRPM5 | ENSG00000070985 | TAPBP | ENSG00000112493 |
| TRPV6 | ENSG00000165125 | ORAI2 | ENSG00000160991 |
| GDE1 | ENSG00000006007 | OR13C3 | ENSG00000204246 |
| MFRP | ENSG00000259159 | OR9I1 | ENSG00000172377 |
| C1QTNF5 | ENSG00000259159 | GP1BB | ENSG00000203618 |
| OR13C4 | ENSG00000148136 | ORAI3 | ENSG00000175938 |
| PIGZ | ENSG00000119227 | VWA9 | ENSG00000138614 |
| GRIN2D | ENSG00000105464 | KLRC4-KLRK1 | ENSG00000255819 |
| ATP2A2 | ENSG00000174437 | ACSL3 | ENSG00000123983 |
| KIR2DL4 | ENSG00000274189 | GJA8 | ENSG00000121634 |
| TMEM174 | ENSG00000164325 |  | ENSG00000105520 |
| OR51T1 | ENSG00000176900 | TM4SF20 | ENSG00000168955 |
| FCAR | ENSG00000275564 | VKORC1 | ENSG00000167397 |
| ERVW-1 | ENSG00000242950 | TMEM128 | ENSG00000132406 |
| KCNK17 | ENSG00000124780 | OR9Q1 | ENSG00000186509 |
| APOL4 | ENSG00000100336 | GPAA1 | ENSG00000197858 |
| PCDH11Y | ENSG00000099715 | GDAP1L1 | ENSG00000124194 |
| DDR1 | ENSG00000230456 | ITGB5 | ENSG00000082781 |
| PET117 | ENSG00000232838 | GPR37L1 | ENSG00000170075 |
| LRRC37A2 | ENSG00000238083 | CYP46A1 | ENSG00000036530 |
| DNAH10 | ENSG00000197653 | HLA-DOB | ENSG00000239457 |
| CDKAL1 | ENSG00000145996 | KCNS3 | ENSG00000170745 |
| CAPZA2 | ENSG00000198898 | MANSC1 | ENSG00000111261 |
| DDX59 | ENSG00000118197 | HEPACAM2 | ENSG00000188175 |
| FREM1 | ENSG00000164946 | CEBPZOS | ENSG00000218739 |
| PCDH7 | ENSG00000169851 | OR12D2 | ENSG00000204690 |
| ITPRIPL2 | ENSG00000205730 | OR6Q1 | ENSG00000279051 |
| GJA5 | ENSG00000265107 | ABHD16A | ENSG00000206403 |
| LRP2 | ENSG00000081479 | NRM | ENSG00000228854 |
| ACSM1 | ENSG00000166743 | DPP7 | ENSG00000176978 |
| KIR2DS4 | ENSG00000276154 | TEX28 | ENSG00000278057 |
|  | ENSG00000254979 | TMEM263 | ENSG00000151135 |
| OR51F1 | ENSG00000280021 | CD1A | ENSG00000158477 |
| P2RY11 | ENSG00000244165 | HIATL1 | ENSG00000148110 |
| FAM26F | ENSG00000188820 | OR5V1 | ENSG00000112461 |
| OR12D3 | ENSG00000204692 | NTN1 | ENSG00000065320 |
| TSPAN2 | ENSG00000134198 | TMEM182 | ENSG00000170417 |
| OR10C1 | ENSG00000204689 | TMEM141 | ENSG00000244187 |
| KIR3DL1 | ENSG00000278856 | MGST2 | ENSG00000085871 |
| KIR2DL1 | ENSG00000278495 | PTGFRN | ENSG00000134247 |
| MARCH5 | ENSG00000198060 | IFNB1 | ENSG00000171855 |
| NCR3 | ENSG00000206430 | HLA-DOA | ENSG00000232962 |
| ZDHHC13 | ENSG00000177054 | SCN11A | ENSG00000168356 |
| NDST2 | ENSG00000166507 | RNF24 | ENSG00000101236 |
| SLC11A1 | ENSG00000018280 | SPATA31D1 | ENSG00000214929 |
| C22orf24 | ENSG00000128254 | TMEM253 | ENSG00000232070 |
| NRM | ENSG00000235773 | OR13C8 | ENSG00000186943 |
| ACSS2 | ENSG00000131069 | PPFIA1 | ENSG00000131626 |
| ACSM2B | ENSG00000066813 | COX15 | ENSG00000014919 |
| SLC16A5 | ENSG00000170190 | PCDHAC2 | ENSG00000243232 |
| OR51F2 | ENSG00000176925 | CNPPD1 | ENSG00000115649 |
| KIR2DL3 | ENSG00000275623 | RNF103-CHMP3 | ENSG00000249884 |
| FAM134C | ENSG00000141699 | TMEM88B | ENSG00000205116 |
| KIR2DS2 | ENSG00000276258 | KCNN4 | ENSG00000104783 |
| CYP2A6 | ENSG00000255974 | SYT15 | ENSG00000204176 |
| TSPAN11 | ENSG00000110900 | HLA-C | ENSG00000204525 |
| C6orf10 | ENSG00000236672 | GALNT15 | ENSG00000131386 |
| TRPC7 | ENSG00000069018 | TPM1 | ENSG00000140416 |
| RNF103 | ENSG00000239305 | CRLF3 | ENSG00000176390 |
| CTAGE5 | ENSG00000150527 | PAQR5 | ENSG00000137819 |
| KIR3DL2 | ENSG00000276424 | ABI3BP | ENSG00000154175 |
| HGSNAT | ENSG00000165102 | SERF1B | ENSG00000205572 |
| SLC5A1 | ENSG00000100170 | ITGA1 | ENSG00000213949 |
| TMEM220 | ENSG00000187824 | PTPRQ | ENSG00000139304 |
| PLD3 | ENSG00000105223 | OR2J2 | ENSG00000204700 |
| TIMM50 | ENSG00000105197 | ATP13A2 | ENSG00000159363 |
| MFRP | ENSG00000235718 | GJA3 | ENSG00000121743 |

TABLE 5-continued

Gene List

| HGNC symbol ID | Ensembl Gene | HGNC symbol ID | Ensembl Gene |
|---|---|---|---|
| HLA-DQA2 | ENSG00000231823 | TMX4 | ENSG00000125827 |
| FZD4 | ENSG00000174804 | PCDH9 | ENSG00000184226 |
| TMEM140 | ENSG00000146859 | LILRB1 | ENSG00000104972 |
| LITAF | ENSG00000189067 | PANX3 | ENSG00000154143 |
| PI16 | ENSG00000164530 | TRPC4 | ENSG00000133107 |
| GAL3ST4 | ENSG00000197093 | PTPRS | ENSG00000105426 |
| HLA-DMA | ENSG00000242361 | OR5D13 | ENSG00000279761 |
| AWAT1 | ENSG00000204195 | FER1L6 | ENSG00000214814 |
| LRRN4CL | ENSG00000177363 | GRIA2 | ENSG00000120251 |
| KCNK3 | ENSG00000171303 | HLA-DQB2 | ENSG00000224305 |
| FZD3 | ENSG00000104290 | OR4F6 | ENSG00000184140 |
| MUC17 | ENSG00000169876 | DDR1 | ENSG00000234078 |
| KIR3DL3 | ENSG00000276328 | KIR3DL2 | ENSG00000276882 |
| RNF43 | ENSG00000108375 | GPR61 | ENSG00000156097 |
| C19orf18 | ENSG00000177025 | OR4F15 | ENSG00000182854 |
| OSTC | ENSG00000198856 | ZDHHC24 | ENSG00000174165 |
|  | ENSG00000117598 | CEND1 | ENSG00000184524 |
| C1QB | ENSG00000173369 | IGSF1 | ENSG00000147255 |
| TAS2R4 | ENSG00000127364 | TMX2 | ENSG00000213593 |
| CLDN12 | ENSG00000157224 | YME1L1 | ENSG00000136758 |
| SLC6A12 | ENSG00000111181 | ACPP | ENSG00000014257 |
| ENPP3 | ENSG00000154269 | C6orf136 | ENSG00000204564 |
| FAT1 | ENSG00000083857 | BRS3 | ENSG00000102239 |
| THSD7A | ENSG00000005108 | P2RX6 | ENSG00000099957 |
| MCHR1 | ENSG00000128285 | SLC15A2 | ENSG00000163406 |
| FZD5 | ENSG00000163251 | LRP1B | ENSG00000168702 |
| CMTM5 | ENSG00000166091 | OR8S1 | ENSG00000197376 |
| AQP1 | ENSG00000240583 | KCNJ12 | ENSG00000184185 |
| KCNJ6 | ENSG00000157542 | KIR2DL2 | ENSG00000275407 |
| CYB5R1 | ENSG00000159348 | FAAH2 | ENSG00000165591 |
| MMEL1 | ENSG00000142606 | OR8J1 | ENSG00000172487 |
| HLA-DOA | ENSG00000235744 | ANO10 | ENSG00000160746 |
| SLC6A19 | ENSG00000174358 | ATP11C | ENSG00000101974 |
| WNT11 | ENSG00000085741 | TMEM133 | ENSG00000170647 |
| SLC39A13 | ENSG00000165915 | SIGLEC5 | ENSG00000105501 |
| LYVE1 | ENSG00000133800 | MIA | ENSG00000261857 |
| ASB18 | ENSG00000182177 | LAG3 | ENSG00000089692 |
| TMEM63B | ENSG00000137216 | BAMBI | ENSG00000095739 |
| DNAJB11 | ENSG00000090520 | KIR3DL1 | ENSG00000276329 |
| HLA-DRA | ENSG00000227993 | NAT2 | ENSG00000156006 |
| SLC7A4 | ENSG00000099960 | RMDN2 | ENSG00000115841 |
| NKAIN2 | ENSG00000188580 | ZNF451 | ENSG00000112200 |
| IL7R | ENSG00000168685 | GGT1 | ENSG00000100031 |
| TMEM33 | ENSG00000109133 | GJD4 | ENSG00000177291 |
| OR4C5 | ENSG00000176540 | TMEM18 | ENSG00000151353 |
| SLC22A11 | ENSG00000168065 | SLC38A11 | ENSG00000169507 |
| OR4C3 | ENSG00000176547 | KCNE4 | ENSG00000152049 |
| PAAF1 | ENSG00000175575 | TMEM255B | ENSG00000184497 |
| ZDHHC22 | ENSG00000177108 | TMEM239 | ENSG00000198326 |
| NLGN4Y | ENSG00000165246 | ABCA5 | ENSG00000154265 |
| CLEC6A | ENSG00000205846 | TMEM143 | ENSG00000161558 |
| CX3CL1 | ENSG00000006210 | ACKR2 | ENSG00000144648 |
| OR2A1 | ENSG00000221970 | KIR2DL5A | ENSG00000276392 |
| GPR25 | ENSG00000170128 | TMEM44 | ENSG00000145014 |
| C6orf10 | ENSG00000204296 | OR1D2 | ENSG00000184166 |
| IGSF23 | ENSG00000216588 | CSMD1 | ENSG00000183117 |
| CDSN | ENSG00000237123 | HCN3 | ENSG00000263324 |
| MAMDC4 | ENSG00000177943 | SIGLEC5 | ENSG00000268500 |
| DISP1 | ENSG00000154309 | OR10AD1 | ENSG00000172640 |
| NPIPB3 | ENSG00000169246 | GOLGA5 | ENSG00000066455 |
| HS3ST2 | ENSG00000122254 | OR4K17 | ENSG00000176230 |
| MAS1L | ENSG00000234954 | KIR3DS1 | ENSG00000276498 |
| G6PC3 | ENSG00000141349 | SLC13A2 | ENSG00000007216 |
| DEXI | ENSG00000182108 | ECSCR | ENSG00000279686 |
| PPAN-P2RY11 | ENSG00000243207 | CD3G | ENSG00000160654 |
| PIEZO2 | ENSG00000154864 | XYLT1 | ENSG00000103489 |
| RHBDD3 | ENSG00000100263 | PVRL2 | ENSG00000130202 |
| ATF7 | ENSG00000170653 | SGCE | ENSG00000127990 |
| RELL2 | ENSG00000164620 | CFTR | ENSG00000001626 |
| ADPRM | ENSG00000170222 | TPTE | ENSG00000274391 |
| OXER1 | ENSG00000162881 | CST9 | ENSG00000173335 |
| C5orf28 | ENSG00000151881 | OR10K1 | ENSG00000173285 |
| ADCY2 | ENSG00000078295 | TAS1R1 | ENSG00000173662 |
| PRDX4 | ENSG00000123131 | GRAMD1B | ENSG00000023171 |
| CD53 | ENSG00000143119 | GRM8 | ENSG00000179603 |

TABLE 5-continued

Gene List

| HGNC symbol ID | Ensembl Gene | HGNC symbol ID | Ensembl Gene |
|---|---|---|---|
| SLC44A4 | ENSG00000229077 | CACNG2 | ENSG00000166862 |
| ATP2B4 | ENSG00000058668 | AOC2 | ENSG00000131480 |
| MOG | ENSG00000236561 | ATRAID | ENSG00000138085 |
| ABCA9 | ENSG00000154258 | TMEM70 | ENSG00000175606 |
| EPHA3 | ENSG00000044524 | ECSCR | ENSG00000249751 |
| LILRB2 | ENSG00000274513 | TMEM87B | ENSG00000153214 |
| HCRTR2 | ENSG00000137252 | OR2B3 | ENSG00000226832 |
| BTNL2 | ENSG00000225845 | ICMT | ENSG00000116237 |
| ATP4B | ENSG00000186009 | KIAA0195 | ENSG00000177728 |
| TFRC | ENSG00000072274 | IL12RB1 | ENSG00000096996 |
| C5orf60 | ENSG00000204661 | FMR1NB | ENSG00000176988 |
| HTR1B | ENSG00000135312 | CLGN | ENSG00000153132 |
| OR4F4 | ENSG00000177693 | E2F5 | ENSG00000133740 |
| KCNJ15 | ENSG00000157551 | DCC | ENSG00000187323 |
| CYP4B1 | ENSG00000142973 | SLC30A4 | ENSG00000104154 |
| LMBRD2 | ENSG00000164187 | TUSC5 | ENSG00000184811 |
| HLA-DPA1 | ENSG00000236177 | GPR173 | ENSG00000184194 |
| SEMA3D | ENSG00000153993 | SP4 | ENSG00000105866 |
| SEMA4F | ENSG00000135622 | GTF3C3 | ENSG00000119041 |
| TMEM262 | ENSG00000187066 | WNT9A | ENSG00000143816 |
| LEPR | ENSG00000116678 | ZNF98 | ENSG00000197360 |
| DDR1 | ENSG00000137332 | OR13C5 | ENSG00000277556 |
| KCNH5 | ENSG00000140015 | PLIN5 | ENSG00000214456 |
| SPCS1 | ENSG00000114902 | SCNN1D | ENSG00000162572 |
| ZFPL1 | ENSG00000162300 | | ENSG00000255439 |
| CTAGE8 | ENSG00000244693 | MUSK | ENSG00000030304 |
| OR10T2 | ENSG00000186306 | ZDHHC2 | ENSG00000104219 |
| FCAR | ENSG00000273738 | SCG2 | ENSG00000171951 |
| OR10K2 | ENSG00000180708 | TMEM199 | ENSG00000244045 |
| IL20RB | ENSG00000174564 | PRTG | ENSG00000166450 |
| KCNN1 | ENSG00000105642 | OR4M2 | ENSG00000274102 |
| SMIM24 | ENSG00000095932 | SIGLEC14 | ENSG00000254415 |
| GPR65 | ENSG00000140030 | PMP22 | ENSG00000109099 |
| SLC27A3 | ENSG00000143554 | ST6GALNAC4 | ENSG00000136840 |
| TAS2R3 | ENSG00000127362 | RRM1 | ENSG00000167325 |
| CD40LG | ENSG00000102245 | RNF145 | ENSG00000145860 |
| PTPRA | ENSG00000132670 | MDK | ENSG00000110492 |
| MLC1 | ENSG00000100427 | SIGMAR1 | ENSG00000147955 |
| MOG | ENSG00000137345 | HLA-G | ENSG00000204632 |
| KIR3DL3 | ENSG00000277028 | KCNJ18 | ENSG00000260458 |
| SORCS3 | ENSG00000156395 | VMP1 | ENSG00000062716 |
| ART3 | ENSG00000156219 | CLEC1A | ENSG00000150048 |
| PXYLP1 | ENSG00000155893 | TMEM52 | ENSG00000178821 |
| FCRL6 | ENSG00000181036 | CSF1 | ENSG00000184371 |
| TMEM248 | ENSG00000106609 | MC2R | ENSG00000185231 |
| EXTL1 | ENSG00000158008 | PNPLA7 | ENSG00000130653 |
| MEGF6 | ENSG00000162591 | SEC11A | ENSG00000140612 |
| RFT1 | ENSG00000163933 | NTRK2 | ENSG00000148053 |
| XPR1 | ENSG00000143324 | GPR124 | ENSG00000020181 |
| CCL5 | ENSG00000271503 | SLC10A5 | ENSG00000253598 |
| | ENSG00000259916 | CELSR3 | ENSG00000008300 |
| KIR3DL1 | ENSG00000273518 | ATP8A2 | ENSG00000132932 |
| TMEM254 | ENSG00000133678 | MICA | ENSG00000233051 |
| OR6C65 | ENSG00000205328 | KIR2DL1 | ENSG00000278738 |
| GPR114 | ENSG00000159618 | TM7SF3 | ENSG00000064115 |
| XYLT2 | ENSG00000015532 | CDHR5 | ENSG00000099834 |
| FIBCD1 | ENSG00000130720 | FAM209B | ENSG00000213714 |
| CYP2F1 | ENSG00000197446 | SLC30A5 | ENSG00000145740 |
| PCDHA9 | ENSG00000204961 | EPSTI1 | ENSG00000133106 |
| TMEM222 | ENSG00000186501 | ADIPOR2 | ENSG00000006831 |
| TLR5 | ENSG00000187554 | ERGIC1 | ENSG00000113719 |
| CES5A | ENSG00000261972 | CHCHD3 | ENSG00000106554 |
| PKD1 | ENSG00000008710 | MFSD3 | ENSG00000167700 |
| TMX2-CTNND1 | ENSG00000254462 | TSPAN8 | ENSG00000127324 |
| DNAJC18 | ENSG00000170464 | OR2J3 | ENSG00000206522 |
| HRK | ENSG00000135116 | C15orf48 | ENSG00000166920 |
| MICA | ENSG00000231225 | SLC27A2 | ENSG00000140284 |
| GALNS | ENSG00000141012 | OR4N5 | ENSG00000184394 |
| HS6ST2 | ENSG00000171004 | FAM134A | ENSG00000144567 |
| MPPE1 | ENSG00000154889 | | ENSG00000206463 |
| ABCB6 | ENSG00000115657 | CST3 | ENSG00000101439 |
| MFSD9 | ENSG00000135953 | ICAM3 | ENSG00000076662 |
| FTO | ENSG00000140718 | HLA-DPB1 | ENSG00000230708 |
| COX10 | ENSG00000006695 | GRIA1 | ENSG00000155511 |
| CLPTM1 | ENSG00000104853 | UGT2B7 | ENSG00000171234 |

TABLE 5-continued

Gene List

| HGNC symbol ID | Ensembl Gene | HGNC symbol ID | Ensembl Gene |
|---|---|---|---|
| GPR42 | ENSG00000126251 | SCAMP5 | ENSG00000198794 |
| OR10R2 | ENSG00000198965 | PTPN2 | ENSG00000175354 |
| FCRL5 | ENSG00000143297 | PCDHA1 | ENSG00000204970 |
| FZD6 | ENSG00000164930 | OR6Y1 | ENSG00000197532 |
| SLC10A2 | ENSG00000125255 | ATG9B | ENSG00000181652 |
| OR13C2 | ENSG00000276119 | COX18 | ENSG00000163626 |
| GJC3 | ENSG00000176402 | OR6P1 | ENSG00000186440 |
| WDR83OS | ENSG00000105583 | OR2H1 | ENSG00000232984 |
| GAL3ST2 | ENSG00000154252 | SLC17A8 | ENSG00000179520 |
| FAM171A1 | ENSG00000148468 | VSTM2B | ENSG00000187135 |
| ST8SIA2 | ENSG00000140557 | OR10X1 | ENSG00000279111 |
| WSCD1 | ENSG00000179314 | LPAR6 | ENSG00000139679 |
| MFSD2B | ENSG00000205639 | CYB5R2 | ENSG00000166394 |
| CLCA2 | ENSG00000137975 | SPINK2 | ENSG00000128040 |
| TNC | ENSG00000041982 | FAM174B | ENSG00000185442 |
| C2orf83 | ENSG00000042304 | LPAR5 | ENSG00000184574 |
| KCNMA1 | ENSG00000156113 | OR2V1 | ENSG00000185372 |
| IYD | ENSG00000009765 | NEU1 | ENSG00000223957 |
| FAM210A | ENSG00000177150 | SMPD1 | ENSG00000166311 |
| ACPT | ENSG00000142513 | GPR141 | ENSG00000187037 |
| HCN1 | ENSG00000164588 | NPFFR1 | ENSG00000148734 |
| SLC7A11 | ENSG00000151012 | RHBDL3 | ENSG00000141314 |
| HTR1E | ENSG00000168830 | RPN1 | ENSG00000163902 |
|  | ENSG00000231350 | SEMA4D | ENSG00000187764 |
| THOC3 | ENSG00000051596 | MRGPRE | ENSG00000184350 |
| OPN4 | ENSG00000122375 | SLC4A3 | ENSG00000114923 |
| SPAST | ENSG00000021574 | C19orf24 | ENSG00000228300 |
| MARCH4 | ENSG00000144583 | IL3RA | ENSG00000185291 |
| TSPAN9 | ENSG00000011105 | MTNR1B | ENSG00000134640 |
| PFKP | ENSG00000067057 | TMC3 | ENSG00000188869 |
| SLC19A1 | ENSG00000173638 | CSMD3 | ENSG00000164796 |
| SLC35D3 | ENSG00000182747 | CKLF-CMTM1 | ENSG00000254788 |
| HAS3 | ENSG00000103044 | TNFRSF10A | ENSG00000104689 |
| CRHR2 | ENSG00000106113 | OR10Z1 | ENSG00000198967 |
| OR4N4 | ENSG00000183706 | FFAR4 | ENSG00000186188 |
| SUSD4 | ENSG00000143502 | LAX1 | ENSG00000122188 |
| TMED9 | ENSG00000184840 | HLA-DPB1 | ENSG00000223826 |
| TRPM8 | ENSG00000144481 | KCNB1 | ENSG00000158445 |
| SLC7A5 | ENSG00000103257 | ATP8B2 | ENSG00000143515 |
| FAM198A | ENSG00000144649 | CADM2 | ENSG00000175161 |
| FCGRT | ENSG00000104870 | KIR2DL4 | ENSG00000277076 |
| FCAR | ENSG00000186431 | SLC6A16 | ENSG00000063127 |
| LTBR | ENSG00000111321 | PRUNE2 | ENSG00000106772 |
| ADORA3 | ENSG00000121933 | NDUFB11 | ENSG00000147123 |
| EPHA8 | ENSG00000070886 | CKLF | ENSG00000217555 |
| PTPRZ1 | ENSG00000106278 | KCNC3 | ENSG00000131398 |
| GPR137C | ENSG00000180998 | SLC31A1 | ENSG00000136868 |
| HIGD2A | ENSG00000146066 | FAM3A | ENSG00000071889 |
| CLEC2D | ENSG00000069493 | GRIK3 | ENSG00000163873 |
| SLC29A4 | ENSG00000164638 | PCDH15 | ENSG00000150275 |
| SLC38A2 | ENSG00000134294 | SCN8A | ENSG00000196876 |
| RBM41 | ENSG00000089682 | ZDHHC16 | ENSG00000171307 |
| ELP6 | ENSG00000163832 | DDR2 | ENSG00000162733 |
| OR2A42 | ENSG00000212807 | UNC93A | ENSG00000112494 |
| AGER | ENSG00000229058 | B4GALNT2 | ENSG00000167080 |
| MEGF10 | ENSG00000145794 | UGT2B11 | ENSG00000213759 |
| P2RY2 | ENSG00000175591 | SLC6A11 | ENSG00000132164 |
| BIK | ENSG00000100290 | TSNARE1 | ENSG00000171045 |
| SYNDIG1L | ENSG00000183379 | ITGB8 | ENSG00000105855 |
| OR9A4 | ENSG00000258083 | TMED4 | ENSG00000158604 |
| KIR3DL1 | ENSG00000275786 | NIPAL4 | ENSG00000172548 |
| NLGN3 | ENSG00000196338 | ATP8B4 | ENSG00000104043 |
| YIPF7 | ENSG00000177752 | GABRP | ENSG00000094755 |
| DRAM1 | ENSG00000136048 | SLC2A9 | ENSG00000109667 |
| MFSD2A | ENSG00000168389 | NEU1 | ENSG00000227315 |
| CLEC5A | ENSG00000258227 | CDH16 | ENSG00000166589 |
| SMDT1 | ENSG00000183172 | TMC8 | ENSG00000167895 |
| DHRS11 | ENSG00000278535 | PKD2L2 | ENSG00000078795 |
| LSR | ENSG00000105699 | LRRTM4 | ENSG00000176204 |
| CD9 | ENSG00000010278 | PDPN | ENSG00000162493 |
| C2CD5 | ENSG00000111731 | PECAM1 | ENSG00000261371 |
| SIGLEC8 | ENSG00000105366 | GPR139 | ENSG00000180269 |
| HLA-E | ENSG00000233904 | POMGNT1 | ENSG00000085998 |
| SHISA2 | ENSG00000180730 | ATP1A3 | ENSG00000105409 |
| PTRH2 | ENSG00000141378 | SHISA9 | ENSG00000237515 |

TABLE 5-continued

Gene List

| HGNC symbol ID | Ensembl Gene | HGNC symbol ID | Ensembl Gene |
|---|---|---|---|
| SLC35E1 | ENSG00000127526 | MS4A13 | ENSG00000204979 |
| SLC12A7 | ENSG00000113504 | CD8B | ENSG00000172116 |
| IHH | ENSG00000163501 | TMEM136 | ENSG00000181264 |
| TMEM139 | ENSG00000178826 | NRM | ENSG00000206484 |
| GPR162 | ENSG00000250510 | CLEC4A | ENSG00000111729 |
| PRRT2 | ENSG00000167371 | KIAA1161 | ENSG00000164976 |
| PKD1L3 | ENSG00000277481 | SLC19A3 | ENSG00000135917 |
| MBOAT7 | ENSG00000125505 | HCN4 | ENSG00000138622 |
| SCAMP4 | ENSG00000227500 | NRG4 | ENSG00000169752 |
| GPR89A | ENSG00000117262 | OR10P1 | ENSG00000175398 |
| IFITM10 | ENSG00000244242 | IMPAD1 | ENSG00000104331 |
| AMFR | ENSG00000159461 | APLNR | ENSG00000134817 |
| FAM76B | ENSG00000077458 | TMEM45B | ENSG00000151715 |
| LINGO1 | ENSG00000169783 | GHRL | ENSG00000157017 |
| EPHA6 | ENSG00000080224 | SLC2A4 | ENSG00000181856 |
| NT5C3A | ENSG00000122643 | SUCNR1 | ENSG00000198829 |
| NCR3 | ENSG00000236979 | KIR2DS2 | ENSG00000276139 |
| ATP6AP1 | ENSG00000071553 | ARL10 | ENSG00000175414 |
| SPINK6 | ENSG00000178172 | CLN3 | ENSG00000188603 |
| CLPSL1 | ENSG00000204140 | LEPROT | ENSG00000213625 |
| ARSD | ENSG00000006756 | CDYL | ENSG00000153046 |
| GOLM1 | ENSG00000135052 | ART4 | ENSG00000111339 |
| CRB2 | ENSG00000148204 | DERL3 | ENSG00000099958 |
| LCLAT1 | ENSG00000172954 | MILR1 | ENSG00000271605 |
| BTNL2 | ENSG00000226127 | SLC35C1 | ENSG00000181830 |
| TMEM183A | ENSG00000163444 | | ENSG00000259753 |
| PON3 | ENSG00000105852 | GPR116 | ENSG00000069122 |
| WDR17 | ENSG00000150627 | GLT8D2 | ENSG00000120820 |
| CD3E | ENSG00000198851 | TRBV25-1 | ENSG00000211751 |
| ITLN2 | ENSG00000158764 | OCIAD1 | ENSG00000109180 |
| SMIM17 | ENSG00000268182 | TMEM229A | ENSG00000234224 |
| CDC27 | ENSG00000004897 | S1PR4 | ENSG00000125910 |
| HLA-DPB1 | ENSG00000223865 | ACSL1 | ENSG00000151726 |
| STX6 | ENSG00000135823 | OR4C15 | ENSG00000181939 |
| UBE2J1 | ENSG00000198833 | LTC4S | ENSG00000213316 |
| LILRA6 | ENSG00000275539 | ALG12 | ENSG00000182858 |
| HLA-DQB2 | ENSG00000228813 | GCNT4 | ENSG00000176928 |
| CLDND2 | ENSG00000160318 | CYP1B1 | ENSG00000138061 |
| LRP1 | ENSG00000123384 | SPI1 | ENSG00000066336 |
| CNR1 | ENSG00000118432 | FAM205A | ENSG00000205108 |
| LPCAT1 | ENSG00000153395 | RYK | ENSG00000163785 |
| LRRC3 | ENSG00000160233 | OR2B3 | ENSG00000231319 |
| ABCB11 | ENSG00000276582 | | ENSG00000172901 |
| BEST3 | ENSG00000127325 | TAP2 | ENSG00000206299 |
| VIPR1 | ENSG00000114812 | C10orf111 | ENSG00000176236 |
| TMEM179 | ENSG00000258986 | TMPRSS15 | ENSG00000154646 |
| HLA-A | ENSG00000206503 | SLC43A1 | ENSG00000149150 |
| KCNQ3 | ENSG00000184156 | OR7G1 | ENSG00000161807 |
| HLA-B | ENSG00000232126 | PCSK5 | ENSG00000099139 |
| PTPRH | ENSG00000080031 | C15orf27 | ENSG00000169758 |
| | ENSG00000268790 | PTGIR | ENSG00000160013 |
| APCDD1 | ENSG00000154856 | CYP8B1 | ENSG00000180432 |
| PCDHA6 | ENSG00000081842 | BTLA | ENSG00000186265 |
| PEX11G | ENSG00000104883 | SLC39A7 | ENSG00000227402 |
| NAAA | ENSG00000138744 | TMPRSS4 | ENSG00000137648 |
| GALNTL5 | ENSG00000106648 | TMEM189-UBE2V1 | ENSG00000124208 |
| CDIP1 | ENSG00000089486 | C2CD2L | ENSG00000172375 |
| CMKLR1 | ENSG00000174600 | C20orf173 | ENSG00000125975 |
| KCNU1 | ENSG00000215262 | CFAP54 | ENSG00000188596 |
| TRPV5 | ENSG00000127412 | CD34 | ENSG00000174059 |
| KIR2DS2 | ENSG00000275735 | ABCC1 | ENSG00000103222 |
| INSR | ENSG00000171105 | FUT1 | ENSG00000174951 |
| SYNDIG1 | ENSG00000101463 | CADM1 | ENSG00000182985 |
| TAS2R1 | ENSG00000169777 | TREM1 | ENSG00000124731 |
| GJB2 | ENSG00000165474 | OCSTAMP | ENSG00000149635 |
| BNIP1 | ENSG00000113734 | MYCT1 | ENSG00000120279 |
| AADAC | ENSG00000114771 | BAI1 | ENSG00000181790 |
| DRAXIN | ENSG00000162490 | KLRC4 | ENSG00000183542 |
| KIR2DL3 | ENSG00000274952 | IL5RA | ENSG00000091181 |
| ZDHHC5 | ENSG00000156599 | SLC7A6 | ENSG00000103064 |
| DRD3 | ENSG00000151577 | CTAGE9 | ENSG00000236761 |
| ELOVL2 | ENSG00000197977 | GPR45 | ENSG00000135973 |
| VCAM1 | ENSG00000162692 | C14orf180 | ENSG00000184601 |
| SLC28A2 | ENSG00000137860 | MR1 | ENSG00000153029 |
| FNDC9 | ENSG00000172568 | TRPC3 | ENSG00000138741 |

TABLE 5-continued

Gene List

| HGNC symbol ID | Ensembl Gene | HGNC symbol ID | Ensembl Gene |
|---|---|---|---|
| SLC22A15 | ENSG00000163393 | C1orf101 | ENSG00000179397 |
| KIR3DL1 | ENSG00000277272 | CHST9 | ENSG00000154080 |
| CD6 | ENSG00000013725 | ZNF546 | ENSG00000187187 |
| GABBR1 | ENSG00000232569 | VANGL1 | ENSG00000173218 |
| P2RY10 | ENSG00000078589 | HS3ST5 | ENSG00000249853 |
| LGR6 | ENSG00000133067 | LRRC32 | ENSG00000137507 |
| ECM1 | ENSG00000143369 | XKR5 | ENSG00000275591 |
| HLA-DQA2 | ENSG00000257473 | MGAT2 | ENSG00000168282 |
| SDSL | ENSG00000139410 | TMEM82 | ENSG00000162460 |
| ULBP1 | ENSG00000111981 | OR5K1 | ENSG00000232382 |
| AGPAT6 | ENSG00000158669 | SLC9A3 | ENSG00000066230 |
| PILRA | ENSG00000085514 | SLC5A6 | ENSG00000138074 |
| SLC39A8 | ENSG00000138821 | ITGB3 | ENSG00000259207 |
| C11orf87 | ENSG00000185742 | ITPR1 | ENSG00000150995 |
| B3GALT4 | ENSG00000235863 | SLC8B1 | ENSG00000089060 |
| SLC2A13 | ENSG00000151229 | HHLA2 | ENSG00000114455 |
| MGAM | ENSG00000257335 | | ENSG00000198843 |
| OR2W1 | ENSG00000229328 | SMARCC1 | ENSG00000173473 |
| OR14J1 | ENSG00000204695 | OR52K2 | ENSG00000181963 |
| MRAP2 | ENSG00000135324 | FAM26E | ENSG00000178033 |
| WNT16 | ENSG00000002745 | HLA-DQB1 | ENSG00000206237 |
| EPHA7 | ENSG00000135333 | LY6D | ENSG00000167656 |
| LRRN2 | ENSG00000170382 | RAMP2 | ENSG00000131477 |
| ELFN2 | ENSG00000166897 | SLC25A33 | ENSG00000171612 |
| GLRB | ENSG00000109738 | ZDHHC14 | ENSG00000175048 |
| MGP | ENSG00000111341 | SFTPD | ENSG00000133661 |
| NPBWR1 | ENSG00000183729 | DUOX2 | ENSG00000140279 |
| RNF167 | ENSG00000108523 | NSDHL | ENSG00000147383 |
| CMTM1 | ENSG00000089505 | TAP1 | ENSG00000226173 |
| LSAMP | ENSG00000185565 | MSMB | ENSG00000263639 |
| HLA-DPB1 | ENSG00000215048 | KLRB1 | ENSG00000111796 |
| FAM19A2 | ENSG00000198673 | EPDR1 | ENSG00000086289 |
| SPCS2 | ENSG00000118363 | CD19 | ENSG00000177455 |
| PLA2G2A | ENSG00000188257 | CHRNA1 | ENSG00000138435 |
| SMDT1 | ENSG00000272901 | SCARB2 | ENSG00000138760 |
| GALR2 | ENSG00000182687 | OCLN | ENSG00000197822 |
| GCNT3 | ENSG00000140297 | ITGAL | ENSG00000005844 |
| BTC | ENSG00000174808 | SECTM1 | ENSG00000141574 |
| EEF1E1 | ENSG00000124802 | TSPAN10 | ENSG00000182612 |
| C9orf91 | ENSG00000157693 | MC3R | ENSG00000124089 |
| KIR3DL3 | ENSG00000278490 | DPAGT1 | ENSG00000172269 |
| HAVCR2 | ENSG00000135077 | PTCHD3 | ENSG00000182077 |
| OR2A4 | ENSG00000180658 | APOC2 | ENSG00000234906 |
| KIR3DL2 | ENSG00000278758 | TYRP1 | ENSG00000107165 |
| TMEM150C | ENSG00000249242 | HDAC2 | ENSG00000196591 |
| CCR7 | ENSG00000126353 | LY6G5C | ENSG00000226404 |
| B3GALT2 | ENSG00000162630 | MKKS | ENSG00000125863 |
| TMEM144 | ENSG00000164124 | KIAA1468 | ENSG00000134444 |
| ADCY5 | ENSG00000173175 | GALNT5 | ENSG00000136542 |
| MAL | ENSG00000172005 | PCDHA10 | ENSG00000250120 |
| FAM69B | ENSG00000165716 | SNN | ENSG00000184602 |
| KIR2DL4 | ENSG00000275456 | RECK | ENSG00000122707 |
| SLC39A7 | ENSG00000224399 | ALG8 | ENSG00000159063 |
| FA2H | ENSG00000103089 | SCNN1A | ENSG00000111319 |
| FMNL1 | ENSG00000184922 | DEFB133 | ENSG00000214643 |
| TMEM47 | ENSG00000147027 | GPR26 | ENSG00000154478 |
| OR52K1 | ENSG00000196778 | CLEC4C | ENSG00000198178 |
| XKR7 | ENSG00000260903 | SPAG9 | ENSG00000008294 |
| SLITRK3 | ENSG00000121871 | SMCO3 | ENSG00000179256 |
| JAM2 | ENSG00000154721 | SPAM1 | ENSG00000106304 |
| NHLRC3 | ENSG00000188811 | PCDH20 | ENSG00000197991 |
| UMODL1 | ENSG00000177398 | KIR2DS1 | ENSG00000275921 |
| TRBV28 | ENSG00000211753 | SLC25A2 | ENSG00000120329 |
| HLA-G | ENSG00000233095 | BFAR | ENSG00000103429 |
| SRPRB | ENSG00000144867 | FAM105A | ENSG00000145569 |
| OR51E2 | ENSG00000167332 | IER3IP1 | ENSG00000134049 |
| TRPV1 | ENSG00000262304 | IL17RC | ENSG00000163702 |
| VAMP3 | ENSG00000049245 | PCDH20 | ENSG00000280165 |
| TMEM191B | ENSG00000278558 | ABCA2 | ENSG00000107331 |
| UGCG | ENSG00000148154 | GPR158 | ENSG00000151025 |
| POPDC2 | ENSG00000121577 | DPY19L3 | ENSG00000178904 |
| KCNS1 | ENSG00000124134 | FAM26D | ENSG00000164451 |
| SLC25A34 | ENSG00000162461 | SMIM5 | ENSG00000204323 |
| CHST13 | ENSG00000180767 | OR4C16 | ENSG00000279514 |
| DPY19L4 | ENSG00000156162 | NRP1 | ENSG00000099250 |

TABLE 5-continued

Gene List

| HGNC symbol ID | Ensembl Gene | HGNC symbol ID | Ensembl Gene |
|---|---|---|---|
| TRHDE | ENSG00000072657 | PRRT1 | ENSG00000225141 |
| PIGP | ENSG00000185808 | UGT2B10 | ENSG00000109181 |
| G6PC | ENSG00000131482 | SMIM19 | ENSG00000176209 |
| B3GALT4 | ENSG00000236802 | SLC4A11 | ENSG00000088836 |
| TMEM180 | ENSG00000138111 | KIR2DL4 | ENSG00000278201 |
| PTPRK | ENSG00000152894 | PLXNA2 | ENSG00000076356 |
| EIF2AK3 | ENSG00000172071 | KRTAP19-6 | ENSG00000186925 |
| KLHDC7A | ENSG00000179023 | FGF10 | ENSG00000070193 |
| ZNF138 | ENSG00000197008 | FLT3 | ENSG00000122025 |
| SERP1 | ENSG00000120742 | OR1L4 | ENSG00000136939 |
| MRC2 | ENSG00000011028 | SPTSSB | ENSG00000196542 |
| VNN2 | ENSG00000112303 | IER3IP1 | ENSG00000267228 |
| TGFBR3 | ENSG00000069702 | EVA1C | ENSG00000166979 |
| SNAP23 | ENSG00000092531 | OR1L6 | ENSG00000171459 |
| AVPR2 | ENSG00000126895 | OR4F21 | ENSG00000176269 |
| CSGALNACT2 | ENSG00000169826 | OR2V2 | ENSG00000182613 |
| SERF1A | ENSG00000172058 | PILRB | ENSG00000121716 |
| KLRK1 | ENSG00000213809 | KRTAP19-7 | ENSG00000244362 |
| KIR2DL3 | ENSG00000277554 | FNDC5 | ENSG00000160097 |
| KLRG1 | ENSG00000139187 | MRGPRX1 | ENSG00000170255 |
| ZNF66 | ENSG00000275050 | ELSPBP1 | ENSG00000169393 |
| TRBC2 | ENSG00000211772 | STX8 | ENSG00000170310 |
| FAM19A5 | ENSG00000219438 | CYP4X1 | ENSG00000186377 |
| CYP26C1 | ENSG00000187553 | HLA-DRB1 | ENSG00000206240 |
| RRM2B | ENSG00000048392 | MMP14 | ENSG00000157227 |
| SMIM6 | ENSG00000259120 | GRIA3 | ENSG00000125675 |
| SCNN1B | ENSG00000168447 | STRADB | ENSG00000082146 |
| GPR156 | ENSG00000175697 | ZDHHC19 | ENSG00000163958 |
| AQP4 | ENSG00000171885 | CHST11 | ENSG00000171310 |
| KIR2DL2 | ENSG00000275546 | CLN6 | ENSG00000128973 |
| GRAMD1A | ENSG00000089351 | ITM2A | ENSG00000078596 |
| SLC48A1 | ENSG00000211584 | NFAM1 | ENSG00000235568 |
| RRH | ENSG00000180245 | DDB1 | ENSG00000167986 |
| SLC40A1 | ENSG00000138449 | WNT3 | ENSG00000108379 |
| BBS4 | ENSG00000140463 | PHLDB2 | ENSG00000144824 |
| A4GALT | ENSG00000128274 | IFITM5 | ENSG00000206013 |
| MARCH6 | ENSG00000145495 | TMED7 | ENSG00000134970 |
| ATP5G2 | ENSG00000135390 | SLC23A3 | ENSG00000213901 |
| NPY4R | ENSG00000204174 | DEFB114 | ENSG00000177684 |
| EMC3 | ENSG00000125037 | FAM171B | ENSG00000144369 |
| HLA-DQB2 | ENSG00000229493 | VAMP1 | ENSG00000139190 |
| SLC10A3 | ENSG00000126903 | MUC1 | ENSG00000185499 |
| SFT2D1 | ENSG00000198818 | KCNC4 | ENSG00000116396 |
| AMIGO2 | ENSG00000139211 | APOL6 | ENSG00000221963 |
| TMEM57 | ENSG00000204178 | PSMD8 | ENSG00000099341 |
| CLDN4 | ENSG00000189143 | CLEC4E | ENSG00000166523 |
| TMEM206 | ENSG00000065600 | TMEM60 | ENSG00000135211 |
| TWSG1 | ENSG00000128791 | PPT2 | ENSG00000228116 |
| GPR153 | ENSG00000158292 | CD81 | ENSG00000110651 |
| PTPLA | ENSG00000165996 | PDE3B | ENSG00000152270 |
| STX1B | ENSG00000099365 | TAAR6 | ENSG00000146383 |
| TAAR9 | ENSG00000237110 | SLC2A2 | ENSG00000163581 |
| TMEM151B | ENSG00000178233 | TNFSF14 | ENSG00000125735 |
| MEP1B | ENSG00000141434 | DPP4 | ENSG00000197635 |
| KCNJ8 | ENSG00000121361 | ASTN2 | ENSG00000148219 |
| TAP1 | ENSG00000232367 | LRP12 | ENSG00000147650 |
| IFNGR2 | ENSG00000159128 | KLB | ENSG00000134962 |
| SOGA3 | ENSG00000255330 | | ENSG00000269881 |
| KIAA0408 | ENSG00000255330 | SPX | ENSG00000134548 |
| ALCAM | ENSG00000170017 | PI3 | ENSG00000124102 |
| SLC25A4 | ENSG00000151729 | UTP18 | ENSG00000011260 |
| ABCA7 | ENSG00000064687 | RNF112 | ENSG00000128482 |
| TTYH1 | ENSG00000276537 | ACKR3 | ENSG00000144476 |
| CPT1C | ENSG00000169169 | LPAR4 | ENSG00000147145 |
| TAAR8 | ENSG00000146385 | SLC26A5 | ENSG00000170615 |
| YIPF3 | ENSG00000137207 | GOSR2 | ENSG00000108433 |
| BNIP2 | ENSG00000140299 | HTR1D | ENSG00000179546 |
| TRPV1 | ENSG00000196689 | APOB | ENSG00000084674 |
| KIR2DL1 | ENSG00000277616 | LIPF | ENSG00000182333 |
| UPK3B | ENSG00000243566 | TMC6 | ENSG00000141524 |
| CANX | ENSG00000127022 | APOO | ENSG00000184831 |
| IGSF6 | ENSG00000140749 | MTCH1 | ENSG00000137409 |
| GNPTAB | ENSG00000111670 | VAPB | ENSG00000124164 |
| VRK2 | ENSG00000028116 | TXNDC16 | ENSG00000087301 |
| SLC2A14 | ENSG00000173262 | CRISPLD2 | ENSG00000103196 |

TABLE 5-continued

Gene List

| HGNC symbol ID | Ensembl Gene | HGNC symbol ID | Ensembl Gene |
|---|---|---|---|
| SLC5A9 | ENSG00000117834 | TMEM95 | ENSG00000182896 |
| RPRML | ENSG00000179673 | ABHD13 | ENSG00000139826 |
| OR52M1 | ENSG00000197790 | HLA-DPA1 | ENSG00000224103 |
| MFSD6L | ENSG00000185156 | DUOXA1 | ENSG00000140254 |
| KIR3DL3 | ENSG00000276875 | PCMT1 | ENSG00000120265 |
| BMP2 | ENSG00000125845 | TNF | ENSG00000232810 |
| PNPLA2 | ENSG00000177666 | OR2J3 | ENSG00000233618 |
| VSIG8 | ENSG00000243284 | OR5C1 | ENSG00000148215 |
| NEU1 | ENSG00000204386 | DRD5 | ENSG00000169676 |
| TMCC3 | ENSG00000057704 | F3 | ENSG00000117525 |
| LILRB5 | ENSG00000273991 | SLC39A12 | ENSG00000148482 |
| IL11RA | ENSG00000137070 | SMIM14 | ENSG00000163683 |
| PDGFRA | ENSG00000134853 | PPY | ENSG00000108849 |
| GJB6 | ENSG00000121742 | TMEM184B | ENSG00000198792 |
| CCR9 | ENSG00000173585 | MOGS | ENSG00000115275 |
| | ENSG00000272916 | OR51D1 | ENSG00000197428 |
| KIR2DS4 | ENSG00000275731 | TMED1 | ENSG00000099203 |
| SMIM15 | ENSG00000188725 | UBE3A | ENSG00000114062 |
| PIGO | ENSG00000165282 | FLRT3 | ENSG00000125848 |
| GLB1L2 | ENSG00000149328 | PLBD2 | ENSG00000151176 |
| SLC18B1 | ENSG00000146409 | SDC1 | ENSG00000115884 |
| TMEM27 | ENSG00000147003 | SLC23A2 | ENSG00000089057 |
| SLC20A2 | ENSG00000168575 | HTRA4 | ENSG00000169495 |
| GPR142 | ENSG00000257008 | ASAH2 | ENSG00000188611 |
| HLA-F | ENSG00000235220 | HLA-DPB1 | ENSG00000229295 |
| ITFG3 | ENSG00000167930 | TMEM50B | ENSG00000142188 |
| KIR3DL1 | ENSG00000278427 | SHISA8 | ENSG00000234965 |
| FCAR | ENSG00000278415 | CTSZ | ENSG00000101160 |
| RNF185 | ENSG00000138942 | CXCL11 | ENSG00000169248 |
| KCNH2 | ENSG00000055118 | PIEZO1 | ENSG00000103335 |
| CYP3A7 | ENSG00000160870 | PPAPDC3 | ENSG00000160539 |
| TAP1 | ENSG00000224212 | NUCB1 | ENSG00000104805 |
| ITGA2B | ENSG00000005961 | HLA-DPA1 | ENSG00000231389 |
| REEP5 | ENSG00000129625 | PEX11B | ENSG00000131779 |
| CDH24 | ENSG00000139880 | SV2C | ENSG00000122012 |
| IL15RA | ENSG00000134470 | WDR33 | ENSG00000136709 |
| SLC9A4 | ENSG00000180251 | C14orf2 | ENSG00000156411 |
| KIR2DP1 | ENSG00000276468 | TAP2 | ENSG00000232326 |
| NDRG4 | ENSG00000103034 | GPRC6A | ENSG00000173612 |
| FAM3C | ENSG00000196937 | WRB | ENSG00000182093 |
| LGI2 | ENSG00000153012 | DEAF1 | ENSG00000177030 |
| DNAJC15 | ENSG00000120675 | ZDHHC3 | ENSG00000163812 |
| GPR174 | ENSG00000147138 | HYOU1 | ENSG00000149428 |
| TMEM14C | ENSG00000111843 | GREM1 | ENSG00000166923 |
| SERINC1 | ENSG00000111897 | GALNT6 | ENSG00000139629 |
| TAAR5 | ENSG00000135569 | ATP2A1 | ENSG00000196296 |
| NINJ2 | ENSG00000171840 | TMEM106C | ENSG00000134291 |
| OR56B4 | ENSG00000180919 | C12orf73 | ENSG00000204954 |
| TMPRSS2 | ENSG00000184012 | OR7D4 | ENSG00000174667 |
| SOGA3 | ENSG00000214338 | OR13D1 | ENSG00000179055 |
| OR52B2 | ENSG00000255307 | CYBRD1 | ENSG00000071967 |
| HLA-A | ENSG00000223980 | DPCR1 | ENSG00000257232 |
| SLAMF8 | ENSG00000158714 | DLK2 | ENSG00000171462 |
| LY6G5C | ENSG00000111971 | CD44 | ENSG00000026508 |
| BCHE | ENSG00000114200 | A3GALT2 | ENSG00000184389 |
| LYSMD3 | ENSG00000176018 | IFITM3 | ENSG00000142089 |
| KDR | ENSG00000128052 | KIR3DL3 | ENSG00000277620 |
| | ENSG00000272442 | PTGDR2 | ENSG00000183134 |
| OR2W1 | ENSG00000204704 | SUSD3 | ENSG00000157303 |
| OR2J2 | ENSG00000234746 | CHST10 | ENSG00000115526 |
| CEACAM18 | ENSG00000213822 | AKAP1 | ENSG00000121057 |
| RNF5 | ENSG00000204308 | ELOVL1 | ENSG00000066322 |
| OR4C11 | ENSG00000172188 | MERTK | ENSG00000153208 |
| TOR2A | ENSG00000160404 | ITGAV | ENSG00000138448 |
| FXYD1 | ENSG00000266964 | FAM3B | ENSG00000183844 |
| HUWE1 | ENSG00000086758 | SLC2A1 | ENSG00000117394 |
| MAN1C1 | ENSG00000117643 | DNAJC5G | ENSG00000163793 |
| ENPEP | ENSG00000138792 | DPCR1 | ENSG00000168631 |
| TGFBI | ENSG00000120708 | ZNF66 | ENSG00000160229 |
| OPN3 | ENSG00000054277 | SLC35D2 | ENSG00000130958 |
| SDK2 | ENSG00000069188 | CD86 | ENSG00000114013 |
| OR52A5 | ENSG00000171944 | EPHB3 | ENSG00000182580 |
| OR4P4 | ENSG00000181927 | UBXN8 | ENSG00000104691 |
| GPR176 | ENSG00000166073 | EXT1 | ENSG00000182197 |
| SIGLEC12 | ENSG00000254521 | TIMM22 | ENSG00000177370 |

TABLE 5-continued

Gene List

| HGNC symbol ID | Ensembl Gene | HGNC symbol ID | Ensembl Gene |
|---|---|---|---|
| NDUFA4 | ENSG00000189043 | PCDH19 | ENSG00000165194 |
| HELZ | ENSG00000198265 | SLC34A3 | ENSG00000198569 |
| OR4C46 | ENSG00000185926 | OR52Z1 | ENSG00000176748 |
| TMBIM6 | ENSG00000139644 | CCL4 | ENSG00000275302 |
| DLK1 | ENSG00000185559 | GALNT3 | ENSG00000115339 |
| CDH23 | ENSG00000107736 | SIL1 | ENSG00000120725 |
| NCMAP | ENSG00000184454 | RNF217 | ENSG00000146373 |
| SCN10A | ENSG00000185313 | SVOPL | ENSG00000157703 |
| PCDH17 | ENSG00000118946 | LPHN3 | ENSG00000150471 |
| TNFRSF9 | ENSG00000049249 | PPP1R3A | ENSG00000154415 |
| CDH4 | ENSG00000179242 | LILRB5 | ENSG00000278437 |
| CNEP1R1 | ENSG00000205423 | OR2B2 | ENSG00000168131 |
| KIR2DL4 | ENSG00000275317 | PARM1 | ENSG00000169116 |
| GPR98 | ENSG00000164199 | MICA | ENSG00000235233 |
| HMOX2 | ENSG00000103415 | TMEM200B | ENSG00000253304 |
| USP27X | ENSG00000273820 | TPST2 | ENSG00000128294 |
| DPP10 | ENSG00000175497 | ACSL5 | ENSG00000197142 |
| STAG3L5P-PVRIG2P-PILRB | ENSG00000272752 | DNAJC25 | ENSG00000059769 |
| TOMM7 | ENSG00000196683 | AVPR1A | ENSG00000166148 |
| OTOL1 | ENSG00000182447 | OR4K5 | ENSG00000176281 |
| FAM24A | ENSG00000203795 | TAPBP | ENSG00000231925 |
| WDR19 | ENSG00000157796 | G6PC2 | ENSG00000278373 |
| SLC8A1 | ENSG00000183023 | GPR161 | ENSG00000143147 |
| KIR2DL3 | ENSG00000273947 | PATE3 | ENSG00000236027 |
| ABCA13 | ENSG00000179869 | OR2W1 | ENSG00000234101 |
| PRSS45 | ENSG00000188086 | TMEM51 | ENSG00000171729 |
| DNAJC1 | ENSG00000136770 | LAMP5 | ENSG00000125869 |
| MBOAT2 | ENSG00000143797 | PRPH2 | ENSG00000112619 |
| SLC22A13 | ENSG00000172940 | RNASEK-C17orf49 | ENSG00000161939 |
| MEST | ENSG00000106484 | COLQ | ENSG00000206561 |
| SLCO3A1 | ENSG00000176463 | ERVV-2 | ENSG00000268964 |
| OR2J3 | ENSG00000233636 | ST6GALNAC5 | ENSG00000117069 |
| GPR88 | ENSG00000181656 | ABCC10 | ENSG00000124574 |
| IFNL3 | ENSG00000197110 | SEZ6 | ENSG00000063015 |
| IL20RA | ENSG00000016402 | GPR68 | ENSG00000119714 |
| TAS2R38 | ENSG00000257138 | TMEM14E | ENSG00000221962 |
| RARRES3 | ENSG00000133321 | PARL | ENSG00000175193 |
| YIPF2 | ENSG00000130733 | EOGT | ENSG00000163378 |
| APLF | ENSG00000169621 | TGFB2 | ENSG00000092969 |
| GABRR3 | ENSG00000183185 | GPR82 | ENSG00000171657 |
| XXYLT1 | ENSG00000173950 | GYPB | ENSG00000250361 |
| SYNE4 | ENSG00000181392 | CHRND | ENSG00000135902 |
| ATP6V0E2 | ENSG00000171130 | CT83 | ENSG00000204019 |
| CGA | ENSG00000135346 | KIR2DL4 | ENSG00000274193 |
| OR52A1 | ENSG00000182070 | OR1N1 | ENSG00000171505 |
| SMIM3 | ENSG00000256235 | OR51V1 | ENSG00000176742 |
| HLA-DOB | ENSG00000243496 | SLC26A6 | ENSG00000225697 |
| TMEM163 | ENSG00000152128 | MRGPRX4 | ENSG00000179817 |
| FGFR1 | ENSG00000077782 | ATP2B1 | ENSG00000070961 |
| VANGL2 | ENSG00000162738 | KCNH8 | ENSG00000183960 |
| BTN2A2 | ENSG00000124508 | LPAR3 | ENSG00000171517 |
| CCL4L1 | ENSG00000276070 | KCNT2 | ENSG00000162687 |
| LST1 | ENSG00000235915 | GYPE | ENSG00000197465 |
| ST3GAL1 | ENSG00000008513 | TMPRSS12 | ENSG00000186452 |
| MEMO1 | ENSG00000162959 | SDC4 | ENSG00000124145 |
| TIMMDC1 | ENSG00000113845 | RPL37A | ENSG00000197756 |
| GPR12 | ENSG00000132975 | COL11A2 | ENSG00000227801 |
| CMTM2 | ENSG00000140932 | LILRB2 | ENSG00000276146 |
| IL1RL2 | ENSG00000115598 | FUT2 | ENSG00000176920 |
| PCDH1 | ENSG00000156453 | RTN2 | ENSG00000125744 |
| EBP | ENSG00000147155 | OR2J2 | ENSG00000226000 |
| FBN2 | ENSG00000138829 | CYP7A1 | ENSG00000167910 |
| GPR62 | ENSG00000180929 | UTS2R | ENSG00000181408 |
| SOAT2 | ENSG00000167780 | CRELD1 | ENSG00000163703 |
| RGR | ENSG00000148604 | CALN1 | ENSG00000183166 |
| PODXL2 | ENSG00000114631 | ELOVL5 | ENSG00000012660 |
| KIAA0040 | ENSG00000235750 | KIR2DL1 | ENSG00000275750 |
| TMEM237 | ENSG00000155755 | UGT2A2 | ENSG00000271271 |
| TSPAN16 | ENSG00000130167 | SLC35G5 | ENSG00000177710 |
| HAS1 | ENSG00000105509 | SFXN1 | ENSG00000164466 |
| ACE2 | ENSG00000130234 | OR6K6 | ENSG00000180433 |
| TCTN2 | ENSG00000168778 | NAT8L | ENSG00000185818 |
| GPBAR1 | ENSG00000179921 | CLEC10A | ENSG00000132514 |
| FADS3 | ENSG00000221968 | DNER | ENSG00000187957 |
| CAV1 | ENSG00000105974 | SLC22A23 | ENSG00000137266 |

TABLE 5-continued

Gene List

| HGNC symbol ID | Ensembl Gene | HGNC symbol ID | Ensembl Gene |
|---|---|---|---|
| SPATA31A5 | ENSG00000276581 | TRPM3 | ENSG00000083067 |
| CD74 | ENSG00000019582 | CCL24 | ENSG00000106178 |
| SLC30A3 | ENSG00000115194 | TRPC6 | ENSG00000137672 |
| KIR3DS1 | ENSG00000274283 | SLC25A45 | ENSG00000162241 |
| SAYSD1 | ENSG00000112167 | HLA-DQA2 | ENSG00000225103 |
| SLC4A4 | ENSG00000080493 | KNCN | ENSG00000162456 |
| HLA-A | ENSG00000235657 | SFT2D3 | ENSG00000173349 |
| CD80 | ENSG00000121594 | CYP2D7 | ENSG00000205702 |
| FAM198B | ENSG00000164125 | BDNF | ENSG00000176697 |
| KMO | ENSG00000117009 | LMF2 | ENSG00000100258 |
| OR7A10 | ENSG00000127515 | MMP20 | ENSG00000137674 |
| PTH1R | ENSG00000160801 | UGT2A1 | ENSG00000173610 |
| OR1N2 | ENSG00000171501 | CNTNAP2 | ENSG00000174469 |
| GALNT4 | ENSG00000257594 | BCAP31 | ENSG00000185825 |
| CDHR4 | ENSG00000187492 | OR11A1 | ENSG00000204694 |
| DCHS1 | ENSG00000166341 | PKDCC | ENSG00000162878 |
| LTK | ENSG00000062524 | KCNQ2 | ENSG00000075043 |
| TMEM125 | ENSG00000179178 | SLC39A11 | ENSG00000133195 |
| SLC22A1 | ENSG00000175003 | CYP2D7 | ENSG00000263181 |
| OR1L8 | ENSG00000171496 | GOLIM4 | ENSG00000173905 |
| COL11A2 | ENSG00000230930 | EFNB3 | ENSG00000108947 |
| OR6K2 | ENSG00000196171 | TMEM14B | ENSG00000137210 |
| CDIPT | ENSG00000103502 | CDH19 | ENSG00000071991 |
| CXCL10 | ENSG00000169245 | CACNA1S | ENSG00000081248 |
| FAT3 | ENSG00000165323 | OR4F16 | ENSG00000273547 |
| CECR1 | ENSG00000093072 | ST6GALNAC3 | ENSG00000184005 |
| TRPM1 | ENSG00000134160 | NRSN2 | ENSG00000125841 |
| OR6K3 | ENSG00000203757 | TRIL | ENSG00000255690 |
| TAS1R2 | ENSG00000179002 | ZDHHC11B | ENSG00000206077 |
| SFT2D2 | ENSG00000213064 | CD99L2 | ENSG00000102181 |
| OR12D2 | ENSG00000280236 | GRIA4 | ENSG00000152578 |
| MAOB | ENSG00000069535 | TMEM72 | ENSG00000187783 |
| TNFSF12 | ENSG00000239697 | CNGA1 | ENSG00000198515 |
| OR7A17 | ENSG00000185385 | P2RX4 | ENSG00000135124 |
| DPCR1 | ENSG00000232251 | C3AR1 | ENSG00000171860 |
| FAM20A | ENSG00000108950 | PTPRCAP | ENSG00000213402 |
| ACER1 | ENSG00000167769 | HLA-DPA1 | ENSG00000228163 |
| WFDC10A | ENSG00000180305 | CLEC17A | ENSG00000187912 |
| UGT2B4 | ENSG00000156096 | SEMA4A | ENSG00000196189 |
| FZD10 | ENSG00000111432 | KIR3DL1 | ENSG00000274146 |
| ORAI1 | ENSG00000276045 | SLC6A5 | ENSG00000165970 |
| PRADC1 | ENSG00000135617 | TMEM196 | ENSG00000173452 |
| CCDC168 | ENSG00000175820 | NRK | ENSG00000123572 |
| KDELR2 | ENSG00000136240 | SLCO1B1 | ENSG00000134538 |
| FCN2 | ENSG00000160339 | HLA-C | ENSG00000237022 |
| GDPD5 | ENSG00000158555 | OR11H2 | ENSG00000258453 |
| TMEM203 | ENSG00000187713 | KIR2DL4 | ENSG00000274945 |
| ATP7A | ENSG00000165240 | SLC5A8 | ENSG00000262217 |
| UNC93B1 | ENSG00000110057 | HLA-DRB3 | ENSG00000196101 |
| HLA-DQB1 | ENSG00000206302 | MPZL3 | ENSG00000160588 |
| OR2B3 | ENSG00000233180 | CLCC1 | ENSG00000121940 |
| OR5V1 | ENSG00000243729 | TMEM215 | ENSG00000188133 |
| LCN10 | ENSG00000187922 | SLC35G6 | ENSG00000259224 |
| NUP50 | ENSG00000093000 | TMEM5 | ENSG00000118600 |
| ATP10A | ENSG00000206190 | OR2J3 | ENSG00000232178 |
| SEC61G | ENSG00000132432 | ISLR2 | ENSG00000167178 |
| OR10C1 | ENSG00000206474 | SYS1 | ENSG00000204070 |
| RNF180 | ENSG00000164197 | PPT2 | ENSG00000227600 |
| GPR111 | ENSG00000164393 | GOSR1 | ENSG00000108587 |
| POM121 | ENSG00000196313 | S1PR2 | ENSG00000267534 |
| LRRC8A | ENSG00000136802 | CD151 | ENSG00000177697 |
| OR6N1 | ENSG00000197403 | NDRG2 | ENSG00000165795 |
| RNF128 | ENSG00000133135 | SLAMF6 | ENSG00000162739 |
| SLC10A6 | ENSG00000145283 | LDHA | ENSG00000134333 |
| TMEM8A | ENSG00000129925 | C6orf25 | ENSG00000206396 |
| ROBO3 | ENSG00000154134 | ASPH | ENSG00000198363 |
| TAP2 | ENSG00000223481 | GRIN2B | ENSG00000273079 |
| OR12D3 | ENSG00000112462 | FUT7 | ENSG00000180549 |
| B3GALT1 | ENSG00000172318 | IFNL4 | ENSG00000272395 |
| CDS1 | ENSG00000163624 | C19orf38 | ENSG00000214212 |
| EMP3 | ENSG00000142227 | ARL6IP5 | ENSG00000144746 |
| WFDC9 | ENSG00000180205 | KCNK10 | ENSG00000100433 |
| PTDSS1 | ENSG00000156471 | OR6N2 | ENSG00000188340 |
| DEFB103A | ENSG00000176797 | OR2G3 | ENSG00000177476 |
| CDSN | ENSG00000204539 | ITGB2 | ENSG00000160255 |

TABLE 5-continued

Gene List

| HGNC symbol ID | Ensembl Gene | HGNC symbol ID | Ensembl Gene |
|---|---|---|---|
| KIR3DL2 | ENSG00000278850 | S100A10 | ENSG00000197747 |
| SELPLG | ENSG00000110876 | GRPR | ENSG00000126010 |
| OR10A5 | ENSG00000166363 | SLC2A12 | ENSG00000146411 |
| YIF1B | ENSG00000167645 | OR4F3 | ENSG00000230178 |
| ATL1 | ENSG00000198513 | OR13G1 | ENSG00000197437 |
| SLC31A2 | ENSG00000136867 | RGMA | ENSG00000182175 |
| NPB | ENSG00000183979 | NDFIP1 | ENSG00000131507 |
| UGT3A2 | ENSG00000168671 | BTN1A1 | ENSG00000124557 |
| ATP1A2 | ENSG00000018625 | SLC12A1 | ENSG00000074803 |
| PLA2G2D | ENSG00000117215 | DUOXA2 | ENSG00000140274 |
| GABRG3 | ENSG00000182256 | PPAP2A | ENSG00000067113 |
| KIR2DL5B | ENSG00000278414 | NOMO2 | ENSG00000185164 |
| KCNH3 | ENSG00000135519 | CLDN18 | ENSG00000066405 |
| UGT2A1 | ENSG00000270386 | FCRL4 | ENSG00000163518 |
| DIP2C | ENSG00000151240 | GPR39 | ENSG00000183840 |
| BTNL2 | ENSG00000229741 | LCAT | ENSG00000213398 |
| SLC22A9 | ENSG00000149742 | KRTAP19-1 | ENSG00000184351 |
| SLC25A18 | ENSG00000182902 | DEGS1 | ENSG00000143753 |
| CXCL16 | ENSG00000161921 | GFRAL | ENSG00000187871 |
| CNTN5 | ENSG00000149972 | SLC18A3 | ENSG00000187714 |
| NPDC1 | ENSG00000107281 | TAS2R7 | ENSG00000121377 |
| TCTA | ENSG00000145022 | OR2B3 | ENSG00000225736 |
| HLA-DRA | ENSG00000230726 | NPIPB4 | ENSG00000185864 |
| WBP1L | ENSG00000166272 | SPEM1 | ENSG00000181323 |
| CALHM2 | ENSG00000138172 | TDGF1 | ENSG00000241186 |
| OR52I2 | ENSG00000226288 | OR4Q3 | ENSG00000182652 |
| OR14K1 | ENSG00000153230 | CCR6 | ENSG00000272980 |
| MRGPRX3 | ENSG00000179826 | DNAJC5 | ENSG00000101152 |
| CSMD2 | ENSG00000121904 | TREML2 | ENSG00000112195 |
| TRPC5 | ENSG00000072315 | TMEM245 | ENSG00000106771 |
| OR2W1 | ENSG00000226463 | GPR89B | ENSG00000188092 |
| MFSD4 | ENSG00000174514 | CERS2 | ENSG00000143418 |
| RXFP2 | ENSG00000133105 | CD101 | ENSG00000134256 |
| TMEM205 | ENSG00000105518 | PYCR1 | ENSG00000183010 |
| CPXM2 | ENSG00000121898 | TMCC1 | ENSG00000172765 |
| KIR3DL2 | ENSG00000277982 | CHRNA2 | ENSG00000120903 |
| GPR115 | ENSG00000153294 | FLRT2 | ENSG00000185070 |
| HTR2A | ENSG00000102468 | CYB5B | ENSG00000103018 |
| HRH1 | ENSG00000196639 | CD320 | ENSG00000167775 |
| ADAM17 | ENSG00000151694 | MST1R | ENSG00000164078 |
| GYPA | ENSG00000170180 | LRRN4 | ENSG00000125872 |
| HLA-A | ENSG00000231834 | PAQR3 | ENSG00000163291 |
| OS9 | ENSG00000135506 | PIGC | ENSG00000135845 |
| OR2B3 | ENSG00000233054 | PPAPDC1A | ENSG00000203805 |
| SLC10A1 | ENSG00000100652 | SERINC3 | ENSG00000132824 |
| HLA-DQB2 | ENSG00000196610 | FTH1 | ENSG00000167996 |
| NOX3 | ENSG00000074771 | OR1D5 | ENSG00000262628 |
| KCNMB2 | ENSG00000197584 | KRTAP19-3 | ENSG00000244025 |
| MTX1 | ENSG00000173171 | OR52I1 | ENSG00000232268 |
| OR2G2 | ENSG00000177489 | CLCN7 | ENSG00000103249 |
| FAM189A1 | ENSG00000104059 | TMX1 | ENSG00000139921 |
| B3GAT1 | ENSG00000109956 | FUNDC2 | ENSG00000165775 |
| TRIM13 | ENSG00000204977 | USP48 | ENSG00000090686 |
| HBD | ENSG00000223609 | OR4N2 | ENSG00000176294 |
| DAGLB | ENSG00000164535 | FRMD3 | ENSG00000172159 |
| CACNA1D | ENSG00000157388 | SLC36A2 | ENSG00000186335 |
| ARMC10 | ENSG00000170632 | HMGCR | ENSG00000113161 |
| ZNF816 | ENSG00000180257 | KIAA0319L | ENSG00000142687 |
| C19orf26 | ENSG00000099625 | TMEM176A | ENSG00000002933 |
| FAR1 | ENSG00000197601 | OR4M1 | ENSG00000176299 |
| SARAF | ENSG00000133872 | SYS1-DBNDD2 | ENSG00000254806 |
| SELP | ENSG00000174175 | CEP95 | ENSG00000258890 |
| SLC30A10 | ENSG00000196660 | B4GALT4 | ENSG00000121578 |
| SCARB1 | ENSG00000073060 | BTN3A2 | ENSG00000186470 |
| SRD5A1 | ENSG00000145545 | NCR1 | ENSG00000189430 |
| COMTD1 | ENSG00000165644 | GRM6 | ENSG00000113262 |
| COX7A2 | ENSG00000112695 | SPTLC1 | ENSG00000090054 |
| EPCAM | ENSG00000119888 | DNAJC4 | ENSG00000110011 |
| NKG7 | ENSG00000105374 | MARCH2 | ENSG00000099785 |
| PROKR1 | ENSG00000169618 | KIR2DL4 | ENSG00000277964 |
| SLC46A2 | ENSG00000119457 | GABRR2 | ENSG00000111886 |
| STEAP1 | ENSG00000164647 | TM9SF1 | ENSG00000100926 |
| EMP1 | ENSG00000134531 | NGLY1 | ENSG00000151092 |
| CSPG5 | ENSG00000114646 | TAS2R8 | ENSG00000272712 |
| SLC1A4 | ENSG00000115902 | BR13BP | ENSG00000184992 |

TABLE 5-continued

Gene List

| HGNC symbol ID | Ensembl Gene | HGNC symbol ID | Ensembl Gene |
|---|---|---|---|
| CNNM4 | ENSG00000158158 | FUT6 | ENSG00000156413 |
| FXYD7 | ENSG00000221946 | TMEM62 | ENSG00000137842 |
| OR6F1 | ENSG00000169214 | CD300LB | ENSG00000178789 |
| NPFFR2 | ENSG00000056291 | OR1G1 | ENSG00000183024 |
| RIC3 | ENSG00000166405 | ATP1B3 | ENSG00000069849 |
| MIEF2 | ENSG00000177427 | IL12RB2 | ENSG00000081985 |
| CDH15 | ENSG00000129910 | FZD2 | ENSG00000180340 |
| DLL4 | ENSG00000128917 | GPR37 | ENSG00000170775 |
| CYP4F12 | ENSG00000186204 | OR7C2 | ENSG00000127529 |
| CYP4F22 | ENSG00000171954 | TAS2R9 | ENSG00000273086 |
| SLC2A6 | ENSG00000160326 | | ENSG00000170091 |
| LGALS16 | ENSG00000249861 | CYP3A5 | ENSG00000106258 |
| COL14A1 | ENSG00000187955 | OR6C76 | ENSG00000185821 |
| BACE1 | ENSG00000186318 | CD300C | ENSG00000167850 |
| EFNB2 | ENSG00000125266 | TAP1 | ENSG00000206297 |
| PTTG1IP | ENSG00000183255 | NOX4 | ENSG00000086991 |
| BCAM | ENSG00000187244 | F2R | ENSG00000181104 |
| CACNG7 | ENSG00000105605 | MAS1L | ENSG00000204687 |
| TSPAN6 | ENSG00000000003 | P2RY4 | ENSG00000186912 |
| KCNMB2 | ENSG00000275163 | TSPAN3 | ENSG00000140391 |
| SLC32A1 | ENSG00000101438 | WLS | ENSG00000116729 |
| FAM132B | ENSG00000178752 | OR8H2 | ENSG00000181767 |
| LYPD1 | ENSG00000150551 | WFS1 | ENSG00000109501 |
| SLCO1B7 | ENSG00000205754 | GDPD2 | ENSG00000130055 |
| ZFYVE27 | ENSG00000155256 | SDCBP | ENSG00000137575 |
| PTGDR | ENSG00000168229 | ENTPD5 | ENSG00000187097 |
| OXA1L | ENSG00000155463 | BET1L | ENSG00000177951 |
| NIPAL1 | ENSG00000163293 | CEP120 | ENSG00000168944 |
| BCAP29 | ENSG00000075790 | MLN | ENSG00000096395 |
| SFXN4 | ENSG00000183605 | DHRS7 | ENSG00000100612 |
| PEMT | ENSG00000133027 | CEACAM1 | ENSG00000079385 |
| EPOR | ENSG00000187266 | HLA-DPA1 | ENSG00000206291 |
| ANO4 | ENSG00000151572 | MOGAT3 | ENSG00000106384 |
| C1orf159 | ENSG00000131591 | NCLN | ENSG00000125912 |
| VOPP1 | ENSG00000154978 | NAT10 | ENSG00000135372 |
| SLC39A4 | ENSG00000147804 | CCR6 | ENSG00000112486 |
| KIR2DS1 | ENSG00000273517 | COL11A2 | ENSG00000235708 |
| ACE | ENSG00000159640 | KIR3DL2 | ENSG00000275629 |
| | ENSG00000272162 | | ENSG00000274243 |
| CD79B | ENSG00000007312 | TECR | ENSG00000099797 |
| PFN2 | ENSG00000070087 | F11R | ENSG00000158769 |
| LY6G5C | ENSG00000204428 | ATP13A1 | ENSG00000105726 |
| HEPACAM | ENSG00000165478 | KIR2DL5A | ENSG00000274676 |
| MARCO | ENSG00000019169 | SLC12A4 | ENSG00000124067 |
| DDOST | ENSG00000244038 | SCAMP1 | ENSG00000085365 |
| UNC5D | ENSG00000156687 | ITGB7 | ENSG00000139626 |
| PRRT3 | ENSG00000163704 | CHRNB1 | ENSG00000170175 |
| PEX2 | ENSG00000164751 | PIGK | ENSG00000142892 |
| C19orf12 | ENSG00000131943 | PLN | ENSG00000198523 |
| CLDN20 | ENSG00000171217 | PCLO | ENSG00000186472 |
| LIFR | ENSG00000113594 | DPY19L2 | ENSG00000177990 |
| KIR2DS5 | ENSG00000277650 | STEAP2 | ENSG00000157214 |
| TNFSF13 | ENSG00000161955 | LAMP3 | ENSG00000078081 |
| HTRA2 | ENSG00000115317 | SLC22A3 | ENSG00000146477 |
| KIR3DL3 | ENSG00000278723 | KIR2DL2 | ENSG00000278731 |
| EXT2 | ENSG00000151348 | ADAMTS1 | ENSG00000154734 |
| RARG | ENSG00000172819 | CLDN22 | ENSG00000177300 |
| TDRKH | ENSG00000182134 | RHO | ENSG00000163914 |
| KRTAP20-4 | ENSG00000206105 | KIR3DL2 | ENSG00000275511 |
| ATP8B3 | ENSG00000130270 | SYT15 | ENSG00000277758 |
| TAS2R8 | ENSG00000121314 | PCNXL2 | ENSG00000135749 |
| BTNL8 | ENSG00000113303 | ARSJ | ENSG00000180801 |
| TMEM86B | ENSG00000180089 | DNAJC24 | ENSG00000170946 |
| ERMARD | ENSG00000130023 | CHPT1 | ENSG00000111666 |
| TM6SF1 | ENSG00000136404 | MAN1A1 | ENSG00000111885 |
| RNF149 | ENSG00000163162 | CD276 | ENSG00000103855 |
| FNDC3B | ENSG00000075420 | TMEM132A | ENSG00000006118 |
| SPPL2A | ENSG00000138600 | CD24 | ENSG00000272398 |
| OPN1MW | ENSG00000268221 | GRAMD1C | ENSG00000178075 |
| SCN3B | ENSG00000166257 | JPH3 | ENSG00000154118 |
| COX4I2 | ENSG00000131055 | PHTF1 | ENSG00000116793 |
| OR10A2 | ENSG00000170790 | OR56A5 | ENSG00000188691 |
| ARMCX3 | ENSG00000102401 | ESYT2 | ENSG00000117868 |
| SLC23A1 | ENSG00000170482 | SLC4A9 | ENSG00000113073 |
| TMEM80 | ENSG00000177042 | OR10G3 | ENSG00000169208 |

TABLE 5-continued

Gene List

| HGNC symbol ID | Ensembl Gene | HGNC symbol ID | Ensembl Gene |
|---|---|---|---|
| CLDN1 | ENSG00000163347 | CYP1A2 | ENSG00000140505 |
| TMED6 | ENSG00000157315 | OR4F5 | ENSG00000186092 |
| SYT13 | ENSG00000019505 | CLCN3 | ENSG00000109572 |
| DCST2 | ENSG00000163354 | TMEM194B | ENSG00000189362 |
| OR56A3 | ENSG00000184478 | BAK1 | ENSG00000030110 |
| MRC1 | ENSG00000260314 | NCR3 | ENSG00000236315 |
| SACM1L | ENSG00000211456 | MMD | ENSG00000108960 |
| CCDC126 | ENSG00000169193 | SLCO1B3 | ENSG00000111700 |
| TMEM109 | ENSG00000110108 | NOTCH4 | ENSG00000235396 |
| HSD3B2 | ENSG00000203859 | HLA-DPB1 | ENSG00000236693 |
| GALNT14 | ENSG00000158089 | KIR2DL1 | ENSG00000273794 |
| SLC35C2 | ENSG00000080189 | NPIPA1 | ENSG00000183426 |
| WNT4 | ENSG00000162552 | HLA-C | ENSG00000225691 |
| C2CD2 | ENSG00000157617 | PRMT3 | ENSG00000185238 |
| CD84 | ENSG00000066294 | TMEM221 | ENSG00000188051 |
| GUCY2F | ENSG00000101890 | SHISA6 | ENSG00000188803 |
| ACP2 | ENSG00000134575 | SLC44A4 | ENSG00000235336 |
| OTOP2 | ENSG00000183034 | FAM163B | ENSG00000196990 |
| MANSC4 | ENSG00000205693 | OR5D14 | ENSG00000186113 |
| OR10A4 | ENSG00000170782 | NFASC | ENSG00000163531 |
| ATL2 | ENSG00000119787 | TMEM260 | ENSG00000070269 |
| TMEM176B | ENSG00000106565 | PCNXL4 | ENSG00000126773 |
| C17orf74 | ENSG00000184560 | KCNK9 | ENSG00000169427 |
| TLR4 | ENSG00000136869 | KCNJ16 | ENSG00000153822 |
| PGRMC1 | ENSG00000101856 | NAALADL1 | ENSG00000168060 |
| ENPP1 | ENSG00000197594 | KISS1R | ENSG00000116014 |
| TAS2R9 | ENSG00000121381 | BRICD5 | ENSG00000182685 |
| PLXNC1 | ENSG00000136040 | CLEC12A | ENSG00000172322 |
| MUC12 | ENSG00000205277 | NAT8 | ENSG00000144035 |
| PTCH1 | ENSG00000185920 | TMEM9 | ENSG00000116857 |
| MOG | ENSG00000232641 | ROS1 | ENSG00000047936 |
| BTNL2 | ENSG00000229597 | SLC16A11 | ENSG00000174326 |
| CTAGE15 | ENSG00000271079 | HS3ST3B1 | ENSG00000125430 |
| CADM4 | ENSG00000105767 | B4GALT3 | ENSG00000158850 |
| BEST1 | ENSG00000167995 | CCDC80 | ENSG00000091986 |
| RNF13 | ENSG00000082996 | SLC38A8 | ENSG00000166558 |
| TIMD4 | ENSG00000145850 | ACVR1C | ENSG00000123612 |
| CLDN16 | ENSG00000113946 | SCN4A | ENSG00000007314 |
| HTR3B | ENSG00000149305 | KCNJ14 | ENSG00000182324 |
| KIR2DS3 | ENSG00000275599 | CISD2 | ENSG00000145354 |
| TIE1 | ENSG00000066056 | CXorf57 | ENSG00000147231 |
| CCDC51 | ENSG00000164051 | UBE2J2 | ENSG00000160087 |
| INPP4A | ENSG00000040933 | GPR15 | ENSG00000154165 |
| MLEC | ENSG00000110917 | KCNK12 | ENSG00000184261 |
| HCAR2 | ENSG00000182782 | EQTN | ENSG00000120160 |
| LYSMD4 | ENSG00000183060 | GPR182 | ENSG00000166856 |
| HCAR3 | ENSG00000255398 | GPR108 | ENSG00000125734 |
| LAT2 | ENSG00000086730 | C10orf54 | ENSG00000107738 |
| TMEM207 | ENSG00000198398 | COLEC12 | ENSG00000158270 |
| MARCH3 | ENSG00000173926 | LAIR1 | ENSG00000274110 |
| MFSD6 | ENSG00000151690 | MRGPRX2 | ENSG00000183695 |
| NRG2 | ENSG00000158458 | CD300LD | ENSG00000204345 |
| CNGA4 | ENSG00000132259 | OR1E1 | ENSG00000180016 |
| DLL3 | ENSG00000090932 | ACKR1 | ENSG00000213088 |
| P2RY1 | ENSG00000169860 | LTB | ENSG00000227507 |
| SCN4B | ENSG00000177098 | FAM69C | ENSG00000187773 |
| TMEM145 | ENSG00000167619 | SLC6A4 | ENSG00000108576 |
| IZUMO3 | ENSG00000205442 | PKD2 | ENSG00000118762 |
| TMPRSS5 | ENSG00000166682 | CPOX | ENSG00000080819 |
| KIR2DL5A | ENSG00000276686 | OR14A2 | ENSG00000241128 |
| MFSD8 | ENSG00000164073 | TMC4 | ENSG00000273722 |
| PDCD1 | ENSG00000188389 | LY6G6D | ENSG00000236902 |
| PLLP | ENSG00000102934 | TMEM218 | ENSG00000150433 |
| MSRB3 | ENSG00000174099 | NRROS | ENSG00000174004 |
| CDH20 | ENSG00000101542 | OR1C1 | ENSG00000221888 |
| | ENSG00000230463 | SSTR1 | ENSG00000139874 |
| SLN | ENSG00000170290 | KCND3 | ENSG00000171385 |
| CTXN2 | ENSG00000233932 | C9orf57 | ENSG00000204669 |
| TACR2 | ENSG00000075073 | PRAC2 | ENSG00000229637 |
| SDF2L1 | ENSG00000128228 | SLC9B1 | ENSG00000164037 |
| KIR3DL3 | ENSG00000276572 | SLC13A5 | ENSG00000141485 |
| OPN1SW | ENSG00000128617 | XCR1 | ENSG00000173578 |
| OR2C3 | ENSG00000196242 | SLCO4A1 | ENSG00000101187 |
| CD27 | ENSG00000139193 | NRG3 | ENSG00000185737 |
| NDST3 | ENSG00000164100 | C3orf52 | ENSG00000114529 |

TABLE 5-continued

Gene List

| HGNC symbol ID | Ensembl Gene | HGNC symbol ID | Ensembl Gene |
|---|---|---|---|
| SLC43A2 | ENSG00000167703 | NPC1 | ENSG00000141458 |
| UGT1A6 | ENSG00000167165 | SIDT2 | ENSG00000149577 |
| CHRNG | ENSG00000196811 | OR8H3 | ENSG00000181761 |
| SLITRK2 | ENSG00000185985 | KCNK1 | ENSG00000135750 |
| VN1R2 | ENSG00000196131 | SIGLEC6 | ENSG00000105492 |
| MYADML2 | ENSG00000185105 | CADM3 | ENSG00000162706 |
| DPP8 | ENSG00000074603 | OR1B1 | ENSG00000280094 |
| VN1R4 | ENSG00000228567 | CLEC4G | ENSG00000182566 |
| CD99 | ENSG00000002586 | TAP2 | ENSG00000204267 |
| CA12 | ENSG00000074410 | GJD2 | ENSG00000159248 |
| SLC4A8 | ENSG00000050438 | ARL6IP6 | ENSG00000177917 |
| HLA-B | ENSG00000224608 | VAMP8 | ENSG00000118640 |
| PMEL | ENSG00000185664 | CD200R1 | ENSG00000163606 |
| CORIN | ENSG00000145244 | NDUFB4 | ENSG00000065518 |
| SLC25A44 | ENSG00000160785 | GXYLT2 | ENSG00000172986 |
| OR1Q1 | ENSG00000165202 | ROR1 | ENSG00000185483 |
| IL2RG | ENSG00000147168 | GDF9 | ENSG00000164404 |
| KIR2DL1 | ENSG00000274692 | SLC25A3 | ENSG00000075415 |
| ATP1B1 | ENSG00000143153 | ADRA2B | ENSG00000274286 |
| SYT2 | ENSG00000143858 | MARCH11 | ENSG00000183654 |
| TAPBPL | ENSG00000139192 | SLC27A5 | ENSG00000083807 |
| OLR1 | ENSG00000173391 | RNASEK | ENSG00000219200 |
| TMEM8B | ENSG00000137103 | FADS1 | ENSG00000149485 |
| OR7D2 | ENSG00000188000 | PIGX | ENSG00000163964 |
| OR4S2 | ENSG00000174982 | CLDND1 | ENSG00000080822 |
| SLC35F2 | ENSG00000110660 | TACSTD2 | ENSG00000184292 |
| ZDHHC4 | ENSG00000136247 | APOL2 | ENSG00000128335 |
| CLEC2B | ENSG00000110852 | SPINK13 | ENSG00000214510 |
| ACVR1B | ENSG00000135503 | KIR2DL3 | ENSG00000275658 |
|  | ENSG00000257743 | ASGR2 | ENSG00000161944 |
| PPM1L | ENSG00000163590 | SPINT4 | ENSG00000149651 |
| ABCB11 | ENSG00000073734 | BNIP3L | ENSG00000104765 |
|  | ENSG00000261832 | OR14A16 | ENSG00000196772 |
| HTR5A | ENSG00000157219 | OR52L1 | ENSG00000183313 |
| LRIG1 | ENSG00000144749 | HLA-DQB1 | ENSG00000179344 |
| NEU1 | ENSG00000234846 | RPS23 | ENSG00000186468 |
| LIM2 | ENSG00000105370 | CLDN2 | ENSG00000165376 |
| VSIG10 | ENSG00000176834 | TMEM161A | ENSG00000064545 |
| TVP23C | ENSG00000175106 | PANX1 | ENSG00000110218 |
| KIR2DS1 | ENSG00000278304 | LPHN2 | ENSG00000117114 |
| SCNN1G | ENSG00000166828 | FUT4 | ENSG00000196371 |
| KIR3DS1 | ENSG00000276534 | ST8SIA3 | ENSG00000177511 |
| OR2B6 | ENSG00000124657 | HLA-DPA1 | ENSG00000235844 |
| SLC44A3 | ENSG00000143036 | C14orf1 | ENSG00000133935 |
| NCR3LG1 | ENSG00000188211 | GPR125 | ENSG00000152990 |
| ZDHHC11 | ENSG00000188818 | GPRC5A | ENSG00000013588 |
| ATP6AP2 | ENSG00000182220 | ITGAD | ENSG00000156886 |
| CLMN | ENSG00000165959 | KCNJ1 | ENSG00000151704 |
| KIR2DL4 | ENSG00000278271 | KIR2DS4 | ENSG00000274947 |
| FAM159B | ENSG00000145642 | CTRB2 | ENSG00000168928 |
| CD8A | ENSG00000153563 | CDH3 | ENSG00000062038 |
| VTCN1 | ENSG00000134258 | SGPL1A5 | ENSG00000119899 |
| TMEM114 | ENSG00000232258 | PCNX | ENSG00000100731 |
| KCNMB1 | ENSG00000145936 | UGT1A9 | ENSG00000241119 |
| LPAR2 | ENSG00000064547 | PKD1L1 | ENSG00000158683 |
| GPATCH2L | ENSG00000089916 | GPR27 | ENSG00000170837 |
| VSTM1 | ENSG00000275962 | FCAR | ENSG00000275136 |
| SLC35F3 | ENSG00000183780 | ESYT1 | ENSG00000139641 |
| IL27RA | ENSG00000104998 | ITFG1 | ENSG00000129636 |
| NUP210 | ENSG00000132182 | RFWD2 | ENSG00000143207 |
| MARVELD3 | ENSG00000140832 | ARMCX4 | ENSG00000196440 |
| NIPA2 | ENSG00000140157 | SLC16A3 | ENSG00000141526 |
| HFE2 | ENSG00000168509 | HLA-DRA | ENSG00000206308 |
| GOLT1B | ENSG00000111711 | SLC15A3 | ENSG00000110446 |
| STX5 | ENSG00000162236 | TNF | ENSG00000223952 |
| KIR2DL3 | ENSG00000276590 | SLC9A8 | ENSG00000197818 |
| AGMO | ENSG00000187546 | OR2W3 | ENSG00000238243 |
|  | ENSG00000148123 | OR51B6 | ENSG00000176239 |
| GALNT18 | ENSG00000110328 | OR51I1 | ENSG00000167359 |
| SLC6A3 | ENSG00000142319 | OR10W1 | ENSG00000172772 |
| GLG1 | ENSG00000090863 | APLP1 | ENSG00000105290 |
| PLA2R1 | ENSG00000153246 | FAM19A1 | ENSG00000183662 |
| SLC25A12 | ENSG00000115840 | ANKLE2 | ENSG00000176915 |
| IL1RAP | ENSG00000196083 | KIR2DL4 | ENSG00000273575 |
| OR11H12 | ENSG00000257115 | NOTCH2 | ENSG00000134250 |

TABLE 5-continued

Gene List

| HGNC symbol ID | Ensembl Gene | HGNC symbol ID | Ensembl Gene |
|---|---|---|---|
| IL12B | ENSG00000113302 | KLRD1 | ENSG00000134539 |
| HLA-DRB3 | ENSG00000231679 | ILDR2 | ENSG00000143195 |
| HSD17B3 | ENSG00000130948 | FXYD5 | ENSG00000089327 |
| SCN2B | ENSG00000149575 | TMC7 | ENSG00000170537 |
| TNFRSF17 | ENSG00000048462 | OR52H1 | ENSG00000181616 |
| KIR2DS2 | ENSG00000278300 | SEMA4B | ENSG00000185033 |
| HERPUD2 | ENSG00000122557 | OR52D1 | ENSG00000181609 |
| PLRG1 | ENSG00000171566 | SPECC1L-ADORA2A | ENSG00000258555 |
| TRPV2 | ENSG00000187688 | HLA-DRB1 | ENSG00000196126 |
| GPR157 | ENSG00000180758 | TXNDC12 | ENSG00000117862 |
| PIGQ | ENSG00000007541 | CRTAM | ENSG00000109943 |
| DLL1 | ENSG00000198719 | KRTAP19-8 | ENSG00000206102 |
| KIR3DL3 | ENSG00000274786 | C1QTNF6 | ENSG00000133466 |
| UNC5A | ENSG00000113763 | PMEPA1 | ENSG00000124225 |
| BET1 | ENSG00000105829 | NCAM2 | ENSG00000154654 |
| KIR3DL2 | ENSG00000278442 | DHRS7C | ENSG00000184544 |
| OR2H1 | ENSG00000235132 | TMEM167B | ENSG00000215717 |
| CALCR | ENSG00000004948 | KIR2DL2 | ENSG00000273578 |
| PAQR6 | ENSG00000160781 | HLA-G | ENSG00000235346 |
| FKRP | ENSG00000181027 | LY6G6F | ENSG00000240957 |
| OR11L1 | ENSG00000197591 | PTGFR | ENSG00000122420 |
| FAF1 | ENSG00000185104 | SLC39A3 | ENSG00000141873 |
| TMEM231 | ENSG00000205084 | WFDC2 | ENSG00000101443 |
| APMAP | ENSG00000101474 | MLNR | ENSG00000102539 |
| MC4R | ENSG00000166603 | TMEM54 | ENSG00000121900 |
| FAM174A | ENSG00000174132 | ADAM7 | ENSG00000069206 |
| SLC25A36 | ENSG00000114120 | ADRB2 | ENSG00000169252 |
| SLC9A2 | ENSG00000115616 | PROKR2 | ENSG00000101292 |
| FLT3LG | ENSG00000090554 | TNFSF12-TNFSF13 | ENSG00000248871 |
| SPINK9 | ENSG00000204909 | SCTR | ENSG00000080293 |
| FAM69A | ENSG00000154511 | GRM5 | ENSG00000168959 |
| SLC35F4 | ENSG00000151812 | CNIH4 | ENSG00000143771 |
| BEST4 | ENSG00000142959 | SLC30A6 | ENSG00000152683 |
| MFSD5 | ENSG00000182544 | TVP23C-CDRT4 | ENSG00000259024 |
| CD207 | ENSG00000116031 | TNFSF11 | ENSG00000120659 |
| EPHA1 | ENSG00000146904 | CCR8 | ENSG00000179934 |
| HLA-DQA2 | ENSG00000237541 | GHSR | ENSG00000121853 |
| EVI2A | ENSG00000126860 | HIAT1 | ENSG00000156875 |
| SPG7 | ENSG00000197912 | BPI | ENSG00000101425 |
| IL17RE | ENSG00000163701 | GPR1 | ENSG00000183671 |
| ATP6V0A2 | ENSG00000185344 | RHD | ENSG00000187010 |
| BTNL2 | ENSG00000225412 | CLEC12B | ENSG00000256660 |
| C17orf78 | ENSG00000278505 | PTPRJ | ENSG00000149177 |
| HLA-DOB | ENSG00000241386 | EGF | ENSG00000138798 |
| OR8J3 | ENSG00000167822 | KIAA1109 | ENSG00000138688 |
| MS4A5 | ENSG00000166930 | CD68 | ENSG00000129226 |
| APH1B | ENSG00000138613 | SLCO1A2 | ENSG00000084453 |
| GABBR2 | ENSG00000136928 | HSD11B1 | ENSG00000117594 |
| GLDN | ENSG00000186417 | JAG2 | ENSG00000184916 |
| IL31 | ENSG00000204671 | PTPLB | ENSG00000206527 |
| CACNG8 | ENSG00000142408 | HLA-DOA | ENSG00000232957 |
| ADORA2A | ENSG00000128271 | EPHA4 | ENSG00000116106 |
| FAM187B | ENSG00000177558 | HCAR1 | ENSG00000196917 |
| MCOLN2 | ENSG00000153898 | OR1A2 | ENSG00000172150 |
|  | ENSG00000214978 | CLEC1B | ENSG00000165682 |
| CLDN19 | ENSG00000164007 | ABCB4 | ENSG00000005471 |
| SLC52A2 | ENSG00000185803 | KIR2DL1 | ENSG00000276625 |
| IL2RB | ENSG00000100385 | ADAMDEC1 | ENSG00000134028 |
| GHR | ENSG00000112964 | FZD8 | ENSG00000177283 |
| TNFRSF1B | ENSG00000028137 | OR10H2 | ENSG00000171942 |
| TLR7 | ENSG00000196664 | CDS2 | ENSG00000101290 |
| DDRGK1 | ENSG00000198171 | PCDH10 | ENSG00000138650 |
| AGER | ENSG00000237405 | GP9 | ENSG00000169704 |
| SLC16A14 | ENSG00000163053 | OR10H3 | ENSG00000171936 |
| CERS4 | ENSG00000090661 | SYNPR | ENSG00000163630 |
| KIZ | ENSG00000088970 | IL13RA1 | ENSG00000131724 |
| CYP2J2 | ENSG00000134716 | MS4A7 | ENSG00000166927 |
| SLC16A9 | ENSG00000165449 | GRAMD4 | ENSG00000075240 |
| SPNS3 | ENSG00000182557 | CRTAP | ENSG00000170275 |
| EXOG | ENSG00000157036 | FIS1 | ENSG00000214253 |
| TMC4 | ENSG00000274384 | PPAPDC1B | ENSG00000147535 |
| HLA-DRB1 | ENSG00000206306 | MCTP1 | ENSG00000175471 |
| SPINT2 | ENSG00000167642 | SLC16A6 | ENSG00000108932 |
| OMG | ENSG00000126861 | TMEM35 | ENSG00000126950 |
| MOGAT2 | ENSG00000166391 | TM2D1 | ENSG00000162604 |

TABLE 5-continued

Gene List

| HGNC symbol ID | Ensembl Gene | HGNC symbol ID | Ensembl Gene |
|---|---|---|---|
| LTB | ENSG00000223448 | KIR2DL2 | ENSG00000277251 |
| MGAT1 | ENSG00000131446 | MOSPD1 | ENSG00000101928 |
| LY6G6E | ENSG00000235769 | EVI2B | ENSG00000185862 |
| LFNG | ENSG00000106003 | FLVCR2 | ENSG00000119686 |
| USP19 | ENSG00000172046 | TIMM23B | ENSG00000204152 |
| MS4A6E | ENSG00000166926 | ACSS1 | ENSG00000154930 |
| SLC45A3 | ENSG00000158715 | KIR2DS1 | ENSG00000276387 |
| KIR2DS2 | ENSG00000275253 | BRCA1 | ENSG00000012048 |
| SLC44A4 | ENSG00000206378 | LETMD1 | ENSG00000050426 |
| FANCM | ENSG00000187790 | GLP1R | ENSG00000112164 |
| KIR3DL3 | ENSG00000274254 | OR2L2 | ENSG00000203663 |
| SMOC2 | ENSG00000112562 | PERP | ENSG00000112378 |
| GALNT12 | ENSG00000119514 | GALNTL6 | ENSG00000174473 |
| MARVELD2 | ENSG00000152939 | OR2AK2 | ENSG00000187080 |
| OR10H4 | ENSG00000176231 | KIR3DL2 | ENSG00000278474 |
| TNFSF9 | ENSG00000125657 | TMEM129 | ENSG00000168936 |
| SLC52A3 | ENSG00000101276 | HTR2C | ENSG00000147246 |
| GJC2 | ENSG00000198835 | IL4R | ENSG00000077238 |
| SLC35G1 | ENSG00000176273 | KIR2DL3 | ENSG00000274830 |
| MXRA8 | ENSG00000162576 | ELN | ENSG00000049540 |
| KIAA1644 | ENSG00000138944 | MCOLN3 | ENSG00000055732 |
| OR2T8 | ENSG00000177462 | PGAM5 | ENSG00000247077 |
| ATP10B | ENSG00000118322 | MADCAM1 | ENSG00000099866 |
| TXNDC15 | ENSG00000113621 | KCNJ13 | ENSG00000115474 |
| OTOP1 | ENSG00000163982 | TMEM249 | ENSG00000261587 |
| OR2AJ1 | ENSG00000177275 | C16orf58 | ENSG00000140688 |
|  | ENSG00000265118 | SLC5A4 | ENSG00000100191 |
| ABCG5 | ENSG00000138075 | DEFB4A | ENSG00000171711 |
| CDH12 | ENSG00000154162 | CYBA | ENSG00000051523 |
| IZUMO2 | ENSG00000161652 | PXMP2 | ENSG00000176894 |
| ACKR4 | ENSG00000129048 | ATP8B1 | ENSG00000081923 |
| CES5A | ENSG00000159398 | DNAJC19 | ENSG00000205981 |
| TMEM202 | ENSG00000187806 | BMPR2 | ENSG00000204217 |
| MSR1 | ENSG00000038945 | GDNF | ENSG00000168621 |
| GPR63 | ENSG00000112218 | RNF121 | ENSG00000137522 |
| HLA-DOB | ENSG00000241106 | TIMM17B | ENSG00000126768 |
| OR2L13 | ENSG00000196071 | VAPA | ENSG00000101558 |
| GPR132 | ENSG00000183484 | OR52E2 | ENSG00000176787 |
| FGFR3 | ENSG00000068078 | TMEM132E | ENSG00000181291 |
| TMEM126A | ENSG00000171202 | CD180 | ENSG00000134061 |
| GULP1 | ENSG00000144366 | CNIH3 | ENSG00000143786 |
| CYP2C8 | ENSG00000138115 | KIR3DL2 | ENSG00000276004 |
| FADS2 | ENSG00000134824 | NXPE3 | ENSG00000144815 |
| KIR3DL2 | ENSG00000278809 | FGFR2 | ENSG00000066468 |
| SLC17A7 | ENSG00000104888 | CAMKMT | ENSG00000143919 |
| NRXN1 | ENSG00000179915 | PTPRT | ENSG00000196090 |
| MMP23B | ENSG00000189409 | NCR3 | ENSG00000225211 |
| GLIPR1L2 | ENSG00000180481 | CLDN3 | ENSG00000165215 |
| KCNK4 | ENSG00000182450 | TARM1 | ENSG00000276355 |
| OR2L5 | ENSG00000197454 | CACNA1I | ENSG00000100346 |
| PLD6 | ENSG00000179598 | NPY1R | ENSG00000164128 |
| IL1R1 | ENSG00000115594 | SLC3A2 | ENSG00000168003 |
| SLC16A1 | ENSG00000155380 | KIR2DL3 | ENSG00000278327 |
| STRC | ENSG00000242866 | KRTAP20-2 | ENSG00000184032 |
| B3GNT6 | ENSG00000198488 | TNFSF10 | ENSG00000121858 |
| SUSD1 | ENSG00000106868 | HSD17B13 | ENSG00000170509 |
| NBAS | ENSG00000151779 | CERS6 | ENSG00000172292 |
| OR52J3 | ENSG00000205495 | PTGER1 | ENSG00000160951 |
| PCSK7 | ENSG00000160613 | ALG5 | ENSG00000120697 |
| SLC29A3 | ENSG00000198246 | APP | ENSG00000142192 |
| PVRIG | ENSG00000213413 | TIMM23 | ENSG00000265354 |
|  | ENSG00000243627 | ST7L | ENSG00000007341 |
| TMIGD1 | ENSG00000182271 | ZNF304 | ENSG00000131845 |
| GDAP1 | ENSG00000104381 | TMEM116 | ENSG00000198270 |
| G6PC2 | ENSG00000152254 | LINGO2 | ENSG00000174482 |
| POTEG | ENSG00000222036 | TNFRSF11A | ENSG00000141655 |
| LRRC24 | ENSG00000254402 | CTAGE6 | ENSG00000271321 |
| TMEM217 | ENSG00000172738 | SLC6A6 | ENSG00000131389 |
| HRH4 | ENSG00000134489 | TMUB1 | ENSG00000164897 |
| TRIQK | ENSG00000205133 | GPA33 | ENSG00000143167 |
| PTPRG | ENSG00000144724 | TMEM131 | ENSG00000075568 |
| KIR2DL2 | ENSG00000275960 | GPR148 | ENSG00000173302 |
| DNAJB12 | ENSG00000148719 | VSIG1 | ENSG00000101842 |
| SLFN12L | ENSG00000205045 | KLHDC10 | ENSG00000128607 |
| KIAA2013 | ENSG00000116685 | GOLGB1 | ENSG00000173230 |

TABLE 5-continued

Gene List

| HGNC symbol ID | Ensembl Gene | HGNC symbol ID | Ensembl Gene |
|---|---|---|---|
| HMOX1 | ENSG00000100292 | TM4SF5 | ENSG00000142484 |
| FCGR1A | ENSG00000150337 | ERBB3 | ENSG00000065361 |
| KIR3DL2 | ENSG00000275838 | HAMP | ENSG00000105697 |
| DPM2 | ENSG00000136908 | MRGPRG | ENSG00000182170 |
| GPR155 | ENSG00000163328 | OR2D2 | ENSG00000166368 |
| SFXN5 | ENSG00000144040 | TAS2R60 | ENSG00000185899 |
| SLC25A26 | ENSG00000144741 | MMP15 | ENSG00000102996 |
| DCT | ENSG00000080166 | XKR8 | ENSG00000158156 |
| MS4A14 | ENSG00000166928 | NKPD1 | ENSG00000179846 |
| PDIA4 | ENSG00000155660 | KIR3DL3 | ENSG00000274556 |
| ATP1A4 | ENSG00000132681 | TMEM79 | ENSG00000163472 |
| TMED10 | ENSG00000170348 | KRT5 | ENSG00000186081 |
| SNX19 | ENSG00000120451 | F2RL2 | ENSG00000164220 |
| JPH1 | ENSG00000104369 | CD200 | ENSG00000091972 |
| OPALIN | ENSG00000197430 | SLC9B2 | ENSG00000164038 |
| HTR1F | ENSG00000179097 | TAS2R41 | ENSG00000221855 |
| HFE | ENSG00000010704 | TMEM130 | ENSG00000166448 |
| ATP6V0B | ENSG00000117410 | C1orf85 | ENSG00000198715 |
| KIR2DL1 | ENSG00000125498 | PRRG3 | ENSG00000130032 |
| LTA | ENSG00000230279 | SLC22A25 | ENSG00000196600 |
| ADAM8 | ENSG00000151651 | KIR3DL2 | ENSG00000240403 |
| RNASE10 | ENSG00000182545 | FES | ENSG00000182511 |
| SLC38A5 | ENSG00000017483 | HTR6 | ENSG00000158748 |
| NETO1 | ENSG00000166342 | EVA1B | ENSG00000142694 |
| SLC35E2B | ENSG00000189339 | TRAM1 | ENSG00000067167 |
| NPY5R | ENSG00000164129 | LCTL | ENSG00000188501 |
| ADRA2A | ENSG00000150594 | GPR33 | ENSG00000214943 |
| ACVRL1 | ENSG00000139567 | FNDC3A | ENSG00000102531 |
| BCL2L10 | ENSG00000137875 | MS4A6A | ENSG00000110077 |
| SMIM1 | ENSG00000235169 | GRM2 | ENSG00000164082 |
| SLC47A2 | ENSG00000180638 | GABRR1 | ENSG00000146276 |
| SLC6A13 | ENSG00000010379 | OR6X1 | ENSG00000221931 |
| MBOAT1 | ENSG00000172197 | OR6M1 | ENSG00000196099 |
| GGT2 | ENSG00000133475 | TAS2R16 | ENSG00000128519 |
| FKBP7 | ENSG00000079150 | GPR128 | ENSG00000144820 |
| DHX36 | ENSG00000174953 | TMEM106A | ENSG00000184988 |
| PHTF2 | ENSG00000006576 | KIR2DS4 | ENSG00000276634 |
| BSG | ENSG00000172270 | C14orf37 | ENSG00000139971 |
| ADAM28 | ENSG00000042980 | GPR149 | ENSG00000174948 |
| TMEM200A | ENSG00000164484 | EPHA5 | ENSG00000145242 |
| FOLH1 | ENSG00000086205 | KIR2DL1 | ENSG00000274926 |
| MUC3A | ENSG00000169894 | AUP1 | ENSG00000115307 |
| LST1 | ENSG00000234514 | OPRM1 | ENSG00000112038 |
| TGFB3 | ENSG00000119699 | CD58 | ENSG00000116815 |
| TMEM104 | ENSG00000109066 | LRCH4 | ENSG00000077454 |
| ST6GALNAC2 | ENSG00000070731 | LRRTM2 | ENSG00000146006 |
| COX16 | ENSG00000133983 | LRRC37B | ENSG00000185158 |
| SLC37A2 | ENSG00000134955 | CCPG1 | ENSG00000260916 |
| TMEM236 | ENSG00000148483 | TMEM69 | ENSG00000159596 |
| STEAP3 | ENSG00000115107 | OR4F29 | ENSG00000278566 |
| OSBPL8 | ENSG00000091039 | CD300E | ENSG00000186407 |
| NKAIN3 | ENSG00000185942 | TMEM246 | ENSG00000165152 |
| SGPP1 | ENSG00000126821 | CMTM8 | ENSG00000170293 |
| KCNE1L | ENSG00000176076 | OR5AN1 | ENSG00000176495 |
| KIR2DS2 | ENSG00000277885 | HLA-F | ENSG00000206509 |
| NCEH1 | ENSG00000144959 | SSBP4 | ENSG00000130511 |
| TMEM198 | ENSG00000188760 | ROBO1 | ENSG00000169855 |
| SMLR1 | ENSG00000256162 | SLC22A10 | ENSG00000184999 |
| CMTM4 | ENSG00000183723 | TPCN2 | ENSG00000162341 |
| MOG | ENSG00000204655 | GPRC5C | ENSG00000170412 |
| AOC3 | ENSG00000131471 | HTR3A | ENSG00000166736 |
| CALCRL | ENSG00000064989 | TCTN3 | ENSG00000119977 |
| ACSL4 | ENSG00000068366 | KLK3 | ENSG00000142515 |
| KIR3DL3 | ENSG00000275062 | SPATA3 | ENSG00000173699 |
| NPIPB5 | ENSG00000243716 | PROS1 | ENSG00000184500 |
| KIRREL2 | ENSG00000126259 | CRHR1 | ENSG00000120088 |
| OR2AE1 | ENSG00000244623 | ADORA1 | ENSG00000163485 |
| SLC20A1 | ENSG00000144136 | CA4 | ENSG00000167434 |
| DCBLD1 | ENSG00000164465 | SLC44A4 | ENSG00000232180 |
| KIR3DL1 | ENSG00000274948 | FMO3 | ENSG00000007933 |
| NPHS1 | ENSG00000161270 | RRBP1 | ENSG00000125844 |
|  | ENSG00000233438 | KIR2DL2 | ENSG00000275914 |
| ST3GAL5 | ENSG00000115525 | HERPUD1 | ENSG00000051108 |
| SLC17A1 | ENSG00000124568 | SLC36A3 | ENSG00000186334 |
| DPP6 | ENSG00000130226 | LDLRAD1 | ENSG00000203985 |

TABLE 5-continued

Gene List

| HGNC symbol ID | Ensembl Gene | HGNC symbol ID | Ensembl Gene |
|---|---|---|---|
| GPR112 | ENSG00000156920 | DSG4 | ENSG00000175065 |
| SEC63 | ENSG00000025796 | CCL11 | ENSG00000172156 |
| KIR2DL2 | ENSG00000276011 | | ENSG00000261717 |
| MICU3 | ENSG00000155970 | CATSPER1 | ENSG00000175294 |
| RNASET2 | ENSG00000026297 | TMEM170A | ENSG00000166822 |
| SLC25A48 | ENSG00000145832 | CACNG4 | ENSG00000075461 |
| LTB | ENSG00000231314 | TRBV13 | ENSG00000276405 |
| TNF | ENSG00000206439 | SLC26A2 | ENSG00000155850 |
| FAM189B | ENSG00000160767 | OTOP3 | ENSG00000182938 |
| OR5A2 | ENSG00000172324 | OR5B17 | ENSG00000197786 |
| ATXN2L | ENSG00000168488 | MBOAT7 | ENSG00000276935 |
| CYP2A13 | ENSG00000197838 | SERPINA1 | ENSG00000197249 |
| ST6GALNAC1 | ENSG00000070526 | TRPC1 | ENSG00000144935 |
| TM9SF4 | ENSG00000101337 | TLR10 | ENSG00000174123 |
| PIK3IP1 | ENSG00000100100 | TRPM4 | ENSG00000130529 |
| ENTPD8 | ENSG00000188833 | SLC22A4 | ENSG00000197208 |
| NPTN | ENSG00000156642 | TMEM120B | ENSG00000188735 |
| NUP210L | ENSG00000143552 | GABRG2 | ENSG00000113327 |
| C2orf66 | ENSG00000187944 | EMC10 | ENSG00000161671 |
| SLC22A24 | ENSG00000197658 | C5AR1 | ENSG00000197405 |
| TMEM225 | ENSG00000204300 | TBXAS1 | ENSG00000059377 |
| UMOD | ENSG00000169344 | NDUFB5 | ENSG00000136521 |
| LBR | ENSG00000143815 | TRBV18 | ENSG00000276557 |
| MME | ENSG00000196549 | FRRS1 | ENSG00000156869 |
| SLC22A5 | ENSG00000197375 | | |
| CA14 | ENSG00000118298 | | |
| CACNG5 | ENSG00000075429 | | |
| COX7A1 | ENSG00000161281 | | |
| FBXL17 | ENSG00000145743 | | |
| MARS | ENSG00000166986 | | |
| CNIH2 | ENSG00000174871 | | |
| ENPP4 | ENSG00000001561 | | |
| RHBG | ENSG00000132677 | | |
| EPHB1 | ENSG00000154928 | | |
| KCNH7 | ENSG00000184611 | | |
| ITM2C | ENSG00000135916 | | |
| CYP51A1 | ENSG00000001630 | | |
| TMEM41A | ENSG00000163900 | | |
| SAMD5 | ENSG00000203727 | | |
| RFNG | ENSG00000169733 | | |
| P4HA2 | ENSG00000072682 | | |
| GPR55 | ENSG00000135898 | | |
| LAIR1 | ENSG00000276163 | | |
| COX11 | ENSG00000166260 | | |
| YIF1A | ENSG00000174851 | | |
| CHSY1 | ENSG00000131873 | | |
| NTRK3 | ENSG00000140538 | | |
| KIR2DL4 | ENSG00000275848 | | |
| CRISP3 | ENSG00000096006 | | |
| SLC18A1 | ENSG00000036565 | | |

REFERENCES

1. Opelz G, Wujciak T, Dohler B, Scherer S, Mytilineos J. HLA compatibility and organ transplant survival. Collaborative Transplant Study. Rev Immunogenet. 1999; 1(3): 334-42.
2. Angaswamy N, Tiriveedhi V, Sarma N, Subramanian V, Klein C, Wellen J, Shenoy S, Chapman W, Mohanakumar T. Interplay between immune responses to HLA and non-HLA self-antigens in allograft rejection. Human Immunology. 2013; November; 74(11):1478-85.
3. Leventhal J R, Mathew J M, Salomon D R, Kurian S M, Suthanthiran M, Tambur A, Friedewald J, Gallon L, Charette J, Levitsky J, Kanwar Y, Abecassis M, Miller J. Genomic biomarkers correlate with HLA-identical renal transplant tolerance. J Am Soc Nephrol. 2013 September; 24(9):1376-85.
4. Handbook of clinical transplantation. 4th edition ed. Danovitch G M, editor.: Lippincott Williams & Wilkins; 2009.
5. Mountain J L, Cavalli-Sforza L L. Multilocus Genotypes, a Tree of Individuals, and Human Evolutionary History. Am J Hum Genet 1997; 61:705-18.
6. Suthanthiran M, Schwartz J E, Ding R, Abecassis M, Dadhania D, Samstein B, Knechtle S J, Friedewald J, Becker Y T, Sharma V K, Williams N M, Chang C S, Hoang C, Muthukumar T, August P, Keslar K S, Fairchild R L, Hricik D E, Heeger P S, Han L, Liu J, Riggs M, Ikle D N, Bridges N D, Shaked A. Urinary-cell mRNA profile and acute cellular rejection in kidney allografts. N Engl J Med. 2013 Jul. 4; 369(1):20-31.
7. Dorff K C, Chambwe N, Zeno Z, Simi M, Shaknovich R, Campagne F. GobyWeb: Simplified Management and Analysis of Gene Expression and DNA Methylation Sequencing Data. PLoS ONE. 2013; 8 (7):e69666.

8. Poge U, Gerhardt T, Palmedo H, Klehr H U, Sauerbruch T, Woitas R P. MDRD equations for estimation of GFR in renal transplant recipients. Am J Transplant. 2005 June; 5(6):1306-11.
9. Mengel M, Sis B, Haas M, Colvin R B, Halloran P F, Racusen L C, Solez K, Cendales L, Demetris A J, Drachenberg C B, Farver C F, Rodriguez E R, Wallace W D, Glotz D. Banff 2011 Meeting report: new concepts in antibody-mediated rejection. Am J Transplant. 2011 March; 12(3):563-70.
10. Campagne F, Dorff K C, Chambwe N, Robinson J. T., Mesirov J P. Compression of structured high-throughput sequencing data. PLOS One. 2013; 8 (11):e79871.
11. Danecek P, Auton A, Abecasis G, Albers C A, Banks E, DePristo M A, Handsaker R E, Lunter G, Marth G T, Sherry S T, McVean G, Durbin R. The variant call format and VCFtools. Bioinformatics. 2011 Aug. 1; 27(15):2156-8.
12. Gondos A, Döhler B, Brenner H, Opelz G. Kidney graft survival in Europe and the United States: strikingly different long-term outcomes. Transplantation [Internet] 2013 [cited 2014 Jun. 13]; 95(2):267-74. Available from: ncbi.nlm.nih.gov/pubmed/23060279
13. Sasaki N, Idica. A. The HLA-matching effect in different cohorts of kidney transplant recipients: 10 years later. Clin Transpl [Internet] 2010 [cited 2014 Oct. 13]; 261-82. Available from: ncbi.nlm.nih.gov/pubmed/21696046
14. Phelan P J, Conlon P J, Sparks M A. Genetic determinants of renal transplant outcome: where do we stand? J Nephrol [Internet] 2014; Available from: ncbi.nlm.nih.gov/pubmed/24515316
15. Kielbasa S M, Wan R, Sato K, Horton P, Frith M C. Adaptive seeds tame genomic sequence comparison. Genome Res [Internet] 2011; 21(3):487-93. Available from: ncbi.nlm.nih.gov/entrez/query.fcgi?cmd=Retrieve&db=PubMed&dopt=Citation&list_uids=21209072
16. Levey A S, Tangri N, Stevens L A. Classification of chronic kidney disease: a step forward. Ann Intern Med [Internet] 2011 [cited 2014 May 24]; 154(1):65-7, Available from: ncbi.nlm.nih.gov/pubmed/21200043
17. Franklin C, Fuentes W I, Motion J, et al. A genome-wide association study of kidney transplant survival: Donors recipients and interactions. [Internet]. In: American Conference of Human Genetics. 201.2. Available from: ashg.org/2012meeting/abstracts/fulltext/f120120818.htm
18. Goldfarb-Rumyantzev A S, Naiman N. Genetic prediction of renal transplant outcome. Curr Opin Nephrol Hypertens [Internet] 2008; 17(6):573-9. Available from: ncbi.nlm.nih.gov/entrez/query.fcgi?cmd=Retrieve&db=PubMed&dopt=Citation&list_uids=18941349
1. Opelz G, Wujciak T, Dohler B, Scherer S, Mytilineos J. HLA compatibility and organ transplant survival. Collaborative Transplant Study. Rev Immunogenct [Internet] 1999; 1(3):334-42. Available from: ncbi.nih.gov/entrez/query.fcgi?cmd=Retrieve&db=PubMed&dopt=Citation&list_uids=11256424
2. Angaswamy N, Tiriveedhi V, Sarma N J, et al. Interplay between immune responses to HLA and non-HLA self-antigens in allograft rejection. Hum Immunol 2013; November; 74(11):1478-85.
3. Leventhal J R, Mathew J M, Salomon D R, et al. Genomic biomarkers correlate with HLA-identical renal transplant tolerance. J Soc Nephrol [Internet] 2013; 24(9):1376-85. Available from: ncbi.nlm.nih.gov/entrez/query.fcgi?cmd=Retrieve&db=PubMed&dopt=Citation&list_uids=23787913
4. Gondos A, Döhler B, Brenner H, Opelz, G. Kidney graft survival in Europe and the United States: strikingly different long-term outcomes. Transplantation [Internet] 2013 [cited 2014 Jun. 13]; 95(2):267-74. Available from: ncbi.nlm.nih.gov/pubmed/23060279
5. Sasaki N, Mica A. The HLA-matching effect in different cohorts of kidney transplant recipients: 10 years later. Clin Transpl [Internet] 2010 [cited 2014 Oct. 13]; 261-82. Available from: ncbi.nlm.nih.gov/pubmed/21696046
6. Phelan P J, Conlon P J, Sparks M A. Genetic determinants of renal transplant outcome: where do we stand? J Nephrol [Internet] 2014; Available from: ncbi.nlm.nih.gov/pubmed/24515316
7. Suthanthiran M, Schwartz J E, Ding R, et al. Urinary-cell mRNA profile and acute cellular rejection in kidney allografts. N Engl J Med [Internet] 2013; 369(1):20-31. Available from: ncbi.nlm.nih.gov/entrez/query.fcgi?cmd=Retrieve&db=PubMed&dopt=Citation&list_uids=23822777
8. Dorff K C, Chambwe N, Zeno Z, Simi M, Shaknovich R, Campagne 1. GobyWeb: simplified management and analysis of gene expression and DNA methylation sequencing data. PLoS One [Internet] 2013 [cited 2013 Nov. 19]; 8(7):e69666. Available from: dx.plos.org/10.1371/journal.pone.0069666
9. Kielbasa S M, Wan R, Sato K, Horton P, Frith M C. Adaptive seeds tame genomic sequence comparison. Genome Res [Internet] 2011; 21(3):487-93, Available from: ncbi.nlm.nih.gov/entrez/query.fcgi?cmd=Retrieve&db=PuhMed&dopt=Citation&list_uids=21209072
10. Campagne F, Dorff K C, Chambwe N, Robinson J. T., Mesirov J P. Compression of structured high-throughput sequencing data. PLoS One 2013; 8(11):e79871.
11. Poge U, Gerhardt T, Palmedo H. Klehr H U, Sauerbruch T, Woitas R P. MDRD equations for estimation of GFR in renal transplant recipients. Am J Transpl [Internet] 2005; 5(6): 1306-11. Available from: ncbi.nlm.nih.gov/entrez/query.fcgi?cmd=Retrieve&db=PubMed&dopt=Citation&list_uids=15888034
12. Levey A S, Tangri N, Stevens L A. Classification of chronic kidney disease: a step forward. Ann Intern Med [Internet] 2011 [cited 2014 May 24]; 154(1):65-7. Available from: ncbi.nlm.nih.gov/pubmed/21200043
13. Franklin C, Fuentes W I, Mollon J, et al. A genome-wide association study of kidney transplant survival: Donors recipients and interactions. [Internet]. In: American Conference of Human Genetics. 201.2. Available from: ashg.org/2012meeting/abstracts/fulltext/f120120818.htm
14. Goldfarb-Rumyantzev A S, Naiman N. Genetic prediction of renal transplant outcome. Curr Opin Nephrol Hypertens [Internet] 2008; 17(6):573-9. Available from: ncbi.nlm.nih.gov/entrez/query.fcgi?cmd=Retrieve&db=PubMed&dopt=Citation&list_uids=8941349
15. O'Brien R P, Phelan P J, Conroy J, et al. A genome-wide association study of recipient genotype and medium-term kidney allograft function. Clin Transpl [Internet] 2013; 27(3):379-87. Available from: ncbi.nlm.nih.gov/entrez/query.fcgi?cmd=Retrieve&db=PubMed&dopt=Citation&list_uids-23432519
16. Varagunam M, Yaqoob M M, Dohler B, Opelz G. C3 polymorphisms and allograft outcome in renal transplantation. N Engl J Med [Internet] 2009; 360(9):874-80. Available from: ncbi.nlm.nih.gov/entrez/query.fcgi?cmd=Retrieve&db=PubMed&dopt=Citation&list_uids=19246358
17. Lv, R, Hu X, Bai Y, et al. Association between IL-6-174G/C polymorphism and acute rejection of renal allograft: evidence from a meta-analysis. Transpl Immunol. [Internet] 2012; 26(1):11-8. Available from: ncbi.nlm.nih.gov/entrez/query.fcgi?cmd=Retrieve&db=PubMed&dopt=Citation&list_uids=22024650

The following statements describe and summarize aspects of the invention.

Statements

1. A method to determine the best match among multiple potential organ donors for a recipient in need of a transplanted organ, where the method comprises:
   (a) determining genotypes of at least several hundred donor genomic DNA segments from the multiple organ donor candidates;
   (b) determining genotypes of the corresponding recipient genomic DNA segments from one or more possible transplant recipients; and
   (c) quantifying an amount of immunological mismatch between the one or more donor genotypes and the recipient genotypes, to thereby determine the best match among multiple potential organ donors and potential recipients in need of a transplanted organ.
2. The method of potential statement 1, wherein the immunological mismatch(es) can result in immunological reactions in the transplant recipient.
3. The method of potential statement 1, wherein an amount of immunological mismatch between a donor candidate and the recipient is a quantitative estimate called an allogenomics mismatch score comprising the sum of all amino acid mismatches between the recipient and the donor that can be recognized as non-self by the recipient.
4. The method of statement 3, wherein a lower (or lowest) allogenomics mismatch score identifies a donor of an organ for the recipient.
5. The method of statement 3, wherein a lower (or lowest) allogenomics mismatch score identifies a better clinical outcome for long-term graft survival and function of a donated organ in the recipient.
6. The method of potential statement 1, where the one or more donor genomic segments and the one or more corresponding recipient genomic segments from the recipient are selected to include genomic segments that can cause an immunologic response in the recipient when an organ of the donor is transplanted in the recipient.
7. The method of statement 1, further comprising defining a set of polymorphism sites for evaluation by sequence determination.
8. A method for identifying at least one match among multiple potential organ donors for at least one recipient in need of a transplanted organ, where the method comprises:
   (a) assaying to determine amino acid mismatches encoded by the donor genomes that at least one selected recipient immune system could recognize as non-self;
   (b) separately summing the number of amino acid mismatches for each donor compared to at least one selected recipient where the mismatches can be recognized as non-self by the selected recipient(s);
   (c) determining an allogenomics mismatch score $\Delta(r,d)$ for each selected recipient r and each donor d, which is a sum of mismatches as shown in Equation 1:

$$\Delta(r,d) = \sum_{p \in P} \delta_p[G_{rp} = \text{genotype}(r, p), G_{dp} = \text{genotype}(d, p)] \quad \text{Equation 1}$$

where:
$\delta_p$ is defined in Equation 2;
P is a set of all genomic positions of interest;
p is a polymorphic site in a set P;
$G_{rp}$ is the genotype of the recipient r at genomic site/position p;
$G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
a is an allele; and
   (d) identifying a match among the multiple potential organ donors for at least one recipient in need of a transplanted organ by identifying one or more donor with an allogenomics mismatch score that is below a threshold value, or by identifying the donor with the lowest allogenomics score for a selected recipient.
9. The method of statement 8, further comprising isolating genomic DNA from the donors and at least one recipient and assaying the number of amino acid differences encoded by the donor genomes that at least one recipient immune system could recognize as non-self.
10. The method of statement 8 or 9, wherein at least 1, or at least 2, or least 5, or at least 10, or at least 15, or at least 20, or at least 30, or at least 50, or at least 75, or at least 100, or at least 125, or at 150, or at least 200, or at 500 donors are assayed for the number of amino acid differences encoded by the donor genomes that at least one recipient immune system could recognize as non-self.
11. The method of statement 8 or 9, wherein at least 1, or at least 2, or least 5, or at least 10, or at least 15, or at least 20, or at least 30, or at least 50, or at least 75, or at least 100, or at least 125, or at 150, or at least 200, or at 500 recipients are assayed for the number of amino acid differences encoded by the donor genomes that at least one recipient immune system could recognize as non-self.
12. The method of any of statements 8-11, wherein mismatches between at least one recipient and the donors that can be recognized as non-self by a recipient do not include mismatches that the recipient has but that the donor does not have.
13. The method of any of statements 8-12, wherein assaying comprises identifying polymorphisms that are present in the donor but not in the recipient.
14. The method of any of statements 8-13, wherein assaying comprises genomic DNA fragmentation, DNA sequencing, primer extension, microarray sequence analysis, SNP analysis, polymerase chain reaction, or a combination thereof.
15. The method of any of statements 8-14, wherein assaying comprises sequencing exons in genomic DNA samples obtained from the donor and separately sequencing exons in genomic DNA samples obtained from the recipient.
16. The method of any of statements 8-15, wherein assaying comprises sequencing exons encoding transmembrane proteins.
17. The method of any of statements 8-16, wherein assaying comprises sequencing exons that do not encode human leukocyte antigens.
18. The method of any of statements 8-17, wherein assaying comprises sequencing exons selected from the genes listed in Table 5 to determine the number of amino acid differences encoded by the donor genome that the recipient immune system could recognize as non-self.
19. The method of any of statements 8-18, wherein amino acid mismatches between the recipient and the donor that can be recognized as non-self by the recipient can cause an immunologic response in the recipient when an organ of the donor is transplanted in the recipient.
20. The method of any of statements 8-19, wherein amino acid mismatches between the recipient and the donor that can be recognized as non-self by the recipient comprise amino acid mismatches in membrane proteins.
21. The method of any of statements 8-20, wherein amino acid mismatches between the recipient and the donor that can be recognized as non-self by the recipient comprise amino acid mismatches in extracellular domains of membrane proteins.
22. The method of any of statements 8-21, wherein summing amino acid mismatches between the recipient and the donor that can be recognized as non-self by the recipient comprises summing polymorphic sites as shown in Equation 2:

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
a is an allele;
P is a set of all genomic positions of interest;
p is a polymorphic site in a set P;
$G_{rp}$ is the genotype of the recipient r at genomic site/position p; and
$G_{dp}$ is the genotype of the donor d at site p.
23. The method of any of statements 8-22, further comprising selecting a donor organ for transplantation into a recipient.
24. The method of any of statements 8-23, further comprising transplanting a selected donor organ into a recipient.
25. A method comprising:
  (a) assaying to determine amino acid mismatches encoded a donor organ genome that the immune system of the recipient of the donor organ could recognize as non-self;
  (b) summing the number of donor amino acid mismatches compared to the recipient where the mismatches can be recognized as non-self by recipient;
  (c) determining an allogenomics mismatch score Δ(r,d) for the recipient r and the donor d, which is a sum of mismatches as shown in Equation 1:

$$\Delta(r, d) = \sum_{p \in P} \delta_p[G_{rp} = \text{genotype}(r, p), G_{dp} = \text{genotype}(d, p)] \quad \text{Equation 1}$$

where:
  $\delta_p$ is defined in Equation 2;
  P is a set of all genomic positions of interest;
  p is a polymorphic site in a set P;
  $G_{rp}$ is the genotype of the recipient rat genomic site/position p;
  $G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where a is an allele;
  (d) determining whether the allogenomics mismatch score is greater than a threshold; and
  (e) identifying whether the recipient is in need of treatment, or may develop a need for treatment, when the allogenomics mismatch score is greater than a threshold value.
26. The method of statement 25, further comprising isolating genomic DNA from the donor or the donor transplant, and the recipient; and assaying the number of amino acid differences encoded by the donor genome that the recipient immune system could recognize as non-self.
27. The method of statement 25 or 26, wherein assaying comprises genomic DNA fragmentation, DNA sequencing, primer extension, microarray sequence analysis, SNP analysis, polymerase chain reaction, or a combination thereof.
28. The method of any of statements 25-27, wherein assaying comprises sequencing exons in genomic DNA samples obtained from the donor and separately sequencing exons in genomic DNA samples obtained from the recipient.
29. The method of any of statements 25-28, wherein assaying comprises sequencing exons encoding transmembrane proteins.
30. The method of any of statements 25-29, wherein assaying comprises sequencing exons that do not encode human leukocyte antigens.
31. The method of any of statements 25-30, wherein assaying comprises sequencing exons selected from the genes listed in Table 5 to determine the number of amino acid differences encoded by the donor genome that the recipient immune system could recognize as non-self.
32. The method of any of statements 25-31, wherein amino acid mismatches between the recipient and the donor that can be recognized as non-self by the recipient can cause an immunologic response in the recipient when an organ of the donor is transplanted in the recipient.
33. The method of any of statements 25-31, wherein amino acid mismatches between the recipient and the donor that can be recognized as non-self by the recipient comprise amino acid mismatches in membrane proteins.
34. The method of any of statements 25-33, wherein amino acid mismatches between the recipient and the donor that can be recognized as non-self by the recipient comprise amino acid mismatches in extracellular domains of membrane proteins.
35. The method of any of statements 25-34, wherein summing amino acid mismatches between the recipient and the donor that can be recognized as non-self by the recipient comprises summing polymorphic sites as shown in Equation 2:

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where
a is an allele;
P is a set of all genomic positions of interest;
p is a polymorphic site in a set P;
$G_{rp}$ is the genotype of the recipient r at genomic site/position p; and
$G_{dp}$ is the genotype of the donor d at site p.

36. The method of any of statements 25-35, further comprising treating the recipient when the allogenomics mismatch score is greater than the threshold value.

37. The method of any of statements 25-36, further comprising treating the recipient for tissue rejection or potential tissue rejection when the allogenomics mismatch score is greater than the threshold value.

38. The method of any of statements 25-37, further comprising administering immunosuppression therapy to the recipient when the allogenomics mismatch score is greater than the threshold value.

39. The method of any of statements 25-38, wherein the threshold value is 1700, 1600, 1500, 1400, 1300, 1200, 1100, or 1000.

40. The method of any of statements 25-39, wherein the organ is a kidney, a heart, a liver, a lung, a bladder, an intestine, a trachea, an esophagus, a pancreas, a stomach, a thymus, an ovary, a cervix, a uterus, a vagina, a penis, a prostate, a testes, or any combination or part thereof; or a tissue selected from the group of vascular tissues, neuronal tissues, muscular tissues, adipose tissues, pancreatic islet tissues, bone tissues, bone marrow, skin, dermal tissues, stem cells, connective tissues, or a combination.

41. An apparatus comprising:
(a) a component for separately assaying amino acid mismatches encoded by multiple donor genomes that at least one selected recipient immune system could recognize as non-self;
(b) a component for separately summing the donor amino acid mismatches assayed by comparison to amino acids encoded by each selected recipient;
(c) a component for determining an allogenomics mismatch score Δ(r,d) for at least one recipient r and one or more donor d, which is a sum of mismatches as shown in Equation 1:

$$\Delta(r,d) = \sum_{p \in P} \delta_p[G_{rp} = \text{genotype}(r, p), G_{dp} = \text{genotype}(d, p)] \quad \text{Equation 1}$$

where:
$\delta_p$ is defined in Equation 2;
P is a set of all genomic positions of interest;
p is a polymorphic site in a set P;
$G_{rp}$ is the genotype of the recipient r at genomic site/position p;
$G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \quad \text{Equation 2}$$

where a is an allele; and
(d) a component for determining a match among potential organ donors for at least one recipient in need of a transplanted organ by identifying one or more donor with a allogenomics mismatch score less than a threshold value, or by identifying the donor with the lowest allogenomics mismatch score for a selected recipient.

42. The apparatus of statement 41, further comprising a component for isolating and/or purifying genomic DNA from the donors and at least one recipient and assaying the number of amino acid differences encoded by the donor genomes that at least one recipient immune system could recognize as non-self.

43. The apparatus of statement 41 or 42, wherein the component for assaying the number of amino acid differences (mismatches) encoded by one or more donor genome that at least one recipient immune system could recognize as non-self can separately assay at least 1, or at least 2, or least 5, or at least 10, or at least 15, or at least 20, or at least 30, or at least 50, or at least 75, or at least 100, or at least 125, or at 150, or at least 200, or at 500 donor samples.

44. The apparatus of any of statements 41 to 43, wherein the component for assaying the number of amino acid differences (mismatches) encoded by one or more donor genome that at least one recipient immune system could recognize as non-self can separately assay at least 1, or at least 2, or least 5, or at least 10, or at least 15, or at least 20, or at least 30, or at least 50, or at least 75, or at least 100, or at least 125, or at 150, or at least 200, or at 500 recipient samples.

45. The apparatus of any of statements 41 to 44, wherein the component for assaying comprises at least one chamber for genomic DNA fragmentation, DNA sequencing, primer extension, microarray sequence analysis, SNP analysis, polymerase chain reaction, or a combination thereof.

46. The apparatus of any of statements 41 to 45, wherein the component for assaying comprises at least one chamber comprising primers for sequencing exons in genomic DNA samples obtained from the donor, and at least one chamber comprising primers for separately sequencing exons in genomic DNA samples obtained from the recipient.

47. The apparatus of any of statements 41 to 46, wherein the component for assaying the number of amino acid differences (mismatches) comprises primers that selectively hybridize to exons encoding transmembrane proteins.

48. The apparatus of any of statements 41 to 47, wherein the component for assaying the number of amino acid differences (mismatches) comprises primers that selectively hybridize to exons that do not encode human leukocyte antigens.

49. The apparatus of any of statements 41 to 48, wherein the component for assaying the number of amino acid differences (mismatches) identifies polymorphisms that are present in the donor but not in the recipient.

50. The apparatus of any of statements 41 to 49, wherein the component for assaying comprises primers that selectively hybridize to exons selected from the genes listed in Table 5 to determine the number of amino acid differences encoded by the donor genome that the recipient immune system could recognize as non-self.

51. The apparatus of any of statements 41 to 50, wherein the component for assaying comprises primers that selectively hybridize to exons that encode a protein segment that can cause an immunologic response in the recipient when an organ of the donor is transplanted in the recipient.

52. The apparatus of any of statements 41 to 51 wherein the component for assaying comprises primers that selectively hybridize to exons encoding membrane proteins.
53. The apparatus of any of statements 41 to 52, wherein the component for assaying comprises primers that selectively hybridize to exons encoding membrane proteins with extracellular domains.
54. The apparatus of any of statements 41 to 53, wherein the component for summing of amino acid mismatches between the recipient(s) and the donor(s) does not sum recipient polymorphisms that are not present in the donor.
55. The apparatus of any of statements 41 to 54, wherein the component for summing of amino acid mismatches between the recipient(s) and the donor(s) sums as shown in Equation 2:

$$\delta_p(G_{rp}, G_{dp}) = \sum_{a \in G_{dp}} \begin{cases} 0 & \text{if } a \in G_{r,p} \\ 1 & \text{otherwise} \end{cases} \qquad \text{Equation 2}$$

where
  a is an allele;
  P is a set of all genomic positions of interest;
  p is a polymorphic site in a set P;
  $G_{rp}$ is the genotype of the recipient r at genomic site/position p; and
  $G_{dp}$ is the genotype of the donor d at site p.
56. The apparatus of any of statements 41 to 55, which selects at least one donor organ for transplantation into at least one recipient.
57. The apparatus of any of statements 41 to 56, further comprising a display or a print-out of one or more allogenomics mismatch score.

The specific methods, compositions, and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which are not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acids or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

In the foregoing description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:
1. A method for identifying at least one match among multiple potential organ donors for at least one selected recipient in need of a transplanted organ, where the method comprises:
   (a) assaying to determine amino acid mismatches encoded by the donor genomes that at least one recipient immune system recognizes as non-self;
   (b) separately summing the number of amino acid mismatches for each donor compared to the at least one selected recipient where the mismatches are recognized as non-self by the at least one selected recipient;
   (c) determining an allogenomics mismatch score Δ(r,d) for the at least one selected recipient r and each donor d, which is a sum of mismatch differences as shown in Equation 1:

$$\Delta(r, d) = \sum_{p \in P} \delta_p[G_{rp} = \text{genotype}(r, p), G_{dp} = \text{genotype}(d, p)] \qquad \text{Equation 1}$$

where: $\delta_p$ is defined in Equation 2;
P is a set of all genomic positions of interest;
p is a polymorphic site in a set P;
$G_{rp}$ is the genotype of the recipient r at genomic site/position p;
$G_{dp}$ is the genotype of the donor d at site p;

$$\delta_p(G_{rp}, G_{dp}) = \sum_{a \in G_{dp}} \begin{cases} 0 & \text{if } a \in G_{r,p} \\ 1 & \text{otherwise} \end{cases} \qquad \text{Equation 2}$$

where a is an allele;
   (d) identifying a match among the multiple potential organ donors for the at least one selected recipient in need of a transplanted organ by identifying a donor of the multiple potential organ donors with an allogenomics mismatch score that is below a threshold value, or by identifying the donor with the lowest allogenomics score for the at least one selected recipient; and (e) transplanting the matched donor organ into the at least one selected recipient.

2. The method of claim 1, further comprising isolating genomic DNA from the donors and the at least one selected recipient for the assaying.

3. The method of claim 1, wherein at least 10 donor samples and/or at least 10 recipient samples are assayed to determine the amino acid mismatches encoded by the donor genomes that the at least one selected recipient immune system recognizes as non-self.

4. The method of claim 1, wherein the assaying comprises genomic DNA fragmentation, DNA sequencing, primer extension, microarray sequence analysis, SNP analysis, polymerase chain reaction, or a combination thereof.

5. The method of claim 1, wherein the assaying comprises sequencing exons in genomic DNA samples obtained from the donors and separately sequencing exons in genomic DNA samples obtained from the at least one recipient.

6. The method of claim 1, wherein the assaying comprises sequencing exons encoding transmembrane proteins.

7. The method of claim 1, wherein the assaying comprises sequencing exons that do not encode human leukocyte antigens.

8. The method of claim 1, wherein the amino acid mismatches between the at least one recipient and the donor that are recognized as non-self by the at least one recipient cause an immunologic response in the at least one recipient when an organ of the donor is transplanted in the at least one recipient.

9. The method of claim 1, wherein the amino acid mismatches between the at least one recipient and the donor that are recognized as non-self by the at least one recipient comprise amino acid mismatches in membrane proteins.

10. The method of claim 1, wherein the amino acid mismatches between the at least one recipient and the donor that are recognized as non-self by the at least one recipient comprise amino add mismatches in extracellular domains of membrane proteins.

11. The method of claim 1, wherein the summing in (b) comprises identifying polymorphisms that are present in the donor but not in the at least one recipient.

12. The method of claim 1, wherein the organ is a kidney, a heart, a liver, a lung, a bladder, an intestine, a trachea, an esophagus, a pancreas, a stomach, a thymus, an ovary, a cervix, a uterus, a vagina, a penis, a prostate, a testes, a vascular tissue, a neuronal tissue, a muscular tissue, an adipose tissue, a pancreatic islet tissue, a bone tissue, bone marrow, skin, dermal tissue, stem cell, connective tissue, or a combination or part thereof.

* * * * *

UNITED STATES PATENT AND TRADEMARK OFFICE
CERTIFICATE OF CORRECTION

PATENT NO. : 10,720,226 B2  
APPLICATION NO. : 15/112105  
DATED : July 21, 2020  
INVENTOR(S) : Campagne et al.

It is certified that error appears in the above-identified patent and that said Letters Patent is hereby corrected as shown below:

In the Claims

In Column 132, Line 14, in Claim 10, delete "add" and insert --acid-- therefor

Signed and Sealed this  
Twenty-ninth Day of December, 2020

Andrei Iancu  
*Director of the United States Patent and Trademark Office*